US009637758B2

(12) United States Patent
Hurwitz et al.

(10) Patent No.: US 9,637,758 B2
(45) Date of Patent: May 2, 2017

(54) MODIFIED SENDAI VIRUS VACCINE AND IMAGING VECTOR

(75) Inventors: Julia Lea Hurwitz, Germantown, TN (US); Toru Takimoto, West Henrietta, NY (US); Charles John Russell, Arlington, TN (US); Allen Portner, Memphis, TN (US); Karen Slobod, Somerville, MA (US)

(73) Assignee: St. Jude Children's Research Hospital, Memphis, TN (US)

( * ) Notice: Subject to any disclaimer, the term of this patent is extended or adjusted under 35 U.S.C. 154(b) by 38 days.

(21) Appl. No.: 14/113,769

(22) PCT Filed: Apr. 13, 2012

(86) PCT No.: PCT/US2012/033482
§ 371 (c)(1),
(2), (4) Date: Jan. 13, 2014

(87) PCT Pub. No.: WO2012/148708
PCT Pub. Date: Nov. 1, 2012

(65) Prior Publication Data
US 2014/0186397 A1    Jul. 3, 2014

Related U.S. Application Data

(60) Provisional application No. 61/480,008, filed on Apr. 28, 2011.

(51) Int. Cl.
*C12N 15/86* (2006.01)
*C07K 14/005* (2006.01)
*C12N 7/00* (2006.01)
*C07K 16/08* (2006.01)
*A61K 39/00* (2006.01)

(52) U.S. Cl.
CPC ............ *C12N 15/86* (2013.01); *C07K 14/005* (2013.01); *C07K 16/08* (2013.01); *C12N 7/00* (2013.01); *A61K 2039/5254* (2013.01); *A61K 2039/5256* (2013.01); *C12N 2760/18534* (2013.01); *C12N 2760/18634* (2013.01); *C12N 2760/18734* (2013.01); *C12N 2760/18821* (2013.01); *C12N 2760/18822* (2013.01); *C12N 2760/18834* (2013.01); *C12N 2760/18843* (2013.01)

(58) Field of Classification Search
None
See application file for complete search history.

(56) References Cited

U.S. PATENT DOCUMENTS

| 4,683,195 | A | 7/1987 | Mullis et al. | 435/6.11 |
| 4,683,202 | A | 7/1987 | Mullis | 435/91.2 |
| 4,965,188 | A | 10/1990 | Mullis et al. | 435/6.12 |
| 6,746,860 | B1 | 6/2004 | Tokusumi et al. | 435/235.1 |
| 7,704,509 | B2 | 4/2010 | Murphy et al. | 435/239 |
| 2004/0137627 | A1 | 7/2004 | Tokusumi et al. | 435/320.1 |
| 2005/0266566 | A1 | 12/2005 | Nagai et al. | 435/320.1 |
| 2006/0110740 | A1 | 5/2006 | Hurwitz et al. | 435/6 |
| 2010/0266633 | A1 | 10/2010 | Kano et al. | 514/44 |
| 2010/0323428 | A1 | 12/2010 | Yoshizaki et al. | 424/211.1 |

FOREIGN PATENT DOCUMENTS

WO    WO/01/92548    12/2001

OTHER PUBLICATIONS

Chambers et al. (PLoS, Jun. 2010, vol. 5, p. 1-13).*
Nishio et al. (Virology, 2004, vol. 329, p. 289-301).*
Chambers et al. (PloS, 2010, vol. 5, p. 1-13).*
Anderson, D. E. et al. (2008) "Region between the Canine Distemper Virus M and F Genes Modulates Virulence by Controlling Fusion Protein Expression," *Journal of Virology* 82(21), 10510-10518.
Anh, D. B. T. et al. (2006) "Differential resistance/susceptibility patterns to pneumovirus infection among inbred mouse strains," *American Journal of Physiology—Lung Cellular and Molecular Physiology* 291(3), L426-L435.
Arkwright, P. D. et al. (2008) "Recently identified factors predisposing children to infectious diseases," *Current Opinion in Infectious Diseases* 21(3), 217-222.
Bhatt, P. N. et al. (1974) "An Epizootic of Sendai Infection with Mortality in a Barrier-Maintained Mouse Colony," *American Journal of Epidemiology* 100(3), 222-229.
Boon, A. C. M. et al. (2009) "Host Genetic Variation Affects Resistance to Infection with a Highly Pathogenic H5N1 Influenza a Virus in Mice," *Journal of Virology* 83(20), 10417-10426.
Bourgeois, F. T. et al. (2009) "Relative Impact of Influenza and Respiratory Syncytial Virus in Young Children," *Pediatrics* 124(6), e1072-e1080.
Bousse, T. et al. (2006) "Human parainfluenza virus type 1 but not Sendai virus replicates in human respiratory cells despite IFN treatment," *Virus Research* 121(1), 23-32.
Bousse, T. et al. (2002) "The Long Noncoding Region of the Human Parainfluenza Virus Type 1 F Gene Contributes to the Read-Through Transcription at the M-F Gene Junction," *Journal of Virology* 76(16), 8244-8251.
Boyce, T. G. et al. (2000) "Rates of hospitalization for respiratory syncytial virus infection among children in Medicaid," *Journal of Pediatrics* 137(6), 865-870.
Brown, S. A. et al. (2007) "A Recombinant Sendai Virus Is Controlled by CD4+ Effector T Cells Responding to a Secreted Human Immunodeficiency Virus Type 1 Envelope Glycoprotein," *Journal of Virology* 81(22), 12535-12542.

(Continued)

*Primary Examiner* — Agnieszka Boesen
(74) *Attorney, Agent, or Firm* — Medlen & Carroll, LLP

(57) ABSTRACT

The present invention relates to a Sendai virus or recombinant Sendai virus vector. In particular the present invention provides methods, vectors, formulations, compositions, and kits for a modified Enders strain Sendai viral vector. An immunogenic vector can be used in any in vitro or in vivo system. Moreover, some embodiments include vectors for imaging virus growth, location and transmission.

15 Claims, 30 Drawing Sheets

(56) References Cited

OTHER PUBLICATIONS

Brownstein, D. G. (1987) "Resistance/susceptibility to lethal Sendai virus infection genetically linked to a mucociliary transport polymorphism," *Journal of Virology* 61(5), 1670-1671.

Brownstein, D. G. et al. (1981) "Sendai virus infection in genetically resistant and susceptible mice," *American Journal of Pathology* 105(2), 156-163.

Brownstein, D. G. et al. (1986) "Genetic resistance to lethal Sendai virus pneumonia: virus replication and interferon production in C57BL/6J and DBA/2J mice," *Lab Animal Science* 36(2), 126-129.

Bukreyev, A. et al. (2006) "Nonsegmented Negative-Strand Viruses as Vaccine Vectors," *Journal of Virology* 80(21), 10293-10306.

Cattaneo, R. et al. (1987) "Altered ratios of measles virus transcripts in diseased human brains," *Virology* 160(2), 523-526.

Chambers, R. et al. (2010) "Trafficking of Sendai Virus Nucleocapsids Is Mediated by Intracellular Vesicles," *PLoS One* 5(6), e10994.

Chanock, R. M. et al. (1963) "Myxoviruses: Parainfluenza," *American Review of Respiratory Disease* 88, SUPPL 152-166.

Dave, V. P. et al. (1994) "Viral Cross-Reactivity and Antigenic Determinants Recognized by Human Parainfluenza Virus Type 1-Specific Cytotoxic T-Cells," *Virology* 199(2), 376-383.

De Swart, R. L. et al. (2007) "Predominant infection of CD150+ lymphocytes and dendritic cells during measles virus infection of macaques," *PLoS Pathogens* 3(11), e178.

Denny, F. W. et al. (1983) "Croup: An 11-Year Study in a Pediatric Practice," *Pediatrics* 71(6), 871.

Devincenzo, J. P. et al. (2010) "Viral Load Drives Disease in Humans Experimentally Infected with Respiratory Syncytial Virus," *American Journal of Respiratory and Critical Care Medicine* 182(10), 1305-1314.

Faisca, P. et al. (2005) "Sendai virus-induced alterations in lung structure/function correlate with viral loads and reveal a wide resistance/susceptibility spectrum among mouse strains," *American Journal of Physiology—Lung Cellular and Molecular Physiology* 289(5), L777-L787.

Faísca, P. et al. (2007) "Sendai virus, the mouse parainfluenza type 1: A longstanding pathogen that remains up-to-date," *Research in Veterinary Science* 82(1), 115-125.

Fujii, Y. et al. (2002) "Involvement of the Leader Sequence in Sendai Virus Pathogenesis Revealed by Recovery of a Pathogenic Field Isolate from cDNA," *Journal of Virology* 76(17), 8540-8547.

Garcin, D. et al. (1997) "A Point Mutation in the Sendai Virus Accessory C Proteins Attenuates Virulence for Mice, but Not Virus Growth in Cell Culture," *Virology* 238(2), 424-431.

Gorman, W. L. et al. (1990) "The hemagglutinin-neuraminidase glycoproteins of human parainfluenza virus type 1 and Sendai virus have high structure-function similarity with limited antigenic cross-reactivity," *Virology* 175(1), 211-221.

Graham, B. S. (2011) "Biological challenges and technological opportunities for respiratory syncytial virus vaccine development," *Immunological Reviews* 239(1), 149-166.

Griesenbach, U. et al. (2008) "In vivo imaging of gene transfer to the respiratory tract," *Biomaterials* 29(10), 1533-1540.

Hall, C. B. (2001) "Respiratory Syncytial Virus and Parainfluenza Virus," *New England Journal of Medicine* 344(25), 1917-1928.

Hall, C. B. et al. (1981) "Modes of transmission of respiratory syncytial virus," *Journal of Pediatrics* 99(1), 100-103.

Hall, C. B. et al. (1981) "Infectivity of respiratory syncytial virus by various routes of inoculation," *Infection and Immunity* 33(3), 779-783.

Hall, C. B. et al. (2009) "The Burden of Respiratory Syncytial Virus Infection in Young Children," *New England Journal of Medicine* 360(6), 588-598.

Hasan, M. K. et al. (1997) "Creation of an infectious recombinant Sendai virus expressing the firefly luciferase gene from the 3' proximal first locus," *Journal of General Virology* 78(11), 2813-2820.

Henrickson, K. J. (2003) "Parainfluenza Viruses," *Clinical Microbiology Reviews* 16(2), 242-264.

Hurwitz, J. L. (2008) "Development of recombinant Sendai virus vaccines for prevention of human parainfluenza and respiratory syncytial virus infections," *Pediatric Infectious Disease Journal* 27(10 Suppl), S126-128.

Hurwitz, J. L. et al. (2008) "Development of Sendai Virus-Based Vaccines to Prevent Pediatric Respiratory Virus Infections," *Pracedia in Vaccinology* 1(1), 41-44.

Hurwitz, J. L. et al. (1997) "Intranasal Sendai virus vaccine protects African green monkeys from infection with human parainfluenza virus-type one," *Vaccine* 15(5), 533-540.

Iida, T. (1972) "Experimental Study on the Transmission of Sendai Virus in Specific Pathogen-free Mice," *Journal of General Virology* 14(1), 69-75.

Ishida, N. et al. (1978) "Sendai virus," *Advances in Virus Research* 23, 349-383.

Itoh, M. et al. (1997) "Isolation of an avirulent mutant of Sendai virus with two amino acid mutations from a highly virulent field strain through adaptation to LLC-MK2 cells," *Journal of General Virology* 78(12), 3207-3215.

Itoh, T. et al. (1991) "Comparative lung pathology of inbred strain of mice resistant and susceptible to Sendai virus infection," *Journal of Veterinary Medical Science* 53(2), 275-279.

Jones, B. et al. (2009) "Human PIV-2 recombinant Sendai virus (rSeV) elicits durable immunity and combines with two additional rSeVs to protect against hPIV-1, hPIV-2, hPIV-3, and RSV," *Vaccine* 27(12), 1848-1857.

Karron, R. A. et al. (2007) "Parainfluenza Viruses," 5th ed., pp. 1497-1526.

Kato, A. et al. (1999) "Sendai Virus Gene Start Signals Are Not Equivalent in Reinitiation Capacity: Moderation at the Fusion Protein Gene," *Journal of Virology* 73(11), 9237-9246.

Kido, H. et al. (1992) "Isolation and characterization of a novel trypsin-like protease found in rat bronchiolar epithelial Clara cells. A possible activator of the viral fusion glycoprotein," *Journal of Biological Chemistry* 267(19), 13573-13579.

Kiyotani, K. et al. (1993) "F0-containing noninfectious Sendai virus can initiate replication in mouse lungs but requires a relatively long incubation period," *Journal of Virology* 67(12), 7618-7622.

Kiyotani, K. et al. (2001) "Attenuation of a field Sendai virus isolate through egg-passages is associated with an impediment of viral genome replication in mouse respiratory cells," *Archives in Virology* 146(5), 893-908.

Köhler, G. et al. (1975) "Continuous cultures of fused cells secreting antibody of predefined specificity," *Nature* 256(5517), 495-497.

Lamb, R. A. et al. (2007) "Paramyxoviridae: The Viruses and Their Replication," 5th ed., pp. 1449-1496, Lippincott, Williams and Wilkins, Philadelphia.

Lemon, K. et al. (2011) "Early target cells of measles virus after aerosol infection of non-human primates," *PLoS Pathogens* 7(1), e1001263.

Lowen, A. C. et al. (2007) "Influenza virus transmission is dependent on relative humidity and temperature," *PLoS Pathogens* 3(10), 1470-1476.

Luker, K. E. et al. (2008) "Applications of bioluminescence imaging to antiviral research and therapy: Multiple luciferase enzymes and quantitation," *Antiviral Research* 78(3), 179-187.

Luque, L. E. et al. (2010) "Residues in the Heptad Repeat a Region of the Fusion Protein Modulate the Virulence of Sendai Virus in Mice," *Journal of Virology* 84(2), 810-821.

Luque, L. E. et al. (2007) "Spring-Loaded Heptad Repeat Residues Regulate the Expression and Activation of Paramyxovirus Fusion Protein," *Journal of Virology* 81(7), 3130-3141.

Manicassamy, B. et al. (2010) "Analysis of in vivo dynamics of influenza virus infection in mice using a GFP reporter virus," *Proceedings of the National Academy of Sciences* 107(25), 11531-11536.

McLean, D. M. et al. (1967) "Myxovirus dissemination by air," *Canadian Medical Association Journal* 96(22), 1449-1453.

(56) References Cited

OTHER PUBLICATIONS

Miyamae, T. (2005) "Differential Invasion by Sendai Virus of Abdominal Parenchymal Organs and Brain Tissues in Cortisone- and Cyclophosphamide-Based Immunosuppressed Mice," *Journal of Veterinary Medical Science* 67(4), 369-377.
Mo, X. Y. et al. (1995) "Induction of cytokines in mice with parainfluenza pneumonia," *Journal of Virology* 69(2), 1288-1291.
Moscona, A. (2005) "Entry of parainfluenza virus into cells as a target for interrupting childhood respiratory disease," *Journal of Clinical Investigation* 115(7), 1688-1698.
Murphy, B. R. et al. (2002) "Live-attenuated virus vaccines for respiratory syncytial and parainfluenza viruses: applications of reverse genetics," *Journal of Clinical Investigation* 110(1), 21-27.
Nagai, Y. (1999) "Paramyxovirus replication and pathogenesis. Reverse genetics transforms understanding," *Reviews in Medical Virology* 9(2), 83-99.
Nakagawa, M. et al. (1980) "Pathogenicity of Sendai virus in mice cage-mated with infectors and their offsprings," *Japanese Journal of Veterinary Science* 42(3), 337-344.
Nishio, M. et al. (2004) "Recombinant Sendai viruses with L1618V mutation in their L polymerase protein establish persistent infection, but not temperature sensitivity," *Virology* 329(2), 289-301.
Paramore, L. C. et al. (2010) "Outpatient RSV lower respiratory infections among high-risk infants and other pediatric populations," *Pediatric Pulmonology* 45(6), 578-584.
Parrott, R. H. et al. (1975) "Potential of attenuated respiratory syncytial virus vaccine for infants and children," *Developments in Biological Standardization* 28, 389-399.
Parrott, R. H. et al. (1959) "Clinical Features of Infection with Hemadsorption Viruses," *New England Journal of Medicine* 260(15), 731-738.
Parrott, R. H. et al. (1962) "Acute respiratory diseases of viral etiology. III. parainfluenza. Myxoviruses," *American Journal of Public Health and the Nation's Health* 52, 907-917.
Profeta, M. L. et al. (1969) "Enzootic Sendai Infection in Laboratory Hamsters," *American Journal of Epidemiology* 89(3), 316-324.
Rassa, J. C. et al. (1998) "Molecular Basis for Naturally Occurring Elevated Readthrough Transcription across the M-F Junction of the Paramyxovirus SV5," *Virology* 247(2), 274-286.
Reichelderfer, T. E. et al. (1958) "Infection of human volunteers with type 2 hemadsorption virus," *Science* 128(3327), 779-780.
Rudd, P. A. et al. (2006) "Canine Distemper Virus Uses both the Anterograde and the Hematogenous Pathway for Neuroinvasion," *Journal of Virology* 80(19), 9361-9370.
Rudraraju, R. et al. (2011) "Phenotypes and functions of persistent Sendai virus-induced antibody forming cells and CD8+ T cells in diffuse nasal-associated lymphoid tissue typify lymphocyte responses of the gut," *Virology* 410(2), 429-436.
Russell, C. (2010) Membrane Fusion Proteins of Influenza and Parainfluenza Viruses in Infection and Disease, Emory University Presentation Feb. 1, 2010.
Sakaguchi, T. et al. (1994) "A field isolate of Sendai virus: its high virulence to mice and genetic divergence form prototype strains," *Archives of Virology* 135(1-2), 159-164.
Sakaguchi, T. et al. (2003) "Masking of the contribution of V protein to sendai virus pathogenesis in an infection model with a highly virulent field isolate," *Virology* 313(2), 581-587.
Sangster, M. et al. (1995) "Distinctive Kinetics of the Antibody-Forming Cell Response to Sendai Virus Infection of Mice in Different Anatomical Compartments," *Virology* 207(1), 287-291.
Schaap-Nutt, A. et al. (2010) "Growth restriction of an experimental live attenuated human parainfluenza virus type 2 vaccine in human ciliated airway epithelium in vitro parallels attenuation in African green monkeys," *Vaccine* 28(15), 2788-2798.
Schickli, J. H. et al. (2009) "Challenges in developing a pediatric RSV vaccine," *Human Vaccines* 5(9), 582-591.
Sealy, R. et al. (2010) "Robust IgA and IgG-producing antibody forming cells in the diffuse-NALT and lungs of Sendai virus-vaccinated cotton rats associate with rapid protection against human parainfluenza virus-type 1," *Vaccine* 28(41), 6749-6756.

Shay, D. K. et al. (1999) "Bronchiolitis-associated hospitalizations among us children, 1980-1996," *JAMA* 282(15), 1440-1446.
Shay, D. K. et al. (2001) "Bronchiolitis-Associated Mortality and Estimates of Respiratory Syncytial Virus—Associated Deaths among US Children, 1979-1997," *Journal of Infectious Diseases* 183(1), 16-22.
Simon, A. Y. et al. (2009) "Multigenic control of resistance to Sendai virus infection in mice," *Infection, Genetics and Evolution* 9(6), 1253-1259.
Skiadopoulos, M. H. et al. (2002) "Sendai Virus, a Murine Parainfluenza Virus Type 1, Replicates to a Level Similar to Human PIV1 in the Upper and Lower Respiratory Tract of African Green Monkeys and Chimpanzees," *Virology* 297(1), 153-160.
Skiadopoulos, M. H. et al. (2002) "Evaluation of the Replication and Immunogenicity of Recombinant Human Parainfluenza Virus Type 3 Vectors Expressing up to Three Foreign Glycoproteins," *Virology* 297(1), 136-152.
Slobod, K. S. et al. (2004) "Safety and immunogenicity of intranasal murine parainfluenza virus type 1 (Sendai virus) in healthy human adults," *Vaccine* 22(23-24), 3182-3186.
Smith, F. S. et al. (1994) "Age-Related Development of Human Memory T-Helper and B-Cell Responses toward Parainfluenza Virus Type-1," *Virology* 205(2), 453-461.
Southam, D. S. et al. (2002) "Distribution of intranasal instillations in mice: effects of volume, time, body position, and anesthesia," *American Journal of Physiology—Lung Cellular and Molecular Physiology* 282(4), L833-L839.
Spriggs, M. K. et al. (1986) "Human parainfluenza virus type 3: messenger RNAs, polypeptide coding assignments, intergenic sequences, and genetic map," *Journal of Virology* 59(3), 646-654.
Stark, J. M. et al. (2002) "Genetic susceptibility to respiratory syncytial virus infection in inbred mice," *Journal of Medical Virology* 67(1), 92-100.
Stephens, H. A. (2010) "HLA and other gene associations with dengue disease severity," *Current Topics in Microbiology and Immunology* 338, 99-114.
Takimoto, T. et al. (2004) "Recombinant Sendai Virus Expressing the G Glycoprotein of Respiratory Syncytial Virus (RSV) Elicits Immune Protection against RSV," *Journal of Virology* 78(11), 6043-6047.
Takimoto, T. et al. (2005) "Recombinant Sendai Virus as a Novel Vaccine Candidate for Respiratory Syncytial Virus," *Viral Immunology* 18(2), 255-266.
Tang, R. S. et al. (2004) "Parainfluenza Virus Type 3 Expressing the Native or Soluble Fusion (F) Protein of Respiratory Syncytial Virus (RSV) Confers Protection from RSV Infection in African Green Monkeys," *Journal of Virology* 78(20), 11198-11207.
Tashiro, M. et al. (1988) "Characterization of a pantropic variant of Sendai virus derived from a host range mutant," *Virology* 165(2), 577-583.
Tashiro, M. et al. (1992) "Tryptase Clara, an activating protease for Sendai virus in rat lungs, is involved in pneumopathogenicity," *Journal of Virology* 66(12), 7211-7216.
Tokusumi, T. et al. (2002) "Recombinant Sendai viruses expressing different levels of a foreign reporter gene," *Virus Research* 86(1-2), 33-38.
Touzelet, O. et al. (2009) "De novo generation of a non-segmented negative strand RNA virus with a bicistronic gene," *Virus Research* 140(1-2), 40-48.
Tyrrell, D. A. et al. (1959) "Inoculation of human volunteers with parainfluenza viruses types 1 and 3 (HA 2 and HA 1)," *British Medical Journal* 2(5157), 909-911.
Van Der Veen, J. et al. (1970) "Experimental transmission of Sendai virus infection in mice," *Archiv fur die Gesamte Virusforschung* 31(3), 237-246.
Villenave, R. et al. (2010) "Cytopathogenesis of Sendai Virus in Well-Differentiated Primary Pediatric Bronchial Epithelial Cells," *Journal of Virology* 84(22), 11718-11728.
Von Messling, V. et al. (2004) "Tropism illuminated: Lymphocyte-based pathways blazed by lethal morbillivirus through the host immune system," *Proceedings of the National Academy of Sciences of the United States of America* 101(39), 14216-14221.

(56) References Cited

OTHER PUBLICATIONS

Williams, J. V. et al. (2010) "Population-Based Incidence of Human Metapneumovirus Infection among Hospitalized Children," *Journal of Infectious Diseases* 201(12), 1890-1898.

Zhan, X. (2006) Development of Sendai Virus Vaccines to Prevent Pediatric Respiratory Infections, Mar. 29-Apr. 1, 2006, http://www4.nationalacademies.org/xpedio/idcplg?IdcService=GET_FILE&dDocName=pga_071845&RevisionSelectionMethod=Latest.

Zhan, X. et al. (2007) "Respiratory syncytial virus (RSV) fusion protein expressed by recombinant Sendai virus elicits B-cell and T-cell responses in cotton rats and confers protection against RSV subtypes A and B," *Vaccine* 25(52), 8782-8793.

Zhan, X. et al. (2008) "Sendai virus recombinant vaccine expressing hPIV-3 HN or F elicits protective immunity and combines with a second recombinant to prevent hPIV-1, hPIV-3 and RSV infections," *Vaccine* 26(27-28), 3480-3488.

Zhang, L. et al. (2005) "Infection of Ciliated Cells by Human Parainfluenza Virus Type 3 in an In Vitro Model of Human Airway Epithelium," *Journal of Virology* 79(2), 1113-1124.

Zhang, L. et al. (2009) "Systems-based candidate genes for human response to influenza infection," *Infection, Genetics and Evolution* 9(6), 1148-1157.

Zurcher, C. et al. (1977) "A naturally occurring epizootic caused by Sendai virus in breeding and aging rodent colonies. I. Infection in the mouse," *Laboratory Animal Science* 27(6), 955-962.

PCT International Search Report of International Application No. PCT/US2012/033482 dated Sep. 25, 2012.

\* cited by examiner pSVc plasmid sequence (SEQ. ID NO.:3)
cgttaatacgactcactataaccaaacaagagaaaaaacatgtatgggatatataatgaagttagacagg
attttagggtcaaagtatccaccctgaggagcaggttccagacccctttgctttgctgccaaagttcacg▓
▓▓gccgggttgttgagcaccttcgatacatttagctctaggaggagcgaaagtattaataagtcgggagg
aggtgctgttatccccggccagaggagcacagtctcagtgttcgtactaggcccaagtgtgactgatgat
gcagacaagttattcattgcaactaccttcctagctcactcattggacacagataagcagcactctcaga
gaggagggttcctcgtctctctgcttgccatggcttacagtagtccagaattgtacttgacaacaaacgg
agtaaacgccgatgtcaaatatgtgatctacaacatagagaaagaccctaagaggacgaagacagacgga
ttcattgtgaagacgagagatatggaatatgagaggaccacagaatggctgtttggacctatggtcaaca
agagcccactcttccagggtcaacgggatgctgcagaccctgacacactccttcaaacctatgggtatcc
tgcatgcctaggagcaataattgtccaagtctggattgtgctggtgaaggccatcacaagcagcgccggc
ttaaggaaagggttcttcaacaggttagaggcgttcagacaagacggcaccgtgaaaggtgccttagttt
tcactggggagacagttgaggggataggctcggttatgagatctcagcaaagccttgtatctctcatggt
tgagacccttgtgactatgaatactgcaagatctgatctcaccacattagagaagaacatccagatcgtt
gggaactacatccgagatgcagggctggcttccttcatgaacactattaaatatggggtggagacaaaga
tggcagctctaacgttgtcaaacctgaggcccgatattaataagattagaagcctcatagacacctacct
gtcaaaaggccccagagctcccttatctgtatcctcaaggaccctgttcatggtgaatttgctccaggc
aattatcctgcactatggagttacgccatgggagtcgccgtcgtacagaacaaggcaatgcagcagtacg
tcacagggaggacataccttgatatggaaatgttcttactaggacaagccgtggcaaaggatgctgaatc
gaagatcagcagtgccctggaagatgagttaggagtgacggatacagccaaggagaggctcagacatcat
ctggcaaacttgtccggtggggatggtgcttaccacaaaccaacaggcggtggtgcaattgaggtagctc
tagacaatgccgatatcgacctagaaacagaagctcatgcggaccaggacgctaggggttggggtggaga
aagtggtgaaagatgggcacgtcaggtgagtggtggccactttgtcacactacatggggctgaacggtta
gaggaggaaaccaatgatgaggatgtatcagacatagagagaagaatagccatgagactcgcagagagac
ggcaagaggattctgcaacccatggagatgaaggccgcaataacggtgtcgatcacgacgaagatgacga
taccgcagcagtagctgggataggaggaatc▓▓gatcatacgaggcttcaaggtacttgatccgtagta
agaaaaacttagggtgaaagttcatccactgatcggctcaggcaaggccacacccaaccccaccgaccac
acccagcagtcgagacagccacggcttcggctacacttaccgc▓▓gatcaag▓▓CCTTCATTCTTAAA
GAAGATTCTGAAGTTGAGAGGGAGGCGCCAGGAGGAAGAGAGTCGCTCTCGGATGTTATCGGATTCCTCG
ATGCTGTCCTGTCGAGTGAACCAACTGACATCGGAGGGGACAGAAGCTGGCTCCACAACACCATCAACAC
TCCCCAAGGACCAGGCTCTGCCCATAGAGCCAAAAGTGAGGGCGAAGGAGAAGTCTCAACACCGTCGACC
CAAGATAATCGATCAGGTGAGGAGAGTAGAGTCTCTGGGAGAACAAGCAAGCCAGAGGCAGAAGCACATG
CTGGAAACCTTGATAAACAAAATATACACCGGGCCTTTGGGGGAAGAACTGGTACAAACTCTGTATCTCA
GGATCTGGGCGATGGAGGAGACTCCGGAATCCTTGAAAATCCTCCAAATGAGAGAGGATATCCGAGATCA
GGTATTGAAGATGAAAACAGAGAGATGGCTGCGCACCCTGATAAGAGGGGAGAAGACCAAGCTGAAGGAC
TTCCAGAAGAGGTACGAGGAGGTACATCCCTACCTGATGAAGGAGAAGGTGGAGCAAGTAATAATGGAAG
AAGCATGGAGCCTGGCAGCTCACATAGTGCAAGAG▓▓ctggggtcctggtgattcctagccccgaactC
gaagaggctgtgctacggaggaacaaaagaagacctaccaacagtgggtccaaacctcttactccagcaa
ccgtgcctggcacccggtccccaccgctgaatcgttacaacagcacagggtcaccaccaggaaaaccccc
atctacacaggatgagcacatcaactctggggacaccccgccgtcagggtcaaagaccggaaaccacca
atagggacccgctctgtctcagattgtccagccaacggccgcccaatccacccgggtctagagaccgact
caacaaaaagggcataggagagaacacatcatctatgaaagagatggctacattgttgacgagtcttgg
tgtaatccagtctgctcaagaattcgagtcatcccgagacgcgagttatgtgtttgcaagacgtgcccta
aagtctgcaaactatgcagagatgacattcaatgtatgcggcctgatcctttctgccgagaaatcttccg
ctcgtaaggtagatgagaacaaacaactgctcaaacagatccaagagagcgtggaatcattccgggatat
ttacaagagattctctgagtatcagaaagaacagaactcattgctgatgtccaacctatctacacttcat
atcatcacagatagaggtggcaagactgacaacacagactcccttacaaggtcccctccgtttttgcaa
aatcaaaagagaacaagactaaggctaccaggtttgacccatctatggagaccctagaagatatgaagta
caaaccggacctaatccgagaggatgaatttagagatgagatccgcaacccggtgtaccaagagagggac
acagaacccagggcctcaaacgcatcacgcctcctcccctccaaagagaagcccacaatgcactctctca
ggctcgtcatagagagcagtcccctaagcagagctgagaaagcagcatatgtgaaatcattatccaagtg
caagacagaccaagaggttaaggcagtcatggaactcgtagaagaggacatagagtcactgaccaac▓▓

FIG. 7A atcccgggtgaggcatcctaccatcctcagtcatagagagatccaattaattaacagcatcagccagtaa
agattaagaaaaacttagggtgaaagaaatttcacctaacacggcgca▒▒gcagatatctatagattcc
ctaagttctcatatgaggataacggtactgtggagccctgcctctgagaactggtccagataagaaagc
catccctacatcaggattatcaaggtaggagaccctcctaaacatggagtgagatacctagatttattg
ctcttgggtttctttgagacaccgaaacaaacaaccaatctagggagcgtatctgacttgacagagcga
ccagctactcaatatgcggctccggtcgttacccataggtgtggccaaatactacgggactgatcagga
actcttaaaggcctgcaccgatctcagaattacggtgaggaggactgttcgagcaggagagatgatcgta
tacatggtggattcgattggtgctccactcctaccatggtcaggcaggctgagacagggaatgatattta
atgcaaacaaggtcgcactagctccccaatgcctccctgtggacaaggacataagattcagagtggtgtt
tgtcaatgggacatctctagggcaatcaccatagccaagatcccaaagacccttgcagaccttgcattg
cccaactctatatccgttaacctactggtgacactcaagaccgggatctccacagaacaaaaggggtac
tcccagtacttgatgatcaaggggagaaaaagctcaattttatggtgcacctcgggttgatcaggagaaa
ggtcgggaagatatactctgttgagtactgcaagagcaagattgagagaatgcggctgatttctcactt
gggttaatcggcggtataagcttccatgttcaggttactgggacactatctaagacattcatgagtcagc
tcgcatggaagagggcagtctgcttcccattaatggatgtgaatcccatatgaacctggtgatttgggc
ggcatctgtagaaatcacaggcgtcgatgcggtgttccaaccggccatcctcgtgatttccgctactac
cctaatgttgtggctaagaacatcggaaggatcagaaagctg▒▒atgtgcacccatcagagacctgcga
caatgccccaagcagacaccacctggcagtcggagccaccgggtcactccttgtcttaaataagaaaaac
ttagggataaagtcccttgtgagtgcttggttgcaaaactctccgtacgggaaac▒▒▒acagcatatatc
cagaggtcacagtgcatctcaacatcactactggttgttctcaccacattggtctcgtgtcagattccca
gggataggctctctaacatagggggtcatagtcgatgaagggaaatcactgaagatagctggatcccacga
atcgaggtacatagtactgagtctagttccggggggtagaccttgagaatgggtgcggaacagcccaggtt
atccagtacaagagcctactgaacaggctgttaatcccattgagggatgccttagatcttcaggaggctc
tgataactgtcaccaatgatacgacacaaaatgccggtgttccacagtcgagattcttcggtgctgtgat
tggtactatcgcacttggagtggcgacatcagcacagatcaccgcagggattgcactagccgaagcgagg
gaggccaaaagagacatagcgctcatcaaagaatcgatgacaaaaacacacaagtctatagaactgctgc
aaaacgctgtggggaacaaattcttgctctaaagacactccaggatttcgtgaatgatgagatcaaacc
cgcaataagcgaattaggctgtgagactgctgccttaagactgggtataaaattgacacagcattactcc
gggctgttaactgcgttcggctcgaatttcggaaccatcggagagaagagcctcacgctgcaggcgctgt
cttcactttactctgctaacattactgagattatgaccacaatcaggacagggcagtctaacatctatga
tgtcatttatacagaacagatcaaggaacggtgatagatgtggatctagagagatacatggttaccctg
tctgtgaagatccctattctttctgaagtcccaggtgtgctcatacacaaggcatcgtctatttcttaca
acatagacggggaggaatggtatgtgactgtccccagccatatactcagtcgtgcttctttcttagggggg
tgcagacataaccgattgtgttgagtccaggttgacctatatatgccccagggatcccgcacaactgata
cctgacagccagcaaaagtgtatcctgggggacacaacaaggtgtcctgtcacaaaagttgtggacagcc
ttatccccaagtttgcttttgtgaatggggcgttgttgctaactgcatagcatccacatgtacctgcgg
gacaggccgaagaccaatcagtcaggatcgctcaaaggtgtagtattcctaacccatgacaactgtggt
cttataggtgtcaatggggtagaattgtatgctaaccggagagggcacgatgccacttgggggtccaga
acttgacagtcggtcctgcaattgctatcagacccgttgatatttctctcaaccttgctgatgctacgaa
tttcttgcaagactctaaggctgagcttgagaaagcacggaaaatcctctctgaggtaggtagatggtac
aactcaagagagactgtgattacgatcatagtagttatggtcgtaatattggtggtcattatagtgatcg
tcatcgtgctttatagactcagaaggtcaatgctaatgggtaatccagatgaccgtataccgagggacac
atatacattagagccgaagatcagacatatgtacacaaacggtgggtttgatgcgatggctgagaaaga
▒▒tcacgagtttaaacagatgtcttgtaaagcaggcatggtatccgttgagatctgtatataataagaa
aaactt▒▒▒▒▒▒▒▒gtgaggtcgcgcggtactttagct▒▒▒▒▒▒acattataagaaaaacttagggt
gaaagtga▒▒▒▒▒▒▒caaacaagcacagatc▒▒gatggtgatagggcaaacgtgactcgtactggtct
acctctccagtggtagcactacaaaattagcatcaggttgggagaggtcaagtaaagttgacacatggt
tgctgattctctcattcacccagtgggctttgtcaattgccacagtgatcatctgtatcataatttctgc
tagacaagggtatagtatgaaagagtactcaatgactgtagaggcattgaacatgagcagcagggaggtg
aaagagtcacttaccagtctaataaggcaagaggttatcgcaagggctgtcaacattcagagctctgtgc
aaaccggaatcccagtcttgttaacaaaaacagcagggatgtcatccagatgattgataagtcgtgcag
cagacaagagctcactcagctctgtgagagtacgatcgcagtccaccatgccagggaattgcccctctt

```
gagccacatagtttctggagatgccctgtcggagaaccgtatcttagctcagatcctaaaatctcattgc
tgcctggtccgagcttgttatctggttctacaacgatctctggatgtgttaggctcccttcactctcaat
tggcgaggcaatctatgcctattcatcaaatctcattacacaaggttgtgctgacatagggaaatcatat
caggtcctgcagctagggtacatatcactcaattcagatatgttccctgatcttaaccccgtagtgtccc
acacttatgacatcaacgacaatcggaaatcatgctctgtggtggcaaccgggactaggggttatcagct
ttgctccatgccgactgtagacgaaagaaccgactactctagtgatggtatcgaggatctggtccttgat
gtcctggatctcaaagggagcactaagtctcaccggtatcgcaacagcgaggtagatcttgatcaccgt
tctctgcactatacccagtgtaggcaacggcattgcaacagaaggctcattgatatttcttgggtatgg
tgggctaaccaccccctctacagggtgatacaaaatgtaggacccaaggatgccaacaggtgtcgcaagac
acatgcaatgaggctctgaaaattacatggctaggagggaaacaggtggtcagcgtgatcatccaggtca
atgactatctctcagagaggccaaagataagagtcacaaccattccaatcactcaaaactatctcggggc
ggaaggtagattattaaaattgggtgatcgggtgtacatctatacaagatcatcaggctggcactctcaa
ctgcagataggagtacttgatgtcagccacccttgactatcaactggacacctcatgaagccttgtcta
gaccaggaaatgaagagtgcaattggtacaatacgtgtccgaaggaatgcatatcaggcgtatacactga
tgcttatccattgtccctgatgcagctaacgtcgctaccgtcacgctatatgccaatacatcgcgtgtc
aacccaacaatcatgtattctaacactactaacattataaatatgttaaggataaaggatgttcaattag
aggctgcatataccacgacatcgtgtatcacgcatttttggtaaaggctactgctttcacatcatcgagat
caatcagaagagcctgaataccttacagccgatgctctttaagactagcatccctaaattatgcaaggcc
gagtct[atg]atttaactgactagcaggctggcgcgccttgctgacactagagtcatctccgaacatccac
aatatctctcagtctcttacgtctctcacagtattaagaaaaacccagggtgaatgggaagcttgccata
ggtc[atg]gatgggcaggagtcctcccaaaacccttctgacatactctatccagaatgccacctgaactct
cccatagtcaggggaagatagcacagttgcacgtcttgttagatgtgaaccagccctacagactgaagg
acgacagcataataaatattacaaagcacaaaattaggaacggaggattgtcccccgtcaaattaagat
caggtctctgggtaaggctcttcaacgcacaataaaggatttagaccgatacacgtttgaaccgtaccca
acctactctcaggaattacttaggcttgatataccagagatatgtgacaaaatccgatccgtcttcgcgg
tctcggatcggctgaccagggagttatctagtgggttccaggatctttggttgaatatcttcaagcaact
aggcaatatagaaggaagagaggggtacgatccgttgcaggatatcggcaccatcccggagataactgat
aagtacagcaggaatagatggtataggccattcctaacttggttcagcatcaaatatgacatgcggtgga
tgcagaagaccagaccgggggggacccccttgatacctctaattcacataacctcctagaatgcaaatcata
cactctagtaacatacggagatcttgtcatgatactgaacaagttgacattgacagggtatatcctaacc
cctgagctggtcttgatgtattgtgatgttgtagaaggaaggtggaatatgtctgctgcagggcatctag
ataagaagtccattgggataacaagcaaaggtgaggaattatgggaactagtggattccctcttctcaag
tcttggagaggaaatatacaatgtcatcgcactattggagcccctatcacttgctctcatacaactaaat
gatcctgttatacctctacgtggggcatttatgaggcatgtgttgacagagctacagactgttttaacaa
gtagagacgtgtacacagatgctgaagcagacactattgtggagtcgttactcgccattttccatggaac
ctctattgatgagaaagcagagatcttttccttctttaggacatttggccaccccagcttagaggctgtc
actgccgccgacaaggtaagggcccatatgtatgcacaaaaggcaataaagcttaagaccctatacgagt
gtcatgcagttttttgcactatcatcataaatgggtatagagagaggcatggcggacagtggccccctg
tgacttccctgatcacgtgtgtctagaactaaggaacgctcaagggtccaatacggcaatctcttatgaa
tgtgctgtagacaactatacaagtttcataggcttcaagtttcggaagtttatagaaccacaactagatg
aagatctcacaatatatgaaagacaaagcactatcccccaggaaggaggcatgggactctgtatacccc
ggatagtaatctgtactataaagccccagagtctgaagagacccggcggcttattgaagtgttcataaat
gatgagaatttcaacccagaagaaattatcaattatgtggagtcaggagattggttgaaagacgaggagt
tcaacatctcgtacagtctcaaagagaaagagatcaagcaagagggtcgtctattcgcaaaaatgactta
taagatgcgagccgtacaggtgctggcagagacactactggctaaaggaataggagagctattcagggaa
aatgggatggttaagggagagatagacctacttaaaagattgactactctttctgtctcaggcgtcccca
ggactgattcagtgtacaataactctaaatcatcagagaagagaaacgaaggcatggaaaataagaactc
tggggggtactgggacgaaaagaagaggtccagacatgaattcaaggcaacagattcatcaacagacggc
tatgaaacgttaagttgcttcctcacaacagacctcaagaaatactgcttaaactggagatttgagagta
ctgcattgtttggtcagagatgcaacgagatatttggcttcaagaccttctttaactggatgcatccagt
ccttgaaaggtgtacaatatatgttggagatccttactgtccagtcgccgaccggatgcatcgacaactc
caggatcatgcagactctggcattttcatacataatcctaggggggggcatagaaggttactgccagaagc
```

FIG. 7A continued

```
tgtggaccttaatctcaatcagtgcaatccacctagcagctgtgagagtgggtgtcagggtctctgcaat
ggttcagggtgacaatcaagctatagccgtgacatcaagagtacctgtagctcagacttacaagcagaag
aaaaatcatgtctatgaggagatcaccaaatatttcggtgctctaagacacgtcatgtttgatgtagggc
acgagctaaaattgaacgagaccatcattagtagcaagatgtttgtctatagtaaaaggatatactatga
tgggaagattttaccacagtgcctgaaagccttgaccaagtgtgtattctggtccgagacactggtagat
gaaaacagatctgcttgttcgaacatctcaacatccatagcaaaagctatcgaaatgggtattctccta
tactaggctactgcattgcgttgtataagacctgtcagcaggtgtgcatatcactagggatgactataaa
tccaactatcagcccgaccgtaagagatcaatactttaagggtaagaattggctgagatgtgcagtgttg
attccagcaaatgttggaggattcaactacatgtctacatctagatgctttgttagaaatattggagacc
ccgcagtagcagccctagctgatctcaaaagattcatcagagcggatctgttagacaagcaggtattata
cagggtcatgaatcaagaacccggtgactctagttttctagattgggcttcagacccttattcgtgtaac
ctcccgcattctcagagtataactacgattataaagaatatcactgctagatctgtgctgcaggaatccc
cgaatcctctactgtctggtctcttcaccgagactagtggagaagaggatctcaacctggcctcgttcct
tatggaccggaaagtcatcctgccgagagtggctcatgagatcctgggtaattccttaactggagttagg
gaggcgattgcagggatgcttgatacgaccaagtctctagtgagagccagcgttaggaaaggaggattat
catatgggatattgaggaggcttgtcaattatgatctattgcagtacgagacactgactagaactctcag
gaaaccggtgaaagacaacatcgaatatgagtatatgtgttcagttgagctagctgtcggtctaaggcag
aaaatgtggatccacctgacttacgggagacccatacatgggttagaaacaccagacccttttagagctct
tgaggggaatatttatcgaaggttcagaggtgtgcaagctttgcaggtctgaaggagcagaccccatcta
tacatggttctatcttcctgacaatatagacctggacacgcttacaaacggatgtccggctataagaatc
ccctatttggatcagccactgatgaaaggtcggaagcccaactcgggtatgtaagaaatctaagcaaac
ccgcaaaggcggccatccggatagctatggtgtatacgtgggcctacgggactgatgagatatcgtggat
ggaagccgctcttatagcccaaacaagagctaatctgagcttagagaatctaaagctgctgactcctgtt
tcaacctccactaatctatctcataggttgaaagatacggcaacccagatgaagttctctagtgcaacac
tagtccgtgcaagtcggttcataacaatatcaaatgataacatggcactcaaagaagcaggggagtcgaa
ggatactaatctcgtgtatcagcagattatgctaactgggctaagcttgttcgagttcaatatgagatat
aagaaaggttccttagggaagccactgatattgcacttacatcttaataacgggtgctgtataatggagt
ccccacaggaggcgaatatcccccaaggtccacattagatttagagattacacaagagaacaataaatt
gatctatgatcctgatccactcaaggatgtggaccttgagctatttagcaaggtcagagatgttgtacat
acagttgacatgacttattggtcagatgatgaagttatcagagcaaccagcatctgtactgcaatgacga
tagctgatacaatgtctcaattagatagagacaacttaaaagagatgatcgcactagtaaatgacgatga
tgtcaacagcttgattactgagtttatggtgattgatgttccttttattttgctcaacgttcgggggtatt
ctagtcaatcagtttgcatactcactctacggcttaaacatcagaggaagggaagaaatatggggacatg
tagtccggattcttaaagatacctcccacgcagttctaaaagtcttatctaatgctctatcccatcccaa
aatcttcaaacgattctggaatgcaggtgtcgtggaacctgtgtatgggcctaacctctcaaatcaggat
aagatactcttggccctctctgtctgtgaatattctgtggatctattcatgcacgactggcaaggggtg
taccgcttgagatctttatctgtgacaatgacccagatgtggccgacatgaggaggtcctctttcttggc
aagacatcttgcatacctatgcagcttggcagagatatctagggatgggccaagattagaatcaatgaac
tctctagagaggctcgagtcactaaagagttacctggaactcacatttcttgatgacccggtactgaggt
acagtcagttgactggcctagtcatcaaagtattcccatctactttgacctatatccggaagtcatctat
aaaagtgttaaggacaagaggtataggagtccctgaagtcttagaagattgggatcccgaggcagataat
gcactgttagatggtatcgcggcagaaatacaacgaatattcctttgggacatcagactagagcccctt
tttgggggttgagagtatccaagtcacaggtactgcgtctccgggggtacaaggagatcacaagaggtga
gataggcagatcaggtgttggtctgacgttaccattcgatggaagatatctatctcaccagctgaggctc
tttggcatcaacagtactagctgcttgaaagcacttgaacttacctaccattgagccccttagttgaca
aggataaagataggctatatttaggggaaggagctggggccatgctttcctgttatgacgctactcttgg
cccatgcatcaactattataactcaggggtatactcttgtgatgtcaatgggcagagagagttaaatata
tatcctgctgaggtggcactagtgggaaagaaattaaacaatgttactagtctgggtcaaagagttaaag
tgttattcaacgggaatcctggctcgacatggattgggaatgatgagtgtgaggctttgatttggaatga
attacagaatagctcgataggcctagtccactgtgacatggagggaggagatcataaggatgatcaagtt
gtactgcatgagcattacagtgtaatccggatcgcgtatctggtgggggatcgagacgttgtgcttataa
gcaagattgctcccaggctgggcacggattggaccaggcagctcagcctatatctgagatactgggacga
```

FIG. 7A continued

```
ggttaacctaatagtgcttaaaacatctaaccctgcttccacagagatgtatctcctatcgaggcacccc
aaatctgacattatagaggacagcaagacagtgttagctagtctcctccctttgtcaaaagaagatagca
tcaagatagaaaagtggatcttaatagagaaggcaaaggctcacgaatgggttactcgggaattgagaga
aggaagctcttcatcagggatgcttagaccttaccatcaagcactgcagacgtttggctttgaaccaaac
ttgtataaattgagcagagatttcttgtccaccatgaacatagctgatacacacaactgcatgatagctt
tcaacagggttttgaaggatacaatcttcgaatgggctagaataactgagtcagataaaaggcttaaact
aactggtaagtatgacctgtatcctgtgagagattcaggcaagttgaagacaatttctagaagacttgtg
ctatcttggatatctttatctatgtccacaagattggtaactgggtcattccctgaccagaagtttgaag
caagacttcaattgggaatagtttcattatcatcccgtgaaatcaggaacctgagggttatcacaaaaac
tttattatacaggtttgaggatattatacatagtataacgtatagattcctcaccaaagaaataaagatt
ttgatgaagattttaggggcagtcaagatgttcggggccaggcaaaatgaatacacgaccgtgattgatg
atggatcactaggtgatatcgagccatatgacagctcg   taattagtccctatcgtgcagaacgatcg
aagctccgcggtacctggaagtcttggacttgtccatatgacaatagtaagaaaaacttacaagaagaca
agaaaatttaaaaggatacatatctcttaaactcttgtctggtgggtcggcatggcatctccacctcctc
gcggtccgacctgggcatccgaaggaggacgtcgtccactcggatggctaagggaggggccccgcgggg
ctgctaacaaagcccgaaaggaagctgagttggctgctgccaccgctgagcaataactagcataacccct
tggggcctctaaacgggtcttgaggggttttttgctgaaaggaggaactatatccggatcgagacctcga
tgccggctgatgcggtattttctccttacgcatctgtgcggtatttcacaccgcatatggtgcactctca
gtacaatctgctctgatgccgcatagttaagccagccccgacacccgccaacacccgctgacgcgccctg
acgggcttgtctgctcccggcatccgcttacagacaagctgtgaccgtctccgggagctgcatgtgtcag
aggttttcaccgtcatcaccgaaacgcgcgagacgaaagggcctcgtgatacgcctatttttataggtta
atgtcatgataataatggtttcttagacgtcaggtggcacttttcggggaaatgtgcgcggaaccccctat
ttgtttatttttctaaatacattcaaatatgtatccgctcatgagacaataaccctgataaatgcttcaa
taatattgaaaaaggaagagtatgagtattcaacatttccgtgtcgcccttattccttttttgcggcat
tttgccttcctgtttttgctcacccagaaacgctggtgaaagtaaaagatgctgaagatcagttgggtgc
acgagtgggttacatcgaactggatctcaacagcggtaagatccttgagagttttcgccccgaagaacgt
tttccaatgatgagcacttttaaagttctgctatgtggcgcggtattatcccgtattgacgccgggcaag
agcaactcggtcgccgcatacactattctcagaatgacttggttgagtactcaccagtcacagaaaagca
tcttacggatggcatgacagtaagagaattatgcagtgctgccataaccatgagtgataacactgcggcc
aacttacttctgacaacgatcggaggaccgaaggagctaaccgcttttttgcacaacatgggggatcatg
taactcgccttgatcgttgggaaccggagctgaatgaagccataccaaacgacgagcgtgacaccacgat
gcctgtagcaatggcaacaacgttgcgcaaactattaactggcgaactacttactctagcttcccggcaa
caattaatagactggatggaggcggataaagttgcaggaccacttctgcgctcggcccttccggctggct
ggtttattgctgataaatctggagccggtgagcgtgggtctcgcggtatcattgcagcactggggccaga
tggtaagccctcccgtatcgtagttatctacacgacggggagtcaggcaactatggatgaacgaaataga
cagatcgctgagataggtgcctcactgattaagcattggtaactgtcagaccaagtttactcatatatac
tttagattgatttaaaacttcattttaatttaaaaggatctaggtgaagatcctttttgataatctcat
gaccaaaatcccttaacgtgagttttcgttccactgagcgtcagaccccgtagaaaagatcaaggatct
tcttgagatcctttttttctgcgcgtaatctgctgcttgcaaacaaaaaaaccaccgctaccagcggtgg
tttgtttgccggatcaagagctaccaactcttttttccgaaggtaactggcttcagcagagcgcagatacc
aaatactgtccttctagtgtagccgtagttaggccaccacttcaagaactctgtagcaccgcctacatac
ctcgctctgctaatcctgttaccagtggctgctgccagtggcgataagtcgtgtcttaccgggttggact
caagacgatagttaccggataaggcgcagcggtcgggctgaacggggggttcgtgcacacagcccagctt
ggagcgaacgacctacaccgaactgagatacctacagcgtgagctatgagaaagcgccacgcttcccgaa
gggagaaaggcggacaggtatccggtaagcggcagggtcggaacaggagagcgcacgagggagcttccag
ggggaaacgcctggtatctttatagtcctgtcgggtttcgccacctctgacttgagcgtcgatttttgtg
atgctcgtcagggggcggagcctatggaaaaacgccagcaacgcggcctttttacggttcctggccttt
tgctggccttttgctcacatgttctttcctgcgttatcccctgattctgtggataaccgtattaccgcct
ttgagtgagctgataccgctcgccgcagccgaacgaccgagcgcagcgagtcagtgagcgaggaagcgga
agagcgcccaatacgcaaaccgcctctccccgcgcgttggccgattcattaatgcagctggcacgacagg
tttcccgactggaaagcgggcagtgagcgcaacgcaattaatgtgagttagctcactcattaggcacccc
aggctttacactttatgcttccggctcgtatgttgtgtggaattgtgagcggataacaatttcacacagg
``` aaacagctatgaccatgattacgccaagcttgcatgcctgcaggtcgacg

FIG. 7A continued

NP cDNA: (SEQ. ID. NO.:4)

atggccgggttgttgagcaccttcgatacatttagctctaggaggagcgaaagtattaataagtcgggag
gaggtgctgttatccccggccagaggagcacagtctcagtgttcgtactaggcccaagtgtgactgatga
tgcagacaagttattcattgcaactaccttcctagctcactcattggacacagataagcagcactctcag
agaggagggttcctcgtctctctgcttgccatggcttacagtagtccagaattgtacttgacaacaaacg
gagtaaacgccgatgtcaaatatgtgatctacaacatagagaagaccctaagaggacgaagacagacgg
attcattgtgaagacgagagatatggaatatgagaggaccacagaatggctgtttggacctatggtcaac
aagagcccactcttccagggtcaacgggatgctgcagaccctgacacactccttcaaacctatgggtatc
ctgcatgcctaggagcaataattgtccaagtctggattgtgctggtgaaggccatcacaagcagcgccgg
cttaaggaaagggttcttcaacaggttagaggcgttcagacaagacggcaccgtgaaggtgccttagtt
ttcactggggagacagttgaggggataggctcggttatgagatctcagcaaagccttgtatctctcatgg
ttgagacccttgtgactatgaatactgcaagatctgatctcaccacattagagaagaacatccagatcgt
tgggaactacatccgagatgcagggctggcttccttcatgaacactattaaatatggggtggagacaaag
atggcagctctaacgttgtcaaacctgaggcccgatattaataagattagaagcctcatagacacctacc
tgtcaaaaggccccagagctcccctttatctgtatcctcaaggaccctgttcatggtgaatttgctccagg
caattatcctgcactatggagttacgccatgggagtcgccgtcgtacagaacaaggcaatgcagcagtac
gtcacagggaggacataccttgatatggaaatgttcttactaggacaagccgtggcaaaggatgctgaat
cgaagatcagcagtgccctggaagatgagttaggagtgacggatacagccaaggagaggctcagacatca
tctggcaaacttgtccggtggggatggtgcttaccacaaaccaacaggcggtggtgcaattgaggtagct
ctagacaatgccgatatcgacctagaaacagaagctcatgcggaccaggacgctaggggttggggtggag
aaagtggtgaaagatgggcacgtcaggtgagtggtggccactttgtcacactacatggggctgaacggtt
agaggaggaaaccaatgatgaggatgtatcagacatagagaagaatagccatgagactcgcagagaga
cggcaagaggattctgcaacccatggagatgaaggccgcaataacggtgtcgatcacgacgaagatgacg
ataccgcagcagtagctgggataggaggaatctag

FIG. 7B

P cDNA: (SEQ. ID. NO.:6)

```
atggatcaagatgccttcattcttaaagaagattctgaagttgagagggaggcgccaggaggaagagagt
cgctctcggatgttatcggattcctcgatgctgtcctgtcgagtgaaccaactgacatcggaggggacag
aagctggctccacaacaccatcaacactccccaaggaccaggctctgcccatagagccaaaagtgagggc
gaaggagaagtctcaacaccgtcgacccaagataatcgatcaggtgaggagagtagagtctctgggagaa
caagcaagccagaggcagaagcacatgctggaaaccttgataaacaaaatatacaccgggcctttggggg
aagaactggtacaaactctgtatctcaggatctgggcgatggaggagactccggaatccttgaaaatcct
ccaaatgagagaggatatccgagatcaggtattgaagatgaaaacagagagatggctgcgcaccctgata
agaggggagaagaccaagctgaaggacttccagaagaggtacgaggaggtacatccctacctgatgaagg
agaaggtggagcaagtaataatggaagaagcatggagcctggcagctcacatagtgcaagagtaactggg
gtcctggtgattcctagccccgaactcgaagaggctgtgctacggaggaacaaaagaagacctaccaaca
gtgggtccaaacctcttactccagcaaccgtgcctggcacccggtccccaccgctgaatcgttacaacag
cacagggtcaccaccaggaaaacccccatctacacaggatgagcacatcaactctggggacaccccgcc
gtcagggtcaaagaccggaaaccaccaatagggacccgctctgtctcagattgtccagccaacggccgcc
caatccacccgggtctagagaccgactcaacaaaaaagggcataggagagaacacatcatctatgaaaga
gatggctacattgttgacgagtcttggtgtaatccagtctgctcaagaattcgagtcatcccgagacgcg
agttatgtgtttgcaagacgtgccctaaagtctgcaaactatgcagagatgacattcaatgtatgcggcc
tgatcctttctgccgagaaatcttccgctcgtaagg tagatgagaacaaacaactgctcaaacagatcca
agagagcgtggaatcattccgggatatttacaagagattctctgagtatcagaaagaacagaactcattg
ctgatgtccaacctatctacacttcatatcatcacagatagaggtggcaagactgacaacacagactccc
ttacaaggtcccccctccgttttt gcaaaatcaaaagagaacaagactaaggctaccaggtttgacccatc
tatggagaccctagaagatatgaagtacaaaccggacctaatccgagaggatgaatttagagatgagatc
cgcaacccggtgtaccaagagagggacacagaacccagggcctcaaacgcatcacgcctcctcccctcca
aagagaagcccacaatgcactctctcaggctcgtcatagagagcagtcccctaagcagagctgagaaagc
agcatatgtgaaatcattatccaagtgcaagacagaccaagaggttaaggcagtcatggaactcgtagaa
gaggacatagagtcactgaccaactag
```

FIG. 7C

C cDNA    (SEQ. ID. NO.:8)

```
ATGCCTTCATTCTTAAAGAAGATTCTGAAGTTGAGAGGGAGGCGCCAGGAGGAAGAGAGTCGCTCTCGGATGTTATCGGAT
TCCTCGATGCTGTCCTGTCGAGTGAACCAACTGACATCGGAGGGGACAGAAGCTGGCTCCACAACACCATCAACACTCCCC
AAGGACCAGGCTCTGCCCATAGAGCCAAAAGTGAGGGCGAAGGAGAAGTCTCAACACCGTCGACCCAAGATAATCGATCAG
GTGAGGAGAGTAGAGTCTCTGGGAGAACAAGCAAGCCAGAGGCAGAAGCACATGCTGGAAACCTTGATAAACAAAATATAC
ACCGGGCCTTTGGGGGAAGAACTGGTACAAACTCTGTATCTCAGGATCTGGGCGATGGAGGAGACTCCGGAATCCTTGAAA
ATCCTCCAAATGAGAGAGGATATCCGAGATCAGGTATTGAAGATGAAAACAGAGAGATGGCTGCGCACCCTGATAAGAGGG
GAGAAGACCAAGCTGAAGGACTTCCAGAAGAGGTACGAGGAGGTACATCCCTACCTGATGAAGGAGAAGGTGGAGCAAGTA
ATAATGGAAGAAGCATGGAGCCTGGCAGCTCACATAGTGCAAGAGTAA
```

FIG. 7D

M cDNA: (SEQ. ID. NO.:10)

atggcagatatctatagattccctaagttctcatatgaggataacggtactgtggagcccctgcctctga
gaactggtccagataagaaagccatcccctacatcaggattatcaaggtaggagaccctcctaaacatgg
agtgagatacctagatttattgctcttgggtttctttgagacaccgaaacaaacaaccaatctagggagc
gtatctgacttgacagagccgaccagctactcaatatgcggctccgggtcgttacccataggtgtggcca
aatactacgggactgatcaggaactcttaaaggcctgcaccgatctcagaattacggtgaggaggactgt
tcgagcaggagagatgatcgtatacatggtggattcgattggtgctccactcctaccatggtcaggcagg
ctgagacagggaatgatatttaatgcaaacaaggtcgcactagctcccaatgcctccctgtggacaagg
acataagattcagagtggtgtttgtcaatgggacatctctaggggcaatcaccatagccaagatcccaaa
gacccttgcagaccttgcattgcccaactctatatccgttaacctactggtgacactcaagaccgggatc
tccacagaacaaaagggggtactcccagtacttgatgatcaaggggagaaaaagctcaattttatggtgc
acctcggggttgatcaggagaaaggtcgggaagatatactctgttgagtactgcaagagcaagattgagag
aatgcggctgatttctcacttgggttaatcggcggtataagcttccatgttcaggttactgggacacta
tctaagacattcatgagtcagctcgcatggaagagggcagtctgcttcccattaatggatgtgaatcccc
atatgaacctggtgatttgggcggcatctgtagaaatcacaggcgtcgatgcggtgttccaaccggccat
ccctcgtgatttccgctactaccctaatgttgtggctaagaacatcggaaggatcagaaagctgtaa

FIG. 7E

F cDNA (SEQ. ID. NO.:12)

atgacagcatatatccagaggtcacagtgcatctcaacatcactactggttgttctcaccacattggtct
cgtgtcagattcccagggataggctctctaacataggggtcatagtcgatgaagggaaatcactgaagat
agctggatcccacgaatcgaggtacatagtactgagtctagttccgggggtagaccttgagaatgggtgc
ggaacagcccaggttatccagtacaagagcctactgaacaggctgttaatcccattgagggatgccttag
atcttcaggaggctctgataactgtcaccaatgatacgacacaaaatgccggtgttccacagtcgagatt
cttcggtgctgtgattggtactatcgcacttggagtggcgacatcagcacagatcaccgcagggattgca
ctagccgaagcgagggaggccaaaagagacatagcgctcatcaaagaatcgatgacaaaaacacacaagt
ctatagaactgctgcaaaacgctgtggggaacaaattcttgctctaaagacactccaggatttcgtgaa
tgatgagatcaaacccgcaataagcgaattaggctgtgagactgctgccttaagactgggtataaaattg
acacagcattactccgggctgttaactgcgttcggctcgaatttcggaaccatcggagagaagagcctca
cgctgcaggcgctgtcttcactttactctgctaacattactgagattatgaccacaatcaggacagggca
gtctaacatctatgatgtcatttatacagaacagatcaaaggaacggtgatagatgtggatctagagaga
tacatggttaccctgtctgtgaagatccctattctttctgaagtcccaggtgtgctcatacacaaggcat
cgtctatttcttacaacatagacggggaggaatggtatgtgactgtccccagccatatactcagtcgtgc
ttctttcttaggggggtgcagacataaccgattgtgttgagtccaggttgacctatatatgccccagggat
cccgcacaactgatacctgacagccagcaaaagtgtatcctgggggacacaacaaggtgtcctgtcacaa
aagttgtggacagccttatccccaagtttgcttttgtgaatggggcgttgttgctaactgcatagcatc
cacatgtacctgcgggacaggccgaagaccaatcagtcaggatcgctctaaaggtgtagtattcctaacc
catgacaactgtggtcttataggtgtcaatggggtagaattgtatgctaaccggagagggcacgatgcca
cttgggggtccagaacttgacagtcggtcctgcaattgctatcagacccgttgatatttctctcaacct
tgctgatgctacgaatttcttgcaagactctaaggctgagcttgagaaagcacggaaaatcctctctgag
gtaggtagatggtacaactcaagagagactgtgattacgatcatagtagttatggtcgtaatattggtgg
tcattatagtgatcgtcatcgtgctttatagactcagaaggtcaatgctaatgggtaatccagatgaccg
tataccgagggacacatatacattagagccgaagatcagacatatgtacacaaacggtgggtttgatgcg
atggctgagaaaagatga

FIG. 7F

HN cDNA (SEQ. ID. NO.:14)

atggatggtgatagg
ggcaaacgtgactcgtactggtctacctctcctagtggtagcactacaaaattagcatcaggttgggaga
ggtcaagtaaagttgacacatggttgctgattctctcattcacccagtgggctttgtcaattgccacagt
gatcatctgtatcataatttctgctagacaagggtatagtatgaaagagtactcaatgactgtagaggca
ttgaacatgagcagcagggaggtgaaagagtcacttaccagtctaataaggcaagaggttatcgcaaggg
ctgtcaacattcagagctctgtgcaaaccggaatcccagtcttgttgaacaaaaacagcagggatgtcat
ccagatgattgataagtcgtgcagcagacaagagctcactcagctctgtgagagtacgatcgcagtccac
catgccagggaattgcccctcttgagccacatagtttctggagatgccctgtcggagaaccgtatctta
gctcagatcctaaaatctcattgctgcctggtccgagcttgttatctggttctacaacgatctctggatg
tgttaggctcccttcactctcaattggcgaggcaatctatgcctattcatcaaatctcattacacaaggt
tgtgctgacatagggaaatcatatcaggtcctgcagctagggtacatatcactcaattcagatatgttcc
ctgatcttaaccccgtagtgtcccacacttatgacatcaacgacaatcggaaatcatgctctgtggtggc
aaccgggactaggggttatcagctttgctccatgccgactgtagacgaaagaaccgactactctagtgat
ggtatcgaggatctggtccttgatgtcctggatctcaaaggagcactaagtctcaccggtatcgcaaca
gcgaggtagatcttgatcacccgttctctgcactataccccagtgtaggcaacggcattgcaacagaagg
ctcattgatatttcttgggtatggtgggctaaccacccctctacagggtgatacaaaatgtaggacccaa
ggatgccaacaggtgtcgcaagacacatgcaatgaggctctgaaaattacatggctaggagggaaacagg
tggtcagcgtgatcatccaggtcaatgactatctctcagagaggccaaagataagagtcacaaccattcc
aatcactcaaaactatctcggggcggaaggtagattattaaaattgggtgatcgggtgtacatctataca
agatcatcaggctggcactctcaactgcagataggagtacttgatgtcagccacccctttgactatcaact
ggacacctcatgaagccttgtctagaccaggaaatgaagagtgcaattggtacaatacgtgtccgaagga
atgcatatcaggcgtatacactgatgcttatccattgtccctgatgcagctaacgtcgctaccgtcacg
ctatatgccaatacatcgcgtgtcaacccaacaatcatgtattctaacactactaacattataaatatgt
taaggataaaggatgttcaattagaggctgcatataccacgacatcgtgtatcacgcattttggtaaagg
ctactgctttcacatcatcgagatcaatcagaagagcctgaataccttacagccgatgctctttaagact
agcatccctaaattatgcaaggccgagtcttaa

FIG. 7G

L cDNA (SEQ. ID. NO.:16)

atggatgggcaggag
tcctcccaaaacccttctgacatactctatccagaatgccacctgaactctcccatagtcaggggggaaga
tagcacagttgcacgtcttgttagatgtgaaccagccctacagactgaaggacgacagcataataaatat
tacaaagcacaaaattaggaacggaggattgtcccccgtcaaattaagatcaggtctctgggtaaggct
cttcaacgcacaataaggatttagaccgatacacgtttgaaccgtacccaacctactctcaggaattac
ttaggcttgatataccagagatatgtgacaaaatccgatccgtcttcgcggtctcggatcggctgaccag
ggagttatctagtgggttccaggatctttggttgaatatcttcaagcaactaggcaatatagaaggaaga
gaggggtacgatccgttgcaggatatcggcaccatcccggagataactgataagtacagcaggaatagat
ggtataggccattcctaacttggttcagcatcaaatatgacatgcggtggatgcagaagaccagaccggg
gggaccccttgatacctctaattcacataacctcctagaatgcaaatcatacactctagtaacatacgga
gatcttgtcatgatactgaacaagttgacattgacagggtatatcctaaccccctgagctggtcttgatgt
attgtgatgttgtagaaggaaggtggaatatgtctgctgcagggcatctagataagaagtccattgggat
aacaagcaaaggtgaggaattatgggaactagtggattccctcttctcaagtcttggagaggaaatatac
aatgtcatcgcactattggagcccctatcacttgctctcatacaactaaatgatcctgttataccttctac
gtggggcatttatgaggcatgtgttgacagagctacagactgttttaacaagtagagacgtgtacacaga
tgctgaagcagacactattgtggagtcgttactcgccattttccatggaacctctattgatgagaaagca
gagatcttttccttctttaggacatttggccaccccagcttagaggctgtcactgccgccgacaaggtaa
gggcccatatgtatgcacaaaaggcaataaagcttaagaccctatacgagtgtcatgcagttttttgcac

FIG. 7H

```
tatcatcataaatgggtatagagagaggcatggcggacagtggccccCctgtgacttccctgatcacgtg
tgtctagaactaaggaacgctcaagggtccaatacggcaatctcttatgaatgtgctgtagacaactata
caagtttcataggcttcaagtttcggaagtttatagaaccacaactagatgaagatctcacaatatatat
gaaagacaaagcactatcccccaggaaggaggcatgggactctgtatacccggatagtaatctgtactat
aaagccccagagtctgaagagacccggcggcttattgaagtgttcataaatgatgagaatttcaacccag
aagaaattatcaattatgtggagtcaggagattggttgaaagacgaggagttcaacatctcgtacagtct
caaagagaaagagatcaagcaagagggtcgtctattcgcaaaaatgacttataagatgcgagccgtacag
gtgctggcagagacactactggctaaaggaataggagagctattcagggaaatgggatggttaagggag
agatagacctacttaaaagattgactactctttctgtctcaggcgtccccaggactgattcagtgtacaa
taactctaaatcatcagagaagagaaacgaaggcatggaaaataagaactctgggggtactgggacgaa
aagaagaggtccagacatgaattcaaggcaacagattcatcaacagacggctatgaaacgttaagttgct
tcctcacaacagacctcaagaaatactgcttaaactggagatttgagagtactgcattgtttggtcagag
atgcaacgagatatttggcttcaagaccttctttaactggatgcatccagtccttgaaaggtgtacaata
tatgttggagatccttactgtccagtcgccgaccggatgcatcgacaactccaggatcatgcagactctg
gcattttcatacataatcctagggggggcatagaaggttactgccagaagctgtggaccttaatctcaat
cagtgcaatccacctagcagctgtgagagtgggtgtcagggtctctgcaatggttcagggtgacaatcaa
gctatagccgtgacatcaagagtacctgtagctcagacttacaagcagaagaaaaatcatgtctatgagg
agatcaccaaatatttcggtgctctaagacacgtcatgtttgatgtagggcacgagctaaaattgaacga
gaccatcattagtagcaagatgtttgtctatagtaaaaggatatactatgatgggaagattttaccacag
tgcctgaaagccttgaccaagtgtgtattctggtccgagacactggtagatgaaaacagatctgcttgtt
cgaacatctcaacatccatagcaaaagctatcgaaaatgggtattctcctatactaggctactgcattgc
gttgtataagacctgtcagcaggtgtgcatatcactagggatgactataaatccaactatcagcccgacc
gtaagagatcaatactttaagggtaagaattggctgagatgtgcagtgttgattccagcaaatgttggag
gattcaactacatgtctacatctagatgctttgttagaaatattggagaccccgcagtagcagccctagc
tgatctcaaaagattcatcagagcggatctgttagacaagcaggtattatacagggtcatgaatcaagaa
cccggtgactctagttttctagattgggcttcagaccttattcgtgtaacctcccgcattctcagagta
taactacgattataaagaatatcactgctagatctgtgctgcaggaatccccgaatcctctactgtctgg
tctcttcaccgagactagtggagaagaggatctcaacctggcctcgttccttatggaccggaaagtcatc
ctgccgagagtggctcatgagatcctgggtaattccttaactggagttagggaggcgattgcagggatgc
ttgatacgaccaagtctctagtgagagccagcgttaggaaggaggattatcatatgggatattgaggag
gcttgtcaattatgatctattgcagtacgagacactgactagaactctcaggaaaccggtgaaagacaac
atcgaatatgagtatatgtgttcagttgagctagctgtcggtctaaggcagaaaatgtggatccacctga
cttacgggagacccatacatgggttagaaacaccagaccctttagagctcttgaggggaatatttatcga
aggttcagaggtgtgcaagctttgcaggtctgaaggagcagaccccatctatacatggttctatcttcct
gacaatatagacctggacacgcttacaaacggatgtccggctataagaatcccctatttggatcagcca
ctgatgaaaggtcggaagcccaactcgggtatgtaagaaatctaagcaaacccgcaaaggcggccatccg
gatagctatggtgtatacgtgggcctacgggactgatgagatatcgtggatggaagccgctcttatagcc
caaacaagagctaatctgagcttagagaatctaaagctgctgactcctgtttcaacctccactaatctat
ctcataggttgaaagatacggcaacccagatgaagttctctagtgcaacactagtccgtgcaagtcggtt
cataacaatatcaaatgataacatggcactcaaagaagcaggggagtcgaaggatactaatctcgtgtat
cagcagattatgctaactgggctaagcttgttcgagttcaatatgagatataagaaaggttccttaggga
agccactgatattgcacttacatcttaataacgggtgctgtataatggagtccccacaggaggcgaatat
cccCCCaaggtccacattagatttagagattacacaagagaacaataaattgatctatgatcctgatcca
ctcaaggatgtggaccttgagctatttagcaaggtcagagatgttgtacatacagttgacatgacttatt
ggtcagatgatgaagttatcagagcaaccagcatctgtactgcaatgacgatagctgatacaatgtctca
attagatagagacaacttaaaagagatgatcgcactagtaaatgacgatgatgtcaacagcttgattact
gagtttatggtgattgatgttcctttattttgctcaacgttcgggggtattctagtcaatcagtttgcat
actcactctacggcttaaacatcagaggaagggaagaaatatggggacatgtagtccggattcttaaaga
tacctcccacgcagttctaaaagtcttatctaatgctctatcccatcccaaaatcttcaaacgattctgg
aatgcaggtgtcgtggaacctgtgtatgggcctaacctctcaaatcaggataagatactcttggccctct
ctgtctgtgaatattctgtggatctattcatgcacgactggcaaggggggtgtaccgcttgagatcttat
ctgtgacaatgacccagatgtggccgacatgaggaggtcctcttttcttggcaagacatcttgcataccta
```

FIG. 7H continued

```
tgcagcttggcagagatatctagggatgggccaagattagaatcaatgaactctctagagaggctcgagt
cactaaagagttacctggaactcacatttcttgatgacccggtactgaggtacagtcagttgactggcct
agtcatcaaagtattcccatctactttgacctatatccggaagtcatctataaaagtgttaaggacaaga
ggtataggagtccctgaagtcttagaagattgggatcccgaggcagataatgcactgttagatggtatcg
cggcagaaatacaacagaatattcctttgggacatcagactagagcccctttttgggggttgagagtatc
caagtcacaggtactgcgtctccgggggtacaaggagatcacaagaggtgagataggcagatcaggtgtt
ggtctgacgttaccattcgatggaagatatctatctcaccagctgaggctctttggcatcaacagtacta
gctgcttgaaagcacttgaacttacctacctattgagccccttagttgacaaggataaagataggctata
tttaggggaaggagctggggccatgctttcctgttatgacgctactcttggcccatgcatcaactattat
aactcaggggtatactcttgtgatgtcaatgggcagagagagttaaatatatatcctgctgaggtggcac
tagtgggaaagaaattaaacaatgttactagtctgggtcaaagagttaaagtgttattcaacgggaatcc
tggctcgacatggattgggaatgatgagtgtgaggctttgatttggaatgaattacagaatagctcgata
ggcctagtccactgtgacatggagggaggagatcataaggatgatcaagttgtactgcatgagcattaca
gtgtaatccggatcgcgtatctggtgggggatcgagacgttgtgcttataagcaagattgctcccaggct
gggcacggattggaccaggcagctcagcctatatctgagatactgggacgaggttaacctaatagtgctt
aaaacatctaaccctgcttccacagagatgtatctcctatcgaggcaccccaaatctgacattatagagg
acagcaagacagtgttagctagtctcctccctttgtcaaaagaagatagcatcaagatagaaaagtggat
cttaatagagaaggcaaaggctcacgaatgggttactcgggaattgagagaaggaagctcttcatcaggg
atgcttagaccttaccatcaagcactgcagacgtttggctttgaaccaaacttgtataaattgagcagag
atttcttgtccaccatgaacatagctgatacacacaactgcatgatagcttttcaacagggttttgaagga
tacaatcttcgaatgggctagaataactgagtcagataaaaggcttaaactaactggtaagtatgacctg
tatcctgtgagagattcaggcaagttgaagacaatttctagaagacttgtgctatcttggatatctttat
ctatgtccacaagattggtaactgggtcattccctgaccagaagtttgaagcaagacttcaattgggaat
agtttcattatcatcccgtgaaatcaggaacctgagggttatcacaaaaactttattatacaggtttgag
gatattatacatagtataacgtatagattcctcaccaaagaaataaagattttgatgaagattttagggg
cagtcaagatgttcggggccaggcaaaatgaatacacgaccgtgattgatgatggatcactaggtgatat
cgagccatatgacagctcgtaataattagtccctatc
```

MODIFIED SENDAI VIRUS VACCINE AND IMAGING VECTOR

CROSS-REFERENCE TO RELATED APPLICATIONS

This application is the U.S. National stage filing of, and claims priority to, PCT Application No. PCT/US2012/033482, filed on Apr. 13, 2012, now abandoned, which claims priority to U.S. Provisional Application Ser. No. 61/480,008 filed Apr. 28, 2011, now abandoned. The above-identified applications are incorporated herein by reference in their entirety.

GOVERNMENT FUNDING

This invention was made in part with U.S. Government support under National Institutes of Health (NIH) NIAID grant numbers P01 AI054955, R01 AI088729, R01 AI083370, R56 AI083370, R01 A1056974, R01 AI038956 and R01 AI11949, and NCI P30-CA21765. The U.S. Government has certain rights in this invention. The invention was also made in part with support by American Lebanese Syrian Associated Charities (ALSAC).

A Sequence Listing has been submitted in an ASCII text file named "17340.GTK$_{13}$ ST25.txt," created on Oct. 15, 2015, consisting of 120 kilo bytes, the entire content of which is herein incorporated by reference.

FIELD OF THE INVENTION

The present invention relates to recombinant virus vectors, methods for constructing vectors, and use of such vectors. In particular the present invention provides methods, recombinant virus constructions and compositions, and kits for a modified Enders strain Sendai viral vector for protection against pathogens. Moreover, some embodiments include vectors for imaging or tracing viral spread, clearance, and transmission.

BACKGROUND OF THE INVENTION

Vaccination is the single most effective mechanism for the control of infectious disease, yet there remain numerous pathogens for which no vaccines exist. For example, the paramyxoviruses include a number of important human pathogens transmitted via the respiratory route such as human respiratory syncytial virus (RSV), the parainfluenza viruses (PIVs), human metapneumovirus, measles virus, and mumps virus (Brown et al. 2007 J. Virol 81:12535; Hall et al. 2009 N. Engl. J. Med. 360:588). The human PIVs (hPIVs) consist of four serotypes (hPIV1-4) and, along with RSV and metapneumovirus, are the most common causes of respiratory tract viral infections in children. The PIVs, RSV, and metapneumovirus are efficiently transmitted by direct contact and exposure to nasopharyngeal secretions (Hall et al. 2009 N. Engl. J. Med. 360:588; Hall et al., 1981 J. Pediatr. 99:100). Nearly all children become infected with RSV by age 1, with hPIV3 by age 2, and with hPIV1 and hPIV2 by age 5 (Schickli et. al. 2009 Hum.Vaccin. 5:582; Graham et al. 2011 Immunol Rev. 239:146). In the United States, RSV can account for up to 20% hospitalizations of young children in an RSV season with annual costs as high as 0.4 billion dollars (Hall et al. 2009 N. Engl. J. Med. 360:588; Schickli et. al. 2009 Hum.Vaccin. 5:582; Graham et al. 2011 Immunol. Rev. 239:146; Shay et al.2001 J. Infect. Dis. 183:16; Shay et al. 1999 JAMA 282:1440; Paramore et. al. 2010 Pediatr. Pulmonol. 45:578; Hall et al. 2001 N. Engl. J. Med. 344: 1917; Bourgeois et al. 2009 Pediatrics 124: e1072; Boyce et al. 2000 J. Pediatr. 137: 865). For patients with bronchiolitis and pneumonia, RSV has been identified as the etiologic agent in as many as 90% and 50% cases, respectively (Paramore et. al. 2010 Pediatr. Pulmonol. 45:578; Hall et al. 2001 N. Engl. J. Med. 344: 1917). No licensed vaccines exist for any of these human pathogens.

Sendai virus (SeV) comprises an attractive vaccine and vaccine vector. It can act as a Jennerian vaccine for hPIV-1, the leading cause of laryngotracheobronchitis (pediatric croup), based on amino-acid sequence and antigenic similarities between the two viruses (Gorman et al. 1990 Virology 175: 211; Dave et al. 1994 Virology 199:376; Smith et al. 1994 Virology 205: 453). SeV can also be manipulated by reverse genetics to produce recombinant vaccines that could to vaccinate against virtually any other pathogen(s) of choice. The desirability of a Sendai virus-based vector depends on the following: (i) capacity for facile rescue by reverse genetics, (ii) capacity to carry a marker gene for virus tracking in vivo and in vitro, (iii) support of expression and immunogenicity of foreign proteins when respective genes are introduced into different positions within the SeV genome, (iv) limited growth in primates, (v) sufficient replication-competence to support vaccination and immunogenicity in primates. Because the hPIVs and RSV cause most of the respiratory viral disease infections in the most vulnerable population of children, infants, and elderly, novel methods and compositions are needed to protect humans from parainfluenza virus and respiratory syncytial virus infections.

SUMMARY OF THE INVENTION

The present invention relates to recombinant virus vectors, methods for constructing vectors, and use of such vectors. In one embodiment, the present invention provides methods, recombinant virus constructions and compositions, and kits for a modified Enders strain Sendai viral vector for protection against pathogens. In one embodiment, the modified Enders strain Sendai viral vector is a chimera wherein a portion of the L gene of the Enders strain is replaced with the corresponding portion from the Z-strain of Sendai virus. Some embodiments include vectors for imaging or tracing viral spread, clearance, and transmission. In one embodiment, the present invention relates to a novel recombinant Sendai virus vaccine vector with the following attributes: (i) capacity for facile rescue of recombinant vectors by reverse genetics, (ii) capacity to carry a marker gene for virus tracking in vivo and in vitro, (iii) support of expression and immunogenicity of a foreign protein(s) when respective gene(s) are introduced into different positions within the SeV genome, (iv) limited growth in primates, (v) sufficient replication-competence to support immunogenicity in primates. Further, some embodiments also provide an attribute of (vi) limited growth at 33° C. and even less growth at 37° C. Embodiments of the present invention exhibit an unexpected balance of virus vector attenuation, virus vector growth, capacity for foreign gene expression, and immunogenicity to support each of these desired attributes.

In one embodiment, the present invention provides a vector that is unexpectedly superior to other SeV vectors including unmodified Enders or Z strains in that it can be easily rescued and exhibits both attenuation and immunogenicity in primates. In addition to use as a vaccine, the present invention contemplates in one embodiment that methods, recombinant virus constructions and formulations, and kits will facilitate the use of this Sendai virus vector as a laboratory tool or in a pre-clinical/clinical research setting.

While it is not the intention that the present invention be limited to protection against the paramyxoviruses, it is contemplated that any foreign gene (or portion thereof) encoding an immunogen of interest may be inserted into the vaccine vector of the embodiments of the invention. For example, and not meant to be limiting, the present invention contemplates embodiments where the foreign gene is selected from genes from RSV, PIV, and HIV, including fragments, homologs, analogs, and any other gene of interest for targeting a pathogen/disease of interest. Further in one embodiment, the present invention contemplates a recombinant Sendai viral vector comprising a foreign gene encoding at least one of a respiratory syncytial virus (RSV) protein, a human parainfluenza (hPIV) protein, an antigenic fragment thereof, and combinations thereof. In some embodiments the method further comprises the recombinant Sendai viral vector, wherein the RSV protein is selected from the group of a type A protein G, a type A protein F, a type B protein G, and a type B protein F. In other embodiments the method further comprises the recombinant Sendai viral vector, wherein the hPIV protein is selected from the group of a type 1 protein HN, a type 1 protein F, a type 2 protein HN, a type 2 protein F, a type 3 protein HN, and a type 3 protein F.

In still another embodiment, the present invention contemplates a recombinant Sendai viral vector comprising a modified Enders strain Sendai genome with a foreign gene encoding at least one of a respiratory syncytial virus (RSV) protein. In some embodiments, the recombinant Sendai viral vector includes said foreign gene is inserted between a Sendai virus F gene and a Sendai virus HN gene.

In still another embodiment, the foreign gene or genes may be any other foreign antigen from any pathogen.

In still other embodiments, the foreign gene is inserted between a Sendai virus P gene and a Sendai virus M gene. In still other embodiments, the foreign gene is inserted between a Sendai virus M gene and a Sendai virus F gene.

In further embodiments, the recombinant Sendai viral vector includes methods for the creation of a modified Enders vaccine comprising an Enders/Z strain chimera to facilitate the rescue of an infectious virus vector from cDNA and to ensure the virus is attenuated, but immunogenic in primates. In one embodiment, the Enders/Z strain chimera is a vector wherein a portion of the L gene of the Enders strain is replaced with the corresponding portion from the Z-strain of Sendai virus. In one embodiment, the Sendai virus L gene is modified such that it contains nucleic acid encoding the following amino acid changes from the Z strain: S to G at position 155, R to K at position 258, G to E at position 466, G to E at position 482, S to R at position 581, Q to R at position 717, T to I at position 800, and R to K at position 852.

In another embodiment, the present invention contemplates a composition comprising the recombinant Sendai viral vector and a pharmaceutically acceptable carrier or diluent or any carrier, adjuvant or diluent.

In one embodiment, the present invention contemplates a method, comprising: a) providing: i. a subject in need of vaccination against RSV; ii. one of the novel Sendai vectors described herein wherein the vector comprises an RSV gene or portion thereof; and b) administering said composition to said subject in an amount effective to elicit an immune response.

In yet another embodiment, the present invention contemplates a recombinant Sendai viral vector comprising a modified Enders strain Sendai genome with a foreign gene (or portion thereof) inserted between an intergenic junction selected from the group consisting of a N-P, P-M, an M-F, F-HN an HN-L gene junctions or any other position(s) within the genome. In one embodiment, the foreign gene is a reporter gene. In one embodiment, the reporter gene may be luciferase but may (in other embodiment) be any other reporter gene (e.g. a gene encoding a fluorescent protein).

In further embodiments, the transcription start or stop sequences in the Sendai virus vector genome may be altered to increase or decrease transcription of downstream genes. For example, the Sendai virus transcription start sequence upstream of the Sendai virus F gene may be mutated from AGGGATAAAG (SEQ. ID. NO.:19) to AGGGTGAAAG (SEQ. ID. NO.:20) to increase downstream transcription of an inserted foreign gene inserted between the M and F genes of the Sendai virus genome.

In still other embodiments, the present invention contemplates a kit comprising:
a) providing: i) a Sendai virus vector (i.e. one of the novel vectors described herein) with or without adjuvant and ii) instructions for use to vaccinate against a targeted pathogen.

In other embodiments, the present invention contemplates a kit comprising: a) providing: i) a Sendai virus vector with or without adjuvant and/in combination with another vaccine; and ii) instructions for use to vaccinate against a targeted pathogen.

In yet another embodiment, the present invention contemplates a kit comprising: a) providing: i) a vector carrying a marker gene; and ii) instructions for use to visualize the virus.

In one embodiment, the present invention contemplates a recombinant Sendai viral vector comprising a modified Sendai viral vector in which a portion of Z strain genome is added to the Enders Sendai virus strain genome to create an Enders/Z chimera comprising a modified L gene.

In some embodiments the recombinant Sendai viral vector further comprises, wherein said modified L gene comprises nucleic acid encoding amino acid changes selected from the group comprising S to G at position 155, R to K at position 258, G to E at position 466, G to E at position 482, S to R at position 581, Q to R at position 717, T to I at position 800, R to K at position 852, and combinations thereof.

In yet further embodiments a recombinant Sendai viral vector disclosed herein further comprises a vector with immunogenic properties.

In other embodiments the recombinant Sendai viral vectors disclosed above further comprise having a foreign gene(s) inserted in any position(s) including but not limited to one or more than one intergenic junction selected from the group consisting of a N-P, a P-M, a M-F, a F-HN, a HN-L, and combinations thereof.

In yet other embodiments the recombinant Sendai viral vector with a foreign gene wherein said foreign gene facilitates virus tracking in vitro, in vivo, or combinations thereof.

In another embodiment the recombinant Sendai viral vector wherein said foreign gene for tracking is selected from the group of a luciferase, a green fluorescent protein, and combinations thereof.

In further embodiments the recombinant Sendai viral vectors described herein wherein at least a gene start/stop site is manipulated to alter gene transcription.

In another embodiment the recombinant Sendai viral vectors described herein wherein said foreign gene is a respiratory syncytial virus (RSV) F protein.

In other embodiments the recombinant Sendai viral vectors described herein wherein said foreign gene is a respiratory syncytial virus (RSV) G protein.

In other embodiments the recombinant Sendai viral vectors described herein wherein said foreign gene is a parainfluenza virus type 1 (PIV-1) protein.

In still further embodiments the recombinant Sendai viral vectors described herein wherein said foreign gene is a parainfluenza virus type 2 (PIV-2) protein.

In yet other embodiments the recombinant Sendai viral vectors described herein wherein said foreign gene is a parainfluenza virus type 3 (PIV-3) protein.

In yet other embodiments the recombinant Sendai viral vectors described herein wherein said foreign gene is a parainfluenza virus type 4 (PIV-4) protein.

In one embodiment the recombinant Sendai virus vectors described herein wherein said foreign gene is a reporter gene.

In one embodiment, the present invention contemplates a method of immunizing an animal or a model tissue culture system against infection comprising use of an effective amount of a Sendai viral vector or recombinant Sendai viral vector as described herein.

In one embodiment, the present invention contemplates a composition comprising the Sendai viral vector as described herein and a pharmaceutically acceptable carrier or diluent or any carrier, adjuvant or diluent.

In another embodiment, the present invention contemplates a method, comprising: a) providing: i. a subject in which vaccination is desired wherein said subject includes in vitro, in vivo, and combinations thereof; ii. a Sendai virus vector (i.e. one of the novel vectors described herein) or the composition described herein; and b) administering said vector or composition to said subject in an amount effective to elicit an immune response.

In one embodiment the method further comprises the recombinant Sendai viral vector (i.e. one of the novel vectors described herein) or the composition described herein, wherein said foreign gene is inserted between a Sendai virus P gene and a Sendai virus M gene.

In one embodiment the method further comprises the recombinant Sendai viral vector (i.e. one of the novel vectors described herein) or the composition described herein, wherein said foreign gene is inserted between a Sendai virus M gene and a Sendai virus F gene.

In one embodiment the method further comprises the recombinant Sendai viral vector (i.e. one of the novel vectors described herein) or the composition described herein, wherein said foreign gene is inserted between a Sendai virus F gene and a Sendai virus HN gene.

In yet another embodiment, the present invention contemplates a recombinant Sendai viral vector comprising a modified Enders strain Sendai genome with a foreign gene or portion thereof inserted at an intergenic junction(s) selected from the group consisting of a N-P, a P-M, a M-F, a F-HN, a HN-L, and combinations thereof.

In a further embodiment the recombinant Sendai viral vector further comprises, wherein said modified Enders strain Sendai genome comprises a modified L gene.

In other embodiments the recombinant Sendai viral vector further comprises, wherein a portion of the L gene of the Enders strain is replaced with the corresponding portion from the Z-strain of Sendai virus.

In still other embodiments the recombinant Sendai viral vector further comprises, wherein said foreign gene is a reporter gene.

In one embodiment, the present invention contemplates a kit comprising: a) providing: i) the vector (i.e. one of the novel vectors described herein); and ii) instructions for use to vaccinate against a targeted pathogen.

In one embodiment the present invention contemplates a kit comprising: a) providing: i) the composition (i.e. one of the novel compositions described herein); and ii) instructions for use to vaccinate against a targeted pathogen.

In one embodiment the present invention contemplates a kit comprising: a) providing:

i) the vector (i.e. one of the novel vectors described herein); and ii) instructions for use to visualize the vector.

In one embodiment the present invention contemplates the recombinant Sendai viral vector (i.e. one of the novel vectors described herein) wherein said vector is mixed with at least one other antigen or immunogen.

In yet another embodiment the present invention contemplates a method, comprising:

a) providing: i) a vector comprising an Enders Sendai virus strain genome; and ii) a Z Sendai virus strain genome; and b) replacing at least a portion of a gene of the Enders strain genome with the corresponding portion from the Z-strain of Sendai virus genome so as to generate a modified Sendai viral vector.

In one embodiment the method further comprises, wherein a portion of the L gene of the Enders strain is replaced with the corresponding portion from the Z-strain of Sendai virus so as to generate a modified Sendai viral vector comprising a modified L gene.

In one embodiment the method further comprises, wherein said modified L gene comprises nucleic acid encoding amino acid changes selected from the group comprising S to G at position 155, R to K at position 258, G to E at position 466, G to E at position 482, S to R at position 581, Q to R at position 717, T to I at position 800, R to K at position 852, and combinations thereof.

In one embodiment the method as described herein further comprising, step c) inserting a foreign gene or a portion thereof into said vector wherein said insertion is at an intergenic junction selected from the group consisting of a N-P, a P-M, a M-F, a F-HN, a HN-L, and combinations thereof.

In yet other embodiments the recombinant Sendai viral vectors described herein wherein said foreign gene is a metapneumovirus protein.

In yet other embodiments said nucleic acid encoding amino acid changes selected from the group comprising S to G at position 155, R to K at position 258, G to E at position 466, G to E at position 482, S to R at position 581, Q to R at position 717, T to I at position 800, R to K at position 852 and combinations thereof.

Furthermore, descriptions of embodiments presented are not meant to be limiting and include all equivalent, comparable technologies, reagents, sources, diluents, uses etc. as known by one skilled in the art. For example only and not meant to be limiting, specific sequences are presented but include the related sense, antisense, complementary, homologs, portions, fragments, 5' to 3' and 3' to 5', and analogs as known by one in the related arts such as molecular biology, biotechnology, along with any and all related arts. Moreover, while specific mention of treating humans for respiratory viral infection is presented it is contemplated that the Jennerian vaccine vector might be used as a backbone for development of other vaccines or procedures used in vitro or in vivo to diagnose or treat generally mammals, and more particularly humans. For example only, and not meant to be limiting the vaccine vector contemplates use in non-human mammals such as dogs, cats, horses, cattle, and primates. Moreover, vaccines and/or compositions optionally include pharmaceutically acceptable diluents and/or adjuvants but also include use of research type diluents/adjuvants and/or no diluents/adjuvants.

BRIEF DESCRIPTION OF THE FIGURES

Within the sequence presented in FIG. 7 you can find the different Sendai virus genes by doing a search with the sequences. The sequences presented in FIG. 7B-7H were taken directly from the vector sequence in 7A and are presented individually. Related protein sequences are provided within the detailed description.

FIG. 7. Sequence Listings. FIG. 7A-H are as follows: A, The sequence of a modified SeV construct (pSeVc) (Also see Table 1), and sequences for the individual Sendai virus genes are provided; B, NP cDNA: (SEQ. ID. NO.:4); C, P cDNA: (SEQ. ID. NO.:6); D, C cDNA (SEQ. ID. NO.:8); E, M cDNA: (SEQ. ID. NO.:10); F, F cDNA (SEQ. ID. NO.:12); G, HN cDNA (SEQ. ID. NO.:14); and H, L cDNA (SEQ. ID. NO.:16). Associated translations are shown in the detailed description. The sequences are listed 5' to 3' (left to right). The key to the figure is as follows:

Sequence Key for genes within the pSeVc plasmid

▓ =Start codon
▓ =Stop Codon
Violet=NP gene sequence
Purple=P gene sequence
PURPLE ALL CAPS=C gene sequence (internal start site within the P gene)
orange=M gene sequence
Dark blue=F gene sequence
Pink=FIN gene sequence
Bold black=L gene sequence
▓▓▓▓▓▓▓ =Transcription start signal
▓▓▓▓▓▓▓ =NotI (for cloning in gene of interest e.g. hPIV-2)

Figure 8:
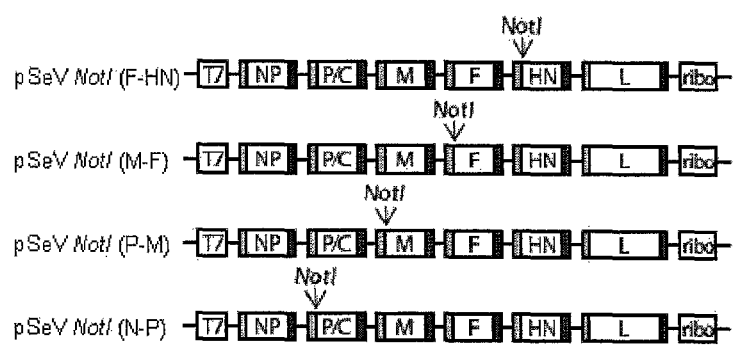

FIG. 8 Examples of sites in which foreign genes may be inserted into the Sendai virus vector genome. Insertion sites may include, but are not limited to, positions upstream of the P, M, F, and HN genes. The foreign gene cassettes are flanked by NotI restriction endonuclease sites, and Sendai virus vector cDNA plasmids have been engineered to have unique NotI restriction endonuclease sites upstream of the various Sendai virus genes.

Figure 9:
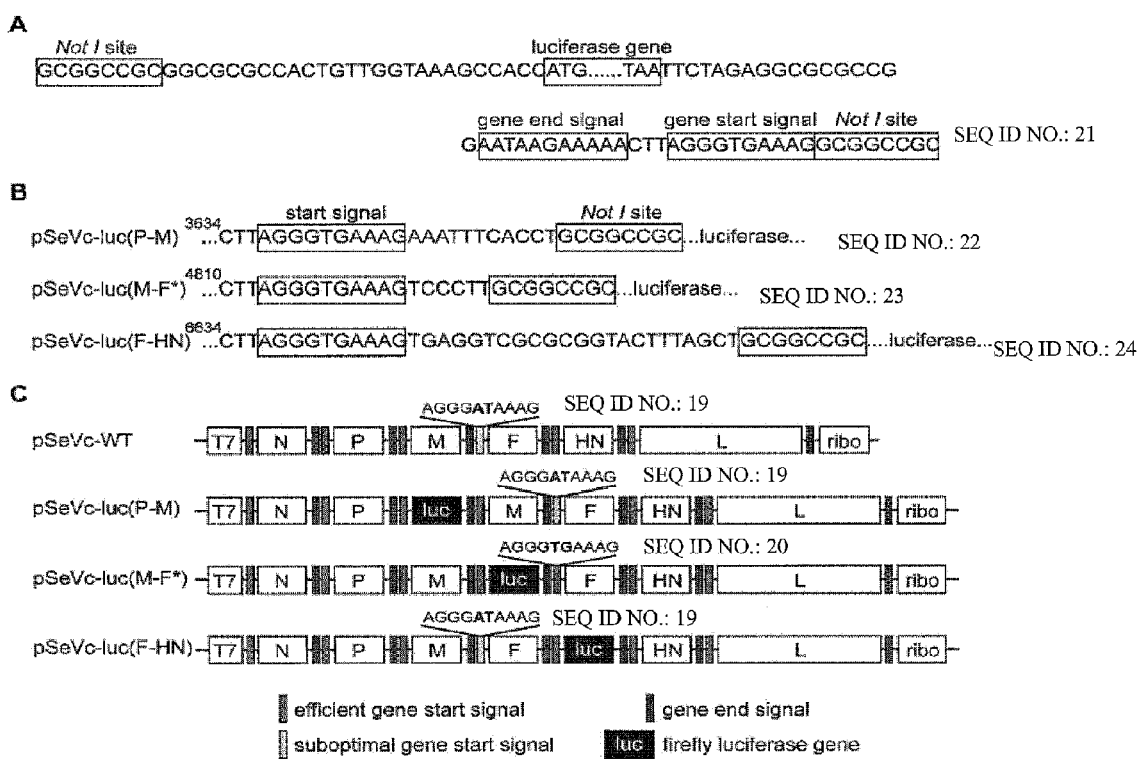

FIG. 9. Construction of luciferase-expressing Sendai viruses. (A) Nucleotide sequence of the firefly luciferase gene cassette. A pGEM3 cloning plasmid was engineered to contain flanking NotI restriction sites, the firefly luciferase reporter gene, gene end and gene start sequences. (B) To insert the luciferase reporter gene cassette into three gene junctions, three pSeV genome plasmids were cloned to contain a unique NotI restriction site in each of the P-M, M-F, and F-HN gene junctions. For the pSeV-luc(M-F*) genome plasmid, the naturally occurring suboptimal start signal AGGGATAAAG (SEQ. ID. NO.: 19) was also mutated to the more efficient start signal AGGGTGAAAG (SEQ. ID. NO.: 20) to compensate for expected attenuation due to the addition of the foreign gene and additional gene junction. The firefly luciferase gene cassette (panel A) was subcloned from the pGEM3 plasmid into the pSeV genome plasmids using the NotI restriction sites. (C) Design of pSeV cDNA plasmids for the rescue of WT and recombinant SeVs containing the luciferase reporter gene (luc). The locations of the SeV genes nucleoprotein (N), polymerase (P), matrix (M), fusion (F), hemagglutinin-neuraminidase (HN), and large (L) protein are shown, as well as the T7 RNA polymerase promoter (T7) and hepatitis delta virus ribozyme sequence (ribo). Gene start sequences are shown in green and the naturally occurring, suboptimal AGGGATAAAG (SEQ. ID. NO.: 19) gene start sequence between the M and F genes of WT SeV is shown in yellow. Gene end sequences are shown in red. The 3' leader sequence upstream of the N gene and the 5' trailer sequence downstream of the L gene are not shown for simplicity.

Figure 10:
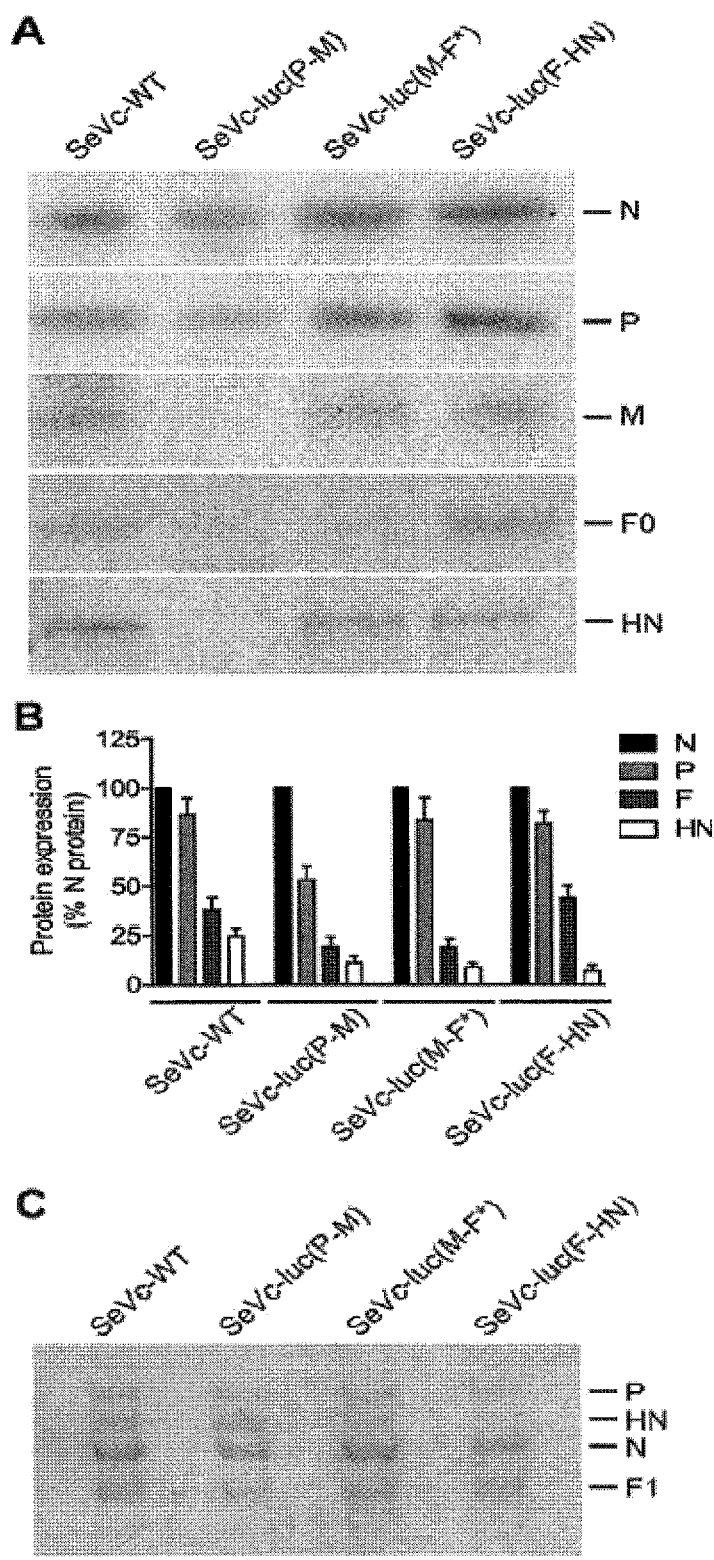

FIG. 10. SeV protein expression and incorporation into virions. (A) SeV protein expression in LLC-MK2 cells. Confluent monolayers of LLC-MK2 cells were infected with recombinant SeVs at an MOI of 5 PFU/cell and incubated for 16 h. Following radiolabeling and immunoprecipitation, viral proteins in the lysates were resolved by SDS-PAGE and visualized with a phosphorimager. (B) Ratios of SeV protein expression. Protein expression was quantified with ImageQuant® 5.2 software and normalized to the expression level of the N protein. The data represent the averages (+/− standard deviation) from three experiments. (C) SeV composition. Recombinant SeVs were harvested from the allantoic cavities of embryonated chicken eggs, purified by centrifugation through a sucrose gradient, separated by SDS-PAGE, and visualized with Coomassie Blue.

Figure 11:
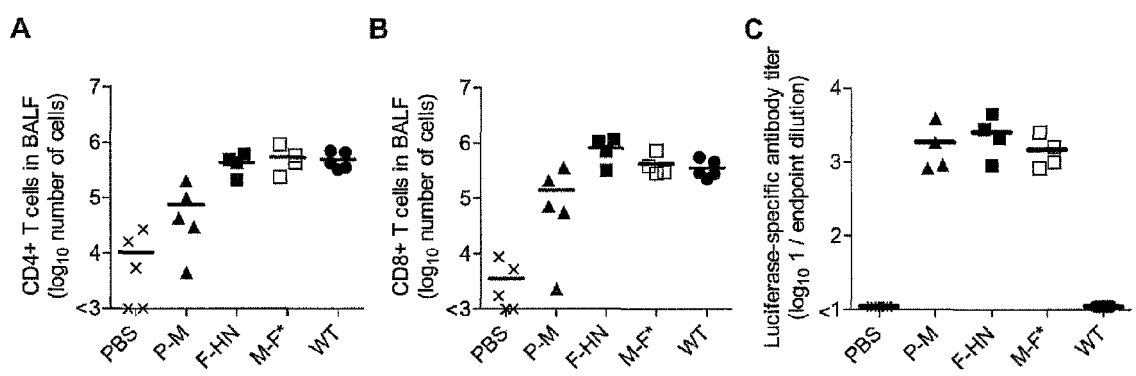

FIG. 11. Immunological responses to infection by recombinant SeVs in mice. Groups of five 8-week-old 129/SvJ mice were intranasally inoculated with 30 μl containing 7,000 PFU of recombinant SeV or PBS. On day 10 p.i., serum was collected and the mice were euthanized to recover bronchoalveolar lavage fluid (BALF). Experiments were performed twice with representative data shown. Each data point represents an individual animal and horizontal bars show group averages. The numbers of CD4+ (A) and CD8+ (B) T cells recovered from BALF were determined by flow cytometry. (C) Luciferase-specific binding antibody titers in sera were determined by ELISA assays and are expressed as reciprocal endpoint dilutions.

Figure 12:
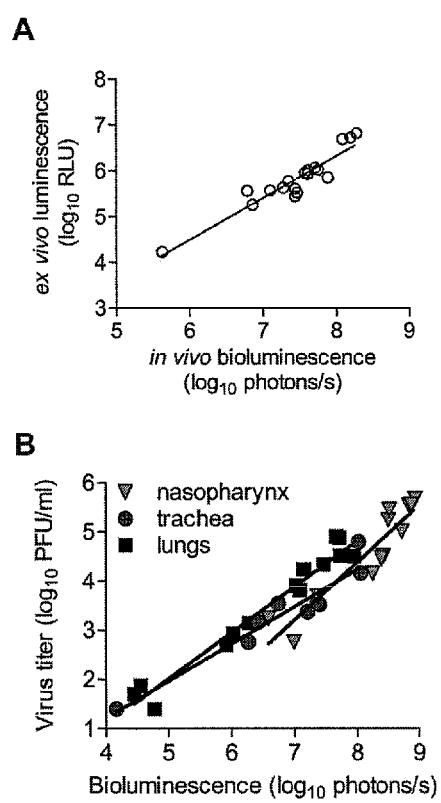

FIG. 12. Bioluminescence and Sendai virus titers in the respiratory tracts of 129/SvJ mice. Groups of three 8-week-old mice were intranasally inoculated with 7,000 PFU of recombinant SeV. (A) In vivo bioluminescence was measured for all three luciferase-expressing viruses on days 4 and 6 p.i., after which lungs were immediately harvested and homogenized so that ex vivo luciferase activity could be measured. A fit of the data with a least squares linear regression model yielded an $R^2$ value of 0.878. RLU denotes relative light units. (B) Comparison between light detected by the camera and viral titers of homogenates from the nasopharynx (triangles), trachea (circles), and lungs (squares). Each point represents data from a single mouse infected with SeVc-luc(M-F*) and studied on day 2, 3, 5 or 7 p.i. Least squares linear regression yielded $R^2$ values of 0.864, 0.915 and 0.961 for the nasopharynx, trachea and lungs, respectively.

Figure 13:
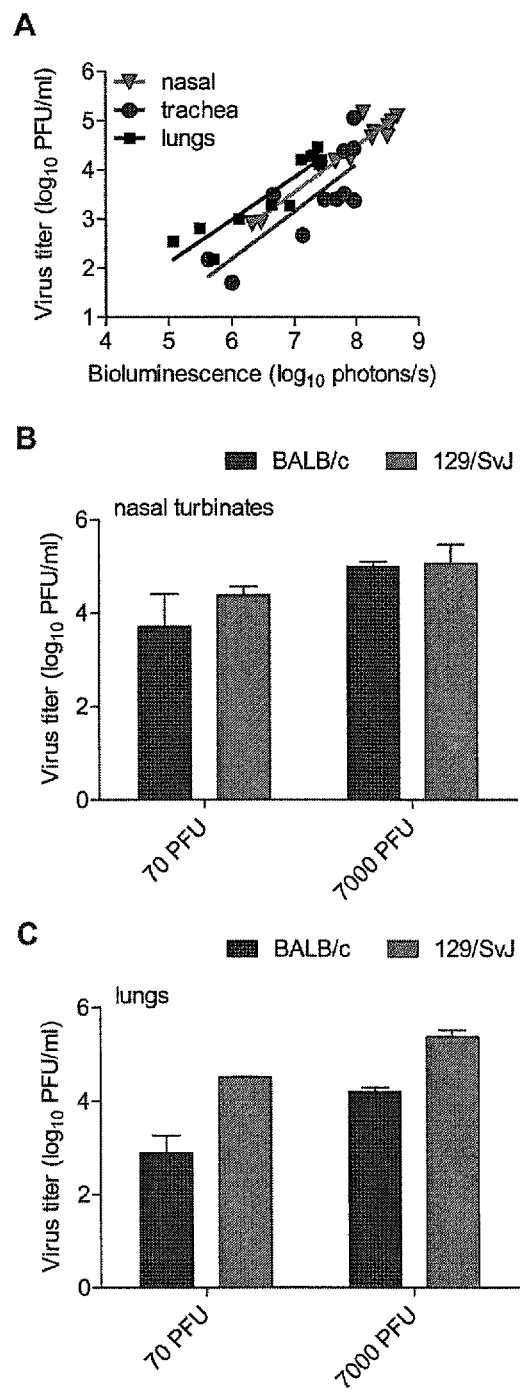

FIG. 13. Bioluminescence and Sendai virus titers in the respiratory tracts of BALB/c and 129/SvJ mice. Groups of three 8-week-old mice were intranasally inoculated with either 70 or 7,000 PFU of SeVc-luc(M-F*). (A) In vivo bioluminescence was measured in BALB/c mice infected with 7,000 PFU of virus on days 2, 3, 5 and 7 p.i. after which the animals were euthanized and tissues were harvested so that virus titers from tissue homogenates could be measured by plaque titration in LLC-MK2 cells. Correlations between virus titers in tissue homogenates and light detected by the camera were found with $R^2$ values of 0.928, 0.656, and 0.846 for the nasopharynx, trachea, and lungs, respectively. Virus titers in homogenates from the nasopharynx (B) and lungs (C) of both BALB/c- and 129-strain mice infected with either 70 or 7,000 PFU of SeVc-luc(M-F*) were measured by plaque titration in LLC-MK2 cells. The data represent the average virus titers of six mice (+/− standard deviation).

Figure 14:
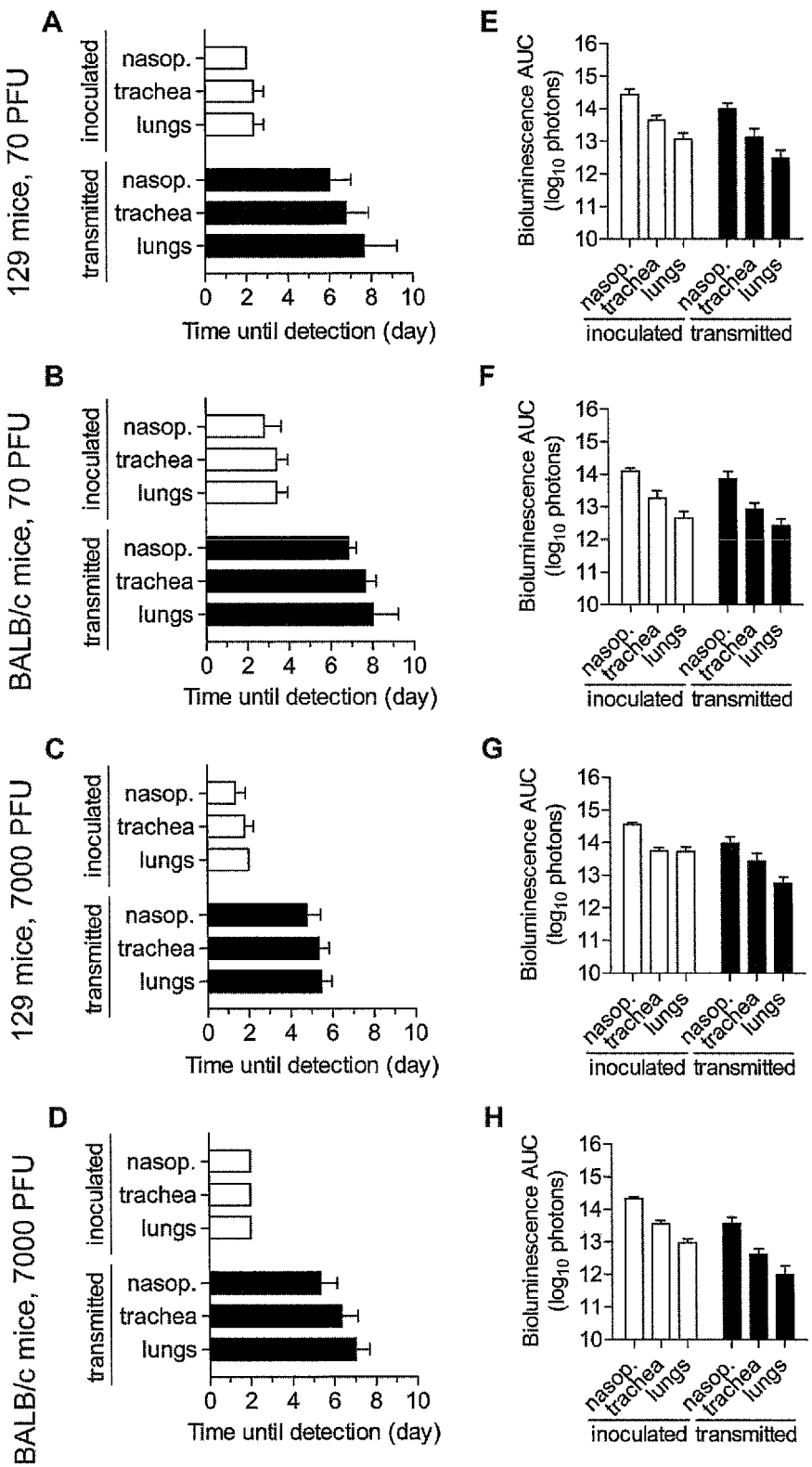

FIG. 14. Tissue-specific timing and magnitude of Sendai virus spread in the respiratory tracts of intact mice after inoculation and contact transmission. In each group, one BALB/c or 129/SvJ mouse was inoculated intranasally with either 70 or 7,000 PFU of SeVc-luc(M-F*) and three contact animals were co-housed one day later as described in FIG. 5. (A-D) Time until detection of bioluminescence in the nasopharynx (nasop.), trachea, and lungs (limit of detection: >6 $\log_{10}$ photons/s) after direct inoculation (open bars) and after contact transmission (solid bars). (E-H) Overall magnitude of infection after direct inoculation (open bars) and after contact transmission (solid bars) as determined by integration of daily measurements of total flux with respect to time. The areas under the curve (AUC) of bioluminescence are expressed as the total amount of photons on a $\log_{10}$ scale. The experiment was performed in triplicate for 129-strain mice (3 donor animals and 9 transmitted) and duplicate for BALB/c-strain mice (2 donor animals and 6 transmitted).

Figure 15:
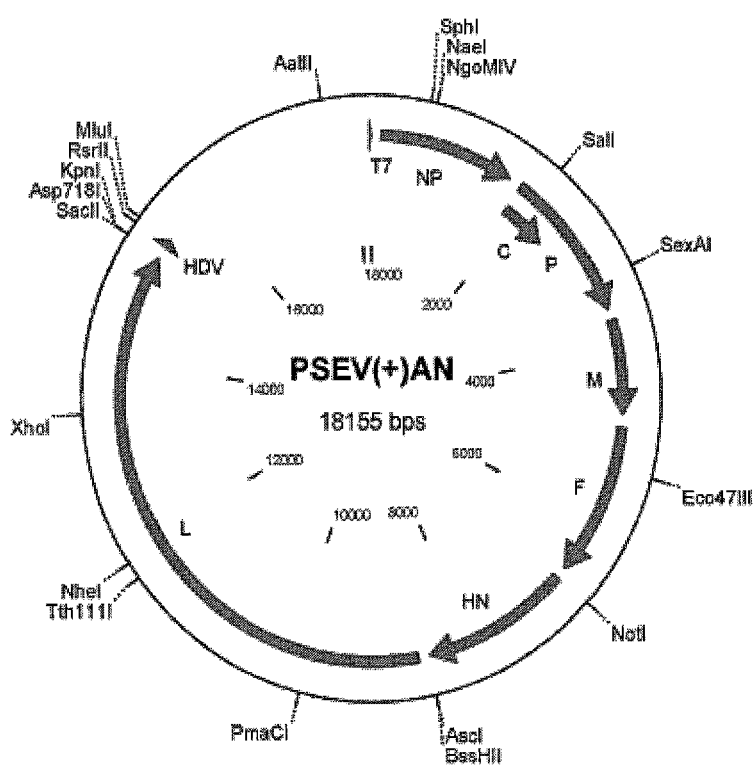

FIG. 15. Diagram of PSEV construction. Sendai virus Enders strain cDNA was cloned into the pUC vector containing a T7 promoter upstream and a RNA self-cleaving HDV sequence downstream.

Figure 16:
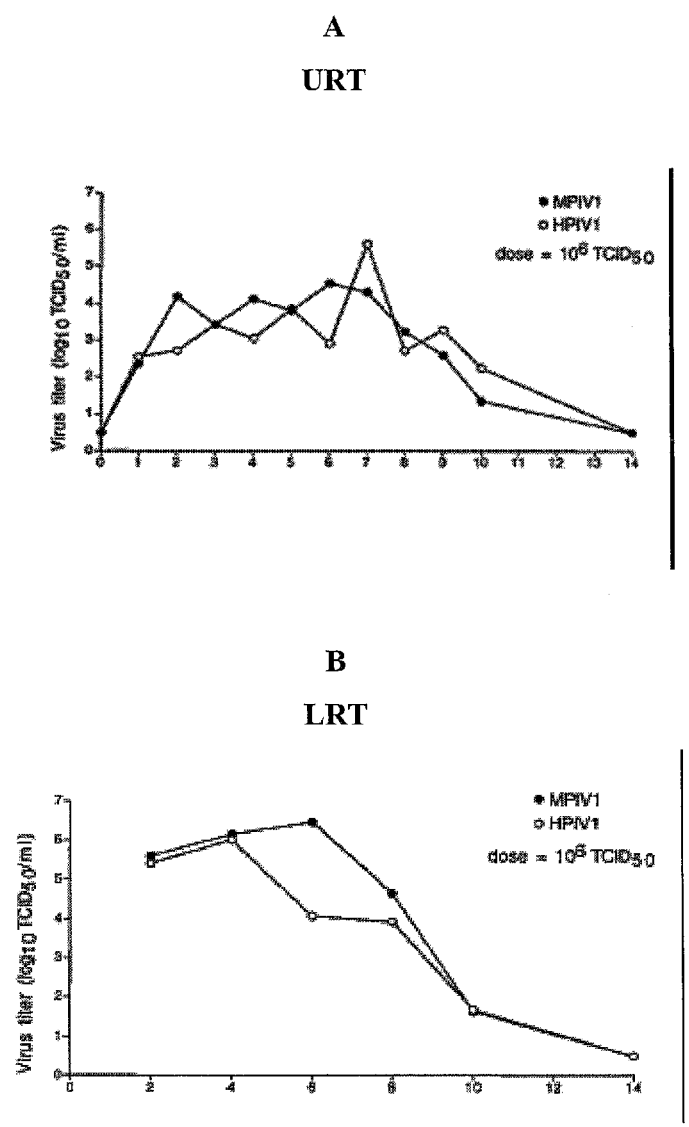
Figure 16:
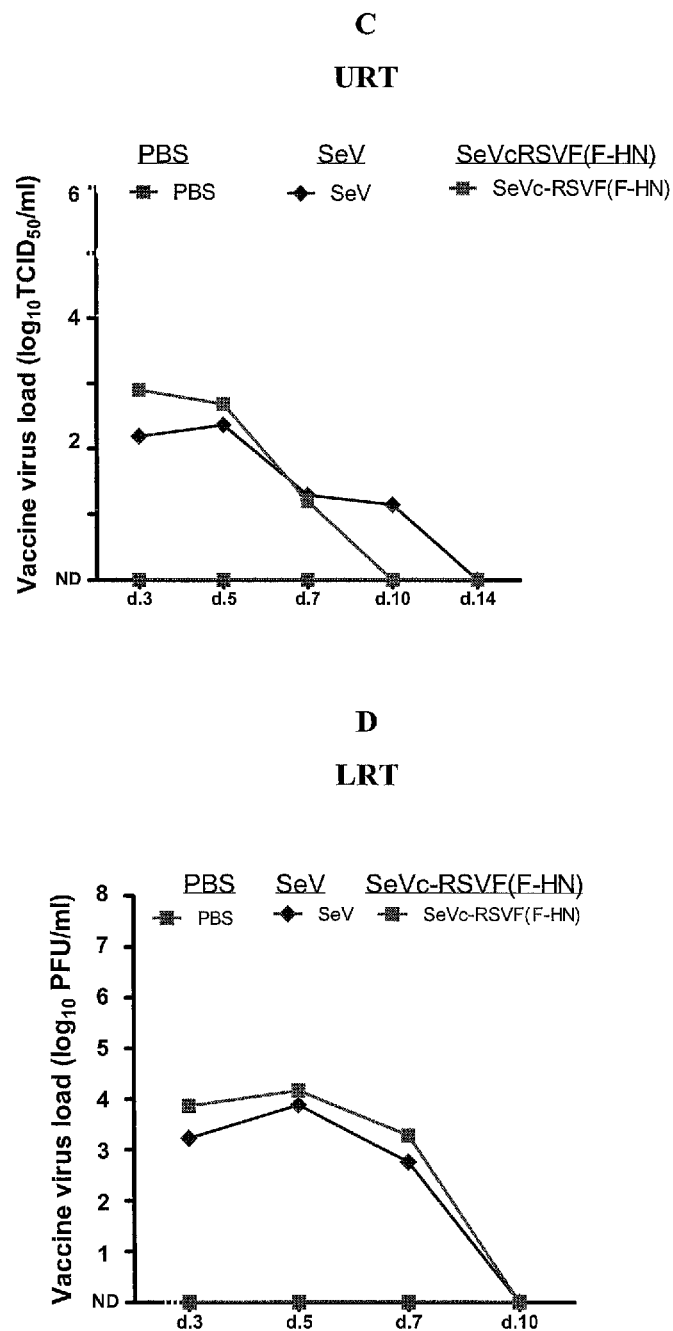

FIG. 16. Persistence of Z strain vaccine and Enders-based vaccines in primates after intranasal and intratracheal inoculation. African green monkeys were inoculated by the intranasal and intratracheal routes with either Sendai virus Z vaccine (A and B (Skiadopoulos et. al. 2002 Virology 297:153)) or Sendai virus Enders-based vaccines (C and D). Virus loads were monitored in the URT or LRT following infections.

Figure 17:
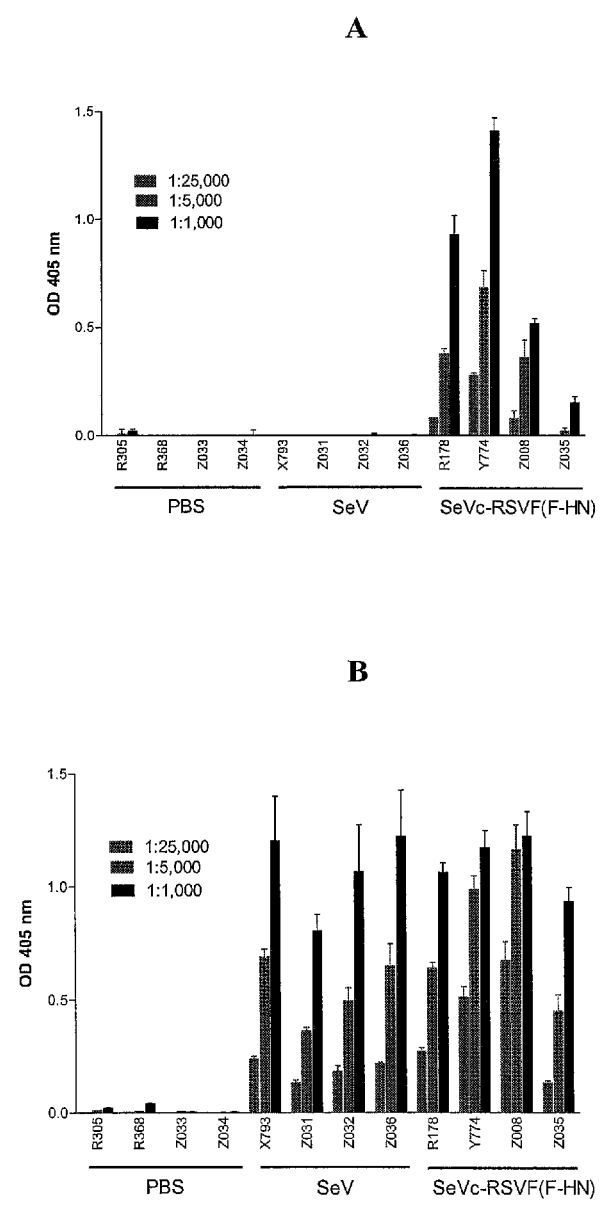

FIG. 17. Immunogenicity of unmodified Enders Sendai virus and a recombinant modified Sendai virus Enders-based vaccine expressing RSV F (SeVc-RSVF(F-HN)) in African green monkeys. Sera were taken 25 days after vaccinations and tested for antibody responses to RSV F (A) and Sendai virus (B) by ELISA.

Figure 18:
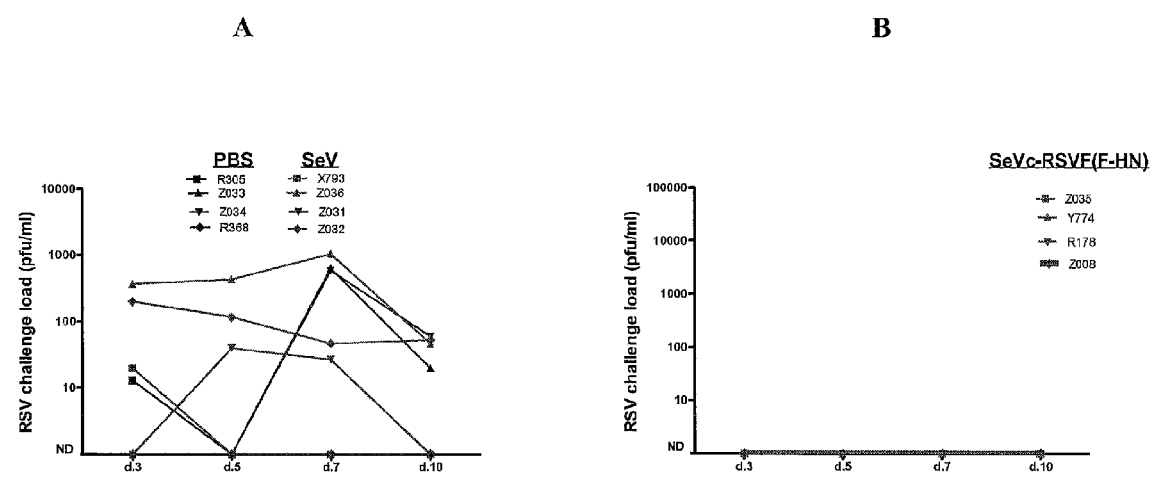

FIG. 18. Modified Sendai virus Enders-based vaccine expressing RSV F protects primates from RSV. Control (left, A) and test (right, B) animals were challenged with RSV approximately 1 month after vaccination. Bronchoalveolar lavage (BAL) samples were collected for 10 days after challenge and tested for RSV growth. All animals that received the modified Sendai virus Enders-based vaccine expressing RSV F (SeVc-RSVF(F-HN)) were protected from RSV infection of the lower respiratory tract.

Figure 19:
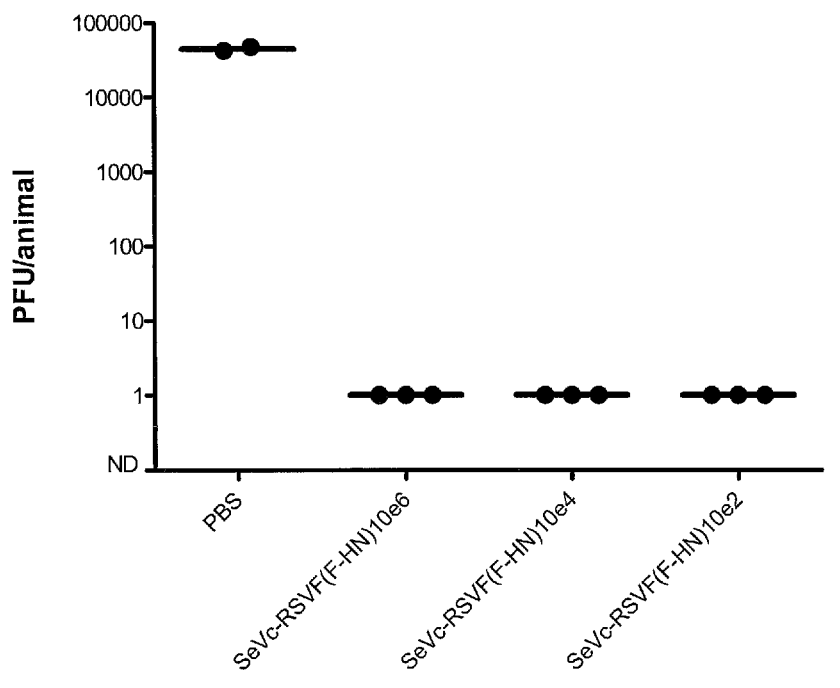

FIG. 19. Modified Sendai virus Enders-based vaccine expressing RSV F (SeVc-RSVF(F—HN)) is protective against RSV at low dose. The modified Sendai virus Enders-based vaccine expressing RSV F was used to vaccinate animals at doses of 10e6, 10e4 and 10e2. All vaccinated animals were protected from RSV challenge as demonstrated by measuring virus in the lung after challenge.

DEFINITIONS

To facilitate the understanding of this invention a number of tei s (set off in quotation marks in this Definitions section) are defined below. Terms defined herein (unless otherwise specified) have meanings as commonly understood by a person of ordinary skill in the areas relevant to the present invention.

Figure 1:
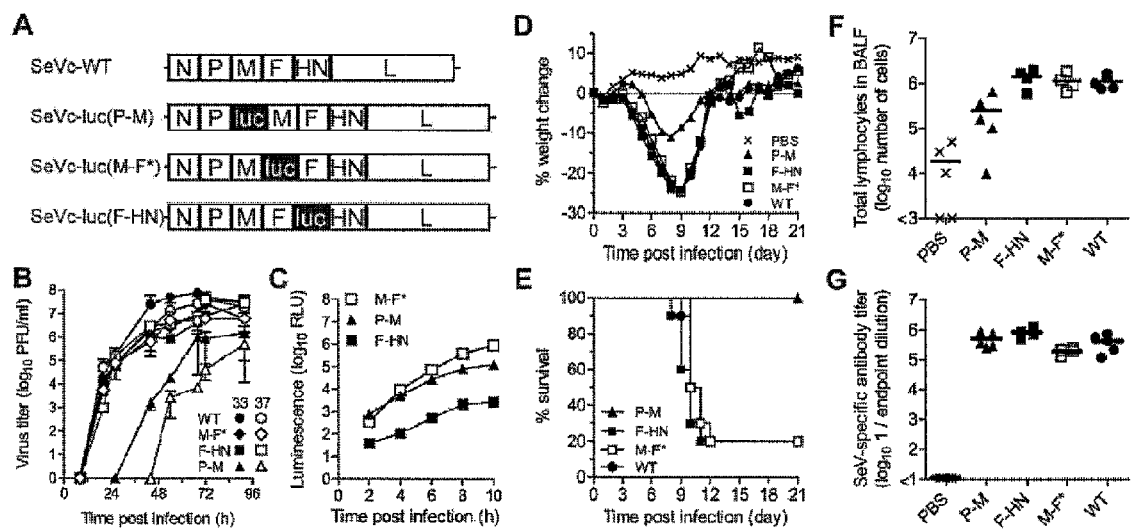
FIG. 1. In vitro and in vivo phenotypes of luciferase-expressing Sendai viruses. (A) Recombinant Sendai viruses were generated that contain the firefly luciferase gene (luc) inserted into the P-M, M-F, and F-FIN gene junctions. (B) Multiple-step replication kinetics of wild-type (WT) and luciferase-expressing SeVs in LLC-MK2 cell cultures infected at a multiplicity of infection (MOI) of 0.01 PFU/cell at 33° C. (closed symbols) and 37° C. (open symbols). (C) Kinetics of luciferase reporter gene expression in LLC-MK2 cells infected with recombinant SeVs at an MOI of 5 PFU/cell, as measured by luminescence. (D) Changes in body weights of mice after intranasal inoculation of SeVs. (E) Percent survival of mice after intranasal inoculation of SeVs. (F) Total numbers of lymphocytes recovered from bronchoalveolar lavage fluid (BALF) of mice 10 days after infection, as measured by flow cytometry. (G) SeV-specific binding antibody titers in sera of mice collected 10 days after infection, as measured by reciprocal endpoint dilutions in ELISA assays. For panels D-G, groups of five 8-week-old 129/Sv-strain mice were intranasally inoculated with 7,000 PFU of recombinant SeV or phosphate buffered saline (PBS) and the experiments were performed twice. Cumulative data are shown in panels D and E, and representative data are shown in panels F and G.

As used herein, the term "subject" or "patient" refers to any organism to which compositions in accordance with the invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In vitro systems may also be used (e.g. to express SeV or other proteins for study within the target cell and/or for isolation). For example only and not meant to be limiting LLC-MK2 cells in culture are contemplated (See FIG. 1).

As used herein, the term "immune response" refers to the alteration in the reactivity of an organism's immune system upon exposure to an antigen. The term "immune response" encompasses but is not limited to one or both of the following responses: antibody production (e.g., humoral immunity), and induction of cell-mediated immunity (e.g., cellular immunity including helper T cell and/or cytotoxic T cell responses).

As used herein, the term "primer" refers to an oligonucleotide, whether occurring naturally (e.g., as in a purified restriction digest) or produced synthetically, capable of acting as a point of initiation of nucleic acid synthesis when placed under conditions in which synthesis of a primer extension product complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. In preferred embodiments, the primer is attached to the end of a nucleic acid such that a hairpin forms from self-hybridization. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method. It is also contemplated that primers can be used in PCR (see below) to artificially insert desired nucleotide sequences at the ends of nucleic acid sequences.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a DNA mixture without cloning or purification. Because the desired amplified segments of the target sequence become the predominant sequences (in terms of concentration) in the mixture, they are said to be "PCR amplified." Similarly, the term "modified PCR" as used herein refers to amplification methods in which a RNA sequence is amplified from a DNA template in the presence of RNA polymerase or in which a DNA sequence is amplified from an RNA template the presence of reverse transcriptase.

As used herein, the terms "restriction endonucleases" and "restriction enzymes" refer to bacterial enzymes, each of which cut double-stranded DNA at or near a specific nucleotide sequence.

The terms "antigen," "antigenic," and "antigenically active," refer to any substance that can be recognized by a specific humoral and/or cell-mediated immune response. The terms "immunogen," "immunogenic" and "immunologically active" refer to any substance that is capable of inducing a specific humoral and/or cell-mediated immune response. An antigen or immunogen generally contains at least one epitope. Antigens and immunogens are exemplified by, but not restricted to molecules, which contain a peptide, polysaccharide, nucleic acid sequence, and/or lipid. Complexes of peptides with lipids, polysaccharides, or with nucleic acid sequences are also contemplated, including (without limitation) glycopeptide, lipopeptide, glycolipid, etc. These complexes are particularly useful immunogens where smaller molecules with few epitopes do not stimulate a satisfactory immune response by themselves.

As used herein the term "nucleic acid sequence" refers to an oligonucleotide, a nucleotide or a polynucleotide, and fragments or portions thereof, and vice versus, and to DNA or RNA of genomic or synthetic origin, which may be single or double-stranded, and represent the sense or antisense strand. Similarly, "amino acid sequence" as used herein refers to peptide or protein sequence.

As used herein the term "antisense" when used in reference to DNA refers to a sequence that is complementary to a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein the term "vaccine" refers to an immunogenic composition that is administered to a host to provide some degree of protection from an infection and/or disease from a target virus or pathogen. Moreover, some degree of protection includes but is not limited to decreasing, reducing, modifying, and/or ameliorating one or more symptoms of an infection and/or disease. Generally, some symptoms of respiratory diseases include common cold symptoms and more particularly for example only and not meant to be limiting, breathing difficulty or labored breathing, cough, fever, croupy cough (often described as a "seal bark" cough), cyanosis (bluish skin color due to lack of oxygen), nasal flaring, stuffy nose, wheezing congested and/or runny nose. Moreover, respiratory diseases can affect their lungs, causing bronchiolitis or pneumonia. Such a composition might include a "pharmaceutically acceptable" diluent and/or carrier or any carrier, adjuvant or diluent. For example only, and not meant to be limiting acceptable diluents and/or carriers can be found in Remingtons "The Science and Practice of Pharmacy," $21^{St}$ Ed. 2005 (herein incorporated by reference in its entirety). The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Numerous vaccine formulations are known to those skilled in the art.

Vaccines can be administered alone or in combination with various adjuvants/carriers. Pharmaceutical carriers are known to those skilled in the art. These most typically would be standard carriers for administration of vaccines to humans, including solutions such as sterile water, saline, and buffered solutions at physiological pH. Other ingredients include excipients, carriers, thickeners, diluents, buffers, preservatives, and surface active.

As used herein the term(s) "administering" and "administer" are used interchangeably and include for example only and not meant to be limiting, administering by aerosol, droplet, parenteral injection (such as intraperitoneal, subcutaneous, or intramuscular), intranasal via droplet, inhalation et al. See Remingtons "The Science and Practice of Phafinacy," $21^{st}$ Ed. 2005.

As used herein the term "Sendai virus" is a mouse parainfluenza virus that is the murine homologue of hPIV-1.

As used herein the term "reporter gene" includes a means of facilitating virus tracking. For example only and not meant to be limiting, the reporter gene as described herein includes luciferase, green fluorescent protein, red fluorescent protein, along with other means of visually tracking (e.g. with marked probes or antibodies) as known to those skilled in the art. Further, while specific examples are given any other means of fluorescent, bioluminescent, luminescent, and related reporter proteins useful for tracking are contemplated by the present invention.

As used herein the term "host cell" refers to any cell capable of replicating and/or transcribing and/or translating a heterologous gene. Thus, a "host cell" refers to any eukaryotic or prokaryotic cell (e.g., such as LLC-MK2 cells (See FIG. 1), bacterial cells, E. coli, yeast cells, mammalian cells, avian cells, amphibian cells, plant cells, fish cells, and insect cells), whether located in vitro or in vivo.

As used herein the term "wild-type" when made in reference to a gene refers to a gene that has the characteristics of a gene isolated from a naturally occurring source. The term "wild-type" when made in reference to a gene product refers to a gene product that has the characteristics of a gene product isolated from a naturally occurring source. The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene.

In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein the term "a modified Enders" means a Enders Sendai virus strain genome comprising a portion of a Z Sendai virus strain meant to be limiting, a Enders Sendai virus strain genome might contain one or more Z Sendai virus strain genes (or portions thereof) such as a Z strain NP gene, a Z strain P gene, a Z strain M gene, a Z strain F gene, a Z strain HN gene, and a Z strain L gene. Additionally, while specific combinations of Enders Sendai strain genome and Z Sendai strain genome have been provided they are not meant to be limiting and encompass use of other equivalent Sendai virus strain genomes.

As used herein a "chimera" means a Enders Sendai virus strain genome containing one or more portions of a different Sendai virus strain genome in operable combination. More particularly, for example only (and not meant to be limiting) in one embodiment, the present invention contemplates a Enders Sendai virus strain genome comprising one or more portions of a Z Sendai virus strain genome. Additionally, while specific combinations of Enders Sendai strain genome and Z Sendai virus strain genome have been provided they are not meant to be limiting and encompass use of other equivalent Sendai virus strain genomes.

As used herein the term "purified" refers to molecules, either nucleic acid or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein the term "purified" or "to purify" also refers to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

As used herein, the term "in vitro" refers to events that occur in an artificial environment, e.g., in a test tube or reaction vessel, in cell culture, etc., rather than within a multi-cellular organism.

As used herein, the term "in vivo" refers to events that occur within a multi-cellular organism. For example only and not meant to be limiting, such as a mammal more particularly a human and/or non-human animal.

As used herein the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The terms also refer to the linkage of amino acid sequences in such a manner so that a functional protein is produced.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "Multiplicity of Infection (MOI)" refers to the ratio of infectious virus particles to target cells (i.e. the ratio of infectious virus particles deposited in a well, relative to the number of target cells in that well). As used herein, the term "Plaque Forming Units (PFU)" refers to a measure of the number of virus particles capable of infecting cells and consequently forming plaques in a target cell monolayer.

As used herein the term "therapeutically effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a sub-portion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term SeVc refers to any construct that is based on the SeVc backbone described below. For example and not meant to be limiting, one embodiment is a SeVc-luc(M-F*) that denotes a modified SeVc construct containing a luciferase reporter gene cloned into the M-F gene junction. See Table 1.

DETAILED DESCRIPTION OF THE INVENTION

The present invention relates to recombinant virus vectors, methods for constructing vectors, and use of such vectors. In one embodiment, the present invention provides methods, recombinant virus constructions and compositions, and kits for a modified Enders strain Sendai viral vector for protection against pathogens. Moreover, some embodiments include vectors for imaging or tracing viral spread, clearance, and transmission. In one embodiment, the present invention contemplates a novel recombinant Sendai virus vaccine vector with the following attributes: (i) capacity for facile rescue of recombinant vectors by reverse genetics, (ii) capacity to carry a marker gene for virus tracking in vivo and in vitro, (iii) support of expression and immunogenicity of a foreign protein(s) when respective gene(s) are introduced into different positions within the SeV genome, (iv) limited growth in primates, (v) sufficient replication-competence to support immunogenicity in primates. Further, some embodiments also provide an attribute of (vi) limited growth at 33° C. and even less growth at 37° C. The present invention exhibits an unexpected balance of virus vector attenuation, virus vector growth, foreign gene expression, and immunogenicity to support each of these desired attributes.

In one embodiment, the present invention provides a vector that is unexpectedly superior to other SeV vectors including unmodified Enders or Z strains in that it can be easily rescued and exhibits both attenuation and immunogenicity in primates. Methods, recombinant virus constructions and formulations, and kits will facilitate the use of this Sendai virus vector as a laboratory tool or in a pre-clinical/clinical research setting.

More particularly the present invention relates to a modified Sendai virus, which can be used as a vaccine. In one embodiment of a method to create recombinant viruses, a plasmid can be used, which contains the entire Sendai virus genome, flanked by a T7 promoter and a hepatitis delta virus ribozyme sequence. See FIG. 8 for examples of four intergenic positions in which foreign genes can be placed prior to virus rescue (Brown et. al. J. Virology, 2007, 81: 12535).

Below are sequences of a RSV F gene, protein sequences for the different Sendai virus genes as presented in a modified Sendai virus construct (pSeVc), and a sequence for the pSeVc recombinant carrying the RSV F gene insert in the F-HN position in the Sendai virus genome (pSeVc-RSVF(F-HN)). Associated translations are also shown. All sequences are listed 5' to 3' (left to right). (Also see FIG. 7 for sequences).

```
RSV F gene sequence (insert from genomic construct)
                                                                                        (SEQ. ID NO.: 1)
atggagttgctaatcctcaaagcaaatgcaattaccacaatcctcactgcagtcacattttgttttgcttctggtcaaaacatcactgaagaat tttatcaatcaacatgcagtgcagttagcaaaggctatcttagtgctctgagaactggttggtataccagtgttataactatagaattaagtaa tatcaagaaaaataagtgtaatggaacagatgccaaggcaaaattgataaaacaagaattagataaatataaaaatgctgtaacagaattgcag ttgctcatgcaaagcacacaagcaacaaacaatcgagccagaagagaactaccaaggtttatgaattatacactcaacaatgccaaaaaaacca atgtaacattaagcaagaaaaggaaaagaagatttcttggtttttgttaggtgttggatctgcaatcgccagtggcgttgctgtatctaaggt cctgcacctagaaggggaagtgaacaagatcaaaagtgctactactatccacaaacaaggctgtagtcagcttatcaaatggagttagtgtctt aaccagcaaagtgttagacctcaaaaactatatagataaacaattgttacctattgtgaacaagcaaagctgcagcatatcaaatatagaaact gtgatagagttccaacaaaagaacaacagactactagagattaccagggaatttagtgttaatgcaggtgtaactacacctgtaagcacttaca tgttaactaatagtgaattattgtcattaatcaatgatatgcctataacaaatgatcagaaaaagttaatgtccaacaatgttcaaatagttag acagcaaagttactctatcatgtccataataaaagaggaagtcttagcatatgtagtacaattaccactatggtgttatggatacacctgtt ggaaactacacacatcccctctatgtacaaccaacacaaaagaagggtccaacatctgtttaacaagaactgacagaggatggtactgtgacaa tgcaggatcagtatctttcttcccacaagctgaaacatgtaaagttcaatcaaatcgagtattttgtgacacaatgaacagtttaacattacca agtgaagtaaatctctgcaatgttgacatattcaaccccaaatatgattgtaaaattatgacctcaaaaacagatgtaagcagctccgttatca catctctaggagccattgtgtcatgctatggcaaaactaaatgtacagcatccaataaaaatcgtggaatcataaagacattttctaacgggtg cgattatgtatcaaataaagggtggacactgtgtctgtaggtaacacattatattatgtaaataagcaagaaggtaaaagtctctatgtaaaa ggtgaaccaataataaatttctatgacccattagtattcccctctgatgaatttgatgcatcaatatctcaagtcaacgagaagattaaccaga gcctagcatttattcgtaaatccgatgaattattacataatgtaattgctggtaaatccaccacaaatATCATGATAACTACTATAATTatagt
```

-continued gattatagtaatattgttatcattaattgctgttggactgctcttatactgtaaggccagaagcacaccagtcacactaagcaaagatcaactg agtggtataaataatattgcatttagtaactaa RSV F Translation sequence (SEQ. ID NO.: 2)

MELLILKANAITTILTAVTFCFASGQNITEEFYQSTCSAVSKGYLSALRTGWYTSVITIELSNIKKNKCNGTDAKAKLIKQELDKYKNAVTELQ
LLMQSTQATNNRARRELPRFMNYTLNNAKKTNVTLSKKRKRRFLGFLLGVGSAIASGVAVSKVLHLEGEVNKIKSALLSTNKAVVSLSNGVSVL
TSKVLDLKNYIDKQLLPIVNKQSCSISNIETVIEFQQKNNRLLEITREFSVNAGVTTPVSTYMLTNSELLSLINDMPITNDQKKLMSNNVQIVR
QQSYSIMSIIKEEVLAYVVQLPLYGVMDTPCWKLHTSPLCTTNTKEGSNICLTRTDRGWYCDNAGSVSFFPQAETCKVQSNRVFCDTMNSLTLP
SEVNLCNVDIFNPKYDCKIMTSKTDVSSSVITSLGAIVSCYGKTKCTASNKNRGIIKTFSNGCDYVSNKGVDTVSVGNTLYYVNKQEGKSLYVK
GEPIINFYDPLVFPSDEFDASISQVNEKINQSLAFIRKSDELLHNVIAGKSTTNIMITTIIIVIIVILLSLIAVGLLLYCKARSTPVTLSKDQL
SGINNIAFSN.

NP protein sequence:

(SEQ. ID NO.: 5)

MAGLLSTFDTFSSRRSESINKSGGGAVIPGQRSTVSVFVLGPSVTDDADKLFIATTFLAHSLDTDKQHSQRGGFLVSLLAMAYSSPELYLTTNG
VNADVKYVIYNIEKDPKRTKTDGFIVKTRDMEYERTTEWLFGPMVNKSPLFQGQRDAADPDTLLQTYGYPACLGAIIVQVWIVLVKAITSSAGL
RKGFFNRLEAFRQDGTVKGALVFTGETVEGIGSVMRSQQSLVSLMVETLVTMNTARSDLTTLEKNIQIVGNYIRDAGLASFMNTIKYGVETKMA
ALTLSNLRPDINKIRSLIDTYLSKGPRAPFICILKDPVHGEFAPGNYPALWSYAMGVAVVQNKAMQQYVTGRTYLDMEMFLLGQAVAKDAESKI
SSALEDELGVTDTAKERLRHHLANLSGGDGAYHKPTGGGAIEVALDNADIDLETEAHADQDARGWGGESGERWARQVSGGHFVTLHGAERLEEE
TNDEDVSDIERRIAMRLAERRQEDSATHGDEGRNNGVDHDEDDDTAAVAGIGGI

P protein sequence:

(SEQ. ID NO.: 7)

MDQDAFILKEDSEVEREAPGGRESLSDVIGFLDAVLSSEPTDIGGDRSWLHNTINTPQGPGSAHRAKSEGEGEVSTPSTQDNRSGEESRVSGRT
SKPEAEAHAGNLDKQNIHRAFGGRTGTNSVSQDLGDGGDSGILENPPNERGYPRSGIEDENREMAAHPDKRGEDQAEGLPEEVRGGTSLPDEGE
GGASNNGRSMEPGSSHSARVTGVLVIPSPELEEAVLRRNKRRPTNSGSKPLTPATVPGTRSPPLNRYNSTGSPPGKPPSTQDEHINSGDTPAVR
VKDRKPPIGTRSVSDCPANGRPIHPGLETDSTKKGIGENTSSMKEMATLLTSLGVIQSAQEFESSRDASYVFARRALKSANYAEMTFNVCGLIL
SAEKSSARKVDENKQLLKQIQESVESFRDIYKRFSEYQKEQNSLLMSNLSTLHIITDRGGKTDNIDSLTRSPSVFAKSKENKTKATRFDPSMET
LEDMKYKPDLIREDEFRDEIRNPVYQERDTEPRASNASRLLPSKEKPTMHSLRLVIESSPLSRAEKAAYVKSLSKCKTDQEVKAVMELVEEDIE
SLTN

C protein sequence (SEQ. ID NO.: 9)

MPSFLKKILKLRGRRQEEESRSRMLSDSSMLSCRVNQLTSEGTEAGSTTPSTLPKDQALPIEPKVRAKEKSQHRRPKIIDQVRRVESLGEQASQ
RQKHMLETLINKIYTGPLGEELVQTLYLRIWAMEETPESLKILQMREDIRDQVLKMKTERWLRTLIRGEKTKLKDFQKRYEEVHPYLMKEKVEQ
VIMEEAWSLAAHIVQE

M protein sequence:

(SEQ. ID NO.: 11)

MADIYRFPKFSYEDNGTVEPLPLRTGPDKKAIPYIRIIKVGDPPKHGVRYLDLLLLGFFETPKQTTNLGSVSDLTEPTSYSICGSGSLPIGVAK
YYGTDQELLKACTDLRITVRRTVRAGEMIVYMVDSIGAPLLPWSGRLRQGMIFNANKVALAPQCLPVDKDIRFRWFVNGTSLGAITIAKIPKTL
ADLALPNSISVNLLVTLKTGISTEQKGVLPVLDDQGEKKLNFMVHLGLIRRKVGKIYSVEYCKSKIERMRLIFSLGLIGGISFHVQVTGTLSKT
FMSQLAWKRAVCFPLMDVNPHMNLVIWAASVEITGVDAVFQPAIPRDFRYYPNVVAKNIGRIRKL

F protein sequence (SEQ. ID NO.: 13)

MTAYIQRSQCISISLLVVLTTLVSCQIPRDRLSNIGVIVDEGKSLKIAGSHESRYIVLSLVPGVDLENGCGTAQVIQYKSLLNRLLIPLRDALD
LQEALITVTNDTTQNAGVPQSRFFGAVIGTIALGVATSAQITAGIALAEAREAKRDIALIKESMTKTHKSIELLQNAVGEQILALKTLQDFVND
EIKPAISELGCETAALRLGIKLTQHYSGLLTAFGSNFGTIGEKSLTLQALSSLYSANITEIMTTIRTGQSNIYDVIYTEQIKGTVIDVDLERYM
VTLSVKIPILSEVPGVLIHKASSISYNIDGEEWYVTVPSHILSRASFLGGADITDCVESRLTYICPRDPAQLIPDSQQKCILGDTTRCPVTKVV
DSLIPKFAFVNGGVVANCIASTCTCGTGRRPISQDRSKGVVFLTHDNCGLIGVNGVELYANRRGHDATWGVQNLTVGPAIAIRPVDISLNLADA
TNFLQDSKAELEKARKILSEVGRWYNSRETVITIIWMVVILVVIIVIVLYRLRRSMLMGNPDDRIPRDTYTLEPKIRHMYTNGGFDAMAEKR

HN protein sequence (SEQ. ID NO.: 15)
MDGQEGKRDSYWSTSPSGSTTKLASGWERSSKVDTWLLILSFTQWALSIATVIICIIISARQGYSMKEYSMTVEALNMSSREVKESLTSLIRQE VIARAVNIQSSVQTGIPVLLNKNSRDVIQMIDKSCSRQELTQLCESTIAVHHAEGIAPLEPHSFWRCPVGEPYLSSDPKISLLPGPSLLSGSTT ISGCVRLPSLSIGEAIYAYSSNLITQGCADIGKSYQVLQLGYISLNSDMFPDLNPVVSHTYDINDNRKSCSVVATGTRGYQLCSMPTVDERTDY SSDGIEDLVLDVLDLKGSTKSHRYRNSEVDLDHPFSALYPSVGNGIATEGSLIFLGYGGLTTPLQGDTKCRTQGCQQVSQDTCNEALKITWLGG KQVVSVIIQVNDYLSERPKIRVTTIPITQNYLGAEGRLLKLGDRVYIYTRSSGWHSQLQIGVLDVSHPLTINWTPHEALSRPGNEECNWYNTCP KECISGVYTDAYPLSPDAANVATVTLYANTSRVNPTIMYSNTTNIINMLRIKDVQLEAAYTTTSCITHFGKGYCFHIIEINQKSLNTLQPMLFK

TSIPKLCKAES

L protein sequence (SEQ. ID NO.: 17)
MDGQESSQNPSDILYPECHLNSPIVRGKIAQLHVLLDVNQPYRLKDDSIINITKHKIRNGGLSPRQIKIRSLGKALQRTIKDLDRYTFEPYPTY SQELLRLDIPEICDKIRSVFAVSDRLTRELSSGFQDLWLNIFKQLGNIEGREGYDPLQDIGTIPEITDKYSRNRWYRPFLTWFSIKYDMRWMQK TRPGGPLDTSNSHNLLECKSYTLVTYGDLVMILNKLTLTGYILTPELVLMYCDVVEGRWNMSAAGHLDKKSIGITSKGEELWELVDSLFSSLGE EIYNVIALLEPLSLALIQLNDPVIPLRGAFMRHVLTELQTVLTSRDVYTDAEADTIVESLLAIFHGTSIDEKAEIFSFFRTFGHPSLEAVTAAD KVRAHMYAQKAIKLKTLYECHAVFCTIIINGYRERHGGQWPPCDFPDHVCLELRNAQGSNTAISYECAVDNYTSFIGFKFRKFIEPQLDEDLTI YMKDKALSPRKEAWDSVYPDSNLYYKAPESEETRRLIEVFINDENFNPEEIINYVESGDWLKDEEFNISYSLKEKEIKQEGRLFAKMTYKMRAV QVLAETLLAKGIGELFRENGMVKGEIDLLKRLTTLSVSGVPRTDSVYNNSKSSEKRNEGMENKNSGGYWDEKKRSRHEFKATDSSTDGYETLSC FLTTDLKKYCLNWRFESTALFGQRCNEIFGFKTFFNWMHPVLERCTIYVGDPYCPVADRMHRQLQDHADSGIFIHNPRGGIEGYCQKLWTLISI SAIHLAAVRVGVRVSAMVQGDNQAIAVTSRVPVAQTYKQKKNHVYEEITKYFGALRHVMFDVGHELKLNETIISSKMFVYSKRIYYDGKILPQC LKALTKCVFWSETLVDENRSACSNISTSIAKAIENGYSPILGYCIALYKTCQQVCISLGMTINPTISPTVRDQYFKGKNWLRCAVLIPANVGGF NYMSTSRCFVRNIGDPAVAALADLKRFIRADLLDKQVLYRVMNQEPGDSSFLDWASDPYSCNLPHSQSITTIIKNITARSVLQESPNPLLSGLF TETSGEEDLNLASFLMDRKVILPRVAHEILGNSLTGVREAIAGMLDTTKSLVRASVRKGGLSYGILRRLVNYDLLQYETLTRTLRKPVKDNIEY EYMCSVELAVGLRQKMWIHLTYGRPIHGLETPDPLELLRGIFIEGSEVCKLCRSEGADPIYTWFYLPDNIDLDTLTNGCPAIRIPYFGSATDER SEAQLGYVRNLSKPAKAAIRIAMVYTWAYGTDEISWMEAALIAQTRANLSLENLKLLTPVSTSTNLSHRLKDTATQMKFSSATLVRASRFITIS NDNMALKEAGESKDTNLVYQQIMLTGLSLFEFNMRYKKGSLGKPLILHLHLNNGCCIMESPQEANIPPRSTLDLEITQENNKLIYDPDPLKDVD LELFSKVRDVVHTVDMTYWSDDEVIRATSICTAMTIADTMSQLDRDNLKEMIALVNDDDVNSLITEFMVIDVPLFCSTFGGILVNQFAYSLYGL NIRGREEIWGHVVRILKDTSHAVLKVLSNALSHPKIFKRFWNAGVVEPVYGPNLSNQDKILLALSVCEYSVDLFMHDWQGGVPLEIFICDNDPD VADMRRSSFLARHLAYLCSLAEISRDGPRLESMNSLERLESLKSYLELTFLDDPVLRYSQLTGLVIKVFPSTLTYIRKSSIKVLRTRGIGVPEV LEDWDPEADNALLDGIAAEIQQNIPLGHQTRAPFWGLRVSKSQVLRLRGYKEITRGEIGRSGVGLTLPFDGRYLSHQLRLFGINSTSCLKALEL TYLLSPLVDKDKDRLYLGEGAGAMLSCYDATLGPCINYYNSGVYSCDVNGQRELNTYPAEVALVGKKLNNVTSLGQRVKVLFNGNPGSTWIGND ECEALIWNELQNSSIGLVHCDMEGGDHKDDQVVLHEHYSVIRIAYLVGDRDVVLISKIAPRLGTDWTRQLSLYLRYWDEVNLIVLKTSNPASTE MYLLSRHPKSDIIEDSKTVLASLLPLSKEDSIKIEKWILIEKAKAHEWVTRELREGSSSSGMLRPYHQALQTFGFEPNLYKLSRDFLSTMNIAD THNCMIAFNRVLKDTIFEWARITESDKRLKLTGKYDLYPVRDSGKLKTISRRLVLSWISLSMSTRLVTGSFPDQKFEARLQLGIVSLSSREIRN

LRVITKTLLYRFEDIIHSITYRFLTKEIKILMKILGAVKMFGARQNEYTTVIDDGSLGDIEPYDSS pSeVc-RSVF(F-HN)

(SEQ. ID NO.: 18)
ACCAAACAAGAGAAAAAACATGTATGGGATATATAATGAAGTTAGACAGGATTTTAGGGTCAAAGTATCCACCCTGAGGAGCAGGTTCCAGACC

CTTTGCTTTGCTGCCAAAGTTCACGATGGCCGGGTTGTTGAGCACCTTCGATACATTTAGCTCTAGGAGGAGCGAAAGTATTAATAAGTCGGGA

GGAGGTGCTGTTATCCCCGGCCAGAGGAGCACAGTCTCAGTGTTCGTACTAGGCCCAAGTGTGACTGATGATGCAGACAAGTTATTCATTGCAA

CTACCTTCCTAGCTCACTCATTGGACACAGATAAGCAGCACTCTCAGAGAGGAGGGTTCCTCGTCTCTCTGCTTGCCATGGCTTACAGTAGTCC

AGAATTGTACTTGACAACAAACGGAGTAAACGCCGATGTCAAATATGTGATCTACAACATAGAGAAAGACCCTAAGAGGACGAAGACAGACGGA

TTCATTGTGAAGACGAGAGATATGGAATATGAGAGGACCACAGAATGGCTGTTTGGACCTATGGTCAACAAGAGCCCACTCTTCCAGGGTCAAC

GGGATGCTGCAGACCCTGACACACTCCTTCAAACCTATGGGTATCCTGCATGCCTAGGAGCAATAATTGTCCAAGTCTGGATTGTGCTGGTGAA

-continued

```
GGCCATCACAAGCAGCGCCGGCTTAAGGAAAGGGTTCTTCAACAGGTTAGAGGCGTTCAGACAAGACGGCACCGTGAAAGGTGCCTTAGTTTTC
ACTGGGGAGACAGTTGAGGGGATAGGCTCGGTTATGAGATCTCAGCAAAGCCTTGTATCTCTCATGGTTGAGACCCTTGTGACTATGAATACTG
CAAGATCTGATCTCACCACATTAGAGAAGAACATCCAGATCGTTGGGAACTACATCCGAGATGCAGGGCTGGCTTCCTTCATGAACACTATTAA
ATATGGGGTGGAGACAAAGATGGCAGCTCTAACGTTGTCAAACCTGAGGCCCGATATTAATAAGATTAGAAGCCTCATAGACACCTACCTGTCA
AAAGGCCCCAGAGCTCCCTTTATCTGTATCCTCAAGGACCCTGTTCATGGTGAATTTGCTCCAGGCAATTATCCTGCACTATGGAGTTACGCCA
TGGGAGTCGCCGTCGTACAGAACAAGGCAATGCAGCAGTACGTCACAGGGAGGACATACCTTGATATGGAAATGTTCTTACTAGGACAAGCCGT
GGCAAAGGATGCTGAATCGAAGATCAGCAGTGCCCTGGAAGATGAGTTAGGAGTGACGGATACAGCCAAGGAGAGGCTCAGACATCATCTGGCA
AACTTGTCCGGTGGGGATGGTGCTTACCACAAACCAACAGGCGGTGGTGCAATTGAGGTAGCTCTAGACAATGCCGATATCGACCTAGAAACAG
AAGCTCATGCGGACCAGGACGCTAGGGGTTGGGGTGGAGAAAGTGGTGAAAGATGGGCACGTCAGGTGAGTGGTGGCCACTTTGTCACACTACA
TGGGGCTGAACGGTTAGAGGAGGAAACCAATGATGAGGATGTATCAGACATAGAGAGAAGAATAGCCATGAGACTCGCAGAGAGACGGCAAGAG
GATTCTGCAACCCATGGAGATGAAGGCCGCAATAACGGTGTCGATCACGACGAAGATGACGATACCGCAGCAGTAGCTGGGATAGGAGGAATCT
AGGATCATACGAGGCTTCAAGGTACTTGATCCGTAGTAAGAAAAACTTAGGGTGAAAGTTCATCCACTGATCGGCTCAGGCAAGGCCACACCCA
ACCCCACCGACCACACCCAGCAGTCGAGACAGCCACGGCTTCGGCTACACTTACCGCATGGATCAAGATGCCTTCATTCTTAAAGAAGATTCTG
AAGTTGAGAGGGAGGCGCCAGGAGGAAGAGAGTCGCTCTCGGATGTTATCGGATTCCTCGATGCTGTCCTGTCGAGTGAACCAACTGACATCGG
AGGGGACAGAAGCTGGCTCCACAACACCATCAACACTCCCCAAGGACCAGGCTCTGCCCATAGAGCCAAAAGTGAGGGCGAAGGAGAAGTCTCA
ACACCGTCGACCCAAGATAATCGATCAGGTGAGGAGAGTAGAGTCTCTGGGAGAACAAGCAAGCCAGAGGCAGAAGCACATGCTGGAAACCTTG
ATAAACAAAATATACACCGGGCCTTTGGGGGAAGAACTGGTACAAACTCTGTATCTCAGGATCTGGGCGATGGAGGAGACTCCGGAATCCTTGA
AAATCCTCCAAATGAGAGAGGATATCCGAGATCAGGTATTGAAGATGAAAACAGAGAGATGGCTGCGCACCCTGATAAGAGGGGAGAAGACCAA
GCTGAAGGACTTCCAGAAGAGGTACGAGGAGGTACATCCCTACCTGATGAAGGAGAAGGTGGAGCAAGTAATAATGGAAGAAGCATGGAGCCTG
GCAGCTCACATAGTGCAAGAGTAACTGGGGTCCTGGTGATTCCTAGCCCCGAACTCGAAGAGGCTGTGCTACGGAGGAACAAAAGAAGACCTAC
CAACAGTGGGTCCAAACCTCTTACTCCAGCAACCGTGCCTGGCACCCGGTCCCCACCGCTGAATCGTTACAACAGCACAGGGTCACCACCAGGA
AAACCCCCATCTACACAGGATGAGCACATCAACTCTGGGGACACCCCCGCCGTCAGGGTCAAAGACCGGAAACCACCAATAGGGACCCGCTCTG
TCTCAGATTGTCCAGCCAACGGCCGCCCAATCCACCCGGGTCTAGAGACCGACTCAACAAAAAAGGGCATAGGAGAGAACACATCATCTATGAA
AGAGATGGCTACATTGTTGACGAGTCTTGGTGTAATCCAGTCTGCTCAAGAATTCGAGTCATCCCGAGACGCGAGTTATGTGTTTGCAAGACGT
GCCCTAAAGTCTGCAAACTATGCAGAGATGACATTCAATGTATGCGGCCTGATCCTTTCTGCCGAGAAATCTTCCGCTCGTAAGGTAGATGAGA
ACAAACAACTGCTCAAACAGATCCAAGAGAGCGTGGAATCATTCCGGGATATTTACAAGAGATTCTCTGAGTATCAGAAAGAACAGAACTCATT
GCTGATGTCCAACCTATCTACACTTCATATCATCACAGATAGAGGTGGCAAGACTGACAACACAGACTCCCTTACAAGGTCCCCCTCCGTTTTT
GCAAAATCAAAAGAGAACAAGACTAAGGCTACCAGGTTTGACCCATCTATGGAGACCCTAGAAGATATGAAGTACAAACCGGACCTAATCCGAG
AGGATGAATTTAGAGATGAGATCCGCAACCCGGTGTACCAAGAGAGGGACACAGAACCCAGGGCCTCAAACGCATCACGCCTCCTCCCCTCCAA
AGAGAAGCCCACAATGCACTCTCTCAGGCTCGTCATAGAGAGCAGTCCCCTAAGCAGAGCTGAGAAAGCAGCATATGTGAAATCATTATCCAAG
TGCAAGACAGACCAAGAGGTTAAGGCAGTCATGGAACTCGTAGAAGAGGACATAGAGTCACTGACCAACTAGATCCCGGGTGAGGCATCCTACC
ATCCTCAGTCATAGAGAGATCCAATTAATTAACAGCATCAGCCAGTAAAGATTAAGAAAAACTTAGGGTGAAAGAAATTTCACCTAACACGGCG
CAATGGCAGATATCTATAGATTCCCTAAGTTCTCATATGAGGATAACGGTACTGTGGAGCCCCTGCCTCTGAGAACTGGTCCAGATAAGAAAGC
CATCCCCTACATCAGGATTATCAAGGTAGGAGACCCTCCTAAACATGGAGTGAGATACCTAGATTTATTGCTCTTGGGTTTCTTTGAGACACCG
AAACAAACAACCAATCTAGGGAGCGTATCTGACTTGACAGAGCCGACCAGCTACTCAATATGCGGCTCCGGGTCGTTACCCATAGGTGTGGCCA
AATACTACGGGACTGATCAGGAACTCTTAAAGGCCTGCACCGATCTCAGAATTACGGTGAGGAGGACTGTTCGAGCAGGAGAGATGATCGTATA
CATGGTGGATTCGATTGGTGCTCCACTCCTACCATGGTCAGGCAGGCTGAGACAGGGAATGATATTTAATGCAAACAAGGTCGCACTAGCTCCC
CAATGCCTCCCTGTGGACAAGGACATAAGATTCAGAGTGGTGTTTGTCAATGGGACATCTCTAGGGGCAATCACCATAGCCAAGATCCCAAAGA
CCCTTGCAGACCTTGCATTGCCCAACTCTATATCCGTTAACCTACTGGTGACACTCAAGACCGGGATCTCCACAGAACAAAAGGGGGTACTCCC
AGTACTTGATGATCAAGGGGAGAAAAAGCTCAATTTTATGGTGCACCTCGGGTTGATCAGGAGAAAGGTCGGGAAGATATACTCTGTTGAGTAC
TGCAAGAGCAAGATTGAGAGAATGCGGCTGATTTTCTCACTTGGGTTAATCGGCGGTATAAGCTTCCATGTTCAGGTTACTGGGACACTATCTA
```

-continued

```
AGACATTCATGAGTCAGCTCGCATGGAAGAGGGCAGTCTGCTTCCCATTAATGGATGTGAATCCCCATATGAACCTGGTGATTTGGGCGGCATC
TGTAGAAATCACAGGCGTCGATGCGGTGTTCCAACCGGCCATCCCTCGTGATTTCCGCTACTACCCTAATGTTGTGGCTAAGAACATCGGAAGG
ATCAGAAAGCTGTAAATGTGCACCCATCAGAGACCTGCGACAATGCCCCAAGCAGACACCACCTGGCAGTCGGAGCCACCGGGTCACTCCTTGT
CTTAAATAAGAAAAACTTAGGGATAAAGTCCCTTGTGAGTGCTTGGTTGCAAAACTCTCCGTACGGGAAACATGACAGCATATATCCAGAGGTC
ACAGTGCATCTCAACATCACTACTGGTTGTTCTCACCACATTGGTCTCGTGTCAGATTCCCAGGGATAGGCTCTCTAACATAGGGGTCATAGTC
GATGAAGGGAAATCACTGAAGATAGCTGGATCCCACGAATCGAGGTACATAGTACTGAGTCTAGTTCCGGGGGTAGACCTTGAGAATGGAGAGC
GTGCGGAACAGCCCAGGTTATCCAGTACACTACTGAACAGGCTGTTAATCCCATTGAGGGATGCCTTAGATCTTCAGGAGGCTCTGATAACTGT
CACCAATGATACGACACAAAATGCCGGTGTTCCACAGTCGAGATTCTTCGGTGCTGTGATTGGTACTATCGCACTTGGAGTGGCGACATCAGCA
CAGATCACCGCAGGGATTGCACTAGCCGAAGCGAGGGAGGCCAAAAGAGACATAGCGCTCATCAAAGAATCGATGACAAAAACACACAAGTCTA
TAGAACTGCTGCAAAACGCTGTGGGGGAACAAATTCTTGCTCTAAAGACACTCCAGGATTTCGTGAATGATGAGATCAAACCCGCAATAAGCGA
ATTAGGCTGTGAGACTGCTGCCTTAAGACTGGGTATAAAATTGACACAGCATTACTCCGGGCTGTTAACTGCGTTCGGCTCGAATTTCGGAACC
ATCGGAGAGAAGAGCCTCACGCTGCAGGCGCTGTCTTCACTTTACTCTGCTAACATTACTGAGATTATGACCACAATCAGGACAGGGCAGTCTA
ACATCTATGATGTCATTTATACAGAACAGATCAAAGGAACGGTGATAGATGTGGATCTAGAGAGATACATGGTTACCCTGTCTGTGAAGATCCC
TATTCTTTCTGAAGTCCCAGGTGTGCTCATACACAAGGCATCGTCTATTTCTTACAACATAGACGGGGAGGAATGGTATGTGACTGTCCCCAGC
CATATACTCAGTCGTGCTTCTTTCTTAGGGGGTGCAGACATAACCGATTGTGTTGAGTCCAGGTTGACCTATATATGCCCCAGGGATCCCGCAC
AACTGATACCTGACAGCCAGCAAAAGTGTATCCTGGGGGACACAACAAGGTGTCCTGTCACAAAAGTTGTGGACAGCCTTATCCCCAAGTTTGC
TTTTGTGAATGGGGGCGTTGTTGCTAACTGCATAGCATCCACATGTACCTGCGGGACAGGCCGAAGACCAATCAGTCAGGATCGCTCTAAAGGT
GTAGTATTCCTAACCCATGACAACTGTGGTCTTATAGGTGTCAATGGGGTAGAATTGTATGCTAACCGGAGAGGGCACGATGCCACTTGGGGGG
TCCAGAACTTGACAGTCGGTCCTGCAATTGCTATCAGACCCGTTGATATTTCTCTCAACCTTGCTGATGCTACGAATTTCTTGCAAGACTCTAA
GGCTGAGCTTGAGAAAGCACGGAAAATCCTCTCTGAGGTAGGTAGATGGTACAACTCAAGAGAGACTGTGATTACGATCATAGTAGTTATGGTC
GTAATATTGGTGGTCATTATAGTGATCGTCATCGTGCTTTATAGACTCAGAAGGTCAATGCTAATGGGTAATCCAGATGACCGTATACCGAGGG
ACACATATACATTAGAGCCGAAGATCAGACATATGTACACAAACGGTGGGTTTGATGCGATGGCTGAGAAAAGATGATCACGAGTTTAAACAGA
TGTCTTGTAAAGCAGGCATGGTATCCGTTGAGATCTGTATATAATAAGAAAAACTTAGGGTGAAAGTGAGGTCGCGCGGTACTTTAGCTGCGGC
CGCACAATGGAGTTGCTAATCCTCAAAGCAAATGCAATTACCACAATCCTCACTGCAGTCACATTTTGTTTTGCTTCTGGTCAAAACATCACTG
AAGAATTTTATCAATCAACATGCAGTGCAGTTAGCAAAGGCTATCTTAGTGCTCTGAGAACTGGTTGGTATACCAGTGTTATAACTATAGAATT
AAGTAATATCAAGAAAAATAAGTGTAATGGAACAGATGCCAAGGCAAAATTGATAAAACAAGAATTAGATAAATATAAAAATGCTGTAACAGAA
TTGCAGTTGCTCATGCAAAGCACACAAGCAACAAACAATCGAGCCAGAAGAGAACTACCAAGGTTTATGAATTATACACTCAACAATGCCAAAA
AAACCAATGTAACATTAAGCAAGAAAAGGAAAAGAAGATTTCTTGGTTTTTGTTAGGTGTTGGATCTGCAATCGCCAGTGGCGTTGCTGTATC
TAAGGTCCTGCACCTAGAAGGGGAAGTGAACAAGATCAAAAGTGCTCTACTATCCACAAACAAGGCTGTAGTCAGCTTATCAAATGGAGTTAGT
GTCTTAACCAGCAAAGTGTTAGACCTCAAAAACTATATAGATAAACAATTGTTACCTATTGTGAACAAGCAAAGCTGCAGCATATCAAATATAG
AAACTGTGATAGAGTTCCAACAAAAGAACAACAGACTACTAGAGATTACCAGGGAATTTAGTGTTAATGCAGGTGTAACTACACCTGTAAGCAC
TTACATGTTAACTAATAGTGAATTATTGTCATTAATCAATGATATGCCTATAACAAATGATCAGAAAAAGTTAATGTCCAACAATGTTCAAATA
GTTAGACAGCAAAGTTACTCTATCATGTCCATAATAAAAGAGGAAGTCTTAGCATATGTAGTACAATTACCACTATATGGTGTTATGGATACAC
CCTGTTGGAAACTACACACATCCCCTCTATGTACAACCAACACAAAAGAAGGGTCCAACATCTGTTTAACAAGAACTGACAGAGGATGGTACTG
TGACAATGCAGGATCAGTATCTTTCTTCCCACAAGCTGAAACATGTAAAGTTCAATCAAATCGAGTATTTTGTGACACAATGAACAGTTTAACA
TTACCAAGTGAAGTAAATCTCTGCAATGTTGACATATTCAACCCCAAATATGATTGTAAAATTATGACCTCAAAAACAGATGTAAGCAGCTCCG
TTATCACATCTCTAGGAGCCATTGTGTCATGCTATGGCAAAACTAAATGTACAGCATCCAATAAAAATCGTGGAATCATAAAGACATTTTCTAA
CGGGTGCGATTATGTATCAAATAAAGGGGTGGACACTGTGTCTGTAGGTAACACATTATATTATGTAAATAAGCAAGAAGGTAAAAGTCTCTAT
GTAAAAGGTGAACCAATAATAAATTTCTATGACCCATTAGTATTCCCCTCTGATGAATTTGATGCATCAATATCTCAAGTCAACGAGAAGATTA
ACCAGAGCCTAGCATTTATTCGTAAATCCGATGAATTATTACATAATGTAATTGCTGGTAAATCCACCACAAATATCATGATAACTACTATAAT
TATAGTGATTATAGTAATATTGTTATCATTAATTGCTGTTGGACTGCTCTTATACTGTAAGGCCAGAAGCACACCAGTCACACTAAGCAAAGAT
```

-continued

```
CAACTGAGTGGTATAAATAATATTGCATTTAGTAACTAATTATAAGAAAAACTTAGGGTGAAAGTGAGCGGCCGCAAACAAGCACAGATCATGG

ATGGTGATAGGGGCAAACGTGACTCGTACTGGTCTACCTCTCCTAGTGGTAGCACTACAAAATTAGCATCAGGTTGGGAGAGGTCAAGTAAAGT

TGACACATGGTTGCTGATTCTCTCATTCACCCAGTGGGCTTTGTCAATTGCCACAGTGATCATCTGTATCATAATTTCTGCTAGACAAGGGTAT

AGTATGAAAGAGTACTCAATGACTGTAGAGGCATTGAACATGAGCAGCAGGGAGGTGAAAGAGTCACTTACCAGTCTAATAAGGCAAGAGGTTA

TCGCAAGGGCTGTCAACATTCAGAGCTCTGTGCAAACCGGAATCCCAGTCTTGTTGAACAAAAACAGCAGGGATGTCATCCAGATGATTGATAA

GTCGTGCAGCAGACAAGAGCTCACTCAGCTCTGTGAGAGTACGATCGCAGTCCACCATGCCGAGGGAATTGCCCCTCTTGAGCCACATAGTTTC

TGGAGATGCCCTGTCGGAGAACCGTATCTTAGCTCAGATCCTAAAATCTCATTGCTGCCTGGTCCGAGCTTGTTATCTGGTTCTACAACGATCT

CTGGATGTGTTAGGCTCCCTTCACTCTCAATTGGCGAGGCAATCTATGCCTATTCATCAAATCTCATTACACAACATATCAGGTCCTGCAGCTA

GGGTACATATCACTCAATTCAGATATGTTCCCTGATCTTAACCCCGTAGTGTCCCACACTTATGACATCAACGACAATCGGAAATCATGCTCTG

TGGTGGCAACCGGGACTAGGGGTTATCAGCTTTGCTCCATGCCGACTGTAGACGAAAGAACCGACTACTCTAGTGATGGTATCGAGGATCTGGT

CCTTGATGTCCTGGATCTCAAAGGGAGCACTAAGTCTCACCGGTATCGCAACAGCGAGGTAGATCCAGTGTACTTGATCACCCGTTCTCTGCAC

TATACCGGCAACGGCATTGCAACAGAAGGCTCATTGATATTTCTTGGGTATGGTGGGCTAACCACCCCTCTACAGGGTGATACAAAATGTAGGA

CCCAAGGATGCCAACAGGTGTCGCAAGACACATGCAATGAGGCTCTGAAAATTACATGGCTAGGAGGGAAACAGGTGGTCAGCGTGATCATCCA

GGTCAATGACTATCTCTCAGAGAGGCCAAAGATAAGAGTCACAACCATTCCAATCACTCAAAACTATCTCGGGGCGGAAGGTAGATTATTAAAA

TTGGGTGATCGGGTGTACATCTATACAAGATCATCAGGCTGGCACTCTCAACTGCAGATAGGAGTACTTGATGTCAGCCACCCTTTGACTATCA

ACTGGACACCTCATGAAGCCTTGTCTAGACCAGGAAATGAAGAGTGCAATTGGTACAATACGTGTCCGAAGGAATGCATATCAGGCGTATACAC

TGATGCTTATCCATTGTCCCCTGATGCAGCTAACGTCGCTACCGTCACGCTATATGCCAATACATCGCGTGTCAACCCAACAATCATGTATTCT

AACACTACTAACATTATAAATATGTTAAGGATAAAGGATGTTCAATTAGAGGCTGCATATACCACGACATCGTGTATCACGCATTTTGGTAAAG

GCTACTGCTTTCACATCATCGAGATCAATCAGAAGAGCCTGAATACCTTACAGCCGATGCTCTTTAAGACTAGCATCCCTAAATTATGCAAGGC

CGAGTCTTAAATTTAACTGACTAGCAGGCTGGCGCGCCTTGCTGACACTAGAGTCATCTCCGAACATCCACAATATCTCTCAGTCTCTTACGTC

TCTCACAGTATTAAGAAAAACCCAGGGTGAATGGGAAGCTTGCCATAGGTCATGGATGGGCAGGAGTCCTCCCAAAACCCTTCTGACATACTCT

ATCCAGAATGCCACCTGAACTCTCCCATAGTCAGGGGGAAGATAGCACAGTTGCACGTCTTGTTAGATGTGAACCAGCCCTACAGACTGAAGGA

CGACAGCATAATAAATATTACAAAGCACAAATTAGGAACGGAGGATTGTCCCCCCGTCAAATTAAGATCAGGTCTCTGGGTAAGGCTCTTCAA

CGCACAATAAAGGATTTAGACCGATACACGTTTGAACCGTACCCAACCTACTCTCAGGAATTACTTAGGCTTGATATACCAGAGATATGTGACA

AAATCCGATCCGTCTTCGCGGTCTCGGATCGGCTGACCAGGGAGTTATCTAGTGGGTTCCAGGATCTTTGGTTGAATATCTTCAAGCAACTAGG

CAATATAGAAGGAAGAGAGGGGTACGATCCGTTGCAGGATATCGGCACCATCCCGGAGATAACTGATAAGTACAGCAGGAATAGATGGTATAGG

CCATTCCTAACTTGGTTCAGCATCAAATATGACATGCGGTGGATGCAGAAGACCAGACCGGGGGGACCCCTTGATACCTCTAATTCACATAACC

TCCTAGAATGCAAATCATACACTCTAGTAACATACGGAGATCTTGTCATGATACTGAACAAGTTGACATTGACAGGGTATATCCTAACCCCTGA

GCTGGTCTTGATGTATTGTGATGTTGTAGAAGGAAGGTGGAATATGTCTGCTGCAGGGCATCTAGATAAGAAGTCCATTGGGATAACAAGCAAA

GGTGAGGAATTATGGGAACTAGTGGATTCCCTCTTCTCAAGTCTTGGAGAGGAAATATACAATGTCATCGCACTATTGGAGCCCCTATCACTTG

CTCTCATACAACTAAATGATCCTGTTATACCTCTACGTGGGGCATTTATGAGGCATGTGTTGACAGAGCTACAGACTGTTTTAACAAGTAGAGA

CGTGTACACAGATGCTGAAGCAGACACTATTGTGGAGTCGTTACTCGCCATTTTCCATGGAACCTCTATTGATGAGAAAGCAGAGATCTTTTCC

TTCTTTAGGACATTTGGCCACCCCAGCTTAGAGGCTGTCACTGCCGCCGACAAGGTAAGGGCCCATATGTATGCACAAAAGGCAATAAAGCTTA

AGACCCTATACGAGTGTCATGCAGTTTTTTGCACTATCATCATAAATGGGTATAGAGAGAGGCATGGCGGACAGTGGCCCCCCTGTGACTTCCC

TGATCACGTGTGTCTAGAACTAAGGAACGCTCAAGGGTCCAATACGGCAATCTCTTATGAATGTGCTGTAGACAACTATACAAGTTTCATAGGC

TTCAAGTTTCGGAAGTTTATAGAACCACAACTAGATGAAGATCTCACAATATATATGAAAGACAAAGCACTATCCCCCAGGAAGGAGGCATGGG

ACTCTGTATACCCGGATAGTAATCTGTACTATAAAGCCCCAGAGTCTGAAGAGACCCGGCGGCTTATTGAAGTGTTCATAAATGATGAGAATTT

CAACCCAGAAGAAATTATCAATTATGTGGAGTCAGGAGATTGGTTGAAAGACGAGGAGTTCAACATCTCGTACAGTCTCAAAGAGAAAGAGATC

AAGCAAGAGGGTCGTCTATTCGCAAAAATGACTTATAAGATGCGAGCCGTACAGGTGCTGGCAGAGACACTACTGGCTAAAGGAATAGGAGAGC

TATTCAGGGAAATGGGATGGTTAAGGGAGAGATAGACCTACTTAAAAGATTGACTACTCTTTCTGTCTCAGGCGTCCCCAGGACTGATTCAGT

GTACAATAACTCTAAATCATCAGAGAAGAGAAACGAAGGCATGGAAAATAAGAACTCTGGGGGGTACTGGGACGAAAAGAAGAGGTCCAGACAT
```

```
GAATTCAAGGCAACAGATTCATCAACAGACGGCTATGAAACGTTAAGTTGCTTCCTCACAACAGACCTCAAGAAATACTGCTTAAACTGGAGAT
TTGAGAGTACTGCATTGTTTGGTCAGAGATGCAACGAGATATTTGGCTTCAAGACCTTCTTTAACTGGATGCATCCAGTCCTTGAAAGGTGTAC
AATATATGTTGGAGATCCTTACTGTCCAGTCGCCGACCGGATGCATCGACAACTCCAGGATCATGCAGACTCTGGCATTTTCATACATAATCCT
AGGGGGGGCATAGAAGGTTACTGCCAGAAGCTGTGGACCTTAATCTCAATCAGTGCAATCCACCTAGCAGCTGTGAGAGTGGGTGTCAGGGTCT
CTGCAATGGTTCAGGGTGACAATCAAGCTATAGCCGTGACATCAAGAGTACCTGTAGCTCAGACTTACAAGCAGAAGAAAATCATGTCTATGA
GGAGATCACCAAATATTTCGGTGCTCTAAGACACGTCATGTTTGATGTAGGGCACGAGCTAAAATTGAACGAGACCATCATTAGTAGCAAGATG
TTTGTCTATAGTAAAAGGATATACTATGATGGGAAGATTTTACCACAGTGCCTGAAAGCCTTGACCAAGTGTGTATTCTGGTCCGAGACACTGG
TAGATGAAAACAGATCTGCTTGTTCGAACATCTCAACATCCATAGCAAAAGCTATCGAAAATGGGTATTCTCCTATACTAGGCTACTGCATTGC
GTTGTATAAGACCTGTCAGCAGGTGTGCATATCACTAGGGATGACTATAAATCCAACTATCAGCCCGACCGTAAGAGATCAATACTTTAAGGGT
AAGAATTGGCTGAGATGTGCAGTGTTGATTCCAGCAAATGTTGGAGGATTCAACTACATGTCTACATCTAGATGCTTTGTTAGAAATATTGGAG
ACCCCGCAGTAGCAGCCCTAGCTGATCTCAAAAGATTCATCAGAGCGGATCTGTTAGACAAGCAGGTATTATACAGGGTCATGAATCAAGAACC
CGGTGACTCTAGTTTTCTAGATTGGGCTTCAGACCCTTATTCGTGTAACCTCCCGCATTCTCAGAGTATAACTACGATTATAAAGAATATCACT
GCTAGATCTGTGCTGCAGGAATCCCCGAATCCTCTACTGTCTGGTCTCTTCACCGAGACTAGTGGAGAAGAGGATCTCAACCTGGCCTCGTTCC
TTATGGACCGGAAAGTCATCCTGCCGAGAGTGGCTCATGAGATCCTGGGTAATTCCTTAACTGGAGTTAGGGAGGCGATTGCAGGGATGCTTGA
TACGACCAAGTCTCTAGTGAGAGCCAGCGTTAGGAAAGGAGGATTATCATATGGGATATTGAGGAGGCTTGTCAATTATGATCTATTGCAGTAC
GAGACACTGACTAGAACTCTCAGGAAACCGGTGAAAGACAACATCGAATATGAGTATATGTGTTCAGTTGAGCTAGCTGTCGGTCTAAGGCAGA
AAATGTGGATCCACCTGACTTACGGGAGACCCATACATGGGTTAGAAACACCAGACCCTTTAGAGCTCTTGAGGGGAATATTTATCGAAGGTTC
AGAGGTGTGCAAGCTTTGCAGGTCTGAAGGAGCAGACCCCATCTATACATGGTTCTATCTTCCTGACAATATAGACCTGGACACGCTTACAAAC
GGATGTCCGGCTATAAGAATCCCCTATTTTGGATCAGCCACTGATGAAAGGTCGGAAGCCCAACTCGGGTATGTAAGAAATCTAAGCAAACCCG
CAAAGGCGGCCATCCGGATAGCTATGGTGTATACGTGGGCCTACGGGACTGATGAGATATCGTGGATGGAAGCCGCTCTTATAGCCCAAACAAG
AGCTAATCTGAGCTTAGAGAATCTAAAGCTGCTGACTCCTGTTTCAACCTCCACTAATCTATCTCATAGGTTGAAAGATACGGCAACCCAGATG
AAGTTCTCTAGTGCAACACTAGTCCGTGCAAGTCGGTTCATAACAATATCAAATGATAACATGGCACTCAAAGAAGCAGGGGAGTCGAAGGATA
CTAATCTCGTGTATCAGCAGATTATGCTAACTGGGCTAAGCTTGTTCGAGTTCAATATGAGATATAAGAAAGGTTCCTTAGGGAAGCCACTGAT
ATTGCACTTACATCTTAATAACGGGTGCTGTATAATGGAGTCCCCACAGGAGGCGAATATCCCCCCAAGGTCCACATTAGATTTAGAGATTACA
CAAGAGAACAATAAATTGATCTATGATCCTGATCCACTCAAGGATGTGGACCTTGAGCTATTTAGCAAGGTCAGAGATGTTGTACATACAGTTG
ACATGACTTATTGGTCAGATGATGAAGTTATCAGAGCAACCAGCATCTGTACTGCAATGACGATAGCTGATACAATGTCTCAATTAGATAGAGA
CAACTTAAAAGAGATGATCGCACTAGTAAATGACGATGATGTCAACAGCTTGATTACTGAGTTTATGGTGATTGATGTTCCTTTATTTTGCTCA
ACGTTCGGGGGTATTCTAGTCAATCAGTTTGCATACTCACTCTACGGCTTAAACATCAGAGGAAGGGAAGAAATATGGGGACATGTAGTCCGGA
TTCTTAAAGATACCTCCCACGCAGTTCTAAAAGTCTTATCTAATGCTCTATCCCATCCCAAAATCTTCAAACGATTCTGGAATGCAGGTGTCGT
GGAACCTGTGTATGGGCCTAACCTCTCAAATCAGGATAAGATACTCTTGGCCCTCTCTGTCTGTGAATATTCTGTGGATCTATTCATGCACGAC
TGGCAAGGGGGTGTACCGCTTGAGATCTTTATCTGTGACAATGACCCAGATGTGGCCGACATGAGGAGGTCCTCTTTCTTGGCAAGACATCTTG
CATACCTATGCAGCTTGGCAGAGATATCTAGGGATGGGCCAAGATTAGAATCAATGAACTCTCTAGAGAGGCTCGAGTCACTAAAGAGTTACCT
GGAACTCACATTTCTTGATGACCCGGTACTGAGGTACAGTCAGTTGACTGGCCTAGTCATCAAAGTATTCCCATCTACTTTGACCTATATCCGG
AAGTCATCTATAAAAGTGTTAAGGACAAGAGGTATAGGAGTCCCTGAAGTCTTAGAAGATTGGGATCCCGAGGCAGATAATGCACTGTTAGATG
GTATCGCGGCAGAAATACAACAGAATATTCCTTTGGGACATCAGACTAGAGCCCCTTTTTGGGGGTTGAGAGTATCCAAGTCACAGGTACTGCG
TCTCCGGGGTACAAGGAGATCACAAGAGGTGAGATAGGCAGATCAGGTGTTGGTCTGACGTTACCATTCGATGGAAGATATCTATCTCACCAG
CTGAGGCTCTTTGGCATCAACAGTACTAGCTGCTTGAAAGCACTTGAACTTACCTACCTATTGAGCCCCTTAGTTGACAAGGATAAAGATAGGC
TATATTTAGGGGAAGGAGCTGGGGCCATGCTTTCCTGTTATGACGCTACTCTTGGCCCATGCATCAACTATTATAACTCAGGGGTATACTCTTG
TGATGTCAATGGGCAGAGAGAGTTAAATATATATCCTGCTGAGGTGGCACTAGTGGGAAAGAAATTAAACAATGTTACTAGTCTGGGTCAAAGA
GTTAAAGTGTTATTCAACGGGAATCCTGGCTCGACATGGATTGGGAATGATGAGTGTGAGGCTTTGATTTGGAATGAATTACAGAATAGCTCGA
TAGGCCTAGTCCACTGTGACATGGAGGGAGGAGATCATAAGGATGATCAAGTTGTACTGCATGAGCATTACAGTGTAATCCGGATCGCGTATCT
```

-continued

```
GGTGGGGGATCGAGACGTTGTGCTTATAAGCAAGATTGCTCCCAGGCTGGGCACGGATTGGACCAGGCAGCTCAGCCTATATCTGAGATACTGG
GACGAGGTTAACCTAATAGTGCTTAAAACATCTAACCCTGCTTCCACAGAGATGTATCTCCTATCGAGGCACCCCAAATCTGACATTATAGAGG
ACAGCAAGACAGTGTTAGCTAGTCTCCTCCCTTTGTCAAAAGAAGATAGCATCAAGATAGAAAAGTGGATCTTAATAGAGAAGGCAAAGGCTCA
CGAATGGGTTACTCGGGAATTGAGAGAAGGAAGCTCTTCATCAGGGATGCTTAGACCTTACCATCAAGCACTGCAGACGTTTGGCTTTGAACCA
AACTTGTATAAATTGAGCAGAGATTTCTTGTCCACCATGAACATAGCTGATACACACAACTGCATGATAGCTTTCAACAGGGTTTTGAAGGATA
CAATCTTCGAATGGGCTAGAATAACTGAGTCAGATAAAAGGCTTAAACTAACTGGTAAGTATGACCTGTATCCTGTGAGAGATTCAGGCAAGTT
GAAGACAATTTCTAGAAGACTTGTGCTATCTTGGATATCTTTATCTATGTCCACAAGATTGGTAACTGGGTCATTCCCTGACCAGAAGTTTGAA
GCAAGACTTCAATTGGGAATAGTTTCATTATCATCCCGTGAAATCAGGAACCTGAGGGTTATCACAAAAACTTTATTATACAGGTTTGAGGATA
TTATACATAGTATAACGTATAGATTCCTCACCAAAGAAATAAAGATTTTGATGAAGATTTTAGGGGCAGTCAAGATGTTCGGGGCCAGGCAAAA
TGAATACACGACCGTGATTGATGATGGATCACTAGGTGATATCGAGCCATATGACAGCTCGTAATAATTAGTCCCTATCGTGCAGAACGATCGA
AGCTCCGCGGTACCTGGAAGTCTTGGACTTGTCCATATGACAATAGTAAGAAAAACTTACAAGAAGACAAGAAAATTTAAAAGGATACATATCT
CTTAAACTCTTGTCTGGTGGGTCGGCATGGCATCTCCACCTCCTCGCGGTCCGACCTGGGCATCCGAAGGAGGACGTCGTCCACTCGGATGGCT
AAGGGAGGGGCCCCCGCGGGGCTGCTAACAAAGCCCGAAAGGAAGCTGAGTTGGCTGCTGCCACCGCTGAGCAATAACTAGCATAACCCCTTGG
GGCCTCTAAACGGGTCTTGAGGGGTTTTTTGCTGAAAGGAGGAACTATATCCGGATCGAGACCTCGATGCCGGCTGATGCGGTATTTTCTCCTT
ACGCATCTGTGCGGTATTTCACACCGCATATGGTGCACTCTCAGTACAATCTGCTCTGATGCCGCATAGTTAAGCCAGCCCCGACACCCGCCAA
CACCCGCTGACGCGCCCTGACGGGCTTGTCTGCTCCCGGCATCCGCTTACAGACAAGCTGTGACCGTCTCCGGGAGCTGCATGTGTCAGAGGTT
TTCACCGTCATCACCGAAACGCGCGAGACGAAAGGGCCTCGTGATACGCCTATTTTTATAGGTTAATGTCATGATAATAATGGTTTCTTAGACG
TCAGGTGGCACTTTTCGGGGAAATGTGCGCGGAACCCCTATTTGTTTATTTTTCTAAATACATTCAAATATGTATCCGCTCATGAGACAATAAC
CCTGATAAATGCTTCAATAATATTGAAAAAGGAAGAGTATGAGTATTCAACATTTCCGTGTCGCCCTTATTCCCTTTTTTGCGGCATTTTGCCT
TCCTGTTTTTGCTCACCCAGAAACGCTGGTGAAAGTAAAAGATGCTGAAGATCAGTTGGGTGCACGAGTGGGTTACATCGAACTGGATCTCAAC
AGCGGTAAGATCCTTGAGAGTTTTCGCCCCGAAGAACGTTTTCCAATGATGAGCACTTTTAAAGTTCTGCTATGTGGCGCGGTATTATCCCGTA
TTGACGCCGGGCAAGAGCAACTCGGTCGCCGCATACACTATTCTCAGAATGACTTGGTTGAGTACTCACCAGTCACAGAAAAGCATCTTACGGA
TGGCATGACAGTAAGAGAATTATGCAGTGCTGCCATAACCATGAGTGATAACACTGCGGCCAACTTACTTCTGACAACGATCGGAGGACCGAAG
GAGCTAACCGCTTTTTTGCACAACATGGGGGATCATGTAACTCGCCTTGATCGTTGGGAACCGGAGCTGAATGAAGCCATACCAAACGACGAGC
GTGACACCACGATGCCTGTAGCAATGGCAACAACGTTGCGCAAACTATTAACTGGCGAACTACTTACTCTAGCTTCCCGGCAACAATTAATAGA
CTGGATGGAGGCGGATAAAGTTGCAGGACCACTTCTGCGCTCGGCCCTTCCGGCTGGCTGGTTTATTGCTGATAAATCTGGAGCCGGTGAGCGT
GGGTCTCGCGGTATCATTGCAGCACTGGGGCCAGATGGTAAGCCCTCCCGTATCGTAGTTATCTACACGACGGGGAGTCAGGCAACTATGGATG
AACGAAATAGACAGATCGCTGAGATAGGTGCCTCACTGATTAAGCATTGGTAACTGTCAGACCAAGTTTACTCATATATACTTTAGATTGATTT
AAAACTTCATTTTTAATTTAAAAGGATCTAGGTGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAATCTGCTGCTTGCAAACAAAAAAACCACCGCTAC
CAGCGGTGGTTTGTTTGCCGGATCAAGAGCTACCAACTCTTTTTCCGAAGGTAACTGGCTTCAGCAGAGCGCAGATACCAAATACTGTCCTTCT
AGTGTAGCCGTAGTTAGGCCACCACTTCAAGAACTCTGTAGCACCGCCTACATACCTCGCTCTGCTAATCCTGTTACCAGTGGCTGCTGCCAGT
GGCGATAAGTCGTGTCTTACCGGGTTGGACTCAAGACGATAGTTACCGGATAAGGCGCAGCGGTCGGGCTGAACGGGGGGTTCGTGCACACAGC
CCAGCTTGGAGCGAACGACCTACACCGAACTGAGATACCTACAGCGTGAGCTATGAGAAAGCGCCACGCTTCCCGAAGGGAGAAAGGCGGACAG
GTATCCGGTAAGCGGCAGGGTCGGAACAGGAGAGCGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGATTCTGTGGATAACCGTATTACCGCCTTTGAGTGAGCTGATACCGC
TCGCCGCAGCCGAACGACCGAGCGCAGCGAGTCAGTGAGCGAGGAAGCGGAAGAGCGCCCAATACGCAAACCGCCTCTCCCCGCGCGTTGGCCG
ATTCATTAATGCAGCTGGCACGACAGGTTTCCCGACTGGAAAGCGGGCAGTGAGCGCAACGCAATTAATGTGAGTTAGCTCACTCATTAGGCAC
CCCAGGCTTTACACTTTATGCTTCCGGCTCGTATGTTGTGTGGAATTGTGAGCGGATAACAATTTCACACAGGAAACAGCTATGACCATGATTA
CGCCAAGCTTGCATGCCTGCAGGTCGACGCGTTAATACGACTCACTATA
```

In particular, the present invention provides methods, compositions, recombinant virus constructions and formulations, and kits for a modified Enders strain Sendai viral vector. Viruses can be used to protect humans or other animals from infection or for use in vitro. Moreover, some embodiments include vectors for imaging in vitro or in vivo viral spread, clearance, and transmission. Furthermore, the disclosed embodiments contemplate an Enders Sendai virus vector with insertion of a foreign gene. More particularly, for example only and not meant to be limiting, the foreign gene might be an RSV F gene and/or G gene, an hPIV gene from Type 1-4, for use as a vaccine either alone or in combination with other vectors. Insertion of a foreign gene into any of the intergenic junctions is acceptable; however, it is believed that it might be preferable to insert the foreign gene between the Sendai virus F and FIN genes because it provides sufficient virulence for infection of a primate host while providing sufficient RSV F gene expression to confer protective immunity. Further, studies show that a small amount of inoculum and small dose of Sendai virus might enhance the ratio of upper respiratory tract as compared to lower respiratory tract infection such that there is an increased margin of safety.

While it is not necessary to understand the mechanism of action, it is believed that use of the modified Enders strain to understand the mechanism of action, it is believed these modifications have been demonstrated to enable efficient generation of an infectious clone of an Enders-based Sendai virus from cDNA relative to the unmodified Enders strain genome, and enable an attenuated virus to elicit an immune response in primates.

I. Development of Modified Enders Strain

While it is not necessary to understand the mechanism of action, it is believed that the recombinant Sendai viral vector comprised of a foreign gene and a modified L gene provides an efficient and safe vector for use as a vaccine. Various pSeV gene chimeras were constructed containing Z strain and Enders strain genes in order to be able to identify the region that affects virus rescue and growth. The results of virus rescue and growth indicate that a chimeric Enders/Z viral vector is desired. For example only and not meant to be limiting, it is believed an AscI/NheI fragment containing the N-terminal half of the L gene is important for efficient growth. Viruses containing this part from the Z strain grew better than other test constructs. The construction and virus growth data are summarized in FIG. 15 and Table 1 below.

Summary of Rescue Results for Various Enders Strain/Z Strain Sendai Viruses:

TABLE 1

Comparison of Virus Growth by examination of HA titer from allantoic fluid from injected eggs
Table 1. Rescue of various Enders/Z chimeric SeVs.

| Virus | Portion from Z strain | Portion from pSeVE(3) | NP | P | M | F | HN | L | Maximum HA titer |
|---|---|---|---|---|---|---|---|---|---|
| SeV(E)3 | | | E | E | E | E | E | E | 370 |
| SeVa | KpnI/NotI (15,281-6,670) | KpnI/NotI (6670-15281) | Z | Z | Z | Z | E | E | 730 |
| SeVb | NotI/AscI (6,670-8,441) | NotI/AscI (8,441-6,670) | E | E | E | E | Z | E | 240 |
| SeVc | AscI/NheI (8,441-11,960) | AscI/NheI (11,960-8,441) | E | E | E | E | E | *Z/E(1-1,135 Z; 1,136-2,228E) | 6,600 |
| SeVd | SalI/NotI (6,670-2,074) | SalI/NotI (2,074-6,670) | Z | E | E | E | Z | Z | 2,200 |

(a E/Z chimera) instead of the Z strain, of the Sendai virus, provides greater viral attenuation in primates, yet preserves sufficient replication-competence to support facile virus rescue and the induction of an immune response. Furthermore, embodiments of the present invention contemplate some advantages, for example only and not meant to be limiting, including the following: (i) an unmodified Sendai virus vaccine is well tolerated in humans based on Phase I clinical trials, (ii) humans are not a natural host of Sendai virus and no confirmed cases of Sendai viral infection in humans have been reported, (iii) animal studies have shown production of antibodies and stimulation of cellular immunity upon intranasal inoculation of Sendai virus vaccine along with long term immunity (protection is observed when animals are challenged with pathogen months after inoculation (Jones et al. 2009, Vaccine 27:1848). The modified Sendai viral vector comprises a partial replacement of the Enders L region with the Z strain L portion effectively resulting in eight amino acid changes to the encoded L protein of the modified Enders strain. The modified amino acids are as follows: S155G, R258K, G466E, G482E, S581R, Q717R, T800I, and R852K. While it is not necessary Method: 293T cells in 6 well plates were infected with recombinant vaccinia virus vTF7.3 (10 ul/well) for 1 hour and transfected with full genome Sendai virus cDNAs together with Sendai virus NP, P and L genes in pTF1 vector. The cells were cultured for 2 days, and then, collected cells were injected into embryonated eggs. After three-days culture at 35 C, virus titers in allantoic fluids were measured. Z: Strain Z, E: Strain Enders.

Four chimeras were made to create a full Sendai virus genome, combining genes from Enders and Z origin. Rescued viruses were then tested for growth and measured by maximum HA titer. *In the case of SeVc, the L gene was derived partially from Enders and partially from Z, effectively resulting in a modified Enders strain with eight amino acid changes to the Enders L protein. This modification unexpectedly yielded a virus with capacity for facile rescue by reverse genetics, attenuation in primates, and sufficient replication-competence to support immunogenicity in primates. Sendai viruses SeVb, SeVc and SeVd were also diluted at various concentrations and injected into eggs to see their growth. The data also show that SeVc and SeVd grew much better than SeVb. Thus, while it is not necessary to understand the mechanism of action, based on this data, pSeVc was used for further construction of recombinant viruses. The following describes the behavior of the modified Enders-based vaccine carrying the RSV F gene.

Modified Enders-Based Vaccine is Attenuated in Primates

FIG. 16 shows the difference between growth of the Sendai virus Z, the Sendai virus Enders and a modified Sendai virus Enders-based vaccine SeVc-RSVF(F-HN) in African green monkeys. The Sendai virus Enders vaccine and the Sendai virus Enders-based SeVc-RSVF(F-HN) vaccine grew to a lesser titer in both the upper and lower respiratory tract (URT and LRT) of African green monkeys compared to the SeV Z strain (MPIV1 below).

Referring to FIG. 16, 16A and B show the mean daily virus titers of a Z strain Sendai virus (MPIV1) and the human parainfluenza virus type 1 (HPIV1) in a nasopharyngeal swab (URT) or tracheal lavage (LRT) after intranasal and intratracheal vaccination (Skiadopoulos et. al. 2002 Virology 297:153) respectively. As demonstrated in this panel, the peak MPIV1 titer after a 10e6 dose (administered IT and IN) exceeded 10e4 in the URT and exceeded 10e6 in the LRT.

Referring to FIGS. 16, 16C and D show daily titers following vaccination with the Sendai virus Enders vaccine (SeV) or the recombinant modified Sendai virus Enders-based vaccine expressing RSV F (SeVc-RSVF(F-HN)). When the vaccine doses were 10e6 (administered IT and IN) peak viral titers were lower than with Z. They were approximately 10e3 in the URT (16C, top, 1 log reduced compared to Z) and approximately 10e4 in the LRT (16D, bottom, 2 logs reduced compared to Z). The Enders based Sendai virus vector was clearly attenuated compared to Sendai virus Z, yet it maintained immunogenicity.

The Sendai virus Enders-based vaccines were also considerably lower in titers compared to a b/hPIV-3-based RSV F vaccine after administration to African green monkeys. The b/hPIV-3-based RSV F vaccine is already in clinical trials in infants. The b/hPIV-3-based RSV F vaccine grew to peak titers of >10e5 and 10e7 in the URT and LRT respectively in African green monkeys, even when the vaccine was administered at a dose of only 2×10e5 (Tang et. al. 2004 J. Virol. 78:11198).

Enders Based Sendai Virus Vaccine Elicits an Immune Response in African Green Monkeys.

FIG. 17 shows that the modified Sendai virus Enders-based vaccine carrying the RSV F gene in the F-HN position (SeVc-RSVF(F-HN)) elicits an immune response against RSV F (A) and against the Sendai virus components (B) in African green monkeys. The antibody response against RSV F was demonstrated by testing animal sera in an enzyme-linked immunosorbant assay (ELISA) approximately 3 weeks after vaccination. Control animals were African green monkeys that received PBS by the intranasal and intratracheal routes approximately 3 weeks previously. The second group of animals received an unmodified Sendai virus (SeV) by the same routes and the third group of animals received the modified SeV Enders-based vaccine carrying the RSV F gene in the F-HN position (SeVc-RSVF(F-HN)).

The Recombinant Modified Sendai Virus Enders-Based Vaccine Expressing RSV F (SeVc-RSVF(F—RN)) Protects African Green Monkeys from RSV Infection FIG. 18 shows that the modified Sendai virus Enders-based vaccine carrying the RSV F gene in the F-HN position completely protected African green monkeys from RSV infection of the lower respiratory tract. Results show an analysis of BAL samples from three to ten days after RSV challenge. The test animals that received the modified Sendai virus Enders-based vaccine carrying the RSV F gene (SeVc-RSVF(F-HN)) exhibited no challenge virus in the BAL (green, right panel B) as compared to control animals on the left (blue and red, A).

Low Dose Modified Sendai Virus Enders-Based Vaccine Expressing RSV F is Protective FIG. 19 shows that when the RSV F gene is placed in the F-HN position of the Enders-based SeV (SeVc-RSVF(F-HN)), it also confers complete protection against RSV in cotton rats, even when administered at a dose as low as 10e2. Vaccine activity at such a low dose is attractive, both in terms of vaccine efficacy and in terms of vaccine manufacturing. Results show titers of the RSV challenge virus in the lungs three days after challenge in control and vaccinated cotton rats.

Thus, the SeV Enders-based RSV vaccine with RSV in the F-HN position (possibly also in P-M and M-F or other positions) has sufficient growth to protect both African green monkeys and cotton rats from RSV challenge. Vaccine doses can be as low as 10e2. The virus is attenuated in African green monkeys compared to the SeV Z strain and compared to the b/hPIV3-RSV F vaccine that is currently in clinical trials in infants. It is believed that the SeV Enders-based vaccine appears to be an extremely attractive candidate as an non-recombinant vaccine for hPIV-1 and as a recombinant vaccine for any other pathogen.

II. PIV Model System Utilizing Luciferase

Experimental studies on hPIV infection in tissue culture and animal models have helped reveal basic replication mechanisms and evaluate preclinical vaccine candidates [Murphy et al. 2002, J Clin Invest 110: 21-27; Moscona, A. 2005, J Clin Invest 115: 1688-1698; and Schaap-Nutt et al. 2010, Vaccine 28: 2788-2798]. However, being able to visualize the spread of PIV infection in individual, living animals that are fully susceptible to PIV-associated disease would enable more thorough investigations of PIV pathogenesis, virus-host interactions, and virus transmission. Placement of a marker gene in the Sendai virus backbone can assist the study of virus growth, virus localization and virus transmission both in vivo and in vitro.

As demonstration of the marking system, the luciferase gene was placed in various positions within the modified Sendai virus vector. FIG. 9 demonstrates the strategy. Referring to FIG. 9, in panel A is shown sequences within a pGEM3 cloning plasmid engineered to contain flanking Nod restriction sites, the firefly luciferase reporter gene, gene end and gene start sequences. To insert the luciferase reporter gene cassette into three gene junctions (panel B), three pSeV genome plasmids were cloned to contain a unique Nod restriction site in each of the P-M, M-F, and F-HN gene junctions. For the pSeV-luc(M-F*) genome plasmid, the naturally occurring suboptimal start signal AGGGATAAAG (SEQ. ID NO.: 19) was also mutated to the more efficient start signal AGGGTGAAAG (SEQ. ID NO.: 20) to compensate for expected attenuation due to the addition of the foreign gene and additional gene junction. The firefly luciferase gene cassette (panel a) was subcloned from the pGEM3 plasmid into the pSeV genome plasmids using the Nod restriction sites. Panel C shows the design of pSeV cDNA plasmids for the rescue of WT and recombinant SeVs containing the luciferase reporter gene (luc). The locations of the Sendai virus genes nucleoprotein (N), polymerase (P), matrix (M), fusion (F), hemagglutinin-neuraminidase (HN), and large (L) protein are shown, as well as the T7 RNA polymerase promoter (T7) and hepatitis delta virus ribozyme sequence (ribo). Gene start sequences are shown in green and the naturally occurring, suboptimal AGGGATAAAG (SEQ. ID NO.: 19) gene start sequence between the M and F genes of WT Sendai virus is shown in yellow. Gene end sequences are shown in red. The 3' leader sequence upstream of the N gene and the 5' trailer sequence downstream of the L gene are not shown for simplicity.

Figure 2:
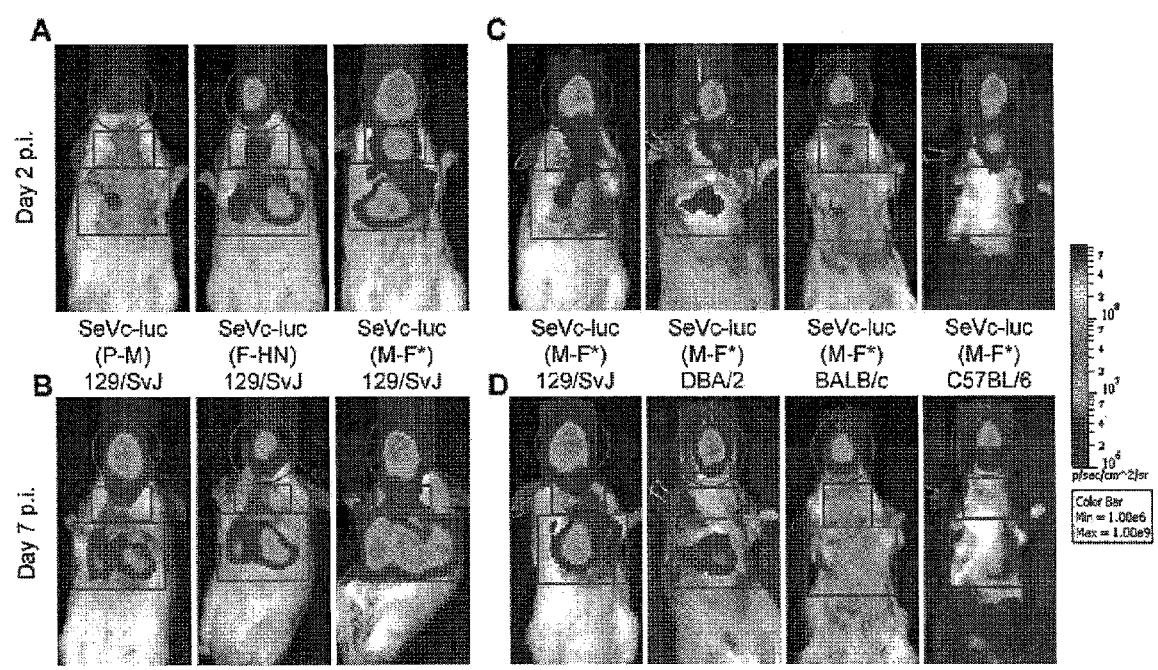
FIG. 2. Non-invasive bioluminescence imaging of SeV infection in the respiratory tracts of living mice. Eight-week-old mice were intranasally inoculated with 7,000 PFU of SeVc-luc(P-M), SeVc-luc(F-HN), or SeVc-luc(M-F*). Every 24 hours the mice were intraperitoneally injected with luciferin substrate, anesthetized with isoflurane, imaged with a Xenogen Lumina device, and then allowed to recover. In one experiment, bioluminescence is shown on day 2 (A) or day 7; (B) post-infection (p.i.) for 129/SvJ mice infected with SeVc-luc(P-M)SeVc-luc(P-M), SeVc-luc(F-HN), or SeVc-luc(M-F*). In a second experiment, bioluminescence is shown on day 2 (C) or day 7 (D) for either 129/SvJ, DBA/2, BALB/c, or C57BL/6 mice infected with SeVc-luc (M-F*). The data are displayed as radiance, a measurement of bioluminescence intensity, on a rainbow log scale. Radiance values range from $1 \times 10^6$ (blue) to $1 \times 10^9$ (red) photons/s/cm$^2$/steradian. Red circles show the regions of interest (ROI) for calculating the total flux (photons/s) in the nasopharynx, and red rectangles show the ROI areas for the trachea and lungs.

The rescued viruses expressing the luciferase gene can be administered to mice and tracked over an extended time course. The upper and lower respiratory tract can be monitored in this way. The non-invasive bioluminescence imaging of Sendai virus infection in the respiratory tracts of living mice is shown in FIG. 2. Eight-week-old mice were intranasally inoculated with 7,000 PFU of SeVc-luc(P-M), SeVc-luc(F-HN), or SeVc-luc(M-F*). Every 24 hours the mice were intraperitoneally injected with luciferin substrate, anesthetized with isoflurane, imaged with a Xenogen Lumina device, and then allowed to recover. Referring to FIG. 2, in one experiment, bioluminescence is shown on day 2 (panel a) or day 7 (panel b) post-infection (p.i.) for 129/SvJ mice infected with SeVc-luc(P-M), SeVc-luc(F-HN), or SeVc-luc(M-F*). In a second experiment, bioluminescence is shown on day 2 (panel c) or day 7 (panel d) for either 129/SvJ, DBA/2, BALB/c, or C57BL/6 mice infected with SeVc-luc(M-F*). The data are displayed as radiance, a measurement of bioluminescence intensity, on a rainbow log scale. Radiance values range from $1 \times 10^6$ (blue) to $1 \times 10^9$ (red) photons/s/cm$^2$/steradian. Red circles show the regions of interest (ROI) for calculating the total flux (photons/s) in the nasopharynx, and red rectangles show the ROI areas for the trachea and lungs. While it is not necessary to understand the mechanism of action, it is believed the methodology can also support (i) studies of virus growth in vitro, (ii) studies of virus in multiple mouse strains (iii) studies of virus transmission between animals, (iv) studies of virus dosing, (v) studies of vaccine volumes and (vi) studies of adjuvants (examples are provided below). The text below describes the luciferase system in greater detail, emphasizing its numerous applications.

A. Introduction

Mice are poorly permissive to infection by the hPIVs, and hPIV infection in cotton rats, hamsters, guinea pigs, and ferrets is usually asymptomatic with minimal or undetectable pathology in the lungs [Karron et al. 2007, Parainfluenza Viruses. 5th Ed. pp. 1497-1526]. As a result, a number of studies have used Sendai virus (SeV) infection in mice as a model to investigate PTV pathogenesis in an experimental setting [Nagai, Y. 1999, Rev Med Virol 9: 83-99 and Faisca et al. 2007, Res Vet Sci 82: 115-125]. Sendai virus is the murine counterpart of hPIV1, the leading cause of laryngotracheobronchitis (pediatric croup) [Denny et al. 1983, Pediatrics 71: 871-876]. Sendai virus and hPIV1 have 78% amino-acid sequence identity [Takimoto et al. 2005, Viral Immunol 18: 255-266], elicit cross-protective immunity [Dave et al. 1994, Virology 199: 376-383; Hurwitz et al. 1997, Vaccine 15: 533-540; and Sangster et al. 1995, Virology 207: 287-291] and share tissue-tropic and epidemiological similarities [Karron et al. 2007, Parainfluenza Viruses. 5th Ed. pp. 1497-1526 and Faisca et al. 2007, Res Vet Sci 82: 115-125]. Moreover, while it is not necessary to understand the mechanism of action, it is believed that Sendai virus shows promise as a Jennerian vaccine for hPIV1 [Slobod et al. 2004, Vaccine 22: 3182-3186] and a vaccine vector for hRSV, hPIV3, and hPIV2 [Jones et al. 2009, Vaccine 27: 1848-1857; Zhan et al. 2007, Vaccine 25: 8782-8793; and Zhan et al. 2008, Vaccine 26: 3480-3488].

Despite Sendai virus and the hPIVs being first isolated in the 1950s and having been studied for over 50 years [Karron et al. 2007, Parainfluenza Viruses. 5th Ed. pp. 1497-1526], fundamental aspects of PIV infection and immunity remain unknown yet would directly bear upon our understanding of PIV pathogenesis and transmission as well the development of control measures. For example, the spatial and temporal spread of natural infection in the respiratory tract after Sendai virus transmission remains unknown because classical experiments measuring virus titers from sacrificed mice were limited by large inter-animal variability and error, resulting in ambiguous results [Iida, T. 1972, J Gen Virol 14: 69-75 and van der Veen et al. 1970, Arch Gesamte Virusforsch 31: 237-246]. It is also unknown how hPIV and Sendai virus transmission often results in immunity without causing severe pathology in their natural host. The contribution of LRT infection to transmission is unknown. Finally, while infection in the lungs and the concomitant host response are clearly associated with disease severity [Karron et al. 2007, Parainfluenza Viruses. 5th Ed. pp. 1497-1526; Faisca et al. 2007, Res Vet Sci 82: 115-125; Hall, C B 2001, N Engl J Med 344: 1917-1928; and Henrickson, K J 2003, Clin Microbiol Rev 16: 242-264], many questions remain about the contribution of infection in the URT and trachea to clinical outcome and protective immunity [Sealy et al. 2010, Vaccine 28: 6749-6756 and Rudraraju et al. 2011, Virology 410: 429-436]. While it is not necessary to understand the mechanism of action, it is believed that there are no published studies investigating how the dose of virus inoculum, replicative fitness of the virus, or genetic susceptibility of the host influences the growth and clearance of Sendai virus in the URT and trachea.

Thus, the present invention contemplates embodiments to measure the in vivo dynamics of PIV infection and immunity in living animals. Therefore, three luciferase-expressing SeVs were generated for non-invasive bioluminescence imaging in mice. Analogous systems have been previously reported for DNA and positive-strand RNA viruses [Luker et al. 2008, Antiviral Res 78: 179-187] but have been elusive for negative-strand RNA viruses until now, largely due to virus attenuation [Hasan et al. 1997, J Gen Virol 78 (Pt 11): 2813-2820] or genetic instability resulting from reporter gene insertion [Manicassamy et al. 2010, Proc Natl Acad Sci USA 107: 11531-11536]. Sendai virus is believed to be an ideal candidate for non-invasive imaging because (i) foreign-gene expression by paramyxovirus vectors is usually stable genetically [Bukreyev et al. 2006, J Virol 80: 10293-10306], (ii) in vivo imaging of a non-replicating Sendai virus in intact mice has been successfully demonstrated [Griesenbach et al. 2008, Biomaterials 29: 1533-1540] and (iii) the match of Sendai virus and the murine host would enable pathogenesis studies [Faisca et al. 2007, Res Vet Sci 82: 115-125]. For the pathogenesis and transmission studies described here, the reporter virus SeVc-luc(M-F*) was engineered, which expresses high levels of luciferase yet replicates and causes disease in mice similar to wild-type (WT) virus. The in vivo dynamics of Sendai virus infection was imaged in living, intact mice after direct inoculation and after contact transmission as a function of virus dose and mouse strain. Unexpectedly, a dichotomous tissue tropism was discovered in which the URT and trachea supported robust virus growth, efficient transmission, and protective immunity even under conditions resulting in little infection in the lungs. Overall, the bioluminescence imaging system and tissue-tropic differences in PIV infection reported here provide a model for understanding in vivo infection and transmission by respiratory paramyxoviruses and a means for targeting antiviral therapies and directing live vaccines on a tissue-specific basis.

B. Materials and Methods

I. Cell culture. Monolayer cultures of LLC-MK2 cells were grown in Dulbecco's minimal essential medium (DMEM) supplemented with 10% fetal bovine serum, 1% L-glutamine, 1% penicillin, and 1% streptomycin at 37° C.+5% $CO_2$.

II. Recombinant Sendai viruses. Unique NotI recognition sites were cloned into the P-M, M-F and F-HN intergenic junctions of an Enders-based pSeV viral genome plasmid, using cloning sites described previously [Tokusumi et al. 2002, Virus Res 86: 33-38]. The firefly luciferase gene was amplified by PCR using the pGL3 Basic vector (Promega) and a pair of AscI tagged primers, subcloned into a shuttle plasmid containing a Sendai virus intergenic junction and flanking NotI restriction sites [Tokusumi et al. 2002, Virus Res 86: 33-38] and then subcloned into the unique NotI site of each of the pSeV viral genome plasmids. Within the pSeV-luc(M-F) plasmid, the start signal upstream of the F protein was changed from AGGGATAAAG (SEQ. ID. NO.: 19) to AGGGTGAAAG (SEQ. ID. NO.: 20) using QuikChange™ Site-Directed Mutagenesis Kit (Stratagene Corp). The recombinant SeVs were rescued from the pSeV genome plasmids as described previously [Zhan et al. 2008, Vaccine 26: 3480-3488]. The modified Enders strain Sendai genome consists of a modified Sendai virus L gene that contains the following amino acid changes: S to G at position 155, R to K at position 258, G to E at position 466, G to E at position 482, S to R at position 581, Q to R at position 717, T to I at position 800, and R to K at position 852.

III. Luciferase Expression in Vitro. SeV-infected LLC-MK2 cells (MOI 5 PFU/cell) were incubated at 33° C.+5% $CO_2$ and lysates collected at various times p.i. Luciferase assays were performed using the Luciferase Assay System (Promega) and the levels of expression measured using an automated luminometer (Turner Biosystems, Inc.) as described previously [Luque et al. 2007, J Virol 81: 3130-3141].

IV. Viral Titers and Bioluminescence Imaging. Virus titers from multistep growth curves (MOI of 0.01 PFU/cell) and homogenized tissues were determined by plaque titration in LLC-MK2 cells as described previously [Luque et al. 2010, J Virol 84: 810-821]. Eight week-old female 129×1/SvJ mice or BALB/c mice (Jackson Laboratories) were anesthetized using isoflurane (Baxter Health Care Corporation) and inoculated intranasally (i.n.) with 30 µl of PBS or virus. For FIGS. 1D, 1E, 2, 3, 4E, 4F, and 12, at 3 d before inoculation with PBS or virus, mice were anesthetized by IP injection of 300 µl avertin (300 mg/kg concentration) and chest hair was removed by shaving and application of a depilatory cream, Animals were monitored daily for weight loss, morbidity and mortality. Prior to imaging, mice were injected intraperitoneally with luciferin (Xenogen Corp) at a dose of 150 mg/kg of body weight and anesthetized with isoflurane for 5 min. In vivo images were acquired with the IVIS CCD camera system (Caliper Life Sciences) and analyzed with Living Image 3.2 software (Caliper Life Sciences) using an exposure of 60 s, 30 s, or 5 s (binning of 4 and an f/stop of 1). Pseudocolor images (representative of bioluminescence) of mice are displayed using a binning of 4 on a colorimetric scale ranging from $1\times10^6$ to $1\times10^9$ surface radiance (photons/s/$cm^2$/steradian), which is defined as the number of photons that leave a $cm^2$ of tissue and radiate into a solid angle of one steradian. To quantify bioluminescence, regions of interest (ROI) were defined manually and graphed data are expressed as total flux (photons/s), which is defined as the radiance in each pixel summed over the ROI area ($cm^2$)×4π. All animal studies were approved by the Animal Care and Use Committee of St. Jude Children's Research Hospital and were performed in compliance with relevant institutional policies, the Association for the Accreditation of Laboratory Animal Care guidelines, the National Institutes of Health regulations and local, state and federal laws.

V. Immunology. Sera and BALF were collected from euthanized animals on day 10 or day 60 p.i. BALF samples (3 ml) were centrifuged to collect cellular material and plated in a tissue culture dish for 1 h at 37° C. to remove adherent cells. Suspension cells were harvested, total lymphocytes were counted microscopically, and red blood cells were lysed. For flow cytometric analyses, cells were stained with FITC-conjugated anti-CD4 (RM4-4) and PE-conjugated anti-CD8b (53-5.8) antibodies (BD Biosciences Pharmingen). Lymphocytes were gated based on forward and side scatter, and the percentages of CD4+ and CD8+ T cell populations were measured within this gate. ELISAs were used to measure the levels of Sendai virus-specific or luciferase-specific antibodies present in the sera. Briefly, 96-well plates were coated overnight with disrupted, purified Sendai virus (10 µg/ml) or firefly luciferase (1 µg/ml, Abeam). Plates were blocked with PBS containing 1% BSA and then incubated with 10-fold serially diluted serum samples. After incubation, plates are washed, incubated with HRP-Goat anti mouse IgG (Southern Biotechnologies) and then washed further. To quantify levels of antibodies, TMB substrate (Kirkegaard and Perry Laboratories) was added to the wells followed by stop solution and absorbance was read at a wavelength of 450 nm GraphPad Prism non-linear regression software was used to calculate antibody titers.

VI. Contact Transmission. Donor animals were inoculated intranasally with 30 µL of SeVc-luc(M-F*) and were individually placed into cages containing 3 naïve contact mice at 24 h p.i. Bioluminescence was monitored daily until levels of luminescence were consistently at background levels (~15 days). Sera were collected on day 60 so that Sendai virus-specific antibody levels could be measured as described above. On day 63, mice were challenged with 7000 PFU SeVc-luc(M-F*) administered intranasally and bioluminescence was measured daily.

C. Supplementary Material and Methods

I. In vitro Expression of Sendai Virus Proteins. Viral protein expression levels were analyzed by radioimmunoprecipitation as previously reported [Luque et al. 2007, J Virol 81: 3130-3141 and Luque et al. 2010, J Virol 84: 810-821]. Briefly, LLC-MK2 cells were infected at an MOI of 5 PFU/cell, labeled with 50 µCi [$^{35}$S]Promix (Amersham Pharmacia Biotech), lysed with ice-cold RIPA buffer and clarified by centrifugation. Supernatant was incubated overnight at 4° C. with mouse anti-NP, P, M, F, and HN monoclonal antibodies, and immune complexes were adsorbed to protein G-Sepharose (GE Healthcare) before fractionation on 12% NuPAGE bis-Tris SDS-PAGE gels (Invitrogen) and visualization as described previously [Luque et al. 2010, J Virol 84: 810-821].

II. Sendai Virus Composition. The allantoic cavities of 10-day-old embryonated hen eggs were inoculated with viruses. Allantoic fluid was harvested 72 hpi and centrifuged 45 min at 3000 rpm to remove cellular debris. Supernatants were layered over a 60-20% sucrose gradient and centrifuged at 24,000 rpm for 3.5 hrs to isolate virions. Isolated virions were diluted in TNE buffer and further purified over a 20% sucrose cushion by centrifugation at 24,000 rpm for 15 hrs. Virus pellets were resuspended in RIPA buffer and total protein concentrations were determined using the BCA protein assay kit (Thermo Sci.). Equal protein levels were run on a 4-12% SDS-PAGE gel, the gel was stained using the Blue BANDit™ protein stain (Amresco), and then dried with a BioRad gel dryer at 60° C. for 45 minutes.

III. In vivo Infection and Transmission. The measurement of T-lymphocyte influx in BALF for CD4+ and CD8+ T-cells is described in the main text. Luciferase-specific ELISAs were performed essentially as Sendai virus-specific ELISAs as described in the main text except using firefly luciferase protein (Abcam) was used to coat 96-well plates. Bioluminescence imaging and viral titer determinations from dissected tissues are also described in the main text. In contact transmission experiments, the time until detection was measured as the first day bioluminescence>$10^6$ $\log_{10}$ photons/s was recorded. Bioluminescence areas under the curve (AUC) were calculated by integrating bioluminescence intensities with respect to time using Igor Pro software (Wavemetrics).

D. Results

I. In vitro Properties of Luciferase-Expressing Viruses

To develop a model in which PIV infection could be visualized non-invasively in intact mice, three recombinant Sendai viruses (SeVc viruses) were generated in which firefly luciferase was inserted into the P-M, M-F and F-HN gene junctions of Sendai virus (FIG. 1a, FIG. 9).

Insertion of an additional gene and gene junction into the Sendai virus genome was expected to decrease downstream viral gene expression and, consequently, reduce virus replication [Tokusumi et al. 2002, Virus Res 86: 33-38]. To generate a luciferase-expressing Sendai virus expected to suffer little or no attenuation, the SeVc-luc(M-F*) virus was constructed to contain both the luciferase reporter gene and a more efficient transcription start sequence AGGGTGAAAG (SEQ. ID. NO.: 20) upstream of the F gene (FIG. 9). Thus, the attenuating effects of reporter gene insertion could be counteracted by optimization of the naturally inefficient gene start sequence upstream of the F gene [Kato et al. 1999, J Virol 73: 9237-9246]. For the SeVc-luc(P-M) and SeVc-luc(F-HN) constructs in which the luciferase gene was inserted into the P-M and F-HN gene junctions, respectively, the naturally occurring suboptimal transcription start sequence upstream of the F gene was left intact (FIG. 9).

To determine if the viruses were attenuated or temperature restricted, multiple-step growth curves at a multiplicity of infection (MOI) of 0.01 PFU/cell were measured in LLC-MK2 cells at 33 and 37° C. (FIG. 1b). Titers of SeVc-luc (M-F*), SeVc-luc(F-HN) and WT were similar at both temperatures and similar to each other, showing these two luciferase-expressing viruses were not substantially attenuated or temperature restricted. In contrast, the SeVc-luc(P-M) virus had reduced growth kinetics at 33° C. and grew even slower at 37° C. To determine how efficiently the SeVc viruses expressed the reporter gene, in vitro luciferase expression in LLC-MK2 cell lysates (MOI 5 PFU/cell) was measured with a luminometer (FIG. 1c). Upstream insertion of the reporter gene in SeVc-luc(P-M) resulted in higher reporter-gene expression than downstream insertion in SeVc-luc(F-HN), as has been described previously for insertions of secreted alkaline phosphatase [Tokusumi et al. 2002, Virus Res 86: 33-38]. Luciferase expression by SeVc-luc (M-F*) exceeded that of SeVc-luc(P-M) within 6 h p.i. (post-infection), showing the enhanced gene start sequence engineered into the M-F* virus (FIG. 9) increases reporter-gene transcription at later time points, perhaps due to greater downstream transcription of the L polymerase gene. To determine how the reporter gene insertions may have altered expression of the Sendai virus genes, Sendai virus protein expression in LLC-MK2 cells (MOI 5 PFU/cell) was measured by radioimmunoprecipitation. Low levels of expression of the M, F, HN and presumably L proteins by the SeVc-luc(P-M) virus (FIG. 10a) most likely caused the high level of attenuation of this virus construct. Viral protein expression by SeVc-luc(M-F*) and SeVc-luc(F-HN) was sufficient to generate virions with WT-like compositions (FIGS. 10b,c), and these two reporter viruses grew to levels similar to wild-type virus in vitro.

II. Virulence of Luciferase-expressing Viruses

An ideal luciferase-reporter virus for non-invasive bioluminescence imaging and pathogenesis studies would express high levels of luciferase without altering virus replication and disease severity in the natural murine host compared to WT virus. To determine if the three luciferase-expressing SeVc viruses generated here retained the virulence of WT Sendai virus in vivo, 129/SvJ mice were inoculated intranasally with 7,000 PFU of virus, a dose known to induce substantial levels of morbidity and mortality in this mouse strain [Faisca et al. 2005, Am J Physiol Lung Cell Mol Physiol 289: L777-787]. In this experiment the mice were anesthetized with isoflurane and intranasally inoculated with virus in a 30 µl volume, a method of inoculation that delivers ~⅓ of the volume to the nasopharynx and ~½ of the volume to the lungs [Southam et al. 2002, Am J Physiol Lung Cell Mol Physiol 282: L833-839]. Infection with WT, SeVc-luc(M-F*), and SeVc-luc(F-HN) resulted in average weight losses of ~25% and mortality rates of 80% (FIGS. 1d,e), showing these two luciferase-expressing viruses remained fully virulent at this dose. In contrast, the attenuated SeVc-luc(P-M) virus induced only 12% weight loss and no mortality. Infection of 129/SvJ mice with 70,000 or 700,000 PFU of SeVc-luc(P-M) also resulted in 100% survival (data not shown), further demonstrating that the attenuated SeVc-luc(P-M) virus is avirulent.

Acute viral pneumonia by Sendai virus induces high levels of lymphocyte infiltration in bronchoalveolar lavage fluid (BALF) with a peak at ~10 dpi [Mo et al. 1995, J Virol 69: 1288-1291]. To determine if the luciferase-expressing viruses promoted lymphocyte influx comparable to WT, 129/SvJ mice infected with 7,000 PFU were sacrificed at 10 dpi for recovery of BALF. Similarly high numbers of total lymphocytes, CD4+ T-lymphocytes, and CD8+ T-lymphocytes were detected in BALF after infection with WT, SeVc-luc(M-F*), and SeVc-luc(F-HN), while lymphocyte influx after infection with attenuated SeVc-luc(P-M) was decreased ~10-fold (FIG. 1f; FIG. 11a-b). To determine the extents to which the reporter viruses elicited antibodies that bind to Sendai virus or luciferase, sera was also collected 10 dpi. All three SeVc viruses elicited anti-Sendai virus antibody titers similar to WT (FIG. 1g). The titers of anti-luciferase antibodies were also similar to each other for the three reporter viruses (FIG. 11c). Thus despite being attenuated and avirulent in 129/SvJ mice, SeVc-luc(P-M) elicited a robust antibody response. SeVc-luc(M-F*) induced WT-like levels of morbidity and mortality while expressing high levels of luciferase, making it best suited as a surrogate for WT virus in bioluminescence imaging experiments on pathogenesis and transmission.

III. Dynamics of Infection in Living Animals

To determine if non-invasive bioluminescence accurately reflected in vivo infection, 129/SvJ mice were intranasally inoculated with 7,000 PFU, imaged with a Xenogen IVIS instrument, and immediately euthanized so respiratory tissues could be collected for ex vivo measurement of luminescence and viral titers. Consistent with previous studies in immunocompetent mice [Tashiro et al. 1988, Virology 165: 577-583 and Miyamae et al. 2005, J Vet Med Sci 67: 369-377], viral titers and bioluminescence were limited to the respiratory tract and in these studies were distinctly visualized in the nasopharynx, trachea, and lungs. As shown in FIG. 12, in vivo bioluminescence intensities in living animals correlated well with ex vivo luminescence ($R^2$ 0.878) and viral titers in the nasopharynx ($R^2$ 0.864), trachea ($R^2$ 0.915), and lungs ($R^2$ 0.961), validating the technique as a means to measure in vivo infection non-invasively. To determine if the luciferase-reporter genes were genetically stable in the three SeVc viruses, lung tissues were recovered from 7,000-PFU-inoculated 129/SvJ mice at 7 dpi, homogenized, and plagued in LLC-MK2 cells. Five plaques for each of the three luciferase-expressing viruses were picked, RT-PCR transcribed, and sequenced. All of the individual plaques contained the luciferase insert, had no mutations, and expressed luciferase after infection in LLC-MK2 cells. While it is not necessary to understand the mechanism of action, it is believed this shows that the luciferase reporter gene was genetically stable in all three of the SeVc viruses after 7 days of replication in vivo.

Figure 3:
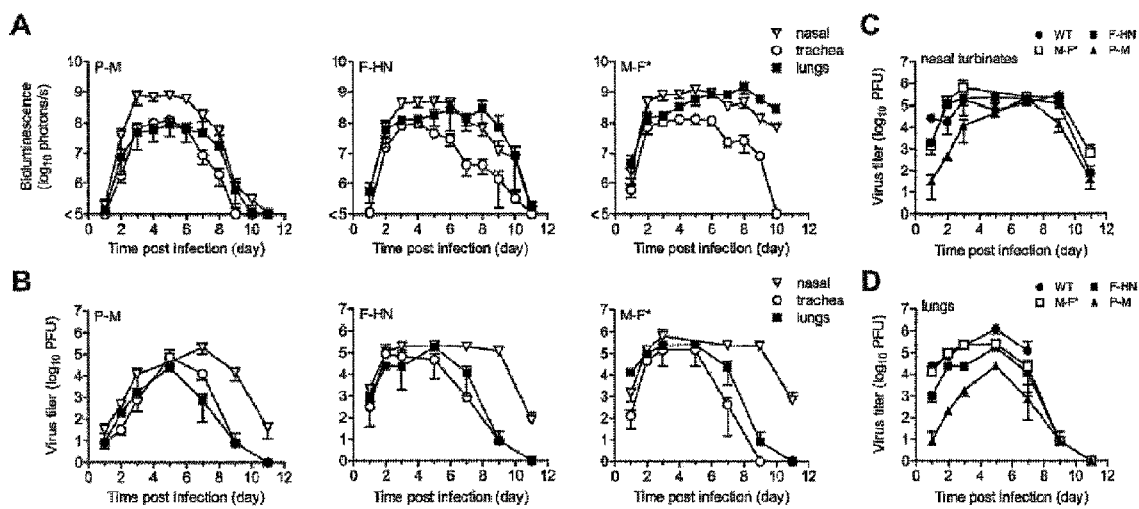
FIG. 3. Kinetics of SeV spread and clearance in the respiratory tracts of 129/Sv mice. (A) The extents of infection were determined by non-invasive bioluminescence imaging of living, anesthetized mice every 24 h. Each data point represents the average bioluminescence of 6 mice. The total flux (photons/s) of bioluminescence intensity is calculated as the sum of radiance in the region of interest. (B-D) The extents of virus replication in the nasal turbinates, trachea, and lungs were determined by sacrificing groups of 3 mice at the reported days and measuring the titers of infectious viruses in LLC-MK2 cells. Both experiments were repeated and representative data is shown.

Using the bioluminescence imaging system presented herein, the kinetics and tropism of infection were measured in intact 129/SvJ mice and compared our results to the conventional method of virus titer determination from dissected tissues (FIGS. 2 and 3). Just as SeVc-luc(M-F*) and SeVc-luc(F-HN) had in vitro replication rates and in vivo pathogenicities similar to WT, these SeVc viruses also had WT-like titers in the nasal turbinates, trachea, and lungs. In the nasal turbinates, high virus titers ($>10^5$ PFU) were detected by 2 dpi and were maintained until 9 dpi, after which rapid clearance occurred (FIG. 3b). High levels of bioluminescence from the nasopharynx ($>10^8$ photons/s) were similarly observed for 129/SvJ mice infected with SeVc-luc(M-F*) between 2 and 9 dpi with a peak around 5 dpi (FIG. 3a). In the lungs, virus titers peaked by 5 dpi and were cleared to low levels by 9 dpi. Infection with the attenuated SeVc-luc(P-M) resulted in peak lung titers of ~$10^4$ PFU at 5 dpi, nearly 100-fold lower than WT (FIG. 3d), and similarly low levels of bioluminescence were observed in the lungs (FIG. 3a), consistent with its attenuated and avirulent phenotype. However, SeVc-luc(P-M) grew to high peak titers (~$10^5$ PFU) in the nasal turbinates, a level similar to WT at 7 dpi (FIG. 3c), and had high levels of bioluminescence in the nasopharynx between 3 and 6 dpi (FIG. 3a).

IV. Tissue Tropism and Viral Dose

While lower inoculating doses of Sendai virus are known to reduce infection and pathology in the lungs, we are unaware of any published studies on the dose dependence of infection in the URT or trachea. Preliminary studies showed that the mouse infectious dose 50 ($MID_{50}$) for SeVc-luc(M-F*) was 9 PFU and that a 70-PFU dose resulted in 100% infection, similar to results obtained for WT Sendai virus in mice [Kiyotani et al. 1993, J Virol 67: 7618-7622] and hPIV1 in humans [Reichelderfer et al. 1958, Science 128: 779-780]. 129/SvJ mice were inoculated intranasally with 70, 700 or 7,000 PFU of SeVc-luc(M-F*) in equal 30 µl volumes and then measured bioluminescence and viral titers. Compared to a 7,000-PFU dose, 70 PFU-inoculation resulted in ~10-fold lower viral titers and bioluminescence in the lungs (FIGS. 4a,b) and lower weight loss (FIG. 4c). In contrast, infection in the nasopharynx and trachea after 70-PFU inoculation was only delayed ~1 d compared to 7,000-PFU, reaching a similar level by ~5 dpi (FIGS. 4a,b) and inducing relatively high titers of Sendai virus-specific antibodies ($>10^5$) (FIG. 4d). Thus, while it is not necessary to understand the mechanism of action, it is believed that low-dose inoculation of WT-like SeVc-luc(M-F*) resulted in infection biased to the URT and trachea, inducing a robust antibody response without causing severe pathogenicity.

V. Tissue Tropism and Host Genetics

Figure 4:
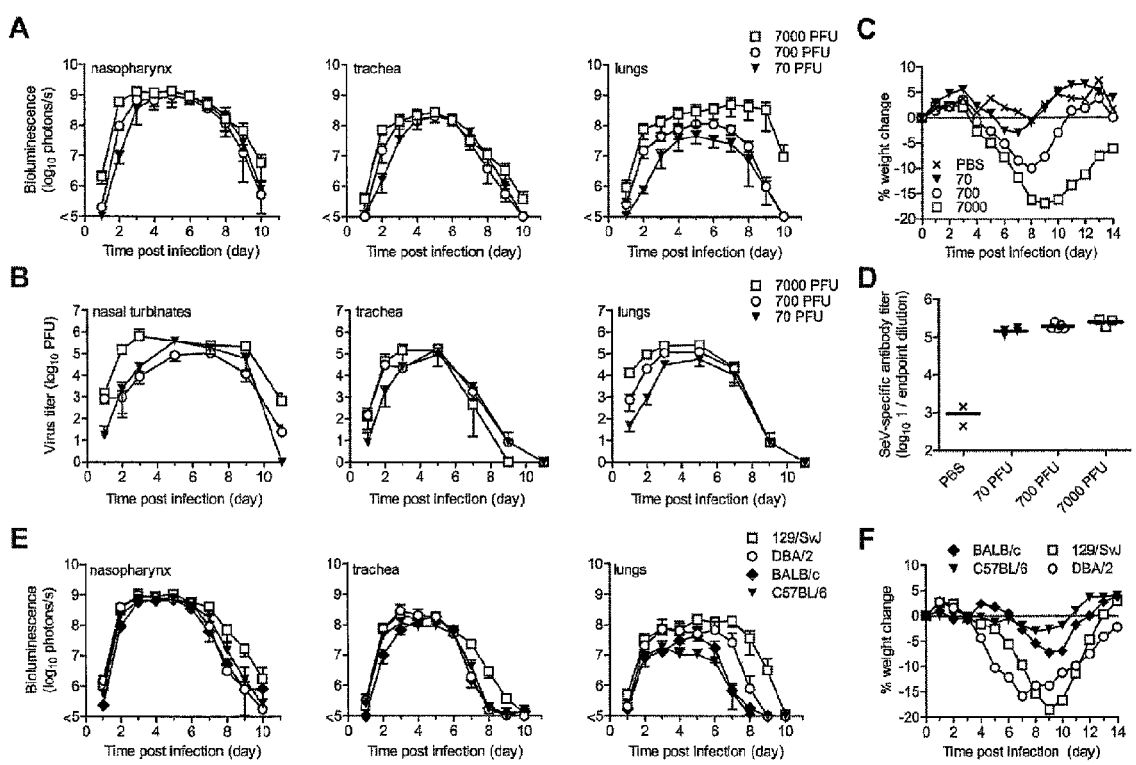
FIG. 4. Virus replication and pathogenesis as a function of virus dose and mouse strain. After intranasal inoculation of 129-strain mice with SeVc-luc(M-F*) at doses ranging from 70 to 7,000 PFU, the total flux of bioluminescence intensities (A) and viral titers (B) were measured as described in FIG. 3. (C) The percentages of body weight change were measured for groups of ten mice after infection of 70 to 7,000 PFU of SeVc-luc(M-F*) in 129-strain mice. The experiment was repeated and representative data is shown. (D) SeV-specific binding antibody titers in sera of 129-strain mice were collected 10 days after inoculation with 70 to 7,000 PFU of SeVc-luc(M-F*) and are reported as the reciprocal endpoint dilutions in ELISA assays. Five infected and two control mice were used in the experiment, which was performed twice. Representative data is shown. (E) The total flux of bioluminescence intensities present in the nasopharynx, trachea, and lungs after 7,000 PFU intranasal inoculation of 129-Sv, DBA/2, BALB/c, or C57BL/6-strain mice with SeVc-luc(M-F*). The averages are for six animals, the experiment was repeated and the results from a representative experiment are shown. (F) The percentages of body weight change were measured for groups of 10 mice after infection with 7,000 PFU of SeVc-luc(M-F*). The experiment was repeated and representative data is shown.

Various strains of recombinant inbred mice differ in their susceptibilities to lung infection by Sendai virus [Faisca et al. 2005, Am J Physiol Lung Cell Mol Physiol 289: L777-787; Brownstein, D G 1987, J Virol 61: 1670-1671; Brownstein et al. 1981, Am J Pathol 105: 156-163; and Brownstein et al. 1986, Lab Anim Sci 36: 126-129]. For example, 129/SvJ and DBA/2 mice are highly susceptible to lung infection and its resulting pathogenesis while BALB/c and C57BL/6 mice are highly resistant. How host genetics affects Sendai virus replication in the URT and trachea has not been previously reported. Therefore, the in vivo dynamics of Sendai virus infection was measured in 129/SvJ, DBA/2, C57BL/6, and BALB/c strains of mice intranasally inoculated with 7,000 PFU of SeVc-luc(M-F*). As expected from previous studies, the extent of infection in the lungs and weight loss correlated with each other and followed the trend C57BL/6<BALB/c<<DBA/2<129/SvJ (FIGS. 2 and 4). In contrast, the URT and trachea were highly permissive to Sendai virus infection, having similarly high levels of bioluminescence for all four strains of mice. Thus, the URT and trachea of BALB/c and C57BL/6 mice were highly permissive to Sendai virus infection despite genetic resistance in the lungs. While it is not necessary to understand the mechanism of action, it is believed that these results show that genetic susceptibility to Sendai virus infection is tissue specific and that reduced infection in the lungs is not due to lower infection in the URT or trachea. In subsequent experiments on transmission, light-coated BALB/c and 129/SvJ strains of mice were used. Therefore, Sendai virus titers in groups of sacrificed BALB/c mice were measured and found that the ex vivo titers correlate with bioluminescence in intact mice (FIG. 13a) just as they had for 129/SvJ mice. Compared to 129/SvJ mice, infection in the lungs of BALB/c mice was decreased at least 10-fold as measured by both bioluminescence (FIG. 4e) and viral titers (FIG. 13b-c). Consequently, the BALB/c mice had only very mild clinical symptoms, including very little weight loss (FIG. 4f). In contrast, nasopharyngeal infection in BALB/c mice reached a level similar to that in 129/SvJ mice by 3 dpi, as measured by both bioluminescence (FIG. 4e) and viral titer (FIG. 13b-c). Overall, it is believed that the bioluminescence imaging studies revealed three conditions in which robust infection in the URT and trachea was observed despite reduced infection in the lungs and little apparent weight loss: an attenuated virus, a low virus dose, and a resistant strain of mouse.

VI. Dynamics of Infection During Contact Transmission

Figure 5:
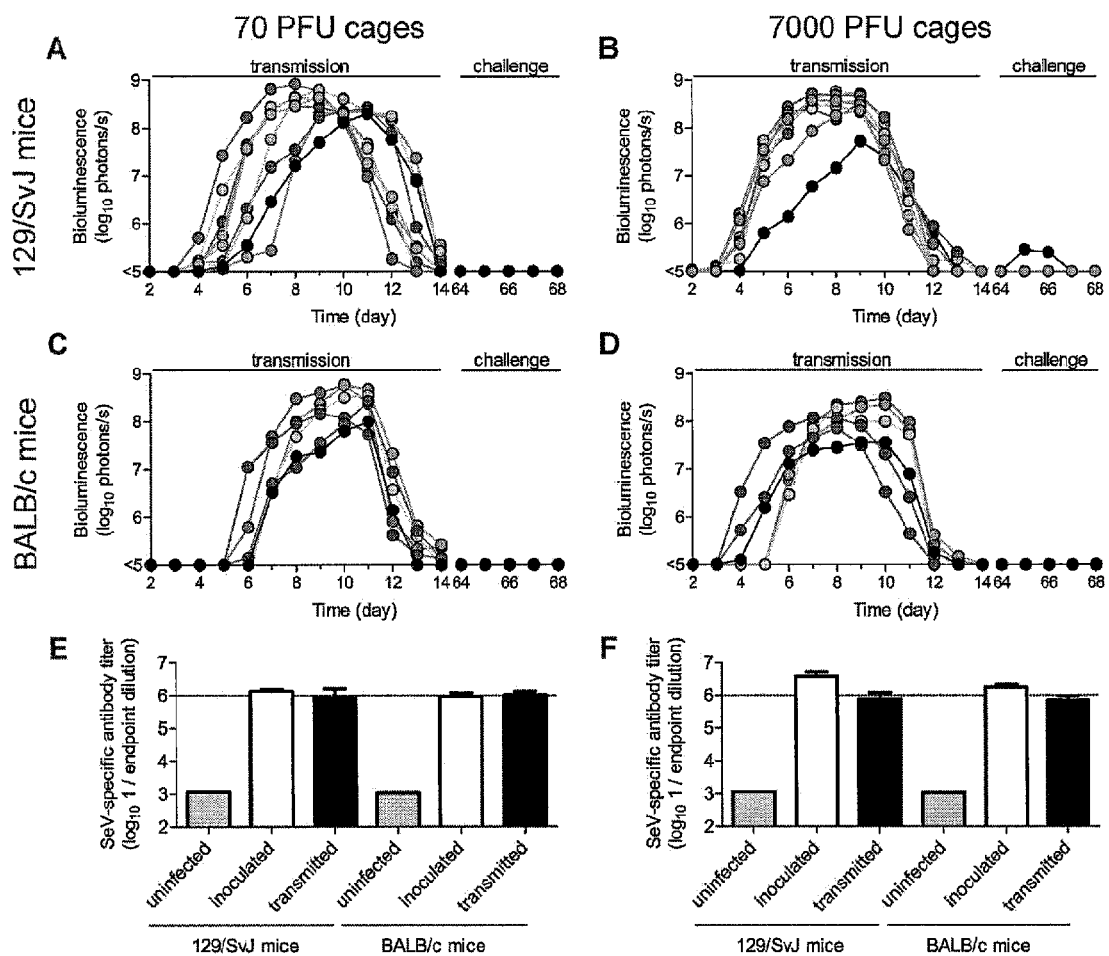
FIG. 5. SeV infection and immunity after contact transmission. One mouse per cage was directly inoculated with either 70 PFU (A,C,E) or 7,000 PFU (B,D,F) of SeVc-luc (M-F*) and then introduced into a cage with 3 naïve animals after one day. The total flux of bioluminescence intensities in the nasopharyngeal cavities of individual 129-strain (A-B) and BALB/c-strain (C-D) mice are shown. Serum was collected on day 60 and the contact mice were challenged with 7,000 PFU of SeVc-luc(M-F*) on day 63 so that potential re-infection could be monitored by bioluminescence. SeV-specific binding antibody titers were measured as reciprocal endpoint dilutions of sera collected on day 60 from mice co-housed with animals inoculated with 70 PFU (E) or 7,000 PFU (F). Open bars correspond to mice directly inoculated on day 0 and solid bars correspond to the contact mice. The experiment was performed in triplicate for 129-strain mice (3 donor animals and 9 transmitted) and duplicate for BALB/c-strain mice (2 donor animals and 6 transmitted).
Figure 6:
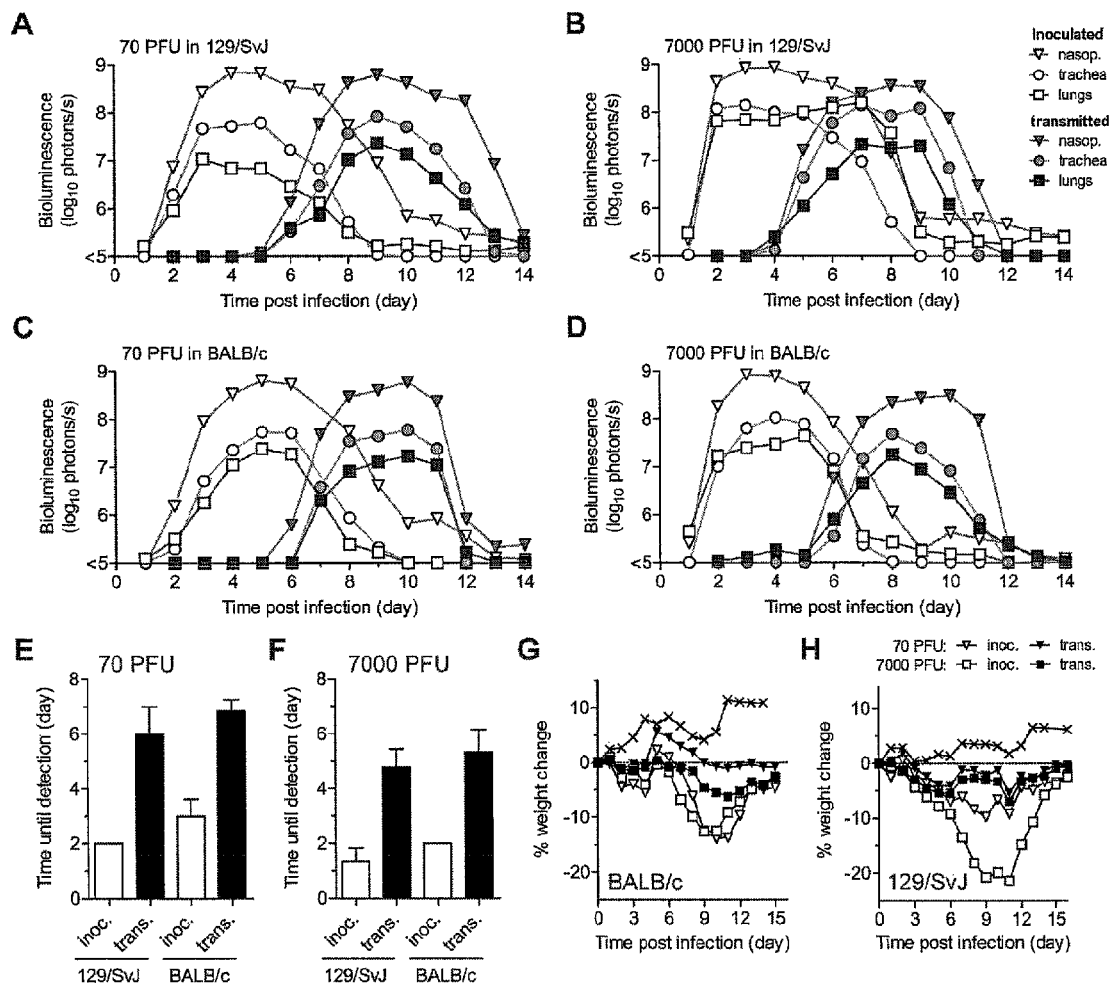
FIG. 6. Timing and tissue-tropic spread of SeV infection after contact transmission. The co-housing of contact mice with mice inoculated with SeVc-luc(M-F*) is described in FIG. 5. The total flux of bioluminescence intensities in individual, representative 129-strain (A-B) and BALB/c-strain (C-D) mice are shown for the nasopharynx (triangles), trachea (circles), and lungs (squares). Time until detection of bioluminescence in the nasopharynx (limit of detection: >6 log$_{10}$ photons/s) after inoculation of donors with either 70 PFU (E) or 7,000 PFU (F). Average percent weight change in BALB/c (G) and 129/SvJ mice (H). The contact transmission experiment was performed in triplicate for 129/SvJ mice and in duplicate for BALB/c mice. Open symbols and bars correspond to directly inoculated mice and solid symbols and bars correspond to the contact mice. In panels g and h, the symbol X corresponds to uninfected, PBS-inoculated control mice.

Infection control requires an understanding of how pathogens are transmitted. Sendai virus, the hPIVs, and hRSV are known to transmit primarily via contact with respiratory secretions as opposed to long-range transmission of small-particle aerosols [Iida, T. 1972, J Gen Virol 14: 69-75; van der Veen et al. 1970, Arch Gesamte Virusforsch 31: 237-246; Henrickson, K. J. 2003, Clin Microbiol Rev 16: 242-264; Hall et al. 1981, J Pediatr 99: 100-103; and McLean et al. 1967, Can Med Assoc J 96: 1449-1453]. It is also known that growth of Sendai virus [Iida, T. 1972, J Gen Virol 14: 69-75] and influenza virus [Lowen et al. 2007, PLoS Pathog 3: 1470-1476] in the URT promotes transmission. Two longstanding, fundamental questions about PIV transmission that remained unknown were (i) how growth of virus in the lungs of donors influences transmission and (ii) what factors determine the timing of transmission and the tissue-specific spread of infection after transmission. To address these fundamental questions about PIV transmission, BALB/c or 129/SvJ donor mice were inoculated with 70 or 7,000 PFU of SeVc-luc(M-F*) and then placed 3 naïve contact mice in a cage with 1 donor mouse at 1 dpi. Bioluminescence was measured daily in inoculated and contact mice until primary infection cleared, collected sera on day 60, challenged the mice with 7,000 PFU of SeVc-luc(M-F*) on day 63, and then imaged the mice daily for reinfection (FIG. 5). It is believed that transmission to every naïve contact mouse was observed by nasopharyngeal bioluminescence and seroconversion, even for resistant BALB/c mice exposed to donor animals inoculated at the lower dose. The timing of transmission was not influenced by the extent of lung infection in donors as lung titers were ~10-fold lower in BALB/c versus 129/SvJ donor mice after 7,000-PFU inoculation (FIG. 13c) yet the transmission times (difference in time until detection in inoculated versus transmitted animals) were a similar 3.3 and 3.4 days, respectively (FIG. 6f). LRT infection occurred in both strains of mice and may contribute to transmission. Regardless, the primary determinant of transmission appeared to be virus shedding in the URT and trachea. For example, high-titer (>$10^5$ PFU) shedding in the nasal cavities and trachea of 129/SvJ donor mice (FIGS. 4a,b) and contact transmission (FIGS. 6e,f) both occurred ~1 day earlier after 7,000-PFU inoculation compared to 70-PFU. Overall, while it is not necessary to understand the mechanism of action, it is believed these results demonstrate how animals that suffer little apparent weight loss are able to promote efficient transmission of Sendai virus Enders strain.

In order to investigate the magnitude of Sendai virus infection after transmission, previous studies measured ex vivo titers in groups of contact mice sacrificed different times after exposure to infected cagemates [Iida, T. 1972, J Gen Virol 14: 69-75 and van der Veen et al. 1970, Arch Gesamte Virusforsch 31: 237-246]. These classical studies yielded highly ambiguous results in which titers varied 100-fold from day to day and the progression of infection in the respiratory tract after transmission was not clear. Therefore, non-invasive bioluminescence imaging was used to measure for the first time the temporal and spatial spread of PIV infection throughout the respiratory tract in individual, living mice after transmission. The inoculated dose was varied in donors and the mouse strain so that viral and host determinants of transmission could be investigated. Under all four conditions tested (129/SvJ or BALB/c mice infected at 70 or 7,000 PFU), the tropism and magnitude of infection in contact animals after transmission was similar to that observed after direct inoculation with a 70-PFU dose of SeVc-luc(M-F*) delivered intranasally. After transmission, bioluminescence was first observed in the nasopharynx and then spread to the trachea and lungs an average of 0.8 and 1.0 days later, respectively (FIG. 14a-d). Robust infection was observed in the nasopharynx and trachea (FIG. 6a-d, FIG. 14e-h), and low levels of lung infection were consistent with little weight loss after transmission (FIG. 6g-h). For all four groups of mice, Sendai virus-specific antibody titers on day 60 were similarly high (~$10^6$) and the animals were universally protected during challenge on day 63 (FIG. 5). After challenge a low level of bioluminescence (<$10^6$ photons/s), but no weight loss, was detected in only 1 contact mouse out of 30, the animal with the lowest level of bioluminescence after primary infection on days 5-12 (FIG. 5b, solid black circles). As this individual animal also had the lowest level of Sendai virus-specific antibodies at day 60 before challenge, a threshold level of infection may be required for protective immunity Overall, while it is not necessary to understand the mechanism of action, it is believed that Sendai virus infection after transmission was observed to be robust enough in the URT and trachea, yet limited enough in the lungs, to induce protective immunity without causing significant weight loss in the matched murine host that is susceptible to Sendai virus infection.

E. Discussion

The current embodiments provide the generation and use of luciferase-reporter viruses to study for the first time the kinetics of PIV infection in living mice after direct inoculation and after contact transmission. Compared to WT Sendai virus, the luciferase-expressing virus SeVc-luc(M-F*) had a similar replication rate in vivo and elicited similar levels of weight loss, mortality, lymphocyte influx in BALF, and serum antibody titers. Both susceptible (129/Sv) and resistant (BALB/c) strains of mice were intranasally infected with 70- and 7,000 PFU doses of SeVc-luc(M-F*), and the spread of infection was measured by both bioluminescence in intact mice and ex vivo virus titers from sacrificed animals. The consequences of infection in the URT and trachea were found to be distinct from infection in the lungs. Unexpectedly, under all conditions tested including 70 PFU inoculation in resistant BALB/c mice, the URT and trachea supported robust Sendai virus growth, efficient contact transmission, and protective immunity independent of the extents of infection in the lungs. In contrast, the extent of infection in the lungs varied by virus dose and mouse strain and also correlated highly with weight loss and mortality. Overall, the results reported here reveal a tissue-specific dichotomy in the respiratory tract in which asymptomatic infection in the URT and trachea supports efficient transmission while the extent of infection and host response in the lungs determines clinical outcome.

While it is not necessary to understand the mechanism of action, the present invention contemplates for the first time the development of a non-invasive, bioluminescence imaging system to visualize infection throughout living animals by a negative-strand RNA virus, using the prototypic respiratory paramyxovirus Sendai virus. The development of a non-attenuated paramyxovirus that expresses high enough levels of a reporter gene for non-invasive imaging in small animals has been a challenge because these non-segmented negative-strand RNA viruses have a polarized transcription mechanism [Lamb et al. 2007, Paramyxoviridae: The Viruses and Their Replication. $5^{th}$ Ed. pp. 1449-1496]. A significant advance described here is the generation of the SeVc-luc(M-F*) virus in which the expected attenuating effects of reporter-gene insertion [Tokusumi et al. 2002, Virus Res 86: 33-38] are counteracted by enhancement of the naturally occurring, suboptimal gene-start sequence upstream of the F gene [Kato et al. 1999, J Virol 73: 9237-9246]. Expression of the F gene, a virulence factor [Anderson et al. 2008, J Virol 82: 10510-10518 and Luque et al. 2010, J Virol 84: 810-821], is also downregulated by hPIV 1 [Bousse et al. 2002, J Virol 76: 8244-8251], hPIV3 [Spriggs et al. 1986, J Virol 59: 646-654], PIV5 [Rassa et al. 1998, Virology 247: 274-286], measles virus [Cattaneo et al. 1987, Virology 160: 523-526] and canine distemper virus (CDV) [Anderson et al. 2008, J Virol 82: 10510-10518] by readthrough transcription or long untranslated regions.

Thus, for example only and not meant to be limiting, the present invention embodiments contemplate that other WT-like reporter paramyxoviruses that express high levels of luciferase could be engineered by inserting the reporter gene into the M-F junction and maintaining F gene expression through compensating mutations. Reporter gene expression without attenuation of Sendai virus has also been achieved by construction of a bicistronic gene that contains an internal ribosome entry site [Touzelet et al. 2009, Virus Res 140: 40-48], although it is not yet clear if this alternative approach yields sufficient luciferase expression for non-invasive imaging of in vivo infection. Insertion of an enhanced green fluorescent protein (eGFP) reporter gene downstream in the H-L junction of a non-attenuated CDV has enabled ex vivo imaging of paramyxovirus dissemination in dissected ferret tissues [Rudd et al. 2006, J Virol 80: 9361-9370 and von Messling et al. 2004, Proc Natl Acad Sci USA 101: 14216-14221]. However, insertion of a luciferase reporter gene near the 5' end of the genome to avoid attenuation is expected to result in relatively low levels of reporter gene expression, limiting the sensitivity of non-invasive imaging techniques as was observed here with the SeVc-luc(F-HN) reporter virus.

While it is not necessary to understand the mechanism of action, it is believed that the use of the luciferase reporter gene in the present work enabled the measurement of infection throughout the entire respiratory tracts of intact animals such that the spread and clearance of infection could be measured after direct inoculation or transmission. Thus it is expected that an alternate form of this Sendai virus vector could be constructed in which a different reporter gene is used including, but not limited to, a fluorescent protein such as eGFP. eGFP-expressing reporter viruses have been also used to study the dynamics of CDV infection in ferrets [Rudd et al. 2006, J Virol 80: 9361-9370 and von Messling et al. 2004, Proc Natl Acad Sci USA 101: 14216-14221] and measles virus infection in monkeys [Lemon et al. 2011, PLoS Pathog 7: e1001263 and de Swart et al. 2007, PLoS Pathog 3: e178]. It is contemplated that an advantage of the eGFP reporter gene is that the tropism of infection in dissected tissues can be studied on a cellular level. Moreover, eGFP-expressing viruses can also be used to quantify and type infected cells in peripheral blood, the skin, and mouths of living animals. eGFP-expressing hPIV3 and SeVs have been used to study the cellular tropism of PIV infection in well differentiated, primary epithelial cultures. In the case of hPIV3, infection was found to be restricted to ciliated epithelial cells and cause little cytopathology [Zhang et al. 2005, J Virol 79: 1113-1124]. In contrast, Sendai virus was found to infect ciliated and non-ciliated cells, but not goblet cells, and was observed to induce ciliostasis, cell sloughing, apoptosis, and cellular degeneration [Villenave et al. 2010, J Virol 84: 11718-11728]. It is unknown if cell-free virus or cell-associated virus is associated with Sendai virus transmission.

Surprisingly, the URT was found here to be highly permissive to Sendai virus infection even under conditions known to limit infection in the lungs: after a low virus dose, for an attenuated virus, and in resistant mouse strains. Intranasal inoculation of RSV in human subjects has also recently been shown to result in equally high peak nasal titers for viral doses that span a 100-fold range [Devincenzo et al. 2010, Am J Respir Crit. Care Med 182: 1305-1314]. Of course, after natural transmission of RSV or hPIVs in humans, high inoculating doses of virus in the lungs may play a role in the development of severe disease, as was observed here for high-dose inoculation of Sendai virus in mice.

Therefore, while it is not necessary to understand the mechanism of action, the present invention embodiments contemplate that Sendai virus is a promising Jennerian vaccine against hPIV1 [Karron et al. 2007, Parainfluenza Viruses. 5th Ed. pp 1497-1526 and Takimoto et al. 2005, Viral Immunol 18: 255-266], and recombinant Sendai virus vaccine vectors containing an envelope gene from RSV, hPIV3 or hPIV2 inserted into the F-HN gene junction have been shown to elicit both B- and T-cell responses that lead to protection from challenge in small-animal models [Jones et al. 2009, Vaccine 27: 1848-1857; Zhan et al. 2007, Vaccine 25: 8782-8793; and Zhan et al. 2008, Vaccine 26: 3480-3488]. While Sendai virus is pathogenic in mice, an ongoing clinical trial has demonstrated Sendai virus to be well tolerated in humans [Slobod et al. 2004, Vaccine 22: 3182-3186]. In non-human primates, Sendai virus has been shown to protect against hPIV1 challenge with no associated adverse events [Hurwitz et al. 1997, Vaccine 15: 533-540 and Skiadopoulos et al. 2002, Virology 297: 153-160]. The results are likely due in part to the sensitivity of Sendai virus to human IFN-mediated innate immunity [Bousse et al. 2006, Virus Res 121: 23-32]. Moreover, embodiments of the present invention also contemplate that as Sendai virus is developed further as a vaccine vector, the luciferase-expressing SeVs and imaging system developed here will be useful in investigating how the vaccine dose, volume, and position of foreign antigen insertion in the Sendai virus genome influence tissue-specific vector growth and the immune response in small animal models. Replacing the luciferase reporter gene in Sendai virus with a vaccine antigen could alter in vivo replication of the vector. For example, three different recombinant hPIV3 vectors expressing hPIV1 HN, hPIV2 HN, or measles virus HA inserted into the P-M gene junction were found to replicate to different levels in hamsters [Skiadopoulos et al. 2002, Virology 297: 136-152].

While it is not necessary to understand the mechanism of action, it is believed that another novel finding here was that the efficiency and timing of Sendai virus transmission occurred independent of the extent of pulmonary infection, clinical symptoms, and host genetics. hPIV1 transmission from asymptomatic human donors has also been observed in an experimental setting [Reichelderfer et al. 1958, Science 128: 779-780] and is consistent with epidemiological observations for PIV outbreaks in general [Hall, C B 2001, N Engl J Med 344: 1917-1928 and Henrickson, K J 2003, Clin Microbiol Rev 16: 242-264]. These observations suggest that LRT infection and the severity of clinical symptoms would be poor predictors of transmission potential for surveillance and infection control efforts. Consistent with previous work [Iida, T. 1972, J Gen Virol 14: 69-75 and Kiyotani et al. 1993, J Virol 67: 7618-7622], it was observed that Sendai virus transmission coincides with high-titer virus growth in the URT and is remarkably efficient because of the high infectivity of the virus (e.g., the $MID_{50}$ of Sendai virus is <10 PFU). hPIV1, hPIV3 and hRSV are similarly highly infectious and also transmit predominantly by direct contact or indirect exposure to nasal secretions [Hall et al. 1981, J Pediatr 99: 100-103; McLean et al. 1967, Can Med Assoc J 96: 1449-1453; Hall et al. 1981, Infect Immun 33: 779-783; Parrott et al. 1975, Dev Biol Stand 28: 389-399; and Tyrrell et al. 1959, Br Med J 2: 909-911]. While it is not necessary to understand the mechanism of action, in the absence of an available prophylactic drug for uninfected individuals in high-risk groups (e.g., premature infants and the immunocompromised), it is believed that the results described here suggest that infection control of PIV would be best focused on reducing URT shedding from infected individuals, disinfecting contaminated surfaces, and hand washing. In contrast to infection control, which would be best served by limiting URT infection, therapeutic antivirals would be better targeted to the LRT to control clinical manifestations of PIV-associated disease.

Genetic factors have been identified that modulate viral susceptibility and disease severity in humans [Stephens, H A 2010, Curr Top Microbiol Immunol 338: 99-114; Zhang et al. 2009, Infect Genet Evol 9: 1148-1157; and Arkwright et al. 2008, Curr Opin Infect Dis 21: 217-222] and in the lungs of mice [Faisca et al. 2005, Am J Physiol Lung Cell Mol Physiol 289: L777-787; Brownstein, DG 1987, J Virol 61: 1670-1671; Brownstein et al. 1986, Lab Anim Sci 36: 126-129; Simon et al. 2009, Infect Genet Evol 9: 1253-1259; Boon et al.2009, J Virol 83: 10417-10426; Anh et al. 2006, Am J Physiol Lung Cell Mol Physiol 291: L426-435; Itoh et al. 1991, J Vet Med Sci 53: 275-279; and Stark et al. 2002, J Med Virol 67: 92-100]. While it is not necessary to understand the mechanism of action, it is believed the present results show for the first time that genetic factors limiting virus growth in the lungs of resistant BALB/c mice, compared to susceptible 129/Sv mice, do not limit robust virus growth in the URT and trachea and, consequently, do not limit transmission. Furthermore, similarly high extents of infection in the URT and trachea and low levels of infection in the lungs were observed after transmission whether BALB/c or 129/Sv mice were exposed to cagemates inoculated at high or low viral doses. While it is not necessary to understand the mechanism of action, it is believed this shows host genetics do not play a major role in PIV transmission, at least for these strains of mice. These observations reinforce the notion presented here that transmission and pathogenesis are independent consequences of URT versus LRT infection, respectively, and may be most effectively countered by tissue-specific strategies. Additional experiments are needed to delineate mechanisms responsible for the high permissivity of the URT and trachea to Sendai virus infection compared to the lungs. While it is not necessary to understand the mechanism of action, it is contemplated that potential mechanisms include the site of inoculation in the nasal cavity, lower temperature in the URT, tissue-specific differences in virus replication and innate immunity, and antiviral mechanisms in the lungs such as the presence of surfactant proteins. One potential contributing factor to reduced replication in the lungs may be lower levels of secreted tryptase Clara, which is required for cleavage of the F protein from an inactivate precursor so that viral entry may occur [Kido et al. 1992, J Biol Chem 267: 13573-13579 and Tashiro et al. 1992, J Virol 66: 7211-7216].

Asymptomatic infection that promotes immunity and transmission represents a balanced relationship that benefits both virus and host. Such has been the case for several enzootic (clinically unapparent) epidemics of Sendai virus in which subclinical infections were maintained in mouse and hamster colonies for years without evolving increased pathogenicity and only occasionally causing apparent disease in suckling and old animals [Profeta et al. 1969, Am J Epidemiol 89: 316-324 and Zurcher et al. 1977, Lab Anim Sci 27: 955-962]. Such epidemiological observations are reminiscent of the low virulence yet high transmissibility of the reverse-genetics engineered Sendai virus described here, which was derived from the Enders strain that had been attenuated through numerous rounds of passage in embryonated chicken eggs and contained modifications to the L gene. While it is not necessary to understand the mechanism of action, it is believed results reported here for the Enders-based strain show that increased shedding of virus in the lungs increases neither the transmission time nor the transmission efficiency, thus there may be no selective advantage for increased Sendai virus replication in the lungs. Instead, the following mechanism for symbiotic virus-host interplay in enzootic epidemics of Sendai virus is suggested: natural infection after transmission is limited enough in the lungs to avoid clinical signs of disease yet robust enough in the nasopharynx and trachea to promote efficient transmission and induce protective immunity.

Epizootic (clinically apparent) outbreaks of Sendai virus have also occurred that caused morbidity and high rates of mortality in mouse colonies [Bhatt et al. 1974, Am J Epidemiol 100: 222-229; Ishida et al. 1978, Adv Virus Res 23: 349-383; and Nakagawa et al. 1980, Nippon Juigaku Zasshi 42: 337-344]. Two closely related, highly pathogenic field isolates of Sendai virus are the Ohita and Hamamatsu strains [Sakaguchi et al. 1994, Arch Virol 135: 159-164 and Itoh et al. 1997, J Gen Virol 78 (Pt 12): 3207-3215]. While inoculation with only a few PFU of unpassaged Hamamatsu strain Sendai virus results in mortality in mice, after 50 passages in eggs the virus was attenuated by as much as 400-fold in $MLD_{50}$ [Kiyotani et al. 2001, Arch Virol 146: 893-908]. Adaptations of the highly pathogenic Ohita and Hamamatsu strains to LLC-MK2 cells and chicken eggs were found to have selected for mutations in the C protein and untranslated leader region, respectively, that increase replication in culture cells but attenuate replication and pathogenesis in the lungs of mice [Garcin et al. 1997, Virology 238: 424-431; Fujii et al. 2002, J Virol 76: 8540-8547; and Sakaguchi et al. 2003, Virology 313: 581-587]. While it is not necessary to understand the mechanism of action, it is believed that, the bioluminescence imaging system described here would be useful in determining if the mutations that attenuate replication in the lungs also attenuate replication in the URT and trachea, thereby reducing transmission, or if the attenuating mutations actually promote sustained transmission by supporting nasal and tracheal shedding of virus while reducing pathogenesis in the lungs. Such experiments may also reveal if the observations on Sendai virus spread and transmission reported here for the attenuated, egg-adapted Enders strain extend to unpassaged, highly pathogenic field isolates.

In summary, while it is not necessary to understand the mechanism of action, it is believed that the development of the non-attenuated reporter virus SeVc-luc(M-F*) has been described, which can be used to quantify tissue-specific infection in living mice, and a candidate vaccine vector SeVc-luc(P-M), which replicates preferentially in the URT. While it is not necessary to understand the mechanism of action, it is contemplated that the results reveal how infection by Sendai virus Enders strain spreads in individual, living animals after direct inoculation and after transmission. A major novel finding was an apparent phenotypic dichotomy of infection in the URT and trachea in comparison to the lungs that results in an observed decoupling of pathogenesis and transmission. While it is not necessary to understand the mechanism of action, it is believed the imaging tools developed here will provide a method to study how the dynamics of infection and transmission are determined by viral factors, host genetics, host age, immune status, environmental conditions, and inoculation mode. For example only and not meant to be limiting, infection can be tracked non-invasively in WT and knockout mice before ex vivo immune responses are measured and then understood in terms of the preceding infection. A similar strategy could also be developed to image infection by other paramyxoviruses in small-animal models. While it is not necessary to understand the mechanism of action, overall, the present invention embodiments contemplate the model system and results, that suggest tissue-targeted approaches to PIV infection control and vaccine development, and the non-invasive bioluminescence imaging technique is expected to assist in preclinical testing of vaccine candidates and antiviral therapeutics.

III. Utilities

Thus in one embodiment the invention contemplates a candidate Sendai virus vector comprising an Enders L gene with substituted amino acids, that can be used as a non-recombinant vector or as a recombinant vector to express any gene, or more than one gene, in any position. In another embodiment the invention contemplates a candidate Sendai virus vaccine vector that is an Enders/Z chimera such as that with a modified Enders/Z L gene, capable of expressing either the RSV F or G gene in the F-HN position of the Sendai virus genome.

In yet another embodiment the foreign gene might be placed in the P-M intergenic junction. Moreover, in other embodiments the foreign gene contemplated by the invention includes a gene or genes from hPIV type 1-4 wherein said gene(s) is inserted in between the P-M and/or F-FIN genes. Further, in other embodiments, the invention also contemplates vaccine candidates with one or more foreign genes from more than one source inserted in one or more intergenic positions such that one or more targeted diseases might be acted upon at one time to elicit a targeted immune response.

While it is not necessary to understand the mechanism of action, it is contemplated that a modified non-recombinant or recombinant SeV vaccine vector may encompass a modified L gene containing the following amino acid substitutions: S155G, R258K, G466E, G482E, S581R, Q717R, T800I, and R852K. Moreover, in a further embodiment the invention contemplates a visual means of tracking infection by use of bioluminescence. The instant disclosure contemplates a system comprising a luciferase vector that is capable of imaging the progression of virus and associated pathogenic disease within a living animal with the ability to investigate candidate vaccine vectors for utility in protecting against targeted diseases. Moreover, in some embodiments, the invention contemplates host cells for expression of viral proteins. In one example, and not meant to be limiting, the expressed viral proteins might be used as an immunogen for eliciting an immune response from a subject against a targeted pathogen or multiple targeted pathogens. For example only and not meant to be limiting, host cells include LLC-MK2 cells (See FIG. 1).

In other embodiments, the present invention contemplates therapeutic and/or diagnostic uses. While it is not necessary to understand the mechanism of action, in some embodiments, the present invention contemplates generation of antibodies for use against the modified virus, modified viral proteins, including fragments, analogs, homologs, peptides, and/or combinations thereof. Such antibodies could be utilized for example within a diagnostic immunoassay such as an ELISA, RIA, and Immunoprecipitation among others for identification/diagnosis of infection and/or disease. Generation of antibodies is known by those of skill in the art. Further, lab procedures/guidance can be found in Antibodies: A Laboratory Manual by Harlow et al. (1988); Using Antibodies: A Laboratory Manual by Harlow et al. (1999); Köhler, G.; Milstein, C. (1975). "Continuous cultures of fused cells secreting antibody of predefined specificity". Nature 256 (5517): 495.

Moreover, in some embodiments, the present invention contemplates use of generated antibodies as a therapeutic for treatment against targeted pathogens including use of the antibodies for delivery of secondary drugs, toxins, among others. Furthermore, it is contemplated that viral proteins can be used for vaccine against virus. Numerous vaccine formulations are known to those skilled in the art. Vaccines can be administered alone or in combination with various adjuvants/carriers. Pharmaceutical carriers are known to those skilled in the art. These most typically would be standard carriers for administration of vaccines to humans, including solutions such as sterile water, saline, and buffered solutions at physiological pH. Other ingredients include excipients, carriers, thickeners, diluents, buffers, preservatives, and surface active.

In other embodiments, while it is not necessary to understand the mechanism of action, the present invention contemplates use of the SeVc backbone alone or in combination with other genes of interest for use as a vaccine, a research tool, a diagnostic tool, a imaging tool, and includes any other similar, equivalent, related uses by one of skill in the art.

EXPERIMENTAL

The following examples serve to illustrate certain preferred embodiments and aspects of the present invention and are not to be construed as limiting the scope thereof.

Example I

Cell culture

Monolayer cultures of LLC-MK2 cells were grown in Dulbecco's minimal essential medium (DMEM) supplemented with 10% fetal bovine serum, 1% L-glutamine, 1% penicillin, and 1% streptomycin at 37° C.+5% $CO_2$.

Example II

Recombinant Sendai Viruses

Unique NotI recognition sites were cloned into the P-M, M-F and F-HN intergenic junctions of an Enders-based pSeV viral genome plasmid, using cloning sites described previously [Tokusumi et al. 2002, Virus Res 86: 33-38]. The firefly luciferase gene was amplified by PCR using the pGL3 Basic vector (Promega) and a pair of AscI tagged primers, subcloned into a shuttle plasmid containing a Sendai virus intergenic junction and flanking NotI restriction sites [Tokusumi et al. 2002, Virus Res 86: 33-38] and then subcloned into the unique NoI site of each of the pSeV viral genome plasmids. Within the pSeV-luc(M-F) plasmid, the start signal upstream of the F protein was changed from AGGGATAAAG (SEQ. ID. NO.: 19) to AGGGTGAAAG (SEQ. ID. NO.: 20) using QuikChange™ Site-Directed Mutagenesis Kit (Stratagene Corp). The recombinant SeVs were rescued from the pSeV genome plasmids as described previously [Zhan et al. 2008, Vaccine 26: 3480-3488]. The modified Enders strain Sendai genome consists of a modified Sendai virus L gene that contains the following amino acid changes: S to G at position 155, R to K at position 258, G to E at position 466, G to E at position 482, S to R at position 581, Q to R at position 717, T to I at position 800, and R to K at position 852.

Example III

Luciferase Expression in vitro

SeV-infected LLC-MK2 cells (MOI 5 PFU/cell) were incubated at 33° C.+5% $CO_2$ and lysates collected at various times p.i. Luciferase assays were performed using the Luciferase Assay System (Promega) and the levels of expression measured using an automated luminometer (Turner Biosystems, Inc.) as described previously [Luque et al. 2007, J Virol 81: 3130-3141].

Example IV

Viral Titers and Bioluminescence Imaging

Virus titers from multistep growth curves (MOI of 0.01 PFU/cell) and homogenized tissues were determined by plaque titration in LLC-MK2 cells as described previously [Luque et al. 2010, J Virol 84: 810-821]. Eight week-old female 129×1/SvJ mice or BALB/c mice (Jackson Laboratories) were anesthetized using isoflurane (Baxter Health Care Corporation) and inoculated intranasally (i.n.) with 30 µl of PBS or virus. For FIGS. 1D, 1E, 2, 3, 4E, 4F, and 12, at 3 d before inoculation with PBS or virus, mice were anesthetized by IP injection of 300 µl avertin (300 mg/kg concentration) and chest hair was removed by shaving and application of a depilatory cream, Animals were monitored daily for weight loss, morbidity and mortality. Prior to imaging, mice were injected intraperitoneally with luciferin (Xenogen Corp) at a dose of 150 mg/kg of body weight and anesthetized with isoflurane for 5 min. In vivo images were acquired with the IVIS CCD camera system (Caliper Life Sciences) and analyzed with Living Image 3.2 software (Caliper Life Sciences) using an exposure of 60 s, 30 s, or 5 s (binning of 4 and an f/stop of 1). Pseudocolor images (representative of bioluminescence) of mice are displayed using a binning of 4 on a colorimetric scale ranging from $1 \times 10^6$ to $1 \times 10^9$ surface radiance (photons/s/cm$^2$/steradian), which is defined as the number of photons that leave a cm$^2$ of tissue and radiate into a solid angle of one steradian. To quantify bioluminescence, regions of interest (ROI) were defined manually and graphed data are expressed as total flux (photons/s), which is defined as the radiance in each pixel summed over the ROI area (cm$^2$)×4π. All animal studies were approved by the Animal Care and Use Committee of St. Jude Children's Research Hospital and were performed in compliance with relevant institutional policies, the Association for the Accreditation of Laboratory Animal Care guidelines, the National Institutes of Health regulations and local, state and federal laws.

Example V

Immunology

Sera and BALF were collected from euthanized animals on day 10 or day 60 p.i. BALF samples (3 nil) were centrifuged to collect cellular material and plated in a tissue culture dish for 1 h at 37° C. to remove adherent cells. Suspension cells were harvested, total lymphocytes were counted microscopically, and red blood cells were lysed. For flow cytometric analyses, cells were stained with FITC-conjugated anti-CD4 (RM4-4) and PE-conjugated anti-CD8b (53-5.8) antibodies (BD Biosciences Pharmingen). Lymphocytes were gated based on forward and side scatter, and the percentages of CD4+ and CD8+ T cell populations were measured within this gate. ELISAs were used to measure the levels of Sendai virus-specific or luciferase-specific antibodies present in the sera. Briefly, 96-well plates were coated overnight with disrupted, purified Sendai virus (10 µg/ml) or firefly luciferase (1 µg/ml, Abeam). Plates were blocked with PBS containing 1% BSA and then incubated with 10-fold serially diluted serum samples. After incubation, plates are washed, incubated with HRP-Goat anti mouse IgG (Southern Biotechnologies) and then washed further. To quantify levels of antibodies, TMB substrate (Kirkegaard and Perry Laboratories) was added to the wells followed by stop solution and absorbance was read at a wavelength of 450 nm. GraphPad Prism non-linear regression software was used to calculate antibody titers.

Example VI

Contact Transmission

Donor animals were inoculated intranasally with 30 µL of SeVc-luc(M-F*) and were individually placed into cages containing 3 naïve contact mice at 24 h p.i. Bioluminescence was monitored daily until levels of luminescence were consistently at background levels (~15 days). Sera were collected on day 60 so that Sendai virus-specific antibody levels could be measured as described above. On day 63, mice were challenged with 7000 PFU SeVc-luc(M-F*) administered intranasally and bioluminescence was measured daily.

Example VII

In vitro Expression of Sendai Virus Proteins

Viral protein expression levels were analyzed by radioimmunoprecipitation as previously reported [Luque et al. 2007, J Virol 81: 3130-3141 and Luque et al. 2010, J Virol 84: 810-821]. Briefly, LLC-MK2 cells were infected at an MOI of 5 PFU/cell, labeled with 50 µCi [$^{35}$S]Promix (Amersham Pharmacia Biotech), lysed with ice-cold RIPA buffer and clarified by centrifugation. Supernatant was incubated overnight at 4° C. with mouse anti-NP, P, M, F, and HN monoclonal antibodies, and immune complexes were adsorbed to protein G-Sepharose (GE Healthcare) before fractionation on 12% NuPAGE bis-Tris SDS-PAGE gels (Invitrogen) and visualization as described previously [Luque et al. 2010, J Virol 84: 810-821].

Example VIII

Sendai Virus Composition

The allantoic cavities of 10-day-old embryonated hen eggs were inoculated with viruses. Allantoic fluid was harvested 72 hpi and centrifuged 45 min at 3000 rpm to remove cellular debris. Supernatants were layered over a 60-20% sucrose gradient and centrifuged at 24,000 rpm for 3.5 hrs to isolate virions. Isolated virions were diluted in TNE buffer and further purified over a 20% sucrose cushion by centrifugation at 24,000 rpm for 15 hrs. Virus pellets were resuspended in RIPA buffer and total protein concentrations were determined using the BCA protein assay kit (Thermo Sci.). Equal protein levels were run on a 4-12% SDS-PAGE gel, the gel was stained using the Blue BAN-Dit™ protein stain (Amresco), and then dried with a BioRad gel dryer at 60° C. for 45 minutes.

Example IX

In vivo Infection and Transmission

The measurement of T-lymphocyte influx in BALF for CD4+ and CD8+ T-cells is described in the main text. Luciferase-specific ELISAs were performed essentially as Sendai virus-specific ELISAs as described in the main text except using firefly luciferase protein (Abeam) was used to coat 96-well plates. Bioluminescence imaging and viral titer determinations from dissected tissues are also described in the main text. In contact transmission experiments, the time until detection was measured as the first day bioluminescence >$10^6$ log$_{10}$ photons/s was recorded. Bioluminescence areas under the curve (AUC) were calculated by integrating bioluminescence intensities with respect to time using Igor Pro software (Wavemetrics).

Example X

In vitro Properties of Luciferase-expressing Viruses

To develop a model in which PIV infection could be visualized non-invasively in intact mice, three recombinant Sendai viruses (SeVc viruses) were generated in which firefly luciferase was inserted into the P-M, M-F and F-FIN gene junctions of Sendai virus (FIG. 1a, FIG. 9).

Insertion of an additional gene and gene junction into the Sendai virus genome was expected to decrease downstream viral gene expression and, consequently, reduce virus replication [Tokusumi et al. 2002, Virus Res 86: 33-38]. To generate a luciferase-expressing Sendai virus expected to suffer little or no attenuation, the SeVc-luc(M-F*) was constructed to contain both the luciferase reporter gene and a more efficient transcription start sequence AGGGT-GAAAG (SEQ. ID. NO.: 20) upstream of the F gene (FIG. 9). Thus, the attenuating effects of reporter gene insertion could be counteracted by optimization of the naturally inefficient gene start sequence upstream of the F gene [Kato et al. 1999, J Virol 73: 9237-9246]. For the SeVc-luc(P-M) and SeVc-luc(F-HN) constructs in which the luciferase gene was inserted into the P-M and F-HN gene junctions, respectively, the naturally occurring suboptimal transcription start sequence upstream of the F gene was left intact (FIG. S1).

To determine if the viruses were attenuated or temperature restricted, multiple-step growth curves at a multiplicity of infection (M01) of 0.01 PFU/cell were measured in LLC-MK2 cells at 33 and 37° C. (FIG. 1b). Titers of SeVc-luc (M-F*), SeVc-luc(F-HN) and WT were similar at both temperatures and similar to each other, showing these two luciferase-expressing viruses were not substantially attenuated or temperature restricted. In contrast, the SeVc-luc(P-M) virus had reduced growth kinetics at 33° C. and grew even slower at 37° C. To determine how efficiently the SeVc viruses expressed the reporter gene, in vitro luciferase expression in LLC-MK2 cell lysates (MOI 5 PFU/cell) was measured with a luminometer (FIG. 1c). Upstream insertion of the reporter gene in SeVc-luc(P-M) resulted in higher reporter-gene expression than downstream insertion in SeVc-luc(F-HN), as has been described previously for insertions of secreted alkaline phosphatase [Tokusumi et al. 2002, Virus Res 86: 33-38]. Luciferase expression by SeVc-luc (M-F*) exceeded that of SeVc-luc(P-M) within 6 h p.i. (post-infection), showing the enhanced gene start sequence engineered into the M-F* virus (FIG. 9) increases reporter-gene transcription at later time points, perhaps due to greater downstream transcription of the L polymerase gene. To determine how the reporter gene insertions may have altered expression of the Sendai virus genes, Sendai virus protein expression in LLC-MK2 cells (MOI 5 PFU/cell) was measured by radioimmunoprecipitation. Low levels of expression of the M, F, HN and presumably L proteins by the SeVc-luc(P-M) virus (FIG. 10a) most likely caused the high level of attenuation of this virus construct. Viral protein expression by SeVc-luc(M-F*) and SeVc-luc(F-HN) was sufficient to generate virions with WT-like compositions (FIGS. 10b,c), and these two reporter viruses grew to levels similar to wild-type virus in vitro.

Example XI

Virulence of Luciferase-expressing Viruses

An ideal luciferase-reporter virus for non-invasive bioluminescence imaging and pathogenesis studies would express high levels of luciferase without altering virus replication and disease severity in the natural murine host compared to WT virus. To determine if the three luciferase-expressing SeVc viruses generated here retained the virulence of WT Sendai virus in vivo, 129/SvJ mice were inoculated intranasally with 7,000 PFU of virus, a dose known to induce substantial levels of morbidity and mortality in this mouse strain [Faisca et al. 2005, Am J Physiol Lung Cell Mol Physiol 289: L777-787]. In this experiment the mice were anesthetized with isoflurane and intranasally inoculated with virus in a 30 µl volume, a method of inoculation that delivers ~⅓ of the volume to the nasopharynx and ~½ of the volume to the lungs [Southam et al. 2002, Am J Physiol Lung Cell Mol Physiol 282: L833-839]. Infection with WT, SeVc-luc(M-F*), and SeVc-luc(F-HN) resulted in average weight losses of ~25% and mortality rates of 80% (FIGS. 1d,e), showing these two luciferase-expressing viruses remained fully virulent at this dose. In contrast, the attenuated SeVc-luc(P-M) virus induced only 12% weight loss and no mortality. Infection of 129/SvJ mice with 70,000 or 700,000 PFU of SeVc-luc(P-M) also resulted in 100% survival (data not shown), further demonstrating that the attenuated SeVc-luc(P-M) virus is avirulent.

Acute viral pneumonia by Sendai virus induces high levels of lymphocyte infiltration in bronchoalveolar lavage fluid (BALF) with a peak at ~10 dpi [Mo et al. 1995, J Virol 69: 1288-1291]. To determine if the luciferase-expressing viruses promoted lymphocyte influx comparable to WT, 129/SvJ mice infected with 7,000 PFU were sacrificed at 10 dpi for recovery of BALF. Similarly high numbers of total lymphocytes, CD4+ T-lymphocytes, and CD8+ T-lymphocytes were detected in BALF after infection with WT, SeVc-luc(M-F*), and SeVc-luc(F-HN), while lymphocyte influx after infection with attenuated SeVc-luc(P-M) was decreased ~10-fold (FIG. 1f; FIG. 11a-b). To determine the extents to which the reporter viruses elicited antibodies that bind to Sendai virus or luciferase, sera was also collected 10 dpi. All three SeVc viruses elicited anti-Sendai virus antibody titers similar to WT (FIG. 1g). The titers of anti-luciferase antibodies were also similar to each other for the three reporter viruses (FIG. 11c). Thus despite being attenuated and avirulent in 129/SvJ mice, SeVc-luc(P-M) elicited a robust antibody response. SeVc-luc(M-F*) induced WT-like levels of morbidity and mortality while expressing high levels of luciferase, making it best suited as a surrogate for WT virus in bioluminescence imaging experiments on pathogenesis and transmission.

Example XII

Dynamics of Infection in Living Animals

To determine if non-invasive bioluminescence accurately reflected in vivo infection, 129/SvJ mice were intranasally inoculated with 7,000 PFU, imaged with a Xenogen IVIS instrument, and immediately euthanized so respiratory tissues could be collected for ex vivo measurement of luminescence and viral titers. Consistent with previous studies in immunocompetent mice [Tashiro et al. 1988, Virology 165: 577-583 and Miyamae et al. 2005, J Vet Med Sci 67: 369-377], viral titers and bioluminescence were limited to the respiratory tract and in these studies were distinctly visualized in the nasopharynx, trachea, and lungs. As shown in FIG. 12, in vivo bioluminescence intensities in living animals correlated well with ex vivo luminescence ($R^2$ 0.878) and viral titers in the nasopharynx ($R^2$ 0.864), trachea ($R^2$ 0.915), and lungs ($R^2$ 0.961), validating the technique as a means to measure in vivo infection non-invasively. To determine if the luciferase-reporter genes were genetically stable in the three SeVc viruses, lung tissues were recovered from 7,000-PFU-inoculated 129/SvJ mice at 7 dpi, homogenized, and plaqued in LLC-MK2 cells. Five plaques for each of the three luciferase-expressing viruses were picked, RT-PCR transcribed, and sequenced. All of the individual plaques contained the luciferase insert, had no mutations, and expressed luciferase after infection in LLC-MK2 cells. While it is not necessary to understand the mechanism of action it is believed, this shows that the luciferase reporter gene was genetically stable in all three of the SeVc viruses after 7 days of replication in vivo.

Using the bioluminescence imaging system presented herein, the kinetics and tropism of infection were measured in intact 129/SvJ mice and compared our results to the conventional method of virus titer determination from dissected tissues (FIGS. 2 and 3). Just as SeVc-luc(M-F*) and SeVc-luc(F-HN) had in vitro replication rates and in vivo pathogenicities similar to WT, these SeVc viruses also had WT-like titers in the nasal turbinates, trachea, and lungs. In the nasal turbinates, high virus titers ($>10^5$ PFU) were detected by 2 dpi and were maintained until 9 dpi, after which rapid clearance occurred (FIG. 3b). High levels of bioluminescence from the nasopharynx ($>10^8$ photons/s) were similarly observed for 129/SvJ mice infected with SeVc-luc(M-F*) between 2 and 9 dpi with a peak around 5 dpi (FIG. 3a). In the lungs, virus titers peaked by 5 dpi and were cleared to low levels by 9 dpi. Infection with the attenuated SeVc-luc(P-M) resulted in peak lung titers of ~$10^4$ PFU at 5 dpi, nearly 100-fold lower than WT (FIG. 3d), and similarly low levels of bioluminescence were observed in the lungs (FIG. 3a), consistent with its attenuated and avirulent phenotype. However, SeVc-luc(P-M) grew to high peak titers (~$10^5$ PFU) in the nasal turbinates, a level similar to WT at 7 dpi (FIG. 3c), and had high levels of bioluminescence in the nasopharynx between 3 and 6 dpi (FIG. 3a).

Example XIII

Tissue Tropism and Viral Dose

While lower inoculating doses of Sendai virus are known to reduce infection and pathology in the lungs, we are unaware of any published studies on the dose dependence of infection in the URT or trachea. Preliminary studies showed that the mouse infectious dose 50 ($MID_{50}$) for SeVc-luc(M-F*) was 9 PFU and that a 70-PFU dose resulted in 100% infection, similar to results obtained for WT Sendai virus in mice [Kiyotani et al. 1993, J Virol 67: 7618-7622] and hPIV1 in humans [Reichelderfer et al. 1958, Science 128: 779-780]. 129/SvJ mice were inoculated intranasally with 70, 700 or 7,000 PFU of SeVc-luc(M-F*) in equal 30 μl volumes and then measured bioluminescence and viral titers. Compared to a 7,000-PFU dose, 70 PFU-inoculation resulted in ~10-fold lower viral titers and bioluminescence in the lungs (FIGS. 4a,b) and lower weight loss (FIG. 4c). In contrast, infection in the nasopharynx and trachea after 70-PFU inoculation was only delayed ~1 d compared to 7,000-PFU, reaching a similar level by ~5 dpi (FIGS. 4a,b) and inducing relatively high titers of Sendai virus-specific antibodies ($>10^5$) (FIG. 4d). Thus, while it is not necessary to understand the mechanism of action, it is believed that low-dose inoculation of WT-like SeVc-luc(M-F*) resulted in infection biased to the URT and trachea, inducing a robust antibody response without causing severe pathogenicity.

Example XIV

Tissue Tropism and Host Genetics

Various strains of recombinant inbred mice differ in their susceptibilities to lung infection by Sendai virus [Faisca et al. 2005, Am J Physiol Lung Cell Mol Physiol 289: L777-787; Brownstein, D G 1987, J Virol 61: 1670-1671; Brownstein et al. 1981, Am J Pathol 105: 156-163; and Brownstein et al. 1986, Lab Anim Sci 36: 126-129]. For example, 129/SvJ and DBA/2 mice are highly susceptible to lung infection and its resulting pathogenesis while BALB/c and C57BL/6 mice are highly resistant. How host genetics affects Sendai virus replication in the URT and trachea has not been previously reported. Therefore, the in vivo dynamics of Sendai virus infection was measured in 129/SvJ, DBA/2, C57BL/6, and BALB/c strains of mice intranasally inoculated with 7,000 PFU of SeVc-luc(M-F*). As expected from previous studies, the extent of infection in the lungs and weight loss correlated with each other and followed the trend C57BL/6<BALB/c<<DBA/2<129/SvJ (FIGS. 2 and 4). In contrast, the URT and trachea were highly permissive to Sendai virus infection, having similarly high levels of bioluminescence for all four strains of mice. Thus, the URT and trachea of BALB/c and C57BL/6 mice were highly permissive to Sendai virus infection despite genetic resistance in the lungs. While it is not necessary to understand the mechanism of action it is believed these results show that genetic susceptibility to Sendai virus infection is tissue specific and that reduced infection in the lungs is not due to lower infection in the URT or trachea. In subsequent experiments on transmission, light-coated BALB/c and 129/SvJ strains of mice were used. Therefore, Sendai virus titers in groups of sacrificed BALB/c mice were measured and found that the ex vivo titers correlate with bioluminescence in intact mice (FIG. 13a) just as they had for 129/SvJ mice. Compared to 129/SvJ mice, infection in the lungs of BALB/c mice was decreased at least 10-fold as measured by both bioluminescence (FIG. 4e) and viral titers (FIG. 13b-c). Consequently, the BALB/c mice had only very mild clinical symptoms, including very little weight loss (FIG. 4f). In contrast, nasopharyngeal infection in BALB/c mice reached a level similar to that in 129/SvJ mice by 3 dpi, as measured by both bioluminescence (FIG. 4e) and viral titer (FIG. 13b-c). Overall, it is believed that the bioluminescence imaging studies revealed three conditions in which robust infection in the URT and trachea was observed despite reduced infection in the lungs and little apparent weight loss: an attenuated virus, a low virus dose, and a resistant strain of mouse.

Example XV

Dynamics of Infection During Contact Transmission

Infection control requires an understanding of how pathogens are transmitted. Sendai virus, the hPIVs, and hRSV are known to transmit primarily via contact with respiratory secretions as opposed to long-range transmission of small-particle aerosols [Iida, T. 1972, J Gen Virol 14: 69-75; van der Veen et al. 1970, Arch Gesamte Virusforsch 31: 237-246; Henrickson, K J 2003, Clin Microbiol Rev 16: 242-264; Hall et al. 1981, J Pediatr 99: 100-103; and McLean et al. 1967, Can Med Assoc J 96: 1449-1453]. It is also known that growth of Sendai virus [Iida, T. 1972, J Gen Virol 14: 69-75] and influenza virus [Lowen et al. 2007, PLoS Pathog 3: 1470-1476] in the URT promotes transmission. Two long-standing, fundamental questions about PIV transmission that remained unknown were (i) how growth of virus in the lungs of donors influences transmission and (ii) what factors determine the timing of transmission and the tissue-specific spread of infection after transmission. To address these fundamental questions about PIV transmission, BALB/c or 129/SvJ donor mice were inoculated with 70 or 7,000 PFU of SeVc-luc(M-F*) and then placed 3 naïve contact mice in a cage with 1 donor mouse at 1 dpi. Bioluminescence was measured daily in inoculated and contact mice until primary infection cleared, collected sera on day 60, challenged the mice with 7,000 PFU of SeVc-luc(M-F*) on day 63, and then imaged the mice daily for reinfection (FIG. 5). It is believed that transmission to every naïve contact mouse was observed by nasopharyngeal bioluminescence and seroconversion, even for resistant BALB/c mice exposed to donor animals inoculated at the lower dose. The timing of transmission was not influenced by the extent of lung infection in donors as lung titers were ~10-fold lower in BALB/c versus 129/SvJ donor mice after 7,000-PFU inoculation (FIG. 13c) yet the transmission times (difference in time until detection in inoculated versus transmitted animals) were a similar 3.3 and 3.4 days, respectively (FIG. 6f). LRT infection occurred in both strains of mice and may contribute to transmission. Regardless, the primary determinant of transmission appeared to be virus shedding in the URT and trachea. For example, high-titer (>$10^5$ PFU) shedding in the nasal cavities and trachea of 129/SvJ donor mice (FIGS. 4a,b) and contact transmission (FIGS. 6e,f) both occurred ~1 day earlier after 7,000-PFU inoculation compared to 70-PFU. Overall, while it is not necessary to understand the mechanism of action, it is believed these results demonstrate how animals that suffer little apparent weight loss are able to promote efficient transmission of Sendai virus Enders strain.

In order to investigate the magnitude of Sendai virus infection after transmission, previous studies measured ex vivo titers in groups of contact mice sacrificed different times after exposure to infected cagemates [Iida, T. 1972, J Gen Virol 14: 69-75 and van der Veen et al. 1970, Arch Gesamte Virusforsch 31: 237-246]. These classical studies yielded highly ambiguous results in which titers varied 100-fold from day to day and the progression of infection in the respiratory tract after transmission was not clear. Therefore, non-invasive bioluminescence imaging was used to measure for the first time the temporal and spatial spread of PIV infection throughout the respiratory tract in individual, living mice after transmission. The inoculated dose was varied in donors and the mouse strain so that viral and host determinants of transmission could be investigated. Under all four conditions tested (129/SvJ or BALB/c mice infected at 70 or 7,000 PFU), the tropism and magnitude of infection in contact animals after transmission was similar to that observed after direct inoculation with a 70-PFU dose of SeVc-luc(M-F*) delivered intranasally. After transmission, bioluminescence was first observed in the nasopharynx and then spread to the trachea and lungs an average of 0.8 and 1.0 days later, respectively (FIG. 14a-d). Robust infection was observed in the nasopharynx and trachea (FIG. 6a-d, FIG. 14e-h), and low levels of lung infection were consistent with little weight loss after transmission (FIG. 6g-h). For all four groups of mice, Sendai virus-specific antibody titers on day 60 were similarly high (~$10^6$) and the animals were universally protected during challenge on day 63 (FIG. 5). After challenge a low level of bioluminescence (<$10^6$ photons/s), but no weight loss, was detected in only 1 contact mouse out of 30, the animal with the lowest level of bioluminescence after primary infection on days 5-12 (FIG. 5b, solid black circles). As this individual animal also had the lowest level of Sendai virus-specific antibodies at day 60 before challenge, a threshold level of infection may be required for protective immunity. Overall, while it is not necessary to understand the mechanism of action, it is believed that Sendai virus infection after transmission was observed to be robust enough in the URT and trachea, yet limited enough in the lungs, to induce protective immunity without causing significant weight loss in the matched murine host that is susceptible to Sendai virus infection.

REFERENCES

All publications and patents mentioned in the above specification are herein incorporated by reference. Various modifications and variations of the described methods and devices of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the subject area of vaccine development, infectious disease, molecular biology, diagnostics, biotechnolgy and-or related fields are intended to be within the scope of the following claims.

Karron R A, Collins P L, editors (2007) Parainfluenza Viruses. 5 ed. Philadelphia: Lippincott, Williams and Wilkins. 1497-1526 p.

Lamb R A, Parks G D, editors (2007) Paramyxoviridae: The Viruses and Their Replication. 5 ed. Philadelphia: Lippincott, Williams and Wilkins. 1449-1496 p.

Williams J V, Edwards K M, Weinberg G A, Griffin M R, Hall C B, et al. (2010) Population-based incidence of human metapneumovirus infection among hospitalized children. J Infect Dis 201: 1890-1898.

Chanock R M, Parrott R H, Johnson K M, Kapikian A Z, Bell J A (1963) Myxoviruses: Parainfluenza. Am Rev Respir Dis 88: S152-S166.

Parrott R H, Vargosko A J, Kimhw, Bell J A, Chanock R M (1962) Acute respiratory diseases of viral etiology. III. parainfluenza. Myxoviruses. Am J Public Health Nations Health 52: 907-917.

Parrott R H, Vargosko A, Luckey A, Kim H W, Cumming C, et al. (1959) Clinical features of infection with hemadsorption viruses. N Engl J Med 260: 731-738.

Murphy B R, Collins P L (2002) Live-attenuated virus vaccines for respiratory syncytial and parainfluenza viruses: applications of reverse genetics. J Clin Invest 110: 21-27.

Moscona A (2005) Entry of parainfluenza virus into cells as a target for interrupting childhood respiratory disease. J Clin Invest 115: 1688-1698.

Schaap-Nutt A, Scull M A, Schmidt A C, Murphy B R, Pickles R J (2010) Growth restriction of an experimental live attenuated human parainfluenza virus type 2 vaccine in human ciliated airway epithelium in vitro parallels attenuation in African green monkeys. Vaccine 28: 2788-2798.

Nagai Y (1999) Paramyxovirus replication and pathogenesis. Reverse genetics transforms understanding. Rev Med Virol 9: 83-99.

Faisca P, Desmecht D (2007) Sendai virus, the mouse parainfluenza type 1: a longstanding pathogen that remains up-to-date. Res Vet Sci 82: 115-125.

Denny F W, Murphy T F, Clyde W A, Jr., Collier A M, Henderson F W (1983) Croup: an 11-year study in a pediatric practice. Pediatrics 71: 871-876.

Takimoto T, Hurwitz J L, Zhan X, Krishnamurthy S, Prouser C, et al. (2005) Recombinant Sendai virus as a novel vaccine candidate for respiratory syncytial virus. Viral Immunol 18: 255-266.

Dave V P, Allan J E, Slobod K S, Smith F S, Ryan K W, et al. (1994) Viral cross-reactivity and antigenic determinants recognized by human parainfluenza virus type 1-specific cytotoxic T-cells. Virology 199: 376-383.

Hurwitz J L, Soike K F, Sangster M Y, Portner A, Sealy R E, et al. (1997) Intranasal Sendai virus vaccine protects African green monkeys from infection with human parainfluenza virus-type one. Vaccine 15: 533-540.

Sangster M, Hyland L, Sealy R, Coleclough C (1995) Distinctive kinetics of the antibody-forming cell response to Sendai virus infection of mice in different anatomical compartments. Virology 207: 287-291.

Slobod K S, Shenep J L, Lujan-Zilbermann J, Allison K, Brown B, et al. (2004) Safety and immunogenicity of intranasal murine parainfluenza virus type 1 (Sendai virus) in healthy human adults. Vaccine 22: 3182-3186.

Jones B, Zhan X, Mishin V, Slobod K S, Surman S, et al. (2009) Human PIV-2 recombinant Sendai virus (rSeV) elicits durable immunity and combines with two additional SeVc viruses to protect against hPIV-1, hPIV-2, hPIV-3, and RSV. Vaccine 27: 1848-1857.

Zhan X, Hurwitz J L, Krishnamurthy S, Takimoto T, Boyd K, et al. (2007) Respiratory syncytial virus (RSV) fusion protein expressed by recombinant Sendai virus elicits B-cell and T-cell responses in cotton rats and confers protection against RSV subtypes A and B. Vaccine 25: 8782-8793.

Zhan X, Slobod K S, Krishnamurthy S, Luque L E, Takimoto T, et al. (2008) Sendai virus recombinant vaccine expressing hPIV-3 HN or F elicits protective immunity and combines with a second recombinant to prevent hPIV-1, hPIV-3 and RSV infections. Vaccine 26: 3480-3488.

Iida T (1972) Experimental study on the transmission of Sendai virus in specific pathogen-free mice. J Gen Virol 14: 69-75.

van der Veen J, Poort Y, Birchfield D J (1970) Experimental transmission of Sendai virus infection in mice. Arch Gesamte Virusforsch 31: 237-246.

Hall C B (2001) Respiratory syncytial virus and parainfluenza virus. N Engl J Med 344: 1917-1928.

Henrickson K J (2003) Parainfluenza viruses. Clin Microbiol Rev 16: 242-264.

Sealy R, Jones B G, Surman S L, Hurwitz J L (2010) Robust IgA and IgG-producing antibody forming cells in the diffuse-NALT and lungs of Sendai virus-vaccinated cotton rats associate with rapid protection against human parainfluenza virus-type 1. Vaccine 28: 6749-6756.

Rudraraju R, Surman S, Jones B, Sealy R, Woodland D L, et al. (2011) Phenotypes and functions of persistent Sendai virus-induced antibody forming cells and CD8+ T cells in diffuse nasal-associated lymphoid tissue typify lymphocyte responses of the gut. Virology 410: 429-436.

Luker K E, Luker G D (2008) Applications of bioluminescence imaging to antiviral research and therapy: multiple luciferase enzymes and quantitation. Antiviral Res 78: 179-187.

Hasan M K, Kato A, Shioda T, Sakai Y, Yu D, et al. (1997) Creation of an infectious recombinant Sendai virus expressing the firefly luciferase gene from the 3' proximal first locus. J Gen Virol 78 (Pt 11): 2813-2820.

Manicassamy B, Manicassamy S, Belicha-Villanueva A, Pisanelli G, Pulendran B, et al. (2010) Analysis of in vivo dynamics of influenza virus infection in mice using a GFP reporter virus. Proc Natl Acad Sci USA 107: 11531-11536.

Bukreyev A, Skiadopoulos M H, Murphy B R, Collins P L (2006) Nonsegmented negative-strand viruses as vaccine vectors. J Virol 80: 10293-10306.

Griesenbach U, Meng C, Farley R, Cheng S H, Scheule R K, et al. (2008) In vivo imaging of gene transfer to the respiratory tract. Biomaterials 29: 1533-1540.

Tokusumi T, Iida A, Hirata T, Kato A, Nagai Y, et al. (2002) Recombinant Sendai viruses expressing different levels of a foreign reporter gene. Virus Res 86: 33-38.

Kato A, Kiyotani K, Hasan M K, Shioda T, Sakai Y, et al. (1999) Sendai virus gene start signals are not equivalent in reinitiation capacity: moderation at the fusion protein gene. J Virol 73: 9237-9246.

Faisca P, Anh D B, Desmecht D J (2005) Sendai virus-induced alterations in lung structure/function correlate with viral loads and reveal a wide resistance/susceptibility spectrum among mouse strains. Am J Physiol Lung Cell Mol Physiol 289: L777-787.

Southam D S, Dolovich M, O'Byrne P M, Inman M D (2002) Distribution of intranasal instillations in mice: effects of volume, time, body position, and anesthesia. Am J Physiol Lung Cell Mol Physiol 282: L833-839.

Mo X Y, Sarawar S R, Doherty P C (1995) Induction of cytokines in mice with parainfluenza pneumonia. J Virol 69: 1288-1291.

Tashiro M, Pritzer E, Khoshnan M A, Yamakawa M, Kuroda K, et al. (1988) Characterization of a pantropic variant of Sendai virus derived from a host range mutant. Virology 165: 577-583.

Miyamae T (2005) Differential invasion by Sendai virus of abdominal parenchymal organs and brain tissues in cortisone- and cyclophosphamide-based immunosuppressed mice. J Vet Med Sci 67: 369-377.

Kiyotani K, Sakaguchi T, Fujii Y, Yoshida T (1993) FO-containing noninfectious Sendai virus can initiate replication in mouse lungs but requires a relatively long incubation period. J Virol 67: 7618-7622.

Reichelderfer T E, Chanock R M, Craighead J E, Huebner R J, Turner H C, et al. (1958) Infection of human volunteers with type 2 hemadsorption virus. Science 128: 779-780.

Brownstein D G (1987) Resistance/susceptibility to lethal Sendai virus infection genetically linked to a mucociliary transport polymorphism. J Virol 61: 1670-1671.

Brownstein D G, Smith A L, Johnson E A (1981) Sendai virus infection in genetically resistant and susceptible mice. Am J Pathol 105: 156-163.

Brownstein D G, Winkler S (1986) Genetic resistance to lethal Sendai virus pneumonia: virus replication and interferon production in C57BL/6J and DBA/2J mice. Lab Anim Sci 36: 126-129.

Hall C B, Douglas R G, Jr. (1981) Modes of transmission of respiratory syncytial virus. J Pediatr 99: 100-103.

McLean D M, Bannatyne R M, Givan K F (1967) Myxovirus dissemination by air. Can Med Assoc J 96: 1449-1453.

Lowen A C, Mubareka S, Steel J, Palese P (2007) Influenza virus transmission is dependent on relative humidity and temperature. PLoS Pathog 3: 1470-1476.

Profeta M L, Lief F S, Plotkin S A (1969) Enzootic sendai infection in laboratory hamsters. Am J Epidemiol 89: 316-324.

Zurcher C, Burek J D, Van Nunen M C, Meihuizen S P (1977) A naturally occurring epizootic caused by Sendai virus in breeding and aging rodent colonies. I. Infection in the mouse. Lab Anim Sci 27: 955-962.

Anderson D E, von Messling V (2008) Region between the canine distemper virus M and F genes modulates virulence by controlling fusion protein expression. J Virol 82: 10510-10518.

Luque L E, Bridges O A, Mason J N, Boyd K L, Portner A, et al. (2010) Residues in the heptad repeat A region of the fusion protein modulate the virulence of Sendai virus in mice. J Virol 84: 810-821.

Bousse T, Matrosovich T, Portner A, Kato A, Nagai Y, et al. (2002) The long noncoding region of the human parainfluenza virus type 1 f gene contributes to the read-through transcription at the m-f gene junction. J Virol 76: 8244-8251.

Spriggs M K, Collins P L (1986) Human parainfluenza virus type 3: messenger RNAs, polypeptide coding assignments, intergenic sequences, and genetic map. J Virol 59: 646-654.

Rassa J C, Parks G D (1998) Molecular basis for naturally occurring elevated readthrough transcription across the M-F junction of the paramyxovirus SV5. Virology 247: 274-286.

Cattaneo R, Rebmann G, Baczko K, ter Meulen V, Billeter M A (1987) Altered ratios of measles virus transcripts in diseased human brains. Virology 160: 523-526.

Touzelet O, Loukili N, Pelet T, Fairley D, Curran J, et al. (2009) De novo generation of a non-segmented negative strand RNA virus with a bicistronic gene. Virus Res 140: 40-48.

Rudd P A, Cattaneo R, von Messling V (2006) Canine distemper virus uses both the anterograde and the hematogenous pathway for neuroinvasion. J Virol 80: 9361-9370.

von Messling V, Milosevic D, Cattaneo R (2004) Tropism illuminated: lymphocyte-based pathways blazed by lethal morbillivirus through the host immune system. Proc Natl Acad Sci USA 101: 14216-14221.

Lemon K, de Vries R D, Mesman A W, McQuaid S, van Amerongen G, et al. (2011) Early target cells of measles virus after aerosol infection of non-human primates. PLoS Pathog 7: e1001263.

de Swart R L, Ludlow M, de Witte L, Yanagi Y, van Amerongen G, et al. (2007) Predominant infection of CD150+ lymphocytes and dendritic cells during measles virus infection of macaques. PLoS Pathog 3: e178.

Zhang L, Bukreyev A, Thompson C I, Watson B, Peeples M E, et al. (2005) Infection of ciliated cells by human parainfluenza virus type 3 in an in vitro model of human airway epithelium. J Virol 79: 1113-1124.

Villenave R, Touzelet O, Thavagnanam S, Sarlang S, Parker J, et al. (2010) Cytopathogenesis of Sendai virus in well-differentiated primary pediatric bronchial epithelial cells. J Virol 84: 11718-11728.

Devincenzo J P, Wilkinson T, Vaishnaw A, Cehelsky J, Meyers R, et al. (2010) Viral load drives disease in humans experimentally infected with respiratory syncytial virus. Am J Respir Crit. Care Med 182: 1305-1314.

Skiadopoulos M H, Surman S R, Riggs J M, Elkins W R, St Claire M, et al. (2002) Sendai virus, a murine parainfluenza virus type 1, replicates to a level similar to human PIV1 in the upper and lower respiratory tract of African green monkeys and chimpanzees. Virology 297: 153-160.

Bousse T, Chambers R L, Scroggs R A, Portner A, Takimoto T (2006) Human parainfluenza virus type 1 but not Sendai virus replicates in human respiratory cells despite IFN treatment. Virus Res 121: 23-32.

Skiadopoulos M H, Surman S R, Riggs J M, Orvell C, Collins P L, et al. (2002) Evaluation of the replication and immunogenicity of recombinant human parainfluenza virus type 3 vectors expressing up to three foreign glycoproteins. Virology 297: 136-152.

Hall C B, Douglas R G, Jr., Schnabel K C, Geiman J M (1981) Infectivity of respiratory syncytial virus by various routes of inoculation. Infect Immun 33: 779-783.

Parrott R H, Kim H W, Brandt C D, Chanock R M (1975) Potential of attenuated respiratory syncytial virus vaccine for infants and children. Dev Biol Stand 28: 389-399.

Tyrrell D A, Bynoe M L, Petersen K B, Sutton R N, Pereira M S (1959) Inoculation of human volunteers with parainfluenza viruses types 1 and 3 (HA 2 and HA 1). Br Med J 2: 909-911.

Stephens H A (2010) HLA and other gene associations with dengue disease severity. Curr Top Microbiol Immunol 338: 99-114.

Zhang L, Katz J M, Gwinn M, Dowling N F, Khoury M J (2009) Systems-based candidate genes for human response to influenza infection. Infect Genet Evol 9: 1148-1157.

Arkwright P D, Abinun M (2008) Recently identified factors predisposing children to infectious diseases. Curr Opin Infect Dis 21: 217-222.

Simon A Y, Moritoh K, Torigoe D, Asano A, Sasaki N, et al. (2009) Multigenic control of resistance to Sendai virus infection in mice. Infect Genet Evol 9: 1253-1259.

Boon AC, deBeauchamp J, Hollmann A, Luke J, Kotb M, et al. (2009) Host genetic variation affects resistance to infection with a highly pathogenic $H_5N_1$ influenza A virus in mice. J Virol 83: 10417-10426.

Anh D B, Faisca P, Desmecht D J (2006) Differential resistance/susceptibility patterns to pneumovirus infection among inbred mouse strains. Am J Physiol Lung Cell Mol Physiol 291: L426-435.

Itoh T, Iwai H, Ueda K (1991) Comparative lung pathology of inbred strain of mice resistant and susceptible to Sendai virus infection. J Vet Med Sci 53: 275-279.

Stark J M, McDowell S A, Koenigsknecht V, Prows D R, Leikauf J E, et al. (2002) Genetic susceptibility to respiratory syncytial virus infection in inbred mice. J Med Virol 67: 92-100.

Kido H, Yokogoshi Y, Sakai K, Tashiro M, Kishino Y, et al. (1992) Isolation and characterization of a novel trypsin-like protease found in rat bronchiolar epithelial Clara cells. A possible activator of the viral fusion glycoprotein. J Biol Chem 267: 13573-13579.

Tashiro M, Yokogoshi Y, Tobita K, Seto J T, Rott R, et al. (1992) Tryptase Clara, an activating protease for Sendai virus in rat lungs, is involved in pneumopathogenicity. J Virol 66: 7211-7216.

Bhatt P N, Jonas A M (1974) An epizootic of Sendai infection with mortality in a barrier-maintained mouse colony. Am J Epidemiol 100: 222-229.

Ishida N, Homma M (1978) Sendai virus. Adv Virus Res 23: 349-383.

Nakagawa M, Saito M, Kinoshita K, Suzuki E, Imaizumi K (1980) Pathogenicity of Sendai virus in mice cage-mated with infectors and their offsprings. Nippon Juigaku Zasshi 42: 337-344.

Sakaguchi T, Kiyotani K, Sakaki M, Fujii Y, Yoshida T (1994) A field isolate of Sendai virus: its high virulence to mice and genetic divergence form prototype strains. Arch Virol 135: 159-164.

Itoh M, Isegawa Y, Hotta H, Homma M (1997) Isolation of an avirulent mutant of Sendai virus with two amino acid mutations from a highly virulent field strain through adaptation to LLC-MK2 cells. J Gen Virol 78 (Pt 12): 3207-3215.

Kiyotani K, Sakaguchi T, Fujii Y, Yoshida T (2001) Attenuation of a field Sendai virus isolate through egg-passages is associated with an impediment of viral genome replication in mouse respiratory cells. Arch Virol 146: 893-908.

Garcin D, Itoh M, Kolakofsky D (1997) A point mutation in the Sendai virus accessory C proteins attenuates virulence for mice, but not virus growth in cell culture. Virology 238: 424-431.

Fujii Y, Sakaguchi T, Kiyotani K, Huang C, Fukuhara N, et al. (2002) Involvement of the leader sequence in Sendai virus pathogenesis revealed by recovery of a pathogenic field isolate from cDNA. J Virol 76: 8540-8547.

Sakaguchi T, Kiyotani K, Watanabe H, Huang C, Fukuhara N, et al. (2003) Masking of the contribution of V protein to Sendai virus pathogenesis in an infection model with a highly virulent field isolate. Virology 313: 581-587.

Luque L E, Russell C J (2007) Spring-loaded heptad repeat residues regulate the expression and activation of paramyxovirus fusion protein. J Virol 81: 3130-3141.

Tokusumi et al., "Recombinant Sendai Viruses Expressing Different Levels of a Foreign Reporter Gene" *Virus Res.,* 86(1-2):33-38 (2002).

Nagai et al., "Recombinant Sendai Virus" U.S. Pat. No. 7,442,544 (Also see U.S. Patent Application Publication No. US 2005/0266566 and related continuations.)

Kano et al., "AIDS Virus Vaccines Using Sendai Virus Vector" U.S. Patent Application Publication No. US 2010/0266633

Xiaoyan Zhan, "Development of Sendai Virus Vaccines to Prevent Pediatric Respiratory Infections"at http://www7.nationalacademies.org/gdestLX_Zhan.GDE-S_China_Presentation.pdf Mar. 29-Apr. 1, 2006.

Takimoto et al., "Recombinant Sendai Virus as a Novel Vaccine Candidate for Respiratory Syncytial Virus" *Viral Immunology,* 18(2):255-265 (2005).

Jones et al., "Human PIV-2 Recombinant Sendai Virus (rSeV) Elicits Durable Immunity and Combines with Two Additional rSeVs to Protect Against hPIV-1, hPIV-2, hPIV-3, and RSV" *Vaccine,* 27:1848-1857, (2009).

Zhan et al., "Sendai Virus Recombinant Vaccine Expressing hPIV-3 HN or F Elicits Protective Immunity and Combines with A Second Recombinant to Prevent hPIV-1, hPIV-3 and RSV Infections" *Vaccine,* 26:3480-3488 (2008).

Hurwitz et al., "Use of Sendai Virus as A Human Parainfluenza Vaccine" U.S. Patent Application Publication No. US 2006/0110740.

Russell, Charles, "Membrane Fusion Proteins of Influenza and Parainfluenza Viruses in Infection and Disease" *Emory University Presentation Feb.* 1, 2010

Hurwitz, Julia L., "Development of Recombinant Sendai Virus Vaccines for Prevention of Human Parainfluenza and Respiratory Syncytial Virus Infections" *Pediatr Infect Dis J,* 27(5):Supplement May 2008

Hurwitz et al., "Development of Sendai Virus-Based Vaccines to Prevent Pediatric Respiratory Virus Infections" *Procedia in Vaccinology,* 1:41-44 (2008).

Zhan et al., "Respiratory Syncytial Virus (RSV) Fusion Protein Expressed By Recombinant Sendai Virus Elicits B-cell and T-cell Responses In Cotton Rats and Confers Protection Against RSV Subtypes A and B" *Vaccine* 25:8782-8793 (2007).

Takimoto et al., "Recombinant Sendai Virus Expressing the G Glycoprotein of Respiratory Syncytial Virus (RSV) Elicits Immune Protection Against RSV" *J. Virol.* 78(11): 6043-6047 (2004).

Tokusumi et al., "Paramyxovirus Vectors Used For Transfer of Foreign Genes" U.S. Patent Application Publication No. US 2004/0137627 (Also see related U.S. Pat. No. 6,746,860.)

Portner et al., "Vaccine and Gene Therapy Vector and Methods of Use Thereof" International Publication No. WO 01/92548.

The invention claimed is:

1. An immunogenic recombinant mutant Enders Sendai viral vector comprising
   a) a modified Enders Sendai virus L gene that encodes a modified L protein containing one or more amino acid mutations of the wild type L protein selected from the group consisting of wild type amino acid S to mutant amino acid G at position 155, wild type amino acid R to mutant amino acid K at position 258, wild type amino acid G to mutant amino acid E at position 466, wild type amino acid G to mutant amino acid E at position 482, wild type amino acid S to mutant amino acid R at position 581, wild type amino acid Q to mutant amino acid R at position 717, wild type amino acid T to mutant amino acid I at position 800, and wild type amino acid R to mutant amino acid K at position 852, and
   b) one or more heterologous genes that comprise a gene encoding an antigen.

2. The recombinant Sendai viral vector of claim 1, wherein said one or more heterologous genes are inserted in one or more intergenic junction selected from the group consisting of N-P junction, P-M junction, M-F junction, F-HN junction, and HN-L junction.

3. The recombinant Sendai viral vector of claim 2, wherein said one or more heterologous genes further comprises a gene that facilitate virus tracking in vitro, in vivo, or both.

4. The recombinant Sendai viral vector of claim 3, wherein said gene that facilitates virus tracking is selected from the group consisting of luciferase, green fluorescent protein, and both luciferase and green fluorescent protein.

5. The recombinant Sendai viral vector of claim 1, further comprising at least one of mutant gene start sequence and of mutant gene stop sequence to alter gene transcription.

6. The recombinant Sendai viral vector of claim 1, wherein said heterologous gene encoding an antigen is selected from the group consisting of respiratory syncytial virus (RSV) F protein, respiratory syncytial virus (RSV) G protein, parainfluenza virus type 1 (PIV-1) protein, parainfluenza virus type 2 (PIV-2) protein, parainfluenza virus type 3 (PIV-3) protein, and parainfluenza virus type 4 (PIV-4) protein.

7. The recombinant Sendai viral vector of claim 3, wherein said gene that facilitates virus tracking is a reporter gene.

8. A method of immunizing an animal comprising administering to the animal an effective amount of the recombinant Sendai viral vector of claim 1.

9. The recombinant Sendai viral vector of claim 2, wherein said one or more heterologous genes are inserted between a Sendai virus P gene and a Sendai virus M gene.

10. The recombinant Sendai viral vector of claim 2, wherein said one or more heterologous genes are inserted between a Sendai virus M gene and a Sendai virus F gene.

11. The recombinant Sendai viral vector of claim 2, wherein said one or more heterologous genes are inserted between a Sendai virus F gene and a Sendai virus HN gene.

12. The recombinant Sendai viral vector of claim 1, wherein said vector further comprises at least one antigen or immunogen.

13. The recombinant Sendai viral vector of claim 5, wherein said mutant start sequence comprises AGGGT-GAAAG (SEQ ID NO: 20).

14. The recombinant Sendai viral vector of claim 1, wherein said modified L protein comprises SEQ ID NO:17.

15. The recombinant Sendai viral vector of claim 6, wherein said one or more heterologous gene encoding an antigen comprise RSV F protein, and said vector comprises SEQ ID NO:18.

* * * * *

UNITED STATES PATENT AND TRADEMARK OFFICE
CERTIFICATE OF CORRECTION

PATENT NO. : 9,637,758 B2
APPLICATION NO. : 14/113769
DATED : May 2, 2017
INVENTOR(S) : Hurwitz et al.

Page 1 of 1

It is certified that error appears in the above-identified patent and that said Letters Patent is hereby corrected as shown below:

In the Specification

Column 1, Lines 18 - 20, should read as follows under GOVERNMENT FUNDING:
This invention was made with government support under grants AI054955, AI083370, AI056974, AI038956, AI011949 and CA021765 awarded by the National Institutes of Health. The government has certain rights in the invention.

Signed and Sealed this
Thirty-first Day of July, 2018

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 1725
<212> TYPE: DNA
<213> ORGANISM: Artificial Sequence
<220> FEATURE:
<223> OTHER INFORMATION: Synthetic

<400> SEQUENCE: 1
atggagttgc taatcctcaa agcaaatgca attaccacaa tcctcactgc agtcacattt     60
tgttttgctt ctggtcaaaa catcactgaa gaattttatc aatcaacatg cagtgcagtt    120
agcaaaggct atcttagtgc tctgagaact ggttggtata ccagtgttat aactatagaa    180
ttaagtaata tcaagaaaaa taagtgtaat ggaacagatg ccaaggcaaa attgataaaa    240
caagaattag ataaatataa aaatgctgta acagaattgc agttgctcat gcaaagcaca    300
caagcaacaa acaatcgagc cagaagagaa ctaccaaggt ttatgaatta tacactcaac    360
aatgccaaaa aaaccaatgt aacattaagc aagaaaagga aaagaagatt tcttggtttt    420
ttgttaggtg ttggatctgc aatcgccagt ggcgttgctg tatctaaggt cctgcaccta    480
gaaggggaag tgaacaagat caaaagtgct ctactatcca caaacaaggc tgtagtcagc    540
```

```
ttatcaaatg gagttagtgt cttaaccagc aaagtgttag acctcaaaaa ctatatagat    600
aaacaattgt tacctattgt gaacaagcaa agctgcagca tatcaaatat agaaactgtg    660
atagagttcc aacaaaagaa caacagacta ctagagatta ccagggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtcc ataataaaag aggaagtctt agcatatgta    900
gtacaattac cactatatgg tgttatggat acaccctgtt ggaaactaca cacatcccct    960
ctatgtacaa ccaacacaaa agaagggtcc aacatctgtt taacaagaac tgacagagga   1020
tggtactgtg acaatgcagg atcagtatct ttcttcccac aagctgaaac atgtaaagtt   1080
caatcaaatc gagtattttg tgacacaatg aacagtttaa cattaccaag tgaagtaaat   1140
ctctgcaatg ttgacatatt caaccccaaa tatgattgta aaattatgac ctcaaaaaca   1200
gatgtaagca gctccgttat cacatctcta ggagccattg tgtcatgcta tggcaaaact   1260
aaatgtacag catccaataa aaatcgtgga atcataaaga cattttctaa cgggtgcgat   1320
tatgtatcaa ataaaggggt ggacactgtg tctgtaggta acacattata ttatgtaaat   1380
aagcaagaag gtaaaagtct ctatgtaaaa ggtgaaccaa taataaattt ctatgaccca   1440
ttagtattcc cctctgatga atttgatgca tcaatatctc aagtcaacga gaagattaac   1500
cagagcctag catttattcg taaatccgat gaattattac ataatgtaat tgctggtaaa   1560
tccaccacaa atatcatgat aactactata attatagtga ttatagtaat attgttatca   1620
ttaattgctg ttggactgct cttatactgt aaggccagaa gcacaccagt cacactaagc   1680
aaagatcaac tgagtggtat aaataatatt gcatttagta actaa                   1725
```

<210> SEQ ID NO 2
<211> LENGTH: 574
<212> TYPE: PRT
<213> ORGANISM: Artificial Sequence
<220> FEATURE:
<223> OTHER INFORMATION: Synthetic

<400> SEQUENCE: 2

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ala Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Gln Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160
```

```
Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
            290                 295                 300

Leu Tyr Gly Val Met Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Ile Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 3
<211> LENGTH: 18180
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---|
| cgttaatacg | actcactata | accaaacaag | agaaaaaaca | tgtatgggat | atataatgaa | 60 |
| gttagacagg | attttagggt | caaagtatcc | accctgagga | gcaggttcca | gacccttgc | 120 |
| tttgctgcca | aagttcacga | tggccgggtt | gttgagcacc | ttcgatacat | ttagctctag | 180 |
| gaggagcgaa | agtattaata | agtcgggagg | aggtgctgtt | atccccggcc | agaggagcac | 240 |
| agtctcagtg | ttcgtactag | gcccaagtgt | gactgatgat | gcagacaagt | tattcattgc | 300 |
| aactaccttc | ctagctcact | cattggacac | agataagcag | cactctcaga | gaggagggtt | 360 |
| cctcgtctct | ctgcttgcca | tggcttacag | tagtccagaa | ttgtacttga | caacaaacgg | 420 |
| agtaaacgcc | gatgtcaaat | atgtgatcta | acatagaa | aaagacccta | agaggacgaa | 480 |
| gacagacgga | ttcattgtga | agacgagaga | tatggaatat | gagaggacca | cagaatggct | 540 |
| gtttggacct | atggtcaaca | agagcccact | cttccagggt | caacgggatg | ctgcagaccc | 600 |
| tgacacactc | cttcaaacct | atgggtatcc | tgcatgccta | ggagcaataa | ttgtccaagt | 660 |
| ctggattgtg | ctggtgaagg | ccatcacaag | cagcgccggc | ttaaggaaag | ggttcttcaa | 720 |
| caggttagag | gcgttcagac | aagacggcac | cgtgaaaggt | gccttagttt | tcactgggga | 780 |
| gacagttgag | gggataggct | cggttatgag | atctcagcaa | agccttgtat | ctctcatggt | 840 |
| tgagacccct | gtgactatga | atactgcaag | atctgatctc | accacattag | agaagaacat | 900 |
| ccagatcgtt | gggaactaca | tccgagatgc | agggctggct | tccttcatga | acactattaa | 960 |
| atatggggtg | gagacaaaga | tggcagctct | aacgttgtca | aacctgaggc | cgatattaa | 1020 |
| taagattaga | agcctcatag | acacctacct | gtcaaaaggc | cccagagctc | cctttatctg | 1080 |
| tatcctcaag | gaccctgttc | atggtgaatt | tgctccaggc | aattatcctg | cactatggag | 1140 |
| ttacgccatg | ggagtcgccg | tcgtacagaa | caaggcaatg | cagcagtacg | tcacagggag | 1200 |
| gacatacctt | gatatggaaa | tgttcttact | aggacaagcc | gtggcaaagg | atgctgaatc | 1260 |
| gaagatcagc | agtgccctgg | aagatgagtt | aggagtgacg | gatacagcca | aggagaggct | 1320 |
| cagacatcat | ctggcaaact | tgtccggtgg | ggatggtgct | taccacaaac | caacaggcgg | 1380 |
| tggtgcaatt | gaggtagctc | tagacaatgc | cgatatcgac | ctagaaacag | aagctcatgc | 1440 |
| ggaccaggac | gctaggggtt | ggggtggaga | aagtggtgaa | agatgggcac | gtcaggtgag | 1500 |
| tggtggccac | tttgtcacac | tacatgggc | tgaacggtta | gaggaggaaa | ccaatgatga | 1560 |
| ggatgtatca | gacatagaga | gaagaatagc | catgagactc | gcagagagac | ggcaagagga | 1620 |
| ttctgcaacc | catggagatg | aaggccgcaa | taacggtgtc | gatcacgacg | aagatgacga | 1680 |
| taccgcagca | gtagctggga | taggaggaat | ctaggatcat | acgaggcttc | aaggtacttg | 1740 |
| atccgtagta | agaaaaactt | agggtgaaag | ttcatccact | gatcggctca | ggcaaggcca | 1800 |
| cacccaaccc | caccgaccac | acccagcagt | cgagacagcc | acggcttcgg | ctacacttac | 1860 |
| cgcatggatc | aagatgcctt | cattcttaaa | gaagattctg | aagttgagag | ggaggcgcca | 1920 |
| ggaggaagag | agtcgctctc | ggatgttatc | ggattcctcg | atgctgtcct | gtcgagtgaa | 1980 |
| ccaactgaca | tcgaggggga | cagaagctgg | ctccacaaca | ccatcaacac | tcccaagga | 2040 |
| ccaggctctg | cccatagagc | caaaagtgag | ggcgaaggag | aagtctcaac | accgtcgacc | 2100 |

-continued

```
caagataatc gatcaggtga ggagagtaga gtctctggga gaacaagcaa gccagaggca   2160
gaagcacatg ctggaaacct tgataaacaa aatatacacc gggcctttgg gggaagaact   2220
ggtacaaact ctgtatctca ggatctgggc gatggaggag actccggaat ccttgaaaat   2280
cctccaaatg agagaggata tccgagatca ggtattgaag atgaaaacag agagatggct   2340
gcgcaccctg ataagagggg agaagaccaa gctgaaggac ttccagaaga ggtacgagga   2400
ggtacatccc tacctgatga aggagaaggt ggagcaagta ataatggaag aagcatggag   2460
cctggcagct cacatagtgc aagagtaact ggggtcctgg tgattcctag ccccgaactc   2520
gaagaggctg tgctacggag gaacaaaaga agacctacca acagtgggtc caaacctctt   2580
actccagcaa ccgtgcctgg cacccggtcc ccaccgctga atcgttacaa cagcacaggg   2640
tcaccaccag gaaaaccccc atctacacag gatgagcaca tcaactctgg ggacaccccc   2700
gccgtcaggg tcaaagaccg gaaaccacca atagggaccc gctctgtctc agattgtcca   2760
gccaacggcc gcccaatcca cccgggtcta gagaccgact caacaaaaaa gggcatagga   2820
gagaacacat catctatgaa agagatggct acattgttga cgagtcttgg tgtaatccag   2880
tctgctcaag aattcgagtc atcccgagac gcgagttatg tgtttgcaag acgtgcccta   2940
aagtctgcaa actatgcaga gatgacattc aatgtatgcg gcctgatcct ttctgccgag   3000
aaatcttccg ctcgtaaggt agatgagaac aaacaactgc tcaaacagat ccaagagagc   3060
gtggaatcat tccgggatat ttacaagaga ttctctgagt atcagaaaga acagaactca   3120
ttgctgatgt ccaacctatc tacacttcat atcatcacag atagaggtgg caagactgac   3180
aacacagact cccttacaag gtccccctcc gtttttgcaa aatcaaaaga gaacaagact   3240
aaggctacca ggtttgaccc atctatggag accctagaag atatgaagta caaaccggac   3300
ctaatccgag aggatgaatt tagagatgag atccgcaacc cggtgtacca agagagggac   3360
acagaaccca gggcctcaaa cgcatcacgc ctcctcccct ccaaagagaa gcccacaatg   3420
cactctctca ggctcgtcat agagagcagt cccctaagca gagctgagaa agcagcatat   3480
gtgaaatcat tatccaagtg caagacagac caagaggtta aggcagtcat ggaactcgta   3540
gaagaggaca tagagtcact gaccaactag atcccgggtg aggcatccta ccatcctcag   3600
tcatagagag atccaattaa ttaacagcat cagccagtaa agattaagaa aaacttaggg   3660
tgaaagaaat ttcacctaac acggcgcaat ggcagatatc tatagattcc ctaagttctc   3720
atatgaggat aacggtactg tggagcccct gcctctgaga actggtccag ataagaaagc   3780
catcccctac atcaggatta tcaaggtagg agaccctcct aaacatggag tgagatacct   3840
agatttattg ctcttgggtt tctttgagac accgaaacaa acaaccaatc tagggagcgt   3900
atctgacttg acagagccga ccagctactc aatatgcggc tccgggtcgt tacccatagg   3960
tgtggccaaa tactacggga ctgatcagga actcttaaag gcctgcaccg atctcagaat   4020
tacggtgagg aggactgttc gagcaggaga gatgatcgta tacatggtgg attcgattgg   4080
tgctccactc ctaccatggt caggcaggct gagacaggga atgatattta atgcaaacaa   4140
ggtcgcacta gctccccaat gcctccctgt ggacaaggac ataagattca gagtggtgtt   4200
tgtcaatggg acatctctag gggcaatcac catagccaag atcccaaaga cccttgcaga   4260
ccttgcattg cccaactcta tatccgttaa cctactggtg acactcaaga ccgggatctc   4320
cacagaacaa aagggggtac tcccagtact tgatgatcaa ggggagaaaa agctcaattt   4380
tatggtgcac ctcgggttga tcaggagaaa ggtcgggaag atatactctg ttgagtactg   4440
caagagcaag attgagagaa tgcggctgat tttctcactt gggttaatcg gcggtataag   4500
```

```
cttccatgtt caggttactg ggacactatc taagacattc atgagtcagc tcgcatggaa    4560
gagggcagtc tgcttcccat taatggatgt gaatccccat atgaacctgg tgatttgggc    4620
ggcatctgta gaaatcacag gcgtcgatgc ggtgttccaa ccggccatcc ctcgtgattt    4680
ccgctactac cctaatgttg tggctaagaa catcggaagg atcagaaagc tgtaaatgtg    4740
cacccatcag agacctgcga caatgcccca agcagacacc acctggcagt cggagccacc    4800
gggtcactcc ttgtcttaaa taagaaaaac ttagggataa agtcccttgt gagtgcttgg    4860
ttgcaaaact ctccgtacgg gaaacatgac agcatatatc cagaggtcac agtgcatctc    4920
aacatcacta ctggttgttc tcaccacatt ggtctcgtgt cagattccca gggataggct    4980
ctctaacata ggggtcatag tcgatgaagg gaaatcactg aagatagctg atcccacga    5040 atcgaggtac atagtactga gtctagttcc gggggtagac cttgagaatg ggtgcggaac    5100
agcccaggtt atccagtaca agagcctact gaacaggctg ttaatcccat tgagggatgc    5160
cttagatctt caggaggctc tgataactgt caccaatgat acgacacaaa atgccggtgt    5220
tccacagtcg agattcttcg gtgctgtgat tggtactatc gcacttggag tggcgacatc    5280
agcacagatc accgcaggga ttgcactagc cgaagcgagg gaggccaaaa gagacatagc    5340
gctcatcaaa gaatcgatga caaaaacaca caagtctata gaactgctgc aaaacgctgt    5400 ggggaacaa attcttgctc taaagacact ccaggatttc gtgaatgatg agatcaaacc    5460
cgcaataagc gaattaggct gtgagactgc tgccttaaga ctgggtataa aattgacaca    5520
gcattactcc gggctgttaa ctgcgttcgg ctcgaatttc ggaaccatcg gagagaagag    5580
cctcacgctg caggcgctgt cttcacttta ctctgctaac attactgaga ttatgaccac    5640
aatcaggaca gggcagtcta acatctatga tgtcatttat acagaacaga tcaaaggaac    5700
ggtgatagat gtggatctag agagatacat ggttaccctg tctgtgaaga tccctattct    5760
ttctgaagtc ccaggtgtgc tcatacacaa ggcatcgtct atttcttaca acatagacgg    5820
ggaggaatgg tatgtgactg tccccagcca tatactcagt cgtgcttctt tcttaggggg    5880
tgcagacata accgattgtg ttgagtccag gttgacctat atatgcccca gggatcccgc    5940
acaactgata cctgacagcc agcaaaagtg tatcctgggg gacacaacaa ggtgtcctgt    6000
cacaaaagtt gtggacagcc ttatccccaa gtttgctttt gtgaatgggg gcgttgttgc    6060
taactgcata gcatccacat gtacctgcgg gacaggccga agaccaatca gtcaggatcg    6120
ctctaaaggt gtagtattcc taacccatga caactgtggt cttataggtg tcaatgggt    6180 agaattgtat gctaaccgga gagggcacga tgccacttgg ggggtccaga acttgacagt    6240
cggtcctgca attgctatca gacccgttga tatttctctc aaccttgctg atgctacgaa    6300
tttcttgcaa gactctaagg ctgagcttga gaaagcacgg aaaatcctct ctgaggtagg    6360
tagatggtac aactcaagag agactgtgat tacgatcata gtagttatgg tcgtaatatt    6420
ggtggtcatt atagtgatcg tcatcgtgct ttatagactc agaaggtcaa tgctaatggg    6480
taatccagat gaccgtatac cgagggacac atatacatta gagccgaaga tcagacatat    6540
gtacacaaac ggtgggtttg atgcgatggc tgagaaaaga tgatcacgag tttaaacaga    6600
tgtcttgtaa agcaggcatg gtatccgttg agatctgtat ataataagaa aaacttaggg    6660
tgaaagtgag gtcgcgcggt actttagctg cggccgcaca ttataagaaa aacttagggt    6720
gaaagtgagc ggccgcaaac aagcacagat catggatggt gatagggca aacgtgactc    6780 gtactggtct acctctccta gtggtagcac tacaaaatta gcatcaggtt gggagaggtc    6840
aagtaaagtt gacacatggt tgctgattct ctcattcacc cagtgggctt tgtcaattgc    6900
```

```
cacagtgatc atctgtatca taatttctgc tagacaaggg tatagtatga aagagtactc    6960
aatgactgta gaggcattga acatgagcag cagggaggtg aaagagtcac ttaccagtct    7020
aataaggcaa gaggttatcg caagggctgt caacattcag agctctgtgc aaaccggaat    7080
cccagtcttg ttgaacaaaa acagcaggga tgtcatccag atgattgata agtcgtgcag    7140
cagacaagag ctcactcagc tctgtgagag tacgatcgca gtccaccatg ccgagggaat    7200
tgcccctctt gagccacata gtttctggag atgccctgtc ggagaaccgt atcttagctc    7260
agatcctaaa atctcattgc tgcctggtcc gagcttgtta tctggttcta caacgatctc    7320
tggatgtgtt aggctcccct cactctcaat tggcgaggca atctatgcct attcatcaaa    7380
tctcattaca caaggttgtg ctgacatagg gaaatcatat caggtcctgc agctagggta    7440
catatcactc aattcagata tgttccctga tcttaacccc gtagtgtccc acacttatga    7500
catcaacgac aatcggaaat catgctctgt ggtggcaacc gggactaggg gttatcagct    7560
ttgctccatg ccgactgtag acgaaagaac cgactactct agtgatggta tcgaggatct    7620
ggtccttgat gtcctggatc tcaaagggag cactaagtct caccggtatc gcaacagcga    7680
ggtagatctt gatcacccgt tctctgcact atacccagt gtaggcaacg gcattgcaac    7740
agaaggctca ttgatatttc ttgggtatgg tgggctaacc accctctac agggtgatac    7800 aaaatgtagg acccaaggat gccaacaggt gtcgcaagac acatgcaatg aggctctgaa    7860
aattacatgg ctaggaggga aacaggtggt cagcgtgatc atccaggtca atgactatct    7920
ctcagagagg ccaaagataa gagtcacaac cattccaatc actcaaaact atctcggggc    7980
ggaaggtaga ttattaaaat tgggtgatcg ggtgtacatc tatacaagat catcaggctg    8040
gcactctcaa ctgcagatag gagtacttga tgtcagccac cctttgacta tcaactggac    8100
acctcatgaa gccttgtcta gaccaggaaa tgaagagtgc aattggtaca atacgtgtcc    8160
gaaggaatgc atatcaggcg tatacactga tgcttatcca ttgtcccctg atgcagctaa    8220
cgtcgctacc gtcacgctat atgccaatac atcgcgtgtc aacccaacaa tcatgtattc    8280
taacactact aacattataa atatgttaag gataaaggat gttcaattag aggctgcata    8340
taccacgaca tcgtgtatca cgcattttgg taaaggctac tgctttcaca tcatcgagat    8400
caatcagaag agcctgaata ccttacagcc gatgctcttt aagactagca tccctaaatt    8460
atgcaaggcc gagtcttaaa tttaactgac tagcaggctg gcgcgccttg ctgacactag    8520
agtcatctcc gaacatccac aatatctctc agtctcttac gtctctcaca gtattaagaa    8580
aaacccaggg tgaatgggaa gcttgccata ggtcatggat gggcaggagt cctcccaaaa    8640
cccttctgac atactctatc cagaatgcca cctgaactct cccatagtca gggggaagat    8700
agcacagttg cacgtcttgt tagatgtgaa ccagccctac agactgaagg acgacagcat    8760
aataaatatt acaaagcaca aaattaggaa cggaggattg tcccccgtc aaattaagat    8820 caggtctctg ggtaaggctc ttcaacgcac aataaaggat ttagaccgat acacgtttga    8880
accgtaccca acctactctc aggaattact taggcttgat ataccagaga tatgtgacaa    8940
aatccgatcc gtcttcgcgg tctcggatcg gctgaccagg gagttatcta gtgggttcca    9000
ggatctttgg ttgaatatct tcaagcaact aggcaatata gaaggaagag aggggtacga    9060
tccgttgcag gatatcggca ccatcccgga gataactgat aagtacagca ggaatagatg    9120
gtataggcca ttcctaactt ggttcagcat caaatatgac atgcggtgga tgcagaagac    9180
cagaccgggg ggaccccttg atacctctaa ttcacataac ctcctagaat gcaaatcata    9240
cactctagta acatacggag atcttgtcat gatactgaac aagttgacat tgacagggta    9300
```

| | | | | | |
|---|---|---|---|---|---|
| tatcctaacc | cctgagctgg | tcttgatgta | ttgtgatgtt | gtagaaggaa | ggtggaatat | 9360 |
| gtctgctgca | gggcatctag | ataagaagtc | cattgggata | acaagcaaag | gtgaggaatt | 9420 |
| atgggaacta | gtggattccc | tcttctcaag | tcttggagag | gaaatataca | atgtcatcgc | 9480 |
| actattggag | cccctatcac | ttgctctcat | acaactaaat | gatcctgtta | tacctctacg | 9540 |
| tggggcattt | atgaggcatg | tgttgacaga | gctacagact | gttttaacaa | gtagagacgt | 9600 |
| gtacacagat | gctgaagcag | acactattgt | ggagtcgtta | ctcgccattt | tccatggaac | 9660 |
| ctctattgat | gagaaagcag | agatcttttc | cttctttagg | acatttggcc | accccagctt | 9720 |
| agaggctgtc | actgccgccg | acaaggtaag | ggcccatatg | tatgcacaaa | aggcaataaa | 9780 |
| gcttaagacc | ctatacgagt | gtcatgcagt | tttttgcact | atcatcataa | atgggtatag | 9840 |
| agagaggcat | ggcggacagt | ggccccccctg | tgacttccct | gatcacgtgt | gtctagaact | 9900 |
| aaggaacgct | caagggtcca | atacggcaat | ctcttatgaa | tgtgctgtag | acaactatac | 9960 |
| aagtttcata | ggcttcaagt | ttcggaagtt | tatagaacca | caactagatg | aagatctcac | 10020 |
| aatatatatg | aaagacaaag | cactatcccc | caggaaggag | gcatgggact | ctgtataccc | 10080 |
| ggatagtaat | ctgtactata | aagccccaga | gtctgaagag | acccggcggc | ttattgaagt | 10140 |
| gttcataaat | gatgagaatt | tcaacccaga | agaaattatc | aattatgtgg | agtcaggaga | 10200 |
| ttggttgaaa | gacgaggagt | tcaacatctc | gtacagtctc | aaagagaaag | agatcaagca | 10260 |
| agagggtcgt | ctattcgcaa | aaatgactta | taagatgcga | gccgtacagg | tgctggcaga | 10320 |
| gacactactg | gctaaaggaa | taggagagct | attcagggaa | aatgggatgg | ttaagggaga | 10380 |
| gatagaccta | cttaaaagat | tgactactct | ttctgtctca | ggcgtcccca | ggactgattc | 10440 |
| agtgtacaat | aactctaaat | catcagagaa | gagaaacgaa | ggcatggaaa | ataagaactc | 10500 |
| tgggggtac | tgggacgaaa | agaagaggtc | cagacatgaa | ttcaaggcaa | cagattcatc | 10560 |
| aacagacggc | tatgaaacgt | taagttgctt | cctcacaaca | gacctcaaga | aatactgctt | 10620 |
| aaactggaga | tttgagagta | ctgcattgtt | tggtcagaga | tgcaacgaga | tatttggctt | 10680 |
| caagaccttc | tttaactgga | tgcatccagt | ccttgaaagg | tgtacaatat | atgttggaga | 10740 |
| tccttactgt | ccagtcgccg | accgatgca | tcgacaactc | caggatcatg | cagactctgg | 10800 |
| cattttcata | cataatccta | ggggggcat | agaaggttac | tgccagaagc | tgtggacctt | 10860 |
| aatctcaatc | agtgcaatcc | acctagcagc | tgtgagagtg | ggtgtcaggg | tctctgcaat | 10920 |
| ggttcagggt | gacaatcaag | ctatagccgt | gacatcaaga | gtacctgtag | ctcagactta | 10980 |
| caagcagaag | aaaaatcatg | tctatgagga | gatcaccaaa | tatttcggtg | ctctaagaca | 11040 |
| cgtcatgttt | gatgtagggc | acgagctaaa | attgaacgag | accatcatta | gtagcaagat | 11100 |
| gtttgtctat | agtaaaagga | tatactatga | tgggaagatt | ttaccacagt | gcctgaaagc | 11160 |
| cttgaccaag | tgtgtattct | ggtccgagac | actggtagat | gaaaacagat | ctgcttgttc | 11220 |
| gaacatctca | acatccatag | caaaagctat | cgaaaatggg | tattctccta | tactaggcta | 11280 |
| ctgcattgcg | ttgtataaga | cctgtcagca | ggtgtgcata | tcactaggga | tgactataaa | 11340 |
| tccaactatc | agcccgaccg | taagagatca | atactttaag | ggtaagaatt | ggctgagatg | 11400 |
| tgcagtgttg | attccagcaa | atgttggagg | attcaactac | atgtctacat | ctagatgctt | 11460 |
| tgttagaaat | attggagacc | ccgcagtagc | agccctagct | gatctcaaaa | gattcatcag | 11520 |
| agcggatctg | ttagacaagc | aggtattata | cagggtcatg | aatcaagaac | ccggtgactc | 11580 |
| tagttttcta | gattgggctt | cagacccttca | ttcgtgtaac | ctcccgcatt | ctcagagtat | 11640 |
| aactacgatt | ataaagaata | tcactgctag | atctgtgctg | caggaatccc | cgaatcctct | 11700 |

```
actgtctggt ctcttcaccg agactagtgg agaagaggat ctcaacctgg cctcgttcct    11760
tatggaccgg aaagtcatcc tgccgagagt ggctcatgag atcctgggta attccttaac    11820
tggagttagg gaggcgattg cagggatgct tgatacgacc aagtctctag tgagagccag    11880
cgttaggaaa ggaggattat catatgggat attgaggagg cttgtcaatt atgatctatt    11940
gcagtacgag acactgacta gaactctcag gaaaccggtg aaagacaaca tcgaatatga    12000
gtatatgtgt tcagttgagc tagctgtcgg tctaaggcag aaaatgtgga tccacctgac    12060
ttacgggaga cccatacatg ggttagaaac accagaccct ttagagctct tgagggaat     12120
atttatcgaa ggttcagagg tgtgcaagct ttgcaggtct gaaggagcag accccatcta    12180
tacatggttc tatcttcctg acaatataga cctggacacg cttacaaacg gatgtccggc    12240
tataagaatc ccctattttg gatcagccac tgatgaaagg tcggaagccc aactcgggta    12300
tgtaagaaat ctaagcaaac ccgcaaaggc ggccatccgg atagctatgg tgtatacgtg    12360
ggcctacggg actgatgaga tatcgtggat ggaagccgct cttatagccc aaacaagagc    12420
taatctgagc ttagagaatc taaagctgct gactcctgtt tcaacctcca ctaatctatc    12480
tcataggttg aaagatacgg caacccagat gaagttctct agtgcaacac tagtccgtgc    12540
aagtcggttc ataacaatat caaatgataa catggcactc aaagaagcag gggagtcgaa    12600
ggatactaat ctcgtgtatc agcagattat gctaactggg ctaagcttgt tcgagttcaa    12660
tatgagatat aagaaaggtt ccttagggaa gccactgata ttgcacttac atcttaataa    12720
cgggtgctgt ataatggagt ccccacagga ggcgaatatc cccccaaggt ccacattaga    12780
tttagagatt acacaagaga acaataaatt gatctatgat cctgatccac tcaaggatgt    12840
ggaccttgag ctatttagca aggtcagaga tgttgtacat acagttgaca tgacttattg    12900
gtcagatgat gaagttatca gagcaaccag catctgtact gcaatgacga tagctgatac    12960
aatgtctcaa ttagatagag acaacttaaa agagatgatc gcactagtaa atgacgatga    13020
tgtcaacagc ttgattactg agtttatggt gattgatgtt cctttatttt gctcaacgtt    13080
cggggggtatt ctagtcaatc agtttgcata ctcactctac ggcttaaaca tcagaggaag    13140
ggaagaaata tggggacatg tagtccggat tcttaaagat acctcccacg cagttctaaa    13200
agtcttatct aatgctctat cccatcccaa aatcttcaaa cgattctgga atgcaggtgt    13260
cgtggaacct gtgtatgggc ctaacctctc aaatcaggat aagatactct tggccctctc    13320
tgtctgtgaa tattctgtgg atctattcat gcacgactgg caagggggtg taccgcttga    13380
gatctttatc tgtgacaatg acccagatgt ggccgacatg aggaggtcct ctttcttggc    13440
aagacatctt gcatacctat gcagcttggc agagatatct agggatgggc caagattaga    13500
atcaatgaac tctctagaga ggctcgagtc actaaagagt tacctggaac tcacattttct   13560
tgatgacccg gtactgaggt acagtcagtt gactggccta gtcatcaaag tattcccatc    13620
tactttgacc tatatccgga agtcatctat aaaagtgtta aggacaagag gtataggagt    13680
ccctgaagtc ttagaagatt gggatcccga ggcagataat gcactgttag atggtatcgc    13740
ggcagaaata caacagaata ttcctttggg acatcagact agagcccctt tttgggggtt    13800
gagagtatcc aagtcacagg tactgcgtct ccgggggtac aaggagatca caagaggtga    13860
gataggcaga tcaggtgttg gtctgacgtt accattcgat ggaagatatc tatctcacca    13920
gctgaggctc tttggcatca acagtactag ctgcttgaaa gcacttgaac ttacctacct    13980
attgagcccc ttagttgaca aggataaaga taggctatat ttaggggaag gagctggggc    14040
catgctttcc tgttatgacg ctactcttgg cccatgcatc aactattata actcaggggt    14100
```

```
atactcttgt gatgtcaatg ggcagagaga gttaaatata tatcctgctg aggtggcact   14160
agtgggaaag aaattaaaca atgttactag tctgggtcaa agagttaaag tgttattcaa   14220
cgggaatcct ggctcgacat ggattgggaa tgatgagtgt gaggctttga tttggaatga   14280
attacagaat agctcgatag gcctagtcca ctgtgacatg gagggaggag atcataagga   14340
tgatcaagtt gtactgcatg agcattacag tgtaatccgg atcgcgtatc tggtgggga    14400 tcgagacgtt gtgcttataa gcaagattgc tcccaggctg ggcacggatt ggaccaggca   14460
gctcagccta tatctgagat actgggacga ggttaaccta atagtgctta aaacatctaa   14520
ccctgcttcc acagagatgt atctcctatc gaggcacccc aaatctgaca ttatagagga   14580
cagcaagaca gtgttagcta gtctcctccc tttgtcaaaa gaagatagca tcaagataga   14640
aaagtggatc ttaatagaga aggcaaaggc tcacgaatgg gttactcggg aattgagaga   14700
aggaagctct tcatcaggga tgcttagacc ttaccatcaa gcactgcaga cgtttggctt   14760
tgaaccaaac ttgtataaat tgagcagaga tttcttgtcc accatgaaca tagctgatac   14820
acacaactgc atgatagctt tcaacagggt tttgaaggat acaatcttcg aatgggctag   14880
aataactgag tcagataaaa ggcttaaact aactggtaag tatgacctgt atcctgtgag   14940
agattcaggc aagttgaaga caatttctag aagacttgtg ctatcttgga tatctttatc   15000
tatgtccaca agattggtaa ctgggtcatt ccctgaccag aagtttgaag caagacttca   15060
attgggaata gtttcattat catcccgtga aatcaggaac ctgagggtta tcacaaaaac   15120
tttattatac aggtttgagg atattataca tagtataacg tatagattcc tcaccaaaga   15180
aataaagatt ttgatgaaga ttttaggggc agtcaagatg ttcggggcca ggcaaaatga   15240
atacacgacc gtgattgatg atggatcact aggtgatatc gagccatatg acagctcgta   15300
ataattagtc cctatcgtgc agaacgatcg aagctccgcg gtacctggaa gtcttggact   15360
tgtccatatg acaatagtaa gaaaaactta caagaagaca agaaaattta aaggataca   15420 tatctcttaa actcttgtct ggtgggtcgg catggcatct ccacctcctc gcggtccgac   15480
ctgggcatcc gaaggaggac gtcgtccact cggatggcta agggaggggc cccgcgggg   15540 ctgctaacaa agcccgaaag gaagctgagt tggctgctgc caccgctgag caataactag   15600
cataacccct tggggcctct aaacgggtct tgaggggttt tttgctgaaa ggaggaacta   15660
tatccggatc gagacctcga tgccggctga tgcggtattt tctccttacg catctgtgcg   15720
gtatttcaca ccgcatatgg tgcactctca gtacaatctg ctctgatgcc gcatagttaa   15780
gccagccccg acaccgcca acacccgctg acgcgccctg acgggcttgt ctgctcccgg   15840
catccgctta cagacaagct gtgaccgtct ccgggagctg catgtgtcag aggttttcac   15900
cgtcatcacc gaaacgcgcg agacgaaagg gcctcgtgat acgcctattt ttataggtta   15960
atgtcatgat aataatggtt tcttagacgt caggtggcac ttttcgggga aatgtgcgcg   16020
gaacccctat ttgttttattt ttctaaatac attcaaatat gtatccgctc atgagacaat   16080
aaccctgata aatgcttcaa taatattgaa aaaggaagag tatgagtatt caacatttcc   16140
gtgtcgccct tattcccttt tttgcggcat tttgccttcc tgttttttgct cacccagaaa   16200 cgctggtgaa agtaaaagat gctgaagatc agttgggtgc acgagtgggt tacatcgaac   16260
tggatctcaa cagcggtaag atccttgaga gttttcgccc cgaagaacgt tttccaatga   16320
tgagcacttt taaagttctg ctatgtggcg cggtattatc ccgtattgac gccgggcaag   16380
agcaactcgg tcgccgcata cactattctc agaatgactt ggttgagtac tcaccagtca   16440
cagaaaagca tcttacggat ggcatgacag taagagaatt atgcagtgct gccataacca   16500
```

| | |
|---|---|
| tgagtgataa cactgcggcc aacttacttc tgacaacgat cggaggaccg aaggagctaa | 16560 |
| ccgcttttt gcacaacatg ggggatcatg taactcgcct tgatcgttgg gaaccggagc | 16620 |
| tgaatgaagc cataccaaac gacgagcgtg acaccacgat gcctgtagca atggcaacaa | 16680 |
| cgttgcgcaa actattaact ggcgaactac ttactctagc ttcccggcaa caattaatag | 16740 |
| actggatgga ggcggataaa gttgcaggac cacttctgcg ctcggccctt ccggctggct | 16800 |
| ggtttattgc tgataaatct ggagccgtg agcgtgggtc tcgcggtatc attgcagcac | 16860 |
| tggggccaga tggtaagccc tcccgtatcg tagttatcta cacgacgggg agtcaggcaa | 16920 |
| ctatggatga acgaaataga cagatcgctg agataggtgc ctcactgatt aagcattggt | 16980 |
| aactgtcaga ccaagtttac tcatatatac tttagattga tttaaaactt cattttaat | 17040 |
| ttaaaaggat ctaggtgaag atccttttg ataatctcat gaccaaaatc ccttaacgtg | 17100 |
| agttttcgtt ccactgagcg tcagaccccg tagaaaagat caaggatctc tcttgagatc | 17160 |
| cttttttct gcgcgtaatc tgctgcttgc aaacaaaaaa accaccgcta ccagcggtgg | 17220 |
| tttgtttgcc ggatcaagag ctaccaactc tttttccgaa ggtaactggc ttcagcagag | 17280 |
| cgcagatacc aaatactgtc cttctagtgt agccgtagtt aggccaccac ttcaagaact | 17340 |
| ctgtagcacc gcctacatac ctcgctctgc taatcctgtt accagtggct gctgccagtg | 17400 |
| gcgataagtc gtgtcttacc gggttggact caagacgata gttaccggat aaggcgcagc | 17460 |
| ggtcgggctg aacggggggt tcgtgcacac agcccagctt ggagcgaacg acctacaccg | 17520 |
| aactgagata cctacagcgt gagctatgag aaagcgccac gcttcccgaa gggagaaagg | 17580 |
| cggacaggta tccggtaagc ggcagggtcg aacaggaga gcgcacgagg gagcttccag | 17640 |
| ggggaaacgc ctggtatctt tatagtcctg tcgggtttcg ccacctctga cttgagcgtc | 17700 |
| gatttttgtg atgctcgtca gggggcgga gcctatggaa aaacgccagc aacgcggcct | 17760 |
| ttttacggtt cctggccttt tgctggcctt ttgctcacat gttctttcct gcgttatccc | 17820 |
| ctgattctgt ggataaccgt attaccgcct ttgagtgagc tgataccgct cgccgcagcc | 17880 |
| gaacgaccga gcgcagcgag tcagtgagcg aggaagcgga agagcgccca atacgcaaac | 17940 |
| cgcctctccc cgcgcgttgg ccgattcatt aatgcagctg gcacgacagg tttcccgact | 18000 |
| ggaaagcggg cagtgagcgc aacgcaatta atgtgagtta gctcactcat taggcacccc | 18060 |
| aggctttaca ctttatgctt ccggctcgta tgttgtgtgg aattgtgagc ggataacaat | 18120 |
| ttcacacagg aaacagctat gaccatgatt acgccaagct tgcatgcctg caggtcgacg | 18180 |

<210> SEQ ID NO 4
<211> LENGTH: 1575
<212> TYPE: DNA
<213> ORGANISM: Sendai virus

<400> SEQUENCE: 4

| | |
|---|---|
| atggccgggt tgttgagcac cttcgataca tttagctcta ggaggagcga aagtattaat | 60 |
| aagtcgggag gaggtgctgt tatccccggc cagaggagca cagtctcagt gttcgtacta | 120 |
| ggcccaagtg tgactgatga tgcagacaag ttattcattg caactacctt cctagctcac | 180 |
| tcattggaca cagataagca gcactctcag agaggagggt cctcgtctc tctgcttgcc | 240 |
| atggcttaca gtagtccaga attgtacttg acaacaaacg gagtaaacgc cgatgtcaaa | 300 |
| tatgtgatct acaacataga gaaagaccct aagaggacga agacagacgg attcattgtg | 360 |
| aagacgagag atatggaata tgagaggacc acagaatggc tgtttggacc tatggtcaac | 420 |
| aagagcccac tcttccaggg tcaacgggat gctgcagacc ctgacacact ccttcaaacc | 480 |

```
tatgggtatc ctgcatgcct aggagcaata attgtccaag tctggattgt gctggtgaag    540
gccatcacaa gcagcgccgg cttaaggaaa gggttcttca acaggttaga ggcgttcaga    600
caagacggca ccgtgaaagg tgccttagtt ttcactgggg agacagttga ggggataggc    660
tcggttatga gatctcagca aagccttgta tctctcatgg ttgagaccct tgtgactatg    720
aatactgcaa gatctgatct caccacatta gagaagaaca tccagatcgt tgggaactac    780
atccgagatg cagggctggc ttccttcatg aacactatta aatatggggt ggagacaaag    840
atggcagctc taacgttgtc aaacctgagg cccgatatta ataagattag aagcctcata    900
gacacctacc tgtcaaaagg ccccagagct ccctttatct gtatcctcaa ggaccctgtt    960
catggtgaat ttgctccagg caattatcct gcactatgga gttacgccat gggagtcgcc    1020
gtcgtacaga acaaggcaat gcagcagtac gtcacaggga ggacataccT tgatatggaa    1080
atgttcttac taggacaagc cgtggcaaag gatgctgaat cgaagatcag cagtgccctg    1140
gaagatgagt taggagtgac ggatacagcc aaggagaggc tcagacatca tctggcaaac    1200
ttgtccggtg gggatggtgc ttaccacaaa ccaacaggcg tggtgcaat tgaggtagct    1260 ctagacaatg ccgatatcga cctagaaaca gaagctcatg cggaccagga cgctaggggt    1320
tggggtggag aaagtggtga agatgggca cgtcaggtga gtggtggcca ctttgtcaca    1380
ctacatgggg ctgaacggtt agaggaggaa accaatgatg aggatgtatc agacatagag    1440
agaagaatag ccatgagact cgcagagaga cggcaagaga ttctgcaac ccatggagat    1500 gaaggccgca ataacggtgt cgatcacgac gaagatgacg ataccgcagc agtagctggg    1560
ataggaggaa tctag                                                    1575
```

<210> SEQ ID NO 5
<211> LENGTH: 524
<212> TYPE: PRT
<213> ORGANISM: Sendai virus

<400> SEQUENCE: 5

```
Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Met Val Asn Lys Ser Pro Leu
    130                 135                 140

Phe Gln Gly Gln Arg Asp Ala Ala Asp Pro Asp Thr Leu Leu Gln Thr
145                 150                 155                 160

Tyr Gly Tyr Pro Ala Cys Leu Gly Ala Ile Ile Val Gln Val Trp Ile
                165                 170                 175
```

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
            195                 200                 205

Leu Val Phe Thr Gly Glu Thr Val Glu Gly Ile Gly Ser Val Met Arg
            210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
            275                 280                 285

Leu Arg Pro Asp Ile Asn Lys Ile Arg Ser Leu Ile Asp Thr Tyr Leu
            290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Gln Asn Lys Ala Met Gln Gln Tyr Val Thr
            340                 345                 350

Gly Arg Thr Tyr Leu Asp Met Glu Met Phe Leu Leu Gly Gln Ala Val
            355                 360                 365

Ala Lys Asp Ala Glu Ser Lys Ile Ser Ser Ala Leu Glu Asp Glu Leu
            370                 375                 380

Gly Val Thr Asp Thr Ala Lys Glu Arg Leu Arg His His Leu Ala Asn
385                 390                 395                 400

Leu Ser Gly Gly Asp Gly Ala Tyr His Lys Pro Thr Gly Gly Gly Ala
                405                 410                 415

Ile Glu Val Ala Leu Asp Asn Ala Asp Ile Asp Leu Glu Thr Glu Ala
            420                 425                 430

His Ala Asp Gln Asp Ala Arg Gly Trp Gly Gly Glu Ser Gly Glu Arg
            435                 440                 445

Trp Ala Arg Gln Val Ser Gly Gly His Phe Val Thr Leu His Gly Ala
            450                 455                 460

Glu Arg Leu Glu Glu Glu Thr Asn Asp Glu Asp Val Ser Asp Ile Glu
465                 470                 475                 480

Arg Arg Ile Ala Met Arg Leu Ala Glu Arg Arg Gln Glu Asp Ser Ala
                485                 490                 495

Thr His Gly Asp Glu Gly Arg Asn Asn Gly Val Asp His Asp Glu Asp
            500                 505                 510

Asp Asp Thr Ala Ala Val Ala Gly Ile Gly Gly Ile
            515                 520

<210> SEQ ID NO 6
<211> LENGTH: 1707
<212> TYPE: DNA
<213> ORGANISM: Sendai virus

<400> SEQUENCE: 6
atggatcaag atgccttcat tcttaaagaa gattctgaag ttgagaggga ggcgccagga      60
ggaagagagt cgctctcgga tgttatcgga ttcctcgatg ctgtcctgtc gagtgaacca     120
actgacatcg gagggacag aagctggctc acaacacca tcaacactcc ccaaggacca     180

```
ggctctgccc atagagccaa aagtgagggc gaaggagaag tctcaacacc gtcgacccaa      240
gataatcgat caggtgagga gagtagagtc tctgggagaa caagcaagcc agaggcagaa      300
gcacatgctg gaaaccttga taaacaaaat atacaccggg cctttggggg aagaactggt      360
acaaactctg tatctcagga tctgggcgat ggaggagact ccggaatcct tgaaaatcct      420
ccaaatgaga gaggatatcc gagatcaggt attgaagatg aaaacagaga gatggctgcg      480
caccctgata gaggggagag agaccaagct gaaggacttc agaagaggt acgaggaggt       540 acatccctac ctgatgaagg agaaggtgga gcaagtaata atggaagaag catggagcct      600
ggcagctcac atagtgcaag agtaactggg gtcctggtga ttcctagccc cgaactcgaa      660
gaggctgtgc tacggaggaa caaaagaaga cctaccaaca gtgggtccaa acctcttact      720
ccagcaaccg tgcctggcac ccggtcccca ccgctgaatc gttacaacag cacagggtca      780
ccaccaggaa acccccatc tacacaggat gagcacatca actctgggga cacccccgcc       840
gtcagggtca agaccggaa accaccaata gggaccgct ctgtctcaga ttgtccagcc        900
aacggccgcc caatccaccc gggtctagag accgactcaa caaaaaaggg cataggagag      960
aacacatcat ctatgaaaga gatggctaca ttgttgacga gtcttggtgt aatccagtct     1020
gctcaagaat tcgagtcatc ccgagacgcg agttatgtgt ttgcaagacg tgccctaaag     1080
tctgcaaact atgcagagat gacattcaat gtatgcggcc tgatcctttc tgccgagaaa     1140
tcttccgctc gtaaggtaga tgagaacaaa caactgctca acagatcca agagagcgtg      1200 gaatcattcc gggatattta caagagattc tctgagtatc agaaagaaca gaactcattg     1260
ctgatgtcca acctatctac acttcatatc atcacagata gaggtggcaa gactgacaac     1320
acagactccc ttacaaggtc cccctccgtt tttgcaaaat caaaagagaa caagactaag     1380
gctaccaggt ttgacccatc tatggagacc ctagaagata tgaagtacaa accggaccta     1440
atccgagagg atgaatttag agatgagatc cgcaacccgg tgtaccaaga gggacacaca     1500
gaacccaggg cctcaaacgc atcacgcctc ctcccctcca agagaagcc cacaatgcac      1560 tctctcaggc tcgtcataga gagcagtccc ctaagcagag ctgagaaagc agcatatgtg     1620
aaatcattat ccaagtgcaa gacagaccaa gaggttaagg cagtcatgga actcgtagaa     1680
gaggacatag agtcactgac caactag                                         1707
```

<210> SEQ ID NO 7
<211> LENGTH: 568
<212> TYPE: PRT
<213> ORGANISM: Sendai virus

<400> SEQUENCE: 7

```
Met Asp Gln Asp Ala Phe Ile Leu Lys Glu Asp Ser Glu Val Glu Arg
1               5                   10                  15

Glu Ala Pro Gly Gly Arg Glu Ser Leu Ser Asp Val Ile Gly Phe Leu
            20                  25                  30

Asp Ala Val Leu Ser Ser Glu Pro Thr Asp Ile Gly Gly Asp Arg Ser
        35                  40                  45

Trp Leu His Asn Thr Ile Asn Thr Pro Gln Gly Pro Gly Ser Ala His
    50                  55                  60

Arg Ala Lys Ser Glu Gly Glu Gly Glu Val Ser Thr Pro Ser Thr Gln
65                  70                  75                  80

Asp Asn Arg Ser Gly Glu Glu Ser Arg Val Ser Gly Arg Thr Ser Lys
                85                  90                  95
```

```
Pro Glu Ala Glu Ala His Ala Gly Asn Leu Asp Lys Gln Asn Ile His
                100                 105                 110

Arg Ala Phe Gly Gly Arg Thr Gly Thr Asn Ser Val Ser Gln Asp Leu
        115                 120                 125

Gly Asp Gly Gly Asp Ser Gly Ile Leu Glu Asn Pro Pro Asn Glu Arg
    130                 135                 140

Gly Tyr Pro Arg Ser Gly Ile Glu Asp Glu Asn Arg Glu Met Ala Ala
145                 150                 155                 160

His Pro Asp Lys Arg Gly Glu Asp Gln Ala Glu Gly Leu Pro Glu Glu
                165                 170                 175

Val Arg Gly Gly Thr Ser Leu Pro Asp Glu Gly Glu Gly Gly Ala Ser
            180                 185                 190

Asn Asn Gly Arg Ser Met Glu Pro Gly Ser Ser His Ser Ala Arg Val
        195                 200                 205

Thr Gly Val Leu Val Ile Pro Ser Pro Glu Leu Glu Glu Ala Val Leu
    210                 215                 220

Arg Arg Asn Lys Arg Arg Pro Thr Asn Ser Gly Ser Lys Pro Leu Thr
225                 230                 235                 240

Pro Ala Thr Val Pro Gly Thr Arg Ser Pro Pro Leu Asn Arg Tyr Asn
                245                 250                 255

Ser Thr Gly Ser Pro Pro Gly Lys Pro Pro Ser Thr Gln Asp Glu His
            260                 265                 270

Ile Asn Ser Gly Asp Thr Pro Ala Val Arg Val Lys Asp Arg Lys Pro
        275                 280                 285

Pro Ile Gly Thr Arg Ser Val Ser Asp Cys Pro Ala Asn Gly Arg Pro
    290                 295                 300

Ile His Pro Gly Leu Glu Thr Asp Ser Thr Lys Lys Gly Ile Gly Glu
305                 310                 315                 320

Asn Thr Ser Ser Met Lys Glu Met Ala Thr Leu Leu Thr Ser Leu Gly
                325                 330                 335

Val Ile Gln Ser Ala Gln Glu Phe Glu Ser Ser Arg Asp Ala Ser Tyr
            340                 345                 350

Val Phe Ala Arg Arg Ala Leu Lys Ser Ala Asn Tyr Ala Glu Met Thr
        355                 360                 365

Phe Asn Val Cys Gly Leu Ile Leu Ser Ala Glu Lys Ser Ser Ala Arg
    370                 375                 380

Lys Val Asp Glu Asn Lys Gln Leu Leu Lys Gln Ile Gln Glu Ser Val
385                 390                 395                 400

Glu Ser Phe Arg Asp Ile Tyr Lys Arg Phe Ser Glu Tyr Gln Lys Glu
                405                 410                 415

Gln Asn Ser Leu Leu Met Ser Asn Leu Ser Thr Leu His Ile Ile Thr
            420                 425                 430

Asp Arg Gly Gly Lys Thr Asp Asn Thr Asp Ser Leu Thr Arg Ser Pro
        435                 440                 445

Ser Val Phe Ala Lys Ser Lys Glu Asn Lys Thr Lys Ala Thr Arg Phe
    450                 455                 460

Asp Pro Ser Met Glu Thr Leu Glu Asp Met Lys Tyr Lys Pro Asp Leu
465                 470                 475                 480

Ile Arg Glu Asp Glu Phe Arg Asp Glu Ile Arg Asn Pro Val Tyr Gln
                485                 490                 495

Glu Arg Asp Thr Glu Pro Arg Ala Ser Asn Ala Ser Arg Leu Leu Pro
            500                 505                 510
```

Ser Lys Glu Lys Pro Thr Met His Ser Leu Arg Leu Val Ile Glu Ser
    515                 520                 525

Ser Pro Leu Ser Arg Ala Glu Lys Ala Ala Tyr Val Lys Ser Leu Ser
    530                 535                 540

Lys Cys Lys Thr Asp Gln Glu Val Lys Ala Val Met Glu Leu Val Glu
545                 550                 555                 560

Glu Asp Ile Glu Ser Leu Thr Asn
                565

<210> SEQ ID NO 8
<211> LENGTH: 615
<212> TYPE: DNA
<213> ORGANISM: Sendai virus

<400> SEQUENCE: 8
atgccttcat tcttaaagaa gattctgaag ttgagaggga ggcgccagga ggaagagagt      60
cgctctcgga tgttatcgga ttcctcgatg ctgtcctgtc gagtgaacca actgacatcg     120
gaggggacag aagctggctc cacaacacca tcaacactcc ccaaggacca ggctctgccc     180
atagagccaa aagtgagggc gaaggagaag tctcaacacc gtcgacccaa gataatcgat     240
caggtgagga gagtagagtc tctgggagaa caagcaagcc agaggcagaa gcacatgctg     300
gaaaccttga taaacaaaat atacaccggg cctttggggg aagaactggt acaaactctg     360
tatctcagga tctgggcgat ggaggagact ccggaatcct tgaaaatcct ccaaatgaga     420
gaggatatcc gagatcaggt attgaagatg aaaacagaga gatggctgcg caccctgata     480
agaggggaga agaccaagct gaaggacttc agaagaggt cgaggaggt acatccctac      540 ctgatgaagg agaaggtgga gcaagtaata atggaagaag catggagcct ggcagctcac     600
atagtgcaag agtaa                                                      615

<210> SEQ ID NO 9
<211> LENGTH: 204
<212> TYPE: PRT
<213> ORGANISM: Sendai virus

<400> SEQUENCE: 9

Met Pro Ser Phe Leu Lys Lys Ile Leu Lys Leu Arg Gly Arg Arg Gln
1               5                   10                  15

Glu Glu Glu Ser Arg Ser Arg Met Leu Ser Asp Ser Ser Met Leu Ser
            20                  25                  30

Cys Arg Val Asn Gln Leu Thr Ser Glu Gly Thr Glu Ala Gly Ser Thr
        35                  40                  45

Thr Pro Ser Thr Leu Pro Lys Asp Gln Ala Leu Pro Ile Glu Pro Lys
    50                  55                  60

Val Arg Ala Lys Glu Lys Ser Gln His Arg Arg Pro Lys Ile Ile Asp
65                  70                  75                  80

Gln Val Arg Arg Val Glu Ser Leu Gly Glu Gln Ala Ser Gln Arg Gln
                85                  90                  95

Lys His Met Leu Glu Thr Leu Ile Asn Lys Ile Tyr Thr Gly Pro Leu
            100                 105                 110

Gly Glu Glu Leu Val Gln Thr Leu Tyr Leu Arg Ile Trp Ala Met Glu
        115                 120                 125

Glu Thr Pro Glu Ser Leu Lys Ile Leu Gln Met Arg Glu Asp Ile Arg
    130                 135                 140

Asp Gln Val Leu Lys Met Lys Thr Glu Arg Trp Leu Arg Thr Leu Ile
145                 150                 155                 160

Arg Gly Glu Lys Thr Lys Leu Lys Asp Phe Gln Lys Arg Tyr Glu Glu
            165                 170                 175

Val His Pro Tyr Leu Met Lys Glu Lys Val Glu Gln Val Ile Met Glu
        180                 185                 190

Glu Ala Trp Ser Leu Ala Ala His Ile Val Gln Glu
    195                 200

<210> SEQ ID NO 10
<211> LENGTH: 1047
<212> TYPE: DNA
<213> ORGANISM: Sendai virus

<400> SEQUENCE: 10
atggcagata tctatagatt ccctaagttc tcatatgagg ataacggtac tgtggagccc      60
ctgcctctga gaactggtcc agataagaaa gccatcccct acatcaggat tatcaaggta     120
ggagaccctc ctaaacatgg agtgagatac ctagatttat tgctcttggg tttctttgag     180
acaccgaaac aaacaaccaa tctagggagc gtatctgact tgacagagcc gaccagctac     240
tcaatatgcg gctccgggtc gttacccata ggtgtggcca atactacgg gactgatcag      300 gaactcttaa aggcctgcac cgatctcaga attacggtga ggaggactgt tcgagcagga     360
gagatgatcg tatacatggt ggattcgatt ggtgctccac tcctaccatg gtcaggcagg     420
ctgagacagg gaatgatatt taatgcaaac aaggtcgcac tagctcccca atgcctccct     480
gtggacaagg acataagatt cagagtggtg tttgtcaatg gacatctct aggggcaatc      540 accatagcca gatcccaaa gacccttgca gaccttgcat tgcccaactc tatatccgtt      600
aacctactgg tgacactcaa gaccgggatc tccacagaac aaaaggggt actcccagta      660 cttgatgatc aaggggagaa aaagctcaat tttatggtgc acctcgggtt gatcaggaga     720
aaggtcggga gatatactc tgttgagtac tgcaagagca gattgagag aatgcggctg       780 attttctcac ttgggttaat cggcggtata agcttccatg ttcaggttac tgggacacta     840
tctaagacat tcatgagtca gctcgcatgg aagagggcag tctgcttccc attaatggat     900
gtgaatcccc atatgaacct ggtgatttgg gcggcatctg tagaaatcac aggcgtcgat    960
gcggtgttcc aaccggccat ccctcgtgat ttccgctact accctaatgt tgtggctaag   1020
aacatcggaa ggatcagaaa gctgtaa                                       1047

<210> SEQ ID NO 11
<211> LENGTH: 348
<212> TYPE: PRT
<213> ORGANISM: Sendai virus

<400> SEQUENCE: 11

Met Ala Asp Ile Tyr Arg Phe Pro Lys Phe Ser Tyr Glu Asp Asn Gly
1               5                   10                  15

Thr Val Glu Pro Leu Pro Leu Arg Thr Gly Pro Asp Lys Lys Ala Ile
            20                  25                  30

Pro Tyr Ile Arg Ile Ile Lys Val Gly Asp Pro Pro Lys His Gly Val
        35                  40                  45

Arg Tyr Leu Asp Leu Leu Leu Gly Phe Phe Glu Thr Pro Lys Gln
    50                  55                  60

Thr Thr Asn Leu Gly Ser Val Ser Asp Leu Thr Glu Pro Thr Ser Tyr
65                  70                  75                  80

Ser Ile Cys Gly Ser Gly Ser Leu Pro Ile Gly Val Ala Lys Tyr Tyr
                85                  90                  95

Gly Thr Asp Gln Glu Leu Leu Lys Ala Cys Thr Asp Leu Arg Ile Thr
            100                 105                 110

Val Arg Arg Thr Val Arg Ala Gly Glu Met Ile Val Tyr Met Val Asp
        115                 120                 125

Ser Ile Gly Ala Pro Leu Leu Pro Trp Ser Gly Arg Leu Arg Gln Gly
    130                 135                 140

Met Ile Phe Asn Ala Asn Lys Val Ala Leu Ala Pro Gln Cys Leu Pro
145                 150                 155                 160

Val Asp Lys Asp Ile Arg Phe Arg Val Val Phe Val Asn Gly Thr Ser
                165                 170                 175

Leu Gly Ala Ile Thr Ile Ala Lys Ile Pro Lys Thr Leu Ala Asp Leu
            180                 185                 190

Ala Leu Pro Asn Ser Ile Ser Val Asn Leu Leu Val Thr Leu Lys Thr
        195                 200                 205

Gly Ile Ser Thr Glu Gln Lys Gly Val Leu Pro Val Leu Asp Asp Gln
    210                 215                 220

Gly Glu Lys Lys Leu Asn Phe Met Val His Leu Gly Leu Ile Arg Arg
225                 230                 235                 240

Lys Val Gly Lys Ile Tyr Ser Val Glu Tyr Cys Lys Ser Lys Ile Glu
                245                 250                 255

Arg Met Arg Leu Ile Phe Ser Leu Gly Leu Ile Gly Gly Ile Ser Phe
            260                 265                 270

His Val Gln Val Thr Gly Thr Leu Ser Lys Thr Phe Met Ser Gln Leu
        275                 280                 285

Ala Trp Lys Arg Ala Val Cys Phe Pro Leu Met Asp Val Asn Pro His
    290                 295                 300

Met Asn Leu Val Ile Trp Ala Ala Ser Val Glu Ile Thr Gly Val Asp
305                 310                 315                 320

Ala Val Phe Gln Pro Ala Ile Pro Arg Asp Phe Arg Tyr Tyr Pro Asn
                325                 330                 335

Val Val Ala Lys Asn Ile Gly Arg Ile Arg Lys Leu
            340                 345

<210> SEQ ID NO 12
<211> LENGTH: 1698
<212> TYPE: DNA
<213> ORGANISM: Sendai virus

<400> SEQUENCE: 12
atgacagcat atatccagag gtcacagtgc atctcaacat cactactggt tgttctcacc      60
acattggtct cgtgtcagat tcccagggat aggctctcta acatagggdt catagtcgat     120
gaagggaaat cactgaagat agctggatcc cacgaatcga ggtacatagt actgagtcta     180
gttccggggg tagaccttga aatgggtgcg ggaacagccc aggttatcca gtacaagagc     240
ctactgaaca ggctgttaat cccattgagg gatgccttag atcttcagga ggctctgata     300
actgtcacca atgatacgac acaaaatgcc ggtgttccac agtcgagatt cttcggtgct     360
gtgattggta ctatcgcact tggagtggcg acatcagcac agatcaccgc agggattgca     420
ctagccgaag cgagggaggc caaaagagac atagcgctca tcaaagaatc gatgacaaaa     480
acacacaagt ctatagaact gctgcaaaac gctgtggggg aacaaattct tgctctaaag     540
acactccagg atttcgtgaa tgatgagatc aaacccgcaa taagcgaatt aggctgtgag     600
actgctgcct taagactggg tataaaattg acacagcatt actccgggct gttaactgcg     660
ttcggctcga atttcggaac catcggagag aagagcctca cgctgcaggc gctgtcttca     720

```
ctttactctg ctaacattac tgagattatg accacaatca ggacagggca gtctaacatc    780
tatgatgtca tttatacaga acagatcaaa ggaacggtga tagatgtgga tctagagaga    840
tacatggtta ccctgtctgt gaagatccct attctttctg aagtcccagg tgtgctcata    900
cacaaggcat cgtctatttc ttacaacata gacggggagg aatggtatgt gactgtcccc    960
agccatatac tcagtcgtgc ttctttctta ggggtgcag acataaccga ttgtgttgag   1020
tccaggttga cctatatatg ccccagggat cccgcacaac tgatacctga cagccagcaa   1080
aagtgtatcc tgggggacac aacaaggtgt cctgtcacaa aagttgtgga cagccttatc   1140
cccaagtttg cttttgtgaa tgggggcgtt gttgctaact gcatagcatc cacatgtacc   1200
tgcgggacag gccgaagacc aatcagtcag gatcgctcta aaggtgtagt attcctaacc   1260
catgacaact gtggtcttat aggtgtcaat ggggtagaat tgtatgctaa ccggagaggg   1320
cacgatgcca cttgggggt ccagaacttg acagtcggtc ctgcaattgc tatcagaccc   1380
gttgatattt ctctcaacct tgctgatgct acgaatttct tgcaagactc taaggctgag   1440
cttgagaaag cacggaaaat cctctctgag gtaggtagat ggtacaactc aagagagact   1500
gtgattacga tcatagtagt tatggtcgta atattggtgg tcattatagt gatcgtcatc   1560
gtgctttata gactcagaag gtcaatgcta atgggtaatc cagatgaccg tataccgagg   1620
gacacatata cattagagcc gaagatcaga catatgtaca caaacggtgg gtttgatgcg   1680
atggctgaga aaagatga                                                 1698

<210> SEQ ID NO 13
<211> LENGTH: 565
<212> TYPE: PRT
<213> ORGANISM: Sendai virus

<400> SEQUENCE: 13

Met Thr Ala Tyr Ile Gln Arg Ser Gln Cys Ile Ser Thr Ser Leu Leu
1               5                   10                  15

Val Val Leu Thr Thr Leu Val Ser Cys Gln Ile Pro Arg Asp Arg Leu
            20                  25                  30

Ser Asn Ile Gly Val Ile Val Asp Glu Gly Lys Ser Leu Lys Ile Ala
        35                  40                  45

Gly Ser His Glu Ser Arg Tyr Ile Val Leu Ser Leu Val Pro Gly Val
    50                  55                  60

Asp Leu Glu Asn Gly Cys Gly Thr Ala Gln Val Ile Gln Tyr Lys Ser
65                  70                  75                  80

Leu Leu Asn Arg Leu Leu Ile Pro Leu Arg Asp Ala Leu Asp Leu Gln
                85                  90                  95

Glu Ala Leu Ile Thr Val Thr Asn Asp Thr Thr Gln Asn Ala Gly Val
            100                 105                 110

Pro Gln Ser Arg Phe Phe Gly Ala Val Ile Gly Thr Ile Ala Leu Gly
        115                 120                 125

Val Ala Thr Ser Ala Gln Ile Thr Ala Gly Ile Ala Leu Ala Glu Ala
    130                 135                 140

Arg Glu Ala Lys Arg Asp Ile Ala Leu Ile Lys Glu Ser Met Thr Lys
145                 150                 155                 160

Thr His Lys Ser Ile Glu Leu Leu Gln Asn Ala Val Gly Glu Gln Ile
                165                 170                 175

Leu Ala Leu Lys Thr Leu Gln Asp Phe Val Asn Asp Glu Ile Lys Pro
            180                 185                 190
```

```
Ala Ile Ser Glu Leu Gly Cys Glu Thr Ala Ala Leu Arg Leu Gly Ile
            195                 200                 205

Lys Leu Thr Gln His Tyr Ser Gly Leu Leu Thr Ala Phe Gly Ser Asn
    210                 215                 220

Phe Gly Thr Ile Gly Glu Lys Ser Leu Thr Leu Gln Ala Leu Ser Ser
225                 230                 235                 240

Leu Tyr Ser Ala Asn Ile Thr Glu Ile Met Thr Thr Ile Arg Thr Gly
                245                 250                 255

Gln Ser Asn Ile Tyr Asp Val Ile Tyr Thr Glu Gln Ile Lys Gly Thr
                260                 265                 270

Val Ile Asp Val Asp Leu Glu Arg Tyr Met Val Thr Leu Ser Val Lys
            275                 280                 285

Ile Pro Ile Leu Ser Glu Val Pro Gly Val Leu Ile His Lys Ala Ser
            290                 295                 300

Ser Ile Ser Tyr Asn Ile Asp Gly Glu Glu Trp Tyr Val Thr Val Pro
305                 310                 315                 320

Ser His Ile Leu Ser Arg Ala Ser Phe Leu Gly Gly Ala Asp Ile Thr
                325                 330                 335

Asp Cys Val Glu Ser Arg Leu Thr Tyr Ile Cys Pro Arg Asp Pro Ala
                340                 345                 350

Gln Leu Ile Pro Asp Ser Gln Gln Lys Cys Ile Leu Gly Asp Thr Thr
            355                 360                 365

Arg Cys Pro Val Thr Lys Val Val Asp Ser Leu Ile Pro Lys Phe Ala
            370                 375                 380

Phe Val Asn Gly Gly Val Val Ala Asn Cys Ile Ala Ser Thr Cys Thr
385                 390                 395                 400

Cys Gly Thr Gly Arg Arg Pro Ile Ser Gln Asp Arg Ser Lys Gly Val
                405                 410                 415

Val Phe Leu Thr His Asp Asn Cys Gly Leu Ile Gly Val Asn Gly Val
                420                 425                 430

Glu Leu Tyr Ala Asn Arg Arg Gly His Asp Ala Thr Trp Gly Val Gln
            435                 440                 445

Asn Leu Thr Val Gly Pro Ala Ile Ala Ile Arg Pro Val Asp Ile Ser
            450                 455                 460

Leu Asn Leu Ala Asp Ala Thr Asn Phe Leu Gln Asp Ser Lys Ala Glu
465                 470                 475                 480

Leu Glu Lys Ala Arg Lys Ile Leu Ser Glu Val Gly Arg Trp Tyr Asn
                485                 490                 495

Ser Arg Glu Thr Val Ile Thr Ile Ile Val Val Met Val Val Ile Leu
                500                 505                 510

Val Val Ile Ile Val Ile Val Ile Val Leu Tyr Arg Leu Arg Arg Ser
            515                 520                 525

Met Leu Met Gly Asn Pro Asp Asp Arg Ile Pro Arg Asp Thr Tyr Thr
            530                 535                 540

Leu Glu Pro Lys Ile Arg His Met Tyr Thr Asn Gly Gly Phe Asp Ala
545                 550                 555                 560

Met Ala Glu Lys Arg
                565

<210> SEQ ID NO 14
<211> LENGTH: 1728
<212> TYPE: DNA
<213> ORGANISM: Sendai virus
```

<400> SEQUENCE: 14

```
atggatggtg ataggggcaa acgtgactcg tactggtcta cctctcctag tggtagcact      60
acaaaattag catcaggttg ggagaggtca agtaaagttg acacatggtt gctgattctc     120
tcattcaccc agtgggcttt gtcaattgcc acagtgatca tctgtatcat aatttctgct     180
agacaagggt atagtatgaa agagtactca atgactgtag aggcattgaa catgagcagc     240
agggaggtga agagtcact taccagtcta ataaggcaag aggttatcgc aagggctgtc      300
aacattcaga gctctgtgca aaccggaatc ccagtcttgt tgaacaaaaa cagcagggat     360
gtcatccaga tgattgataa gtcgtgcagc agacaagagc tcactcagct ctgtgagagt     420
acgatcgcag tccaccatgc cgagggaatt gcccctcttg agccacatag tttctggaga     480
tgccctgtcg gagaaccgta tcttagctca gatcctaaaa tctcattgct gcctggtccg     540
agcttgttat ctggttctac aacgatctct ggatgtgtta ggctcccttc actctcaatt     600
ggcgaggcaa tctatgccta ttcatcaaat ctcattacac aaggttgtgc tgacatanggg    660
aaatcatatc aggtcctgca gctagggtac atatcactca attcagatat gttccctgat     720
cttaaccccg tagtgtccca cacttatgac atcaacgaca tcggaaaatc atgctctgtg     780
gtggcaaccg ggactagggg ttatcagctt tgctccatgc cgactgtaga cgaaagaacc     840
gactactcta gtgatggtat cgaggatctg gtccttgatg tcctggatct caaagggagc     900
actaagtctc accggtatcg caacagcgag gtagatcttg atcacccgtt ctctgcacta     960
tacccccagtg taggcaacgg cattgcaaca gaaggctcat tgatatttct tgggtatggt    1020
gggctaacca cccctctaca gggtgataca aaatgtagga cccaaggatg ccaacaggtg    1080
tcgcaagaca catgcaatga ggctctgaaa attacatggc taggagggaa acaggtggtc   1140
agcgtgatca tccaggtcaa tgactatctc tcagagaggc caaagataag agtcacaacc   1200
attccaatca ctcaaaacta tctcggggcg gaaggtagat tattaaaatt gggtgatcgg   1260
gtgtacatct atacaagatc atcaggctgg cactctcaac tgcagatagg agtacttgat   1320
gtcagccacc ctttgactat caactggaca cctcatgaag ccttgtctag accaggaaat   1380
gaagagtgca attggtacaa tacgtgtccg aaggaatgca tatcaggcgt atacactgat   1440
gcttatccat tgtcccctga tgcagctaac gtcgctaccg tcacgctata tgccaataca    1500
tcgcgtgtca acccaacaat catgtattct aacactacta acattataaa tatgttaagg    1560
ataaaggatg ttcaattaga ggctgcatat accacgacat cgtgtatcac gcattttggt    1620
aaaggctact gctttcacat catcgagatc aatcagaaga gcctgaatac cttacagccg    1680
atgctcttta agactagcat ccctaaatta tgcaaggccg agtcttaa                 1728
```

<210> SEQ ID NO 15
<211> LENGTH: 570
<212> TYPE: PRT
<213> ORGANISM: Sendai virus

<400> SEQUENCE: 15

```
Gly Lys Arg Asp Ser Tyr Trp Ser Thr Ser Pro Ser Gly Ser Thr Thr
1               5                   10                  15

Lys Leu Ala Ser Gly Trp Glu Arg Ser Ser Lys Val Asp Thr Trp Leu
            20                  25                  30

Leu Ile Leu Ser Phe Thr Gln Trp Ala Leu Ser Ile Ala Thr Val Ile
        35                  40                  45

Ile Cys Ile Ile Ile Ser Ala Arg Gln Gly Tyr Ser Met Lys Glu Tyr
    50                  55                  60
```

```
Ser Met Thr Val Glu Ala Leu Asn Met Ser Ser Arg Glu Val Lys Glu
65                  70                  75                  80

Ser Leu Thr Ser Leu Ile Arg Gln Glu Val Ile Ala Arg Ala Val Asn
                85                  90                  95

Ile Gln Ser Ser Val Gln Thr Gly Ile Pro Val Leu Leu Asn Lys Asn
            100                 105                 110

Ser Arg Asp Val Ile Gln Met Ile Asp Lys Ser Cys Ser Arg Gln Glu
        115                 120                 125

Leu Thr Gln Leu Cys Glu Ser Thr Ile Ala Val His His Ala Glu Gly
    130                 135                 140

Ile Ala Pro Leu Glu Pro His Ser Phe Trp Arg Cys Pro Val Gly Glu
145                 150                 155                 160

Pro Tyr Leu Ser Ser Asp Pro Lys Ile Ser Leu Leu Pro Gly Pro Ser
                165                 170                 175

Leu Leu Ser Gly Ser Thr Thr Ile Ser Gly Cys Val Arg Leu Pro Ser
            180                 185                 190

Leu Ser Ile Gly Glu Ala Ile Tyr Ala Tyr Ser Ser Asn Leu Ile Thr
        195                 200                 205

Gln Gly Cys Ala Asp Ile Gly Lys Ser Tyr Gln Val Leu Gln Leu Gly
    210                 215                 220

Tyr Ile Ser Leu Asn Ser Asp Met Phe Pro Asp Leu Asn Pro Val Val
225                 230                 235                 240

Ser His Thr Tyr Asp Ile Asn Asp Asn Arg Lys Ser Cys Ser Val Val
                245                 250                 255

Ala Thr Gly Thr Arg Gly Tyr Gln Leu Cys Ser Met Pro Thr Val Asp
            260                 265                 270

Glu Arg Thr Asp Tyr Ser Ser Asp Gly Ile Glu Asp Leu Val Leu Asp
        275                 280                 285

Val Leu Asp Leu Lys Gly Ser Thr Lys Ser His Arg Tyr Arg Asn Ser
    290                 295                 300

Glu Val Asp Leu Asp His Pro Phe Ser Ala Leu Tyr Pro Ser Val Gly
305                 310                 315                 320

Asn Gly Ile Ala Thr Glu Gly Ser Leu Ile Phe Leu Gly Tyr Gly Gly
                325                 330                 335

Leu Thr Thr Pro Leu Gln Gly Asp Thr Lys Cys Arg Thr Gln Gly Cys
            340                 345                 350

Gln Gln Val Ser Gln Asp Thr Cys Asn Glu Ala Leu Lys Ile Thr Trp
        355                 360                 365

Leu Gly Gly Lys Gln Val Val Ser Val Ile Gln Val Asn Asp Tyr
    370                 375                 380

Leu Ser Glu Arg Pro Lys Ile Arg Val Thr Thr Ile Pro Ile Thr Gln
385                 390                 395                 400

Asn Tyr Leu Gly Ala Glu Gly Arg Leu Leu Lys Leu Gly Asp Arg Val
                405                 410                 415

Tyr Ile Tyr Thr Arg Ser Ser Gly Trp His Ser Gln Leu Gln Ile Gly
            420                 425                 430

Val Leu Asp Val Ser His Pro Leu Thr Ile Asn Trp Thr Pro His Glu
        435                 440                 445

Ala Leu Ser Arg Pro Gly Asn Glu Glu Cys Asn Trp Tyr Asn Thr Cys
    450                 455                 460

Pro Lys Glu Cys Ile Ser Gly Val Tyr Thr Asp Ala Tyr Pro Leu Ser
465                 470                 475                 480
```

```
Pro Asp Ala Ala Asn Val Ala Thr Val Thr Leu Tyr Ala Asn Thr Ser
                485                 490                 495
Arg Val Asn Pro Thr Ile Met Tyr Ser Asn Thr Asn Ile Ile Asn
            500                 505                 510
Met Leu Arg Ile Lys Asp Val Gln Leu Glu Ala Ala Tyr Thr Thr Thr
            515                 520                 525
Ser Cys Ile Thr His Phe Gly Lys Gly Tyr Cys His Ile Ile Glu
    530                 535                 540
Ile Asn Gln Lys Ser Leu Asn Thr Leu Gln Pro Met Leu Phe Lys Thr
545                 550                 555                 560
Ser Ile Pro Lys Leu Cys Lys Ala Glu Ser
                565                 570

<210> SEQ ID NO 16
<211> LENGTH: 6702
<212> TYPE: DNA
<213> ORGANISM: Sendai virus

<400> SEQUENCE: 16
```

| | | |
|---|---|---|
| atggatgggc aggagtcctc ccaaaaccct tctgacatac tctatccaga atgccacctg | 60 |
| aactctccca tagtcagggg gaagatagca cagttgcacg tcttgttaga tgtgaaccag | 120 |
| ccctacagac tgaaggacga cagcataata aatattacaa agcacaaaat taggaacgga | 180 |
| ggattgtccc cccgtcaaat taagatcagg tctctgggta aggctcttca acgcacaata | 240 |
| aaggatttag accgatacac gtttgaaccg tacccaacct actctcagga attacttagg | 300 |
| cttgatatac agagatatg tgacaaaatc cgatccgtct tcgcggtctc ggatcggctg | 360 |
| accagggagt tatctagtgg gttccaggat cttttggttga atatcttcaa gcaactaggc | 420 |
| aatatagaag gaagagaggg gtacgatccg ttgcaggata tcggcaccat cccggagata | 480 |
| actgataagt acagcaggaa tagatggtat aggccattcc taacttggtt cagcatcaaa | 540 |
| tatgacatgc ggtggatgca gaagaccaga ccggggggac cccttgatac ctctaattca | 600 |
| cataacctcc tagaatgcaa atcatacact ctagtaacat acggagatct tgtcatgata | 660 |
| ctgaacaagt tgacattgac agggtatatc ctaaccccctg agctggtctt gatgtattgt | 720 |
| gatgttgtag aaggaaggtg gaatatgtct gctgcagggc atctagataa gaagtccatt | 780 |
| gggataacaa gcaaaggtga ggaattatgg gaactagtgg attccctctt ctcaagtctt | 840 |
| ggagaggaaa tatacaatgt catcgcacta ttggagcccc tatcacttgc ctctcatacaa | 900 |
| ctaaatgatc ctgttatacc tctacgtggg gcatttatga gcatgtgtt gacagagcta | 960 |
| cagactgttt taacaagtag agacgtgtac acagatgctg aagcagacac tattgtggag | 1020 |
| tcgttactcg ccattttcca tggaacctct attgatgaga agcagagat cttttccttc | 1080 |
| tttaggacat ttggccaccc cagcttagag gctgtcactg ccgccgacaa ggtaagggcc | 1140 |
| catatgtatg cacaaaaggc aataaagctt aagaccctat acgagtgtca tgcagttttt | 1200 |
| tgcactatca tcataaatgg gtatagagag aggcatggcg acagtggcc ccctgtgac | 1260 |
| ttccctgatc acgtgtgtct agaactaagg aacgctcaag ggtccaatac ggcaatctct | 1320 |
| tatgaatgtg ctagacaa ctatacaagt ttcataggct tcaagtttcg gaagtttata | 1380 |
| gaaccacaac tagatgaaga tctcacaata tatatgaaag acaaagcact atcccccagg | 1440 |
| aaggaggcat gggactctgt atacccggat agtaatctgt actataaagc cccagagtct | 1500 |
| gaagagaccc ggcggcttat tgaagtgttc ataaatgatg agaatttcaa cccagaagaa | 1560 |
| attatcaatt atgtggagtc aggagattgg ttgaaagacg aggagttcaa catctcgtac | 1620 |

-continued

```
agtctcaaag agaaagagat caagcaagag ggtcgtctat tcgcaaaaat gacttataag    1680
atgcgagccg tacaggtgct ggcagagaca ctactggcta aaggaatagg agagctattc    1740
agggaaaatg ggatggttaa gggagagata gacctactta aaagattgac tactctttct    1800
gtctcaggcg tccccaggac tgattcagtg tacaataact ctaaatcatc agagaagaga    1860
aacgaaggca tggaaaataa gaactctggg gggtactggg acgaaaagaa gaggtccaga    1920
catgaattca aggcaacaga ttcatcaaca gacggctatg aaacgttaag ttgcttcctc    1980
acaacagacc tcaagaaata ctgcttaaac tggagatttg agagtactgc attgtttggt    2040
cagagatgca acgagatatt tggcttcaag accttcttta actggatgca tccagtcctt    2100
gaaaggtgta caatatatgt tggagatcct tactgtccag tcgccgaccg gatgcatcga    2160
caactccagg atcatgcaga ctctggcatt ttcatacata atcctagggg gggcatagaa    2220
ggttactgcc agaagctgtg gaccttaatc tcaatcagtg caatccacct agcagctgtg    2280
agagtgggtg tcagggtctc tgcaatggtt cagggtgaca atcaagctat agccgtgaca    2340
tcaagagtac ctgtagctca gacttacaag cagaagaaaa atcatgtcta tgaggagatc    2400
accaaatatt tcggtgctct aagacacgtc atgtttgatg tagggcacga gctaaaattg    2460
aacgagacca tcattagtag caagatgttt gtctatagta aaaggatata ctatgatggg    2520
aagattttac cacagtgcct gaaagccttg accaagtgtg tattctggtc cgagacactg    2580
gtagatgaaa acagatctgc ttgttcgaac atctcaacat ccatagcaaa agctatcgaa    2640
aatgggtatt ctcctatact aggctactgc attgcgttgt ataagacctg tcagcaggtg    2700
tgcatatcac tagggatgac tataaatcca actatcagcc cgaccgtaag agatcaatac    2760
tttaagggta agaattggct gagatgtgca gtgttgattc cagcaaatgt tggaggattc    2820
aactacatgt ctacatctag atgctttgtt agaaatattg gagaccccgc agtagcagcc    2880
ctagctgatc tcaaaagatt catcagagcg gatctgttag acaagcaggt attatacagg    2940
gtcatgaatc aagaacccgg tgactctagt tttctagatt gggcttcaga cccttattcg    3000
tgtaacctcc cgcattctca gagtataact acgattataa agaatatcac tgctagatct    3060
gtgctgcagg aatccccgaa tcctctactg tctggtctct tcaccgagac tagtggagaa    3120
gaggatctca acctggcctc gttccttatg gaccggaaag tcatcctgcc gagagtggct    3180
catgagatcc tgggtaattc cttaactgga gttaggaggc cgattgcagg gatgcttgat    3240
acgaccaagt ctctagtgag agccagcgtt aggaaaggag gattatcata tgggatattg    3300
aggaggcttg tcaattatga tctattgcag tacgagacac tgactagaac tctcaggaaa    3360
ccggtgaaag acaacatcga atatgagtat atgtgttcag ttgagctagc tgtcggtcta    3420
aggcagaaaa tgtggatcca cctgacttac gggagaccca tacatgggtt agaaacacca    3480
gacccttag agctcttgag gggaatattt atcgaaggtt cagaggtgtg caagctttgc    3540
aggtctgaag gagcagaccc catctataca tggttctatc ttcctgacaa tatagacctg    3600
gacacgctta caaacggatg tccggctata agaatcccct attttggatc agccactgat    3660
gaaaggtcgg aagcccaact cgggtatgta agaaatctaa gcaaacccgc aaaggcggcc    3720
atccggatag ctatggtgta tacgtgggcc tacgggactg atgagatatc gtggatggaa    3780
gccgctctta tagcccaaac aagagctaat ctgagcttag agaatctaaa gctgctgact    3840
cctgttttcaa cctccactaa tctatctcat aggttgaaag atacggcaac ccagatgaag    3900
ttctctagtg caacactagt ccgtgcaagt cggttcataa caatatcaaa tgataacatg    3960
gcactcaaag aagcagggga gtcgaaggat actaatctcg tgtatcagca gattatgcta    4020
```

```
actgggctaa gcttgttcga gttcaatatg agatataaga aaggttcctt agggaagcca    4080
ctgatattgc acttacatct taataacggg tgctgtataa tggagtcccc acaggaggcg    4140
aatatccccc caaggtccac attagattta gagattacac aagagaacaa taaattgatc    4200
tatgatcctg atccactcaa ggatgtggac cttgagctat ttagcaaggt cagagatgtt    4260
gtacatacag ttgacatgac ttattggtca gatgatgaag ttatcagagc aaccagcatc    4320
tgtactgcaa tgacgatagc tgatacaatg tctcaattag atagagacaa cttaaaagag    4380
atgatcgcac tagtaaatga cgatgatgtc aacagcttga ttactgagtt tatggtgatt    4440
gatgttcctt tattttgctc aacgttcggg ggtattctag tcaatcagtt tgcatactca    4500
ctctacggct taaacatcag aggaagggaa gaaatatggg acatgtagt ccggattctt    4560 aaagatacct cccacgcagt tctaaaagtc ttatctaatg ctctatccca tcccaaaatc    4620
ttcaaacgat tctggaatgc aggtgtcgtg gaacctgtgt atgggcctaa cctctcaaat    4680
caggataaga tactcttggc cctctctgtc tgtgaatatt ctgtggatct attcatgcac    4740
gactggcaag ggggtgtacc gcttgagatc tttatctgtg acaatgaccc agatgtggcc    4800
gacatgagga ggtcctcttt cttggcaaga catcttgcat acctatgcag cttggcagag    4860
atatctaggg atgggccaag attagaatca atgaactctc tagagaggct cgagtcacta    4920
aagagttacc tggaactcac atttcttgat dacccggtac tgaggtacag tcagttgact    4980
ggcctagtca tcaaagtatt cccatctact ttgacctata tccggaagtc atctataaaa    5040
gtgttaagga caagaggtat aggagtccct gaagtcttag aagattggga tcccgaggca    5100
gataatgcac tgttagatgg tatcgcggca gaaatacaac agaatattcc tttgggacat    5160
cagactagag ccccttttg ggggttgaga gtatccaagt cacaggtact gcgtctccgg    5220
gggtacaagg agatcacaag aggtgagata ggcagatcag tgttggtct gacgttacca    5280 ttcgatggaa gatatctatc tcaccagctg aggctctttg gcatcaacag tactagctgc    5340
ttgaaagcac ttgaacttac ctacctattg agccccttag ttgacaagga taaagatagg    5400
ctatatttag gggaaggagc tggggccatg ctttcctgtt atgacgctac tcttggccca    5460
tgcatcaact attataactc agggtatac tcttgtgatg tcaatgggca gagagagtta    5520
aatatatatc ctgctgaggt ggcactagtg ggaaagaaat taaacaatgt tactagtctg    5580
ggtcaaagag ttaaagtgtt attcaacggg aatcctggct cgacatggat tgggaatgat    5640
gagtgtgagg ctttgatttg gaatgaatta cagaatagct cgataggcct agtccactgt    5700
gacatggagg gaggagatca taaggatgat caagttgtac tgcatgagca ttacagtgta    5760
atccggatcg cgtatctggt gggggatcga gacgttgtgc ttataagcaa gattgctccc    5820
aggctgggca cggattggac caggcagctc agcctatatc tgagatactg ggacgaggtt    5880
aacctaatag tgcttaaaac atctaaccct gcttccacag agatgtatct cctatcgagg    5940
caccccaaat ctgacattat agaggacagc aagacagtgt tagctagtct cctccctttg    6000
tcaaaagaag atagcatcaa gatagaaaag tggatcttaa tagagaaggc aaaggctcac    6060
gaatgggtta ctcgggaatt gagagaagga agctcttcat cagggatgct tagaccttac    6120
catcaagcac tgcagacgtt tggctttgaa ccaaacttgt ataaattgag cagagatttc    6180
ttgtccacca tgaacatagc tgatacacac aactgcatga tagctttcaa cagggttttg    6240
aaggatacaa tcttcgaatg ggctagaata actgagtcag ataaaaggct taaactaact    6300
ggtaagtatg acctgtatcc tgtgagagat tcaggcaagt tgaagacaat ttctagaaga    6360
cttgtgctat cttggataac tttatctatg tccacaagat tggtaactgg gtcattccct    6420
```

```
gaccagaagt tgaagcaag acttcaattg ggaatagttt cattatcatc ccgtgaaatc    6480
aggaacctga gggttatcac aaaaacttta ttatacaggt ttgaggatat tatacatagt    6540
ataacgtata gattcctcac caaagaaata aagatttga tgaagatttt aggggcagtc    6600
aagatgttcg gggccaggca aaatgaatac acgaccgtga ttgatgatgg atcactaggt    6660
gatatcgagc catatgacag ctcgtaataa ttagtcccta tc                      6702
```

<210> SEQ ID NO 17
<211> LENGTH: 2223
<212> TYPE: PRT
<213> ORGANISM: Sendai virus

<400> SEQUENCE: 17

```
Ser Ser Gln Asn Pro Ser Asp Ile Leu Tyr Pro Glu Cys His Leu Asn
1               5                   10                  15

Ser Pro Ile Val Arg Gly Lys Ile Ala Gln Leu His Val Leu Leu Asp
                20                  25                  30

Val Asn Gln Pro Tyr Arg Leu Lys Asp Asp Ser Ile Ile Asn Ile Thr
            35                  40                  45

Lys His Lys Ile Arg Asn Gly Gly Leu Ser Pro Arg Gln Ile Lys Ile
        50                  55                  60

Arg Ser Leu Gly Lys Ala Leu Gln Arg Thr Ile Lys Asp Leu Asp Arg
65                  70                  75                  80

Tyr Thr Phe Glu Pro Tyr Pro Thr Tyr Ser Gln Glu Leu Leu Arg Leu
                85                  90                  95

Asp Ile Pro Glu Ile Cys Asp Lys Ile Arg Ser Val Phe Ala Val Ser
            100                 105                 110

Asp Arg Leu Thr Arg Glu Leu Ser Ser Gly Phe Gln Asp Leu Trp Leu
        115                 120                 125

Asn Ile Phe Lys Gln Leu Gly Asn Ile Glu Gly Arg Glu Gly Tyr Asp
130                 135                 140

Pro Leu Gln Asp Ile Gly Thr Ile Pro Glu Ile Thr Asp Lys Tyr Ser
145                 150                 155                 160

Arg Asn Arg Trp Tyr Arg Pro Phe Leu Thr Trp Phe Ser Ile Lys Tyr
                165                 170                 175

Asp Met Arg Trp Met Gln Lys Thr Arg Pro Gly Gly Pro Leu Asp Thr
            180                 185                 190

Ser Asn Ser His Asn Leu Leu Glu Cys Lys Ser Tyr Thr Leu Val Thr
        195                 200                 205

Tyr Gly Asp Leu Val Met Ile Leu Asn Lys Leu Thr Leu Thr Gly Tyr
    210                 215                 220

Ile Leu Thr Pro Glu Leu Val Leu Met Tyr Cys Asp Val Val Glu Gly
225                 230                 235                 240

Arg Trp Asn Met Ser Ala Ala Gly His Leu Asp Lys Lys Ser Ile Gly
                245                 250                 255

Ile Thr Ser Lys Gly Glu Glu Leu Trp Glu Leu Val Asp Ser Leu Phe
            260                 265                 270

Ser Ser Leu Gly Glu Glu Ile Tyr Asn Val Ile Ala Leu Leu Glu Pro
        275                 280                 285

Leu Ser Leu Ala Leu Ile Gln Leu Asn Asp Pro Val Ile Pro Leu Arg
    290                 295                 300

Gly Ala Phe Met Arg His Val Leu Thr Glu Leu Gln Thr Val Leu Thr
305                 310                 315                 320
```

-continued

```
Ser Arg Asp Val Tyr Thr Asp Ala Glu Ala Asp Thr Ile Val Glu Ser
            325                 330                 335

Leu Leu Ala Ile Phe His Gly Thr Ser Ile Asp Glu Lys Ala Glu Ile
        340                 345                 350

Phe Ser Phe Phe Arg Thr Phe Gly His Pro Ser Leu Glu Ala Val Thr
            355                 360                 365

Ala Ala Asp Lys Val Arg Ala His Met Tyr Ala Gln Lys Ala Ile Lys
370                 375                 380

Leu Lys Thr Leu Tyr Glu Cys His Ala Val Phe Cys Thr Ile Ile Ile
385                 390                 395                 400

Asn Gly Tyr Arg Glu Arg His Gly Gly Gln Trp Pro Pro Cys Asp Phe
                405                 410                 415

Pro Asp His Val Cys Leu Glu Leu Arg Asn Ala Gln Gly Ser Asn Thr
        420                 425                 430

Ala Ile Ser Tyr Glu Cys Ala Val Asp Asn Tyr Thr Ser Phe Ile Gly
            435                 440                 445

Phe Lys Phe Arg Lys Phe Ile Glu Pro Gln Leu Asp Glu Asp Leu Thr
        450                 455                 460

Ile Tyr Met Lys Asp Lys Ala Leu Ser Pro Arg Lys Glu Ala Trp Asp
465                 470                 475                 480

Ser Val Tyr Pro Asp Ser Asn Leu Tyr Tyr Lys Ala Pro Glu Ser Glu
                485                 490                 495

Glu Thr Arg Arg Leu Ile Glu Val Phe Ile Asn Asp Gly Asn Phe Asn
            500                 505                 510

Pro Glu Glu Ile Ile Asn Tyr Val Glu Ser Gly Asp Trp Leu Lys Asp
        515                 520                 525

Glu Glu Phe Asn Ile Ser Tyr Ser Leu Lys Glu Glu Ile Lys Gln
        530                 535                 540

Glu Gly Arg Leu Phe Ala Lys Met Thr Tyr Lys Met Arg Ala Val Gln
545                 550                 555                 560

Val Leu Ala Glu Thr Leu Leu Ala Lys Gly Ile Gly Glu Leu Phe Arg
                565                 570                 575

Glu Asn Gly Met Val Lys Gly Glu Ile Asp Leu Leu Lys Arg Leu Thr
            580                 585                 590

Thr Leu Ser Val Ser Gly Val Pro Arg Thr Asp Ser Val Tyr Asn Asn
        595                 600                 605

Ser Lys Ser Ser Glu Lys Arg Asn Glu Gly Met Glu Asn Lys Asn Ser
        610                 615                 620

Gly Gly Tyr Trp Asp Glu Lys Lys Arg Ser Arg His Glu Phe Lys Ala
625                 630                 635                 640

Thr Asp Ser Ser Thr Asp Gly Tyr Glu Thr Leu Ser Cys Phe Leu Thr
                645                 650                 655

Thr Asp Leu Lys Lys Tyr Cys Leu Asn Trp Arg Phe Glu Ser Thr Ala
            660                 665                 670

Leu Phe Gly Gln Arg Cys Asn Glu Ile Phe Gly Phe Lys Thr Phe Phe
        675                 680                 685

Asn Trp Met His Pro Val Leu Glu Arg Cys Thr Ile Tyr Val Gly Asp
        690                 695                 700

Pro Tyr Cys Pro Val Ala Asp Arg Met His Arg Gln Leu Gln Asp His
705                 710                 715                 720

Ala Asp Ser Gly Ile Phe Ile His Asn Pro Arg Gly Gly Ile Glu Gly
                725                 730                 735
```

-continued

```
Tyr Cys Gln Lys Leu Trp Thr Leu Ile Ser Ile Ser Ala Ile His Leu
                740                 745                 750

Ala Ala Val Arg Val Gly Val Arg Val Ser Ala Met Val Gln Gly Asp
            755                 760                 765

Asn Gln Ala Ile Ala Val Thr Ser Arg Val Pro Val Ala Gln Thr Tyr
770                 775                 780

Lys Gln Lys Lys Asn His Val Tyr Glu Glu Ile Thr Lys Tyr Phe Gly
785                 790                 795                 800

Ala Leu Arg His Val Met Phe Asp Val Gly His Glu Leu Lys Leu Asn
                805                 810                 815

Glu Thr Ile Ile Ser Ser Lys Met Phe Val Tyr Ser Lys Arg Ile Tyr
            820                 825                 830

Tyr Asp Gly Lys Ile Leu Pro Gln Cys Leu Lys Ala Leu Thr Lys Cys
        835                 840                 845

Val Phe Trp Ser Glu Thr Leu Val Asp Glu Asn Arg Ser Ala Cys Ser
    850                 855                 860

Asn Ile Ser Thr Ser Ile Ala Lys Ala Ile Glu Asn Gly Tyr Ser Pro
865                 870                 875                 880

Ile Leu Gly Tyr Cys Ile Ala Leu Tyr Lys Thr Cys Gln Gln Val Cys
                885                 890                 895

Ile Ser Leu Gly Met Thr Ile Asn Pro Thr Ile Ser Pro Thr Val Arg
            900                 905                 910

Asp Gln Tyr Phe Lys Gly Lys Asn Trp Leu Arg Cys Ala Val Leu Ile
        915                 920                 925

Pro Ala Asn Val Gly Gly Phe Asn Tyr Met Ser Thr Ser Arg Cys Phe
    930                 935                 940

Val Arg Asn Ile Gly Asp Pro Ala Val Ala Ala Leu Ala Asp Leu Lys
945                 950                 955                 960

Arg Phe Ile Arg Ala Asp Leu Leu Asp Lys Gln Val Leu Tyr Arg Val
                965                 970                 975

Met Asn Gln Glu Pro Gly Asp Ser Ser Phe Leu Asp Trp Ala Ser Asp
            980                 985                 990

Pro Tyr Ser Cys Asn Leu Pro His  Ser Gln Ser Ile Thr  Thr Ile Ile
        995                1000                 1005

Lys Asn  Ile Thr Ala Arg Ser  Val Leu Gln Glu Ser  Pro Asn Pro
    1010                1015                1020

Leu Leu  Ser Gly Leu Phe Thr  Glu Thr Ser Gly Glu  Glu Asp Leu
    1025                1030                1035

Asn Leu  Ala Ser Phe Leu Met  Asp Arg Lys Val Ile  Leu Pro Arg
    1040                1045                1050

Val Ala  His Glu Ile Leu Gly  Asn Ser Leu Thr Gly  Val Arg Glu
    1055                1060                1065

Ala Ile  Ala Gly Met Leu Asp  Thr Thr Lys Ser Leu  Val Arg Ala
    1070                1075                1080

Ser Val  Arg Lys Gly Gly Leu  Ser Tyr Gly Ile Leu  Arg Arg Leu
    1085                1090                1095

Val Asn  Tyr Asp Leu Leu Gln  Tyr Glu Thr Leu Thr  Arg Thr Leu
    1100                1105                1110

Arg Lys  Pro Val Lys Asp Asn  Ile Glu Tyr Glu Tyr  Met Cys Ser
    1115                1120                1125

Val Glu  Leu Ala Val Gly Leu  Arg Gln Lys Met Trp  Ile His Leu
    1130                1135                1140
```

-continued

```
Thr Tyr Gly Arg Pro Ile His Gly Leu Glu Thr Pro Asp Pro Leu
    1145                1150                1155
Glu Leu Leu Arg Gly Ile Phe Ile Glu Gly Ser Glu Val Cys Lys
    1160                1165                1170
Leu Cys Arg Ser Glu Gly Ala Asp Pro Ile Tyr Thr Trp Phe Tyr
    1175                1180                1185
Leu Pro Asp Asn Ile Asp Leu Asp Thr Leu Thr Asn Gly Cys Pro
    1190                1195                1200
Ala Ile Arg Ile Pro Tyr Phe Gly Ser Ala Thr Asp Glu Arg Ser
    1205                1210                1215
Glu Ala Gln Leu Gly Tyr Val Arg Asn Leu Ser Lys Pro Ala Lys
    1220                1225                1230
Ala Ala Ile Arg Ile Ala Met Val Tyr Thr Trp Ala Tyr Gly Thr
    1235                1240                1245
Asp Glu Ile Ser Trp Met Glu Ala Ala Leu Ile Ala Gln Thr Arg
    1250                1255                1260
Ala Asn Leu Ser Leu Glu Asn Leu Lys Leu Leu Thr Pro Val Ser
    1265                1270                1275
Thr Ser Thr Asn Leu Ser His Arg Leu Lys Asp Thr Ala Thr Gln
    1280                1285                1290
Met Lys Phe Ser Ser Ala Thr Leu Val Arg Ala Ser Arg Phe Ile
    1295                1300                1305
Thr Ile Ser Asn Asp Asn Met Ala Leu Lys Glu Ala Gly Glu Ser
    1310                1315                1320
Lys Asp Thr Asn Leu Val Tyr Gln Gln Ile Met Leu Thr Gly Leu
    1325                1330                1335
Ser Leu Phe Glu Phe Asn Met Arg Tyr Lys Lys Gly Ser Leu Gly
    1340                1345                1350
Lys Pro Leu Ile Leu His Leu His Leu Asn Asn Gly Cys Cys Ile
    1355                1360                1365
Met Glu Ser Pro Gln Glu Ala Asn Ile Pro Pro Arg Ser Thr Leu
    1370                1375                1380
Asp Leu Glu Ile Thr Gln Glu Asn Asn Lys Leu Ile Tyr Asp Pro
    1385                1390                1395
Asp Pro Leu Lys Asp Val Asp Leu Glu Leu Phe Ser Lys Val Arg
    1400                1405                1410
Asp Val Val His Thr Val Asp Met Thr Tyr Trp Ser Asp Asp Glu
    1415                1420                1425
Val Ile Arg Ala Thr Ser Ile Cys Thr Ala Met Thr Ile Ala Asp
    1430                1435                1440
Thr Met Ser Gln Leu Asp Arg Asp Asn Leu Lys Glu Met Ile Ala
    1445                1450                1455
Leu Val Asn Asp Asp Val Asn Ser Leu Ile Thr Glu Phe Met
    1460                1465                1470
Val Ile Asp Val Pro Leu Phe Cys Ser Thr Phe Gly Gly Ile Leu
    1475                1480                1485
Val Asn Gln Phe Ala Tyr Ser Leu Tyr Gly Leu Asn Ile Arg Gly
    1490                1495                1500
Arg Glu Glu Ile Trp Gly His Val Val Arg Ile Leu Lys Asp Thr
    1505                1510                1515
Ser His Ala Val Leu Lys Val Leu Ser Asn Ala Leu Ser His Pro
    1520                1525                1530
```

Lys Ile Phe Lys Arg Phe Trp Asn Ala Gly Val Val Glu Pro Val
1535                1540                1545

Tyr Gly Pro Asn Leu Ser Asn Gln Asp Lys Ile Leu Leu Ala Leu
1550                1555                1560

Ser Val Cys Glu Tyr Ser Val Asp Leu Phe Met His Asp Trp Gln
1565                1570                1575

Gly Gly Val Pro Leu Glu Ile Phe Ile Cys Asp Asn Asp Pro Asp
1580                1585                1590

Val Ala Asp Met Arg Arg Ser Ser Phe Leu Ala Arg His Leu Ala
1595                1600                1605

Tyr Leu Cys Ser Leu Ala Glu Ile Ser Arg Asp Gly Pro Arg Leu
1610                1615                1620

Glu Ser Met Asn Ser Leu Glu Arg Leu Glu Ser Leu Lys Ser Tyr
1625                1630                1635

Leu Glu Leu Thr Phe Leu Asp Asp Pro Val Leu Arg Tyr Ser Gln
1640                1645                1650

Leu Thr Gly Leu Val Ile Lys Val Phe Pro Ser Thr Leu Thr Tyr
1655                1660                1665

Ile Arg Lys Ser Ser Ile Lys Val Leu Arg Thr Arg Gly Ile Gly
1670                1675                1680

Val Pro Glu Val Leu Glu Asp Trp Asp Pro Glu Ala Asp Asn Ala
1685                1690                1695

Leu Leu Asp Gly Ile Ala Ala Glu Ile Gln Gln Asn Ile Pro Leu
1700                1705                1710

Gly His Gln Thr Arg Ala Pro Phe Trp Gly Leu Arg Val Ser Lys
1715                1720                1725

Ser Gln Val Leu Arg Leu Arg Gly Tyr Lys Glu Ile Thr Arg Gly
1730                1735                1740

Glu Ile Gly Arg Ser Gly Val Gly Leu Thr Leu Pro Phe Asp Gly
1745                1750                1755

Arg Tyr Leu Ser His Gln Leu Arg Leu Phe Gly Ile Asn Ser Thr
1760                1765                1770

Ser Cys Leu Lys Ala Leu Glu Leu Thr Tyr Leu Leu Ser Pro Leu
1775                1780                1785

Val Asp Lys Asp Lys Asp Arg Leu Tyr Leu Gly Glu Gly Ala Gly
1790                1795                1800

Ala Met Leu Ser Cys Tyr Asp Ala Thr Leu Gly Pro Cys Ile Asn
1805                1810                1815

Tyr Tyr Asn Ser Gly Val Tyr Ser Cys Asp Val Asn Gly Gln Arg
1820                1825                1830

Glu Leu Asn Ile Tyr Pro Ala Glu Val Ala Leu Val Gly Lys Lys
1835                1840                1845

Leu Asn Asn Val Thr Ser Leu Gly Gln Arg Val Lys Val Leu Phe
1850                1855                1860

Asn Gly Asn Pro Gly Ser Thr Trp Ile Gly Asn Asp Glu Cys Glu
1865                1870                1875

Ala Leu Ile Trp Asn Glu Leu Gln Asn Ser Ser Ile Gly Leu Val
1880                1885                1890

His Cys Asp Met Glu Gly Gly Asp His Lys Asp Asp Gln Val Val
1895                1900                1905

Leu His Glu His Tyr Ser Val Ile Arg Ile Ala Tyr Leu Val Gly
1910                1915                1920

| | | | | | | | | | | | |
|---|---|---|---|---|---|---|---|---|---|---|---|
| Asp | Arg | Asp | Val | Val | Leu | Ile | Ser | Lys | Ile | Ala | Pro | Arg | Leu | Gly |
| 1925 | | | | 1930 | | | | | 1935 | | |

Asp Arg Asp Val Val Leu Ile Ser Lys Ile Ala Pro Arg Leu Gly
  1925                          1930                     1935

Thr Asp Trp Thr Arg Gln Leu Ser Leu Tyr Leu Arg Tyr Trp Asp
  1940                          1945                     1950

Glu Val Asn Leu Ile Val Leu Lys Thr Ser Asn Pro Ala Ser Thr
  1955                          1960                     1965

Glu Met Tyr Leu Leu Ser Arg His Pro Lys Ser Asp Ile Ile Glu
  1970                          1975                     1980

Asp Ser Lys Thr Val Leu Ala Ser Leu Leu Pro Leu Ser Lys Glu
  1985                          1990                     1995

Asp Ser Ile Lys Ile Glu Lys Trp Ile Leu Ile Glu Lys Ala Lys
  2000                          2005                     2010

Ala His Glu Trp Val Thr Arg Glu Leu Arg Glu Gly Ser Ser Ser
  2015                          2020                     2025

Ser Gly Met Leu Arg Pro Tyr His Gln Ala Leu Gln Thr Phe Gly
  2030                          2035                     2040

Phe Glu Pro Asn Leu Tyr Lys Leu Ser Arg Asp Phe Leu Ser Thr
  2045                          2050                     2055

Met Asn Ile Ala Asp Thr His Asn Cys Met Ile Ala Phe Asn Arg
  2060                          2065                     2070

Val Leu Lys Asp Thr Ile Phe Glu Trp Ala Arg Ile Thr Glu Ser
  2075                          2080                     2085

Asp Lys Arg Leu Lys Leu Thr Gly Lys Tyr Asp Leu Tyr Pro Val
  2090                          2095                     2100

Arg Asp Ser Gly Lys Leu Lys Thr Ile Ser Arg Arg Leu Val Leu
  2105                          2110                     2115

Ser Trp Ile Ser Leu Ser Met Ser Thr Arg Leu Val Thr Gly Ser
  2120                          2125                     2130

Phe Pro Asp Gln Lys Phe Glu Ala Arg Leu Gln Leu Gly Ile Val
  2135                          2140                     2145

Ser Leu Ser Ser Arg Glu Ile Arg Asn Leu Arg Val Ile Thr Lys
  2150                          2155                     2160

Thr Leu Leu Tyr Arg Phe Glu Asp Ile Ile His Ser Ile Thr Tyr
  2165                          2170                     2175

Arg Phe Leu Thr Lys Glu Ile Lys Ile Leu Met Lys Ile Leu Gly
  2180                          2185                     2190

Ala Val Lys Met Phe Gly Ala Arg Gln Asn Glu Tyr Thr Thr Val
  2195                          2200                     2205

Ile Asp Asp Gly Ser Leu Gly Asp Ile Glu Pro Tyr Asp Ser Ser
  2210                          2215                     2220

<210> SEQ ID NO 18
<211> LENGTH: 19905
<212> TYPE: DNA
<213> ORGANISM: Sendai virus

<400> SEQUENCE: 18
accaaacaag agaaaaaaca tgtatgggat atataatgaa gttagacagg attta

```
tggcttacag tagtccagaa ttgtacttga caacaaacgg agtaaacgcc gatgtcaaat   420
atgtgatcta caacatagag aaagacccta agaggacgaa gacagacgga ttcattgtga   480
agacgagaga tatggaatat gagaggacca cagaatggct gtttggacct atggtcaaca   540
agagcccact cttccagggt caacgggatg ctgcagaccc tgacacactc cttcaaacct   600
atgggtatcc tgcatgccta ggagcaataa ttgtccaagt ctggattgtg ctggtgaagg   660
ccatcacaag cagcgccggc ttaaggaaag ggttcttcaa caggttagag gcgttcagac   720
aagacggcac cgtgaaaggt gccttagttt tcactgggga gacagttgag gggataggct   780
cggttatgag atctcagcaa agccttgtat ctctcatggt tgagacccct gtgactatga   840
atactgcaag atctgatctc accacattag agaagaacat ccagatcgtt gggaactaca   900
tccgagatgc agggctggct tccttcatga acactattaa atatgggtg gagacaaaga   960 tggcagctct aacgttgtca aacctgaggc ccgatattaa taagattaga agcctcatag  1020
acacctacct gtcaaaaggc cccagagctc cctttatctg tatcctcaag gaccctgttc  1080
atggtgaatt tgctccaggc aattatcctg cactatggag ttacgccatg ggagtcgccg  1140
tcgtacagaa caaggcaatg cagcagtacg tcacagggag gacatacctt gatatggaaa  1200
tgttcttact aggacaagcc gtggcaaagg atgctgaatc gaagatcagc agtgccctgg  1260
aagatgagtt aggagtgacg gatacagcca aggagaggct cagacatcat ctggcaaact  1320
tgtccggtgg ggatggtgct taccacaaac caacaggcgg tggtgcaatt gaggtagctc  1380
tagacaatgc cgatatcgac ctagaaacag aagctcatgc ggaccaggac gctaggggtt  1440 gggggtggaga aagtggtgaa agatgggcac gtcaggtgag tggtggccac tttgtcacac  1500
tacatggggc tgaacggtta gaggaggaaa ccaatgatga ggatgtatca gacatagaga  1560
gaagaatagc catgagactc gcagagagac ggcaagagga ttctgcaacc catggagatg  1620
aaggccgcaa taacggtgtc gatcacgacg aagatgacga taccgcagca gtagctggga  1680
taggaggaat ctaggatcat acgaggcttc aaggtacttg atccgtagta agaaaaactt  1740
agggtgaaag ttcatccact gatcggctca ggcaaggcca cacccaaccc caccgaccac  1800
acccagcagt cgagacagcc acggcttcgg ctacacttac cgcatggatc aagatgcctt  1860
cattcttaaa gaagattctg aagttgagag ggaggcgcca ggaggaagag agtcgctctc  1920
ggatgttatc ggattcctcg atgctgtcct gtcgagtgaa ccaactgaca tcggaggga   1980 cagaagctgg ctccacaaca ccatcaacac tccccaagga ccaggctctg cccatagagc  2040
caaaagtgag ggcgaaggag aagtctcaac accgtcgacc aagataatc gatcaggtga  2100 ggagagtaga gtctctggga gaacaagcaa gccagaggca gaagcacatg ctggaaacct  2160
tgataaacaa aatatacacc gggcctttgg gggaagaact ggtacaaact ctgtatctca  2220
ggatctgggc gatggaggag actccggaat ccttgaaaat cctccaaatg agaggata    2280 tccgagatca ggtattgaag atgaaaacag agagatggct cgcaccctg ataagagggg   2340 agaagaccaa gctgaaggac ttccagaaga ggtacgagga ggtacatccc tacctgatga  2400
aggagaaggt ggagcaagta ataatggaag aagcatggag cctggcagct cacatagtgc  2460
aagagtaact ggggtcctgg tgattcctag ccccgaactc gaagaggctg tgctacggag  2520
gaacaaaaga agacctacca acagtgggtc caaacctctt actccagcaa ccgtgcctgg  2580 caccggtcc ccaccgctga atcgttacaa cagcacaggg tcaccaccag gaaaaccccc   2640
atctacacag gatgagcaca tcaactctgg ggacaccccc gccgtcaggg tcaaagaccg  2700
gaaaccacca ataggaccc gctctgtctc agattgtcca gccaacggcc gcccaatcca   2760
```

```
cccgggtcta gagaccgact caacaaaaaa gggcatagga gagaacacat catctatgaa    2820
agagatggct acattgttga cgagtcttgg tgtaatccag tctgctcaag aattcgagtc    2880
atcccgagac gcgagttatg tgtttgcaag acgtgcccta aagtctgcaa actatgcaga    2940
gatgacattc aatgtatgcg gcctgatcct ttctgccgag aaatcttccg ctcgtaaggt    3000
agatgagaac aaacaactgc tcaaacagat ccaagagagc gtggaatcat tccgggatat    3060
ttacaagaga ttctctgagt atcagaaaga acagaactca ttgctgatgt ccaacctatc    3120
tacacttcat atcatcacag atagaggtgg caagactgac aacacagact cccttacaag    3180 gtcccccctcc gttttttgcaa aatcaaaaga gaacaagact aaggctacca ggtttgaccc    3240
atctatggag accctagaag atatgaagta caaaccggac ctaatccgag aggatgaatt    3300
tagagatgag atccgcaacc cggtgtacca agagagggac acagaaccca gggcctcaaa    3360
cgcatcacgc ctcctcccct ccaaagagaa gcccacaatg cactctctca ggctcgtcat    3420
agagagcagt cccctaagca gagctgaaaa agcagcatat gtgaaatcat tatccaagtg    3480
caagacagac caagaggtta aggcagtcat ggaactcgta aagaggaca tagagtcact    3540 gaccaactag atcccggggtg aggcatccta ccatcctcag tcatagagag atccaattaa    3600
ttaacagcat cagccagtaa agattaagaa aaacttaggg tgaaagaaat ttcacctaac    3660
acggcgcaat ggcagatatc tatagattcc ctaagttctc atatgaggat aacggtactg    3720
tggagcccct gcctctgaga actggtccag ataagaaagc catcccctac atcaggatta    3780
tcaaggtagg agaccctcct aaacatggag tgagatacct agatttattg ctcttgggtt    3840
tctttgagac accgaaacaa caaccaatc tagggagcgt atctgacttg acagagccga    3900
ccagctactc aatatgcggc tccgggtcgt tacccatagg tgtggccaaa tactacggga    3960
ctgatcagga actcttaaag gcctgcaccg atctcagaat tacggtgagg aggactgttc    4020
gagcaggaga gatgatcgta tacatggtgg attcgattgg tgctccactc ctaccatggt    4080
caggcaggct gagacaggga atgatattta atgcaaacaa ggtcgcacta gctccccaat    4140
gcctccctgt ggacaaggac ataagattca gagtggtgtt tgtcaatggg acatctctag    4200
gggcaatcac catagccaag atcccaaaga cccttgcaga ccttgcattg cccaactcta    4260
tatccgttaa cctactggtg acactcaaga ccgggatctc cacagaacaa aaggggggtac    4320 tcccagtact tgatgatcaa ggggagaaaa agctcaattt tatggtgcac ctcgggttga    4380
tcaggagaaa ggtcgggaag atatactctg ttgagtactg caagagcaag attgagagaa    4440
tgcggctgat tttctcactt gggttaatcg gcggtataag cttccatgtt caggttactg    4500
ggacactatc taagacattc atgagtcagc tcgcatggaa gagggcagtc tgcttcccat    4560
taatggatgt gaatccccat atgaacctgg tgatttgggc ggcatctgta gaaatcacag    4620
gcgtcgatgc ggtgttccaa ccggccatcc ctcgtgattt ccgctactac cctaatgttg    4680
tggctaagaa catcggaagg atcagaaagc tgtaaatgtg cacccatcag agacctgcga    4740
caatgcccca agcagacacc acctggcagt cggagccacc gggtcactcc ttgtcttaaa    4800
taagaaaaac ttagggataa agtcccttgt gagtgcttgg ttgcaaaact ctccgtacgg    4860
gaaacatgac agcatatatc cagaggtcac agtgcatctc aacatcacta ctggttgttc    4920
tcaccacatt ggtctcgtgt cagattccca gggataggct ctctaacata ggggtcatag    4980
tcgatgaagg gaaatcactg aagatagctg atcccacga atcgaggtac atagtactga    5040
gtctagttcc gggggtagac cttgagaatg ggtgcgaaac agcccaggtt atccagtaca    5100
agagcctact gaacaggctg ttaatcccat tgagggatgc cttagatctt caggaggctc    5160
```

```
tgataactgt caccaatgat acgacacaaa atgccggtgt tccacagtcg agattcttcg   5220
gtgctgtgat tggtactatc gcacttggag tggcgacatc agcacagatc accgcaggga   5280
ttgcactagc cgaagcgagg gaggccaaaa gagacatagc gctcatcaaa gaatcgatga   5340
caaaaacaca caagtctata gaactgctgc aaaacgctgt gggggaacaa attcttgctc   5400
taaagacact ccaggatttc gtgaatgatg agatcaaacc cgcaataagc gaattaggct   5460
gtgagactgc tgccttaaga ctgggtataa aattgacaca gcattactcc gggctgttaa   5520
ctgcgttcgg ctcgaatttc ggaaccatcg gagagaagag cctcacgctg caggcgctgt   5580
cttcacttta ctctgctaac attactgaga ttatgaccac aatcaggaca gggcagtcta   5640
acatctatga tgtcatttat acagaacaga tcaaaggaac ggtgatagat gtggatctag   5700
agagatacat ggttaccctg tctgtgaaga tccctattct ttctgaagtc ccaggtgtgc   5760
tcatacacaa ggcatcgtct atttcttaca acatagacgg ggaggaatgg tatgtgactg   5820
tccccagcca tatactcagt cgtgcttctt tcttaggggg tgcagacata accgattgtg   5880
ttgagtccag gttgacctat atatgcccca gggatcccgc acaactgata cctgacagcc   5940
agcaaaagtg tatcctgggg gacacaacaa ggtgtcctgt cacaaaagtt gtggacagcc   6000
ttatccccaa gtttgctttt gtgaatgggg gcgttgttgc taactgcata gcatccacat   6060
gtacctgcgg gacaggccga agaccaatca gtcaggatcg ctctaaaggt gtagtattcc   6120
taacccatga caactgtggt cttataggtg tcaatggggt agaattgtat gctaaccgga   6180
gagggcacga tgccacttgg ggggtccaga acttgacagt cggtcctgca attgctatca   6240
gacccgttga tatttctctc aaccttgctg atgctacgaa tttcttgcaa gactctaagg   6300
ctgagcttga gaaagcacgg aaaatcctct ctgaggtagg tagatggtac aactcaagag   6360
agactgtgat tacgatcata gtagttatgg tcgtaatatt ggtggtcatt atagtgatcg   6420
tcatcgtgct ttatagactc agaaggtcaa tgctaatggg taatccagat gaccgtatac   6480
cgagggacac atatacatta gagccgaaga tcagacatat gtacacaaac ggtgggtttg   6540
atgcgatggc tgagaaaaga tgatcacgag tttaaacaga tgtcttgtaa agcaggcatg   6600
gtatccgttg agatctgtat ataataagaa aaacttaggg tgaaagtgag gtcgcgcggt   6660
actttagctg cggccgcaca atggagttgc taatcctcaa agcaaatgca attaccacaa   6720
tcctcactgc agtcacattt tgttttgctt ctggtcaaaa catcactgaa gaattttatc   6780
aatcaacatg cagtgcagtt agcaaaggct atcttagtgc tctgagaact ggttggtata   6840
ccagtgttat aactatagaa ttaagtaata tcaagaaaaa taagtgtaat ggaacagatg   6900
ccaaggcaaa attgataaaa caagaattag ataaatataa aaatgctgta acagaattgc   6960
agttgctcat gcaaagcaca caagcaacaa acaatcgagc cagaagagaa ctaccaaggt   7020
ttatgaatta tacactcaac aatgccaaaa aaccaatgt aacattaagc aagaaaagga   7080
aaagaagatt tcttggtttt ttgttaggtg ttggatctgc aatcgccagt ggcgttgctg   7140
tatctaaggt cctgcaccta gaaggggaag tgaacaagat caaagtgct ctactatcca   7200 caaacaaggc tgtagtcagc ttatcaaatg gagttagtgt cttaaccagc aaagtgttag   7260
acctcaaaaa ctatatagat aaacaattgt tacctattgt gaacaagcaa agctgcagca   7320
tatcaaatat agaaactgtg atagagttcc aacaaaagaa caacagacta ctagagatta   7380
ccagggaatt tagtgttaat gcaggtgtaa ctacacctgt aagcacttac atgttaacta   7440
atagtgaatt attgtcatta atcaatgata tgcctataac aaatgatcag aaaaagttaa   7500
tgtccaacaa tgttcaaata gttagacagc aaagttactc tatcatgtcc ataataaaag   7560
```

| | |
|---|---|
| aggaagtctt agcatatgta gtacaattac cactatatgg tgttatggat acaccctgtt | 7620 |
| ggaaactaca cacatcccct ctatgtacaa ccaacacaaa agaagggtcc aacatctgtt | 7680 |
| taacaagaac tgacagagga tggtactgtg acaatgcagg atcagtatct ttcttcccac | 7740 |
| aagctgaaac atgtaaagtt caatcaaatc gagtattttg tgacacaatg aacagtttaa | 7800 |
| cattaccaag tgaagtaaat ctctgcaatg ttgacatatt caaccccaaa tatgattgta | 7860 |
| aaattatgac ctcaaaaaca gatgtaagca gctccgttat cacatctcta ggagccattg | 7920 |
| tgtcatgcta tggcaaaact aaatgtacag catccaataa aaatcgtgga atcataaaga | 7980 |
| cattttctaa cgggtgcgat tatgtatcaa ataaaggggt ggacactgtg tctgtaggta | 8040 |
| acacattata ttatgtaaat aagcaagaag gtaaaagtct ctatgtaaaa ggtgaaccaa | 8100 |
| taataaattt ctatgaccca ttagtattcc cctctgatga atttgatgca tcaatatctc | 8160 |
| aagtcaacga gaagattaac cagagcctag catttattcg taaatccgat gaattattac | 8220 |
| ataatgtaat tgctggtaaa tccaccacaa atatcatgat aactactata attatagtga | 8280 |
| ttatagtaat attgttatca ttaattgctg ttggactgct cttatactgt aaggccagaa | 8340 |
| gcacaccagt cacactaagc aaagatcaac tgagtggtat aaataatatt gcatttagta | 8400 |
| actaattata agaaaaactt agggtgaaag tgagcggccg caaacaagca cagatcatgg | 8460 |
| atggtgatag ggcaaacgt gactcgtact ggtctacctc tcctagtggt agcactacaa | 8520 |
| aattagcatc aggttgggag aggtcaagta aagttgacac atggttgctg attctctcat | 8580 |
| tcacccagtg ggctttgtca attgccacag tgatcatctg tatcataatt tctgctagac | 8640 |
| aagggtatag tatgaaagag tactcaatga ctgtagaggc attgaacatg agcagcaggg | 8700 |
| aggtgaaaga gtcacttacc agtctaataa ggcaagaggt tatcgcaagg gctgtcaaca | 8760 |
| ttcagagctc tgtgcaaacc ggaatcccag tcttgttgaa caaaaacagc agggatgtca | 8820 |
| tccagatgat tgataagtcg tgcagcagac aagagctcac tcagctctgt gagagtacga | 8880 |
| tcgcagtcca ccatgccgag ggaattgccc ctcttgagcc acatagtttc tggagatgcc | 8940 |
| ctgtcggaga accgtatctt agctcagatc ctaaaatctc attgctgcct ggtccgagct | 9000 |
| tgttatctgg ttctacaacg atctctggat gtgttaggct cccttcactc tcaattggcg | 9060 |
| aggcaatcta tgcctattca tcaaatctca ttacacaagg ttgtgctgac atagggaaat | 9120 |
| catatcaggt cctgcagcta gggtacatat cactcaattc agatatgttc cctgatctta | 9180 |
| accccgtagt gtcccacact tatgacatca acgacaatcg gaaatcatgc tctgtggtgg | 9240 |
| caaccgggac taggggttat cagctttgct ccatgccgac tgtagacgaa agaaccgact | 9300 |
| actctagtga tggtatcgag gatctggtcc ttgatgtcct ggatctcaaa gggagcacta | 9360 |
| agtctcaccg gtatcgcaac agcgaggtag atcttgatca cccgttctct gcactatacc | 9420 |
| ccagtgtagg caacggcatt gcaacagaag gctcattgat atttcttggg tatggtgggc | 9480 |
| taaccacccc tctacagggt gatacaaaat gtaggaccca aggatgccaa caggtgtcgc | 9540 |
| aagacacatg caatgaggct ctgaaaatta catggctagg agggaaacag gtggtcagcg | 9600 |
| tgatcatcca ggtcaatgac tatctctcag agaggccaaa gataagagtc acaaccattc | 9660 |
| caatcactca aaactatctc ggggcggaag gtagattatt aaaattgggt gatcgggtgt | 9720 |
| acatctatac aagatcatca ggctggcact ctcaactgca gataggagta cttgatgtca | 9780 |
| gccaccctt gactatcaac tggacacctc atgaagcctt gtctagacca ggaaatgaag | 9840 |
| agtgcaattg gtacaatacg tgtccgaagg aatgcatatc aggcgtatac actgatgctt | 9900 |
| atccattgtc ccctgatgca gctaacgtcg ctaccgtcac gctatatgcc aatacatcgc | 9960 |

```
gtgtcaaccc aacaatcatg tattctaaca ctactaacat tataaatatg ttaaggataa   10020
aggatgttca attagaggct gcatatacca cgacatcgtg tatcacgcat tttggtaaag   10080
gctactgctt tcacatcatc gagatcaatc agaagagcct gaataccta cagccgatgc   10140 tctttaagac tagcatccct aaattatgca aggccgagtc ttaaatttaa ctgactagca   10200
ggctggcgcg ccttgctgac actagagtca tctccgaaca tccacaatat ctctcagtct   10260
cttacgtctc tcacagtatt aagaaaaacc cagggtgaat gggaagcttg ccataggtca   10320
tggatgggca ggagtcctcc caaaaccctt ctgacatact ctatccagaa tgccacctga   10380
actctcccat agtcaggggg aagatagcac agttgcacgt cttgttagat gtgaaccagc   10440
cctacagact gaaggacgac agcataataa atattacaaa gcacaaaatt aggaacggag   10500
gattgtcccc ccgtcaaatt aagatcaggt ctctgggtaa ggctcttcaa cgcacaataa   10560
aggatttaga ccgatacacg tttgaaccgt acccaaccta ctctcaggaa ttacttaggc   10620
ttgatatacc agagatatgt gacaaaatcc gatccgtctt cgcggtctcg gatcggctga   10680
ccagggagtt atctagtggg ttccaggatc tttggttgaa tatcttcaag caactaggca   10740
atatagaagg aagagagggg tacgatccgt tgcaggatat cggcaccatc ccggagataa   10800
ctgataagta cagcaggaat agatggtata ggccattcct aacttggttc agcatcaaat   10860
atgacatgcg gtggatgcag aagaccagac cgggggggacc ccttgatacc tctaattcac   10920
ataacctcct agaatgcaaa tcatacactc tagtaacata cggagatctt gtcatgatac   10980
tgaacaagtt gacattgaca gggtatatcc taacccctga gctggtcttg atgtattgtg   11040
atgttgtaga aggaaggtgg aatatgtctg ctgcagggca tctagataag aagtccattg   11100
ggataacaag caaaggtgag gaattatggg aactagtgga ttccctcttc tcaagtcttg   11160
gagaggaaat atacaatgtc atcgcactat tggagcccct atcacttgct ctcatacaac   11220
taaatgatcc tgttataacct ctacgtgggg catttatgag gcatgtgttg acagagctac   11280
agactgtttt aacaagtaga gacgtgtaca cagatgctga agcagacact attgtggagt   11340
cgttactcgc cattttccat ggaacctcta ttgatgagaa agcagagatc ttttccttct   11400
ttaggacatt tggccacccc agcttagagg ctgtcactgc cgccgacaag gtaagggccc   11460
atatgtatgc acaaaaggca ataaagctta agaccctata cgagtgtcat gcagtttttt   11520
gcactatcat cataaatggg tatagagaga ggcatggcgg acagtggccc ccctgtgact   11580
tccctgatca cgtgtgtcta gaactaagga acgctcaagg gtccaatacg gcaatctctt   11640
atgaatgtgc tgtagacaac tatacaagtt tcataggctt caagtttcgg aagtttatag   11700
aaccacaact agatgaagat ctcacaatat atatgaaaga caaagcacta tcccccagga   11760
aggaggcatg ggactctgta tacccggata gtaatctgta ctataaagcc ccagagtctg   11820
aagagacccg gcggcttatt gaagtgttca taaatgatga gaatttcaac ccagaagaaa   11880
ttatcaatta tgtggagtca ggagattggt tgaaagacga ggagttcaac atctcgtaca   11940
gtctcaaaga gaaagagatc aagcaagagg gtcgtctatt cgcaaaaatg acttataaga   12000
tgcgagccgt acaggtgctg gcagagacac tactggctaa ggaatagga gagctattca   12060 gggaaaatgg gatggttaag ggagagatag acctacttaa aagattgact actctttctg   12120
tctcaggcgt ccccaggact gattcagtgt acaataactc taaatcatca gagaagagaa   12180
acgaaggcat ggaaaataag aactctgggg ggtactggga cgaaaagaag aggtccagac   12240
atgaattcaa ggcaacagat tcatcaacag acggctatga aacgttaagt tgcttcctca   12300
caacagacct caagaaatac tgcttaaact ggagatttga gagtactgca ttgtttggtc   12360
```

```
agagatgcaa cgagatattt ggcttcaaga ccttctttaa ctggatgcat ccagtccttg    12420
aaaggtgtac aatatatgtt ggagatcctt actgtccagt cgccgaccgg atgcatcgac    12480
aactccagga tcatgcagac tctggcattt tcatacataa tcctaggggg ggcatagaag    12540
gttactgcca gaagctgtgg accttaatct caatcagtgc aatccaccta gcagctgtga    12600
gagtgggtgt cagggtctct gcaatggttc agggtgacaa tcaagctata gccgtgacat    12660
caagagtacc tgtagctcag acttacaagc agaagaaaaa tcatgtctat gaggagatca    12720
ccaaatattt cggtgctcta agacacgtca tgtttgatgt agggcacgag ctaaaattga    12780
acgagaccat cattagtagc aagatgtttg tctatagtaa aaggatatac tatgatggga    12840
agattttacc acagtgcctg aaagccttga ccaagtgtgt attctggtcc gagacactgg    12900
tagatgaaaa cagatctgct tgttcgaaca tctcaacatc catagcaaaa gctatcgaaa    12960
atgggtattc tcctatacta ggctactgca ttgcgttgta aagacctgt cagcaggtgt     13020
gcatatcact agggatgact ataaatccaa ctatcagccc gaccgtaaga gatcaatact    13080
ttaagggtaa gaattggctg agatgtgcag tgttgattcc agcaaatgtt ggaggattca    13140
actacatgtc tacatctaga tgctttgtta gaaatattgg agaccccgca gtagcagccc    13200
tagctgatct caaaagattc atcagagcgg atctgttaga caagcaggta ttatacaggg    13260
tcatgaatca agaacccggt gactctagtt ttctagattg ggcttcagac ccttattcgt    13320
gtaacctccc gcattctcag agtataacta cgattataaa gaatatcact gctagatctg    13380
tgctgcagga atccccgaat cctctactgt ctggtctctt caccgagact agtggagaag    13440
aggatctcaa cctggcctcg ttccttatgg accggaaagt catcctgccg agagtggctc    13500
atgagatcct gggtaattcc ttaactggag ttagggaggc gattgcaggg atgcttgata    13560
cgaccaagtc tctagtgaga gccagcgtta ggaaaggagg attatcatat gggatattga    13620
ggaggcttgt caattatgat ctattgcagt acgagacact gactagaact ctcaggaaac    13680
cggtgaaaga caacatcgaa tatgagtata tgtgttcagt tgagctagct gtcggtctaa    13740
ggcagaaaat gtggatccac ctgacttacg ggagacccat acatgggtta gaaacaccag    13800
accctttaga gctcttgagg ggaatattta tcgaaggttc agaggtgtgc aagctttgca    13860
ggtctgaagg agcagacccc atctatacat ggttctatct tcctgacaat atagacctgg    13920
acacgcttac aaacggatgt ccggctataa gaatccccta ttttggatca gccactgatg    13980
aaaggtcgga agcccaactc gggtatgtaa gaaatctaag caaacccgca aaggcggcca    14040
tccggatagc tatggtgtat acgtgggcct acgggactga tgagatatcg tggatggaag    14100
ccgctcttat agcccaaaca agagctaatc tgagcttaga gaatctaaag ctgctgactc    14160
ctgtttcaac ctccactaat ctatctcata ggttgaaaga tacggcaacc cagatgaagt    14220
tctctagtgc aacactagtc cgtgcaagtc ggttcataac aatatcaaat gataacatgg    14280
cactcaaaga agcaggggag tcgaaggata ctaatctcgt gtatcagcag attatgctaa    14340
ctgggctaag cttgttcgag ttcaatatga gatataagaa aggttcctta gggaagccac    14400
tgatattgca cttacatctt aataacgggt gctgtataat ggagtcccca caggaggcga    14460
atatccccc aaggtccaca ttagatttag agattacaca agagaacaat aaattgatct    14520
atgatcctga tccactcaag gatgtggacc ttgagctatt tagcaaggtc agagatgttg    14580
tacatacagt tgacatgact tattggtcag atgatgaagt tatcagagca accagcatct    14640
gtactgcaat gacgatagct gatacaatgt ctcaattaga tagagacaac ttaaaagaga    14700
tgatcgcact agtaaatgac gatgatgtca acagcttgat tactgagttt atggtgattg    14760
```

```
atgttccttt attttgctca acgttcgggg gtattctagt caatcagttt gcatactcac    14820
tctacggctt aaacatcaga ggaagggaag aaatatgggg acatgtagtc cggattctta    14880
aagatacctc ccacgcagtt ctaaaagtct tatctaatgc tctatcccat cccaaaatct    14940
tcaaacgatt ctggaatgca ggtgtcgtgg aacctgtgta tgggcctaac ctctcaaatc    15000
aggataagat actcttggcc ctctctgtct gtgaatattc tgtggatcta ttcatgcacg    15060
actggcaagg gggtgtaccg cttgagatct ttatctgtga caatgaccca gatgtggccg    15120
acatgaggag gtcctctttc ttggcaagac atcttgcata cctatgcagc ttggcagaga    15180
tatctaggga tgggccaaga ttagaatcaa tgaactctct agagaggctc gagtcactaa    15240
agagttacct ggaactcaca tttcttgatg acccggtact gaggtacagt cagttgactg    15300
gcctagtcat caaagtattc ccatctactt tgacctatat ccggaagtca tctataaaag    15360
tgttaaggac aagaggtata ggagtccctg aagtcttaga agattgggat cccgaggcag    15420
ataatgcact gttagatggt atcgcggcag aaatacaaca gaatattcct ttgggacatc    15480
agactagagc ccctttttgg ggggttgagag tatccaagtc acaggtactg cgtctccggg    15540
ggtacaagga gatcacaaga ggtgagatag gcagatcagg tgttggtctg acgttaccat    15600
tcgatggaag atatctatct caccagctga ggctctttgg catcaacagt actagctgct    15660
tgaaagcact tgaacttacc tacctattga gccccttagt tgacaaggat aaagataggc    15720
tatatttagg ggaaggagct ggggccatgc tttcctgtta tgacgctact cttggcccat    15780
gcatcaacta ttataactca ggggtatact cttgtgatgt caatgggcag agagagttaa    15840
atatatatcc tgctgaggtg gcactagtgg gaaagaaatt aaacaatgtt actagtctgg    15900
gtcaaagagt taaagtgtta ttcaacggga atcctggctc gacatggatt gggaatgatg    15960
agtgtgaggc tttgatttgg aatgaattac agaatagctc gataggccta gtccactgtg    16020
acatggaggg aggagatcat aaggatgatc aagttgtact gcatgagcat tacagtgtaa    16080
tccggatcgc gtatctggtg ggggatcgag acgttgtgct tataagcaag attgctccca    16140
ggctgggcac ggattggacc aggcagctca gcctatatct gagatactgg gacgaggtta    16200
acctaatagt gcttaaaaca tctaaccctg cttccacaga gatgtatctc ctatcgaggc    16260
accccaaatc tgacattata gaggacagca agacagtgtt agctagtctc ctcccttgt    16320 caaaagaaga tagcatcaag atagaaaagt ggatcttaat agagaaggca aaggctcacg    16380
aatgggttac tcgggaattg agagaaggaa gctcttcatc agggatgctt agaccttacc    16440
atcaagcact gcagacgttt ggctttgaac caaacttgta taaattgagc agagatttct    16500
tgtccaccat gaacatagct gatacacaca actgcatgat agctttcaac agggttttga    16560
aggatacaat cttcgaatgg gctagaataa ctgagtcaga taaaaggctt aaactaactg    16620
gtaagtatga cctgtatcct gtgagagatt caggcaagtt gaagacaatt tctagaagac    16680
ttgtgctatc ttggatatct ttatctatgt ccacaagatt ggtaactggg tcattccctg    16740
accagaagtt tgaagcaaga cttcaattgg gaatagtttc attatcatcc cgtgaaatca    16800
ggaacctgag ggttatcaca aaaactttat tatacaggtt tgaggatatt atacatagta    16860
taacgtatag attcctcacc aaagaaataa agatttgat gaagattta ggggcagtca    16920 agatgttcgg ggccaggcaa aatgaataca cgaccgtgat tgatgatgga tcactaggtg    16980
atatcgagcc atatgacagc tcgtaataat tagtccctat cgtgcagaac gatcgaagct    17040
ccgcggtacc tggaagtctt ggacttgtcc atatgacaat agtaagaaaa acttacaaga    17100
agacaagaaa atttaaaagg atacatatct cttaaactct tgtctggtgg gtcggcatgg    17160
```

```
catctccacc tcctcgcggt ccgacctggg catccgaagg aggacgtcgt ccactcggat    17220
ggctaaggga ggggccccg cggggctgct aacaaagccc gaaaggaagc tgagttggct     17280
gctgccaccg ctgagcaata actagcataa ccccttgggg cctctaaacg ggtcttgagg    17340
ggttttttgc tgaaaggagg aactatatcc ggatcgagac ctcgatgccg gctgatgcgg    17400
tattttctcc ttacgcatct gtgcggtatt tcacaccgca tatggtgcac tctcagtaca    17460
atctgctctg atgccgcata gttaagccag ccccgacacc cgccaacacc cgctgacgcg    17520
ccctgacggg cttgtctgct cccggcatcc gcttacagac aagctgtgac cgtctccggg    17580
agctgcatgt gtcagaggtt ttcaccgtca tcaccgaaac gcgcgagacg aaagggcctc    17640
gtgatacgcc tattttttata ggttaatgtc atgataataa tggtttctta cacgtcaggt    17700
ggcacttttc ggggaaatgt gcgcggaacc cctatttgtt tattttttcta aatacattca    17760 aatatgtatc cgctcatgag acaataaccc tgataaatgc ttcaataata ttgaaaaagg    17820
aagagtatga gtattcaaca tttccgtgtc gcccttattc ccttttttgc ggcattttgc    17880
cttcctgttt ttgctcaccc agaaacgctg gtgaaagtaa aagatgctga agatcagttg    17940
ggtgcacgag tgggttacat cgaactggat ctcaacagcg gtaagatcct tgagagtttt    18000
cgccccgaag aacgttttcc aatgatgagc acttttaaag ttctgctatg tggcgcggta    18060
ttatcccgta ttgacgccgg gcaagagcaa ctcggtcgcc gcatacacta ttctcagaat    18120
gacttggttg agtactcacc agtcacagaa aagcatctta cggatggcat gacagtaaga    18180
gaattatgca gtgctgccat aaccatgagt gataacactg cggccaactt acttctgaca    18240
acgatcggag gaccgaagga gctaaccgct tttttgcaca acatggggga tcatgtaact    18300
cgccttgatc gttgggaacc ggagctgaat gaagccatac caaacgacga gcgtgacacc    18360
acgatgcctg tagcaatggc aacaacgttg cgcaaactat taactggcga actacttact    18420
ctagcttccc ggcaacaatt aatagactgg atggaggcgg ataaagttgc aggaccactt    18480
ctgcgctcgg cccttccggc tggctggttt attgctgata atctggagc cggtgagcgt    18540 gggtctcgcg gtatcattgc agcactgggg ccagatggta agccctcccg tatcgtagtt    18600
atctacacga cggggagtca ggcaactatg gatgaacgaa atagacagat cgctgagata    18660
ggtgcctcac tgattaagca ttggtaactg tcagaccaag tttactcata tactttag     18720 attgatttaa aacttcattt ttaatttaaa aggatctagg tgaagatcct ttttgataat    18780
ctcatgacca aaatccctta acgtgagttt tcgttccact gagcgtcaga ccccgtagaa    18840
aagatcaaag gatcttcttg agatcctttt tttctgcgcg taatctgctg cttgcaaaca    18900
aaaaaaccac cgctaccagc ggtggtttgt ttgccggatc aagagctacc aactcttttt    18960
ccgaaggtaa ctggcttcag cagagcgcag ataccaaata ctgtccttct agtgtagccg    19020
tagttaggcc accacttcaa gaactctgta gcaccgccta catacctcgc tctgctaatc    19080
ctgttaccag tggctgctgc cagtggcgat aagtcgtgtc ttaccgggtt ggactcaaga    19140
cgatagttac cggataaggc gcagcggtcg ggctgaacgg ggggttcgtg cacacagccc    19200
agcttggagc gaacgaccta caccgaactg agatacctac agcgtgagct atgagaaagc    19260
gccacgcttc ccgaagggag aaaggcggac aggtatccgg taagcggcag gtcggaaca    19320 ggagagcgca cgagggagct tccaggggga aacgcctggt atctttatag tcctgtcggg    19380
tttcgccacc tctgacttga gcgtcgattt ttgtgatgct cgtcaggggg gcggagccta    19440
tggaaaaacg ccagcaacgc ggcctttta cggttcctgg ccttttgctg gccttttgct    19500
cacatgttct ttcctgcgtt atcccctgat tctgtggata accgtattac cgcctttgag    19560
```

-continued

```
tgagctgata ccgctcgccg cagccgaacg accgagcgca gcgagtcagt gagcgaggaa    19620
gcggaagagc gcccaatacg caaaccgcct ctccccgcgc gttggccgat tcattaatgc    19680
agctggcacg acaggtttcc cgactggaaa gcgggcagtg agcgcaacgc aattaatgtg    19740
agttagctca ctcattaggc accccaggct ttacactttta tgcttccggc tcgtatgttg    19800
tgtggaattg tgagcggata acaatttcac acaggaaaca gctatgacca tgattacgcc    19860
aagcttgcat gcctgcaggt cgacgcgtta atacgactca ctata                    19905
```

<210> SEQ ID NO 19
<211> LENGTH: 10
<212> TYPE: DNA
<213> ORGANISM: Sendai virus

<400> SEQUENCE: 19
agggataaag                                                           10

<210> SEQ ID NO 20
<211> LENGTH: 10
<212> TYPE: DNA
<213> ORGANISM: Artificial Sequence
<220> FEATURE:
<223> OTHER INFORMATION: Synthetic

<400> SEQUENCE: 20
agggtgaaag                                                           10

<210> SEQ ID NO 21
<211> LENGTH: 33
<212> TYPE: DNA
<213> ORGANISM: Artificial sequence
<220> FEATURE:
<223> OTHER INFORMATION: Synthetic

<400> SEQUENCE: 21
gaataagaaa aacttagggt gaaaggcggc cgc                                 33

<210> SEQ ID NO 22
<211> LENGTH: 32
<212> TYPE: DNA
<213> ORGANISM: Artificial sequence
<220> FEATURE:
<223> OTHER INFORMATION: Synthetic

<400> SEQUENCE: 22
cttagggtga agaaatttc acctgcggcc gc                                   32

<210> SEQ ID NO 23
<211> LENGTH: 27
<212> TYPE: DNA
<213> ORGANISM: Artificial sequence
<220> FEATURE:
<223> OTHER INFORMATION: Synthetic

<400> SEQUENCE: 23
cttagggtga agtcccttg cggccgc                                         27

<210> SEQ ID NO 24
<211> LENGTH: 44
<212> TYPE: DNA
<213> ORGANISM: Artificial sequence
<220> FEATURE:
<223> OTHER INFORMATION: Synthetic

```
<400> SEQUENCE: 24
cttagggtga aagtgaggtc gcgcggtact ttagctgcgg ccgc                    44
```